US011584743B2

(12) United States Patent
Crew et al.

(10) Patent No.: US 11,584,743 B2
(45) Date of Patent: *Feb. 21, 2023

(54) INDOLE DERIVATIVES AS ESTROGEN RECEPTOR DEGRADERS

(71) Applicant: Arvinas Operations, Inc., New Haven, CT (US)

(72) Inventors: Andrew P. Crew, Guilford, CT (US); Yimin Qian, Plainsboro, NJ (US); Hanging Dong, Madison, CT (US); Jing Wang, Milford, CT (US)

(73) Assignee: Arvinas Operations, Inc., New Haven, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/082,839

(22) Filed: Oct. 28, 2020

(65) Prior Publication Data

US 2021/0040081 A1 Feb. 11, 2021

Related U.S. Application Data

(63) Continuation of application No. 16/376,225, filed on Apr. 5, 2019, now Pat. No. 10,865,202, which is a continuation of application No. 15/706,064, filed on Sep. 15, 2017, now abandoned.

(60) Provisional application No. 62/395,228, filed on Sep. 15, 2016.

(51) Int. Cl.

| | |
|---|---|
| ***C07D 417/14*** | (2006.01) |
| ***C07K 5/062*** | (2006.01) |
| ***C07D 403/12*** | (2006.01) |
| ***C07D 403/14*** | (2006.01) |
| ***C07D 413/14*** | (2006.01) |

(52) U.S. Cl.

CPC ......... *C07D 417/14* (2013.01); *C07D 403/12* (2013.01); *C07D 403/14* (2013.01); *C07D 413/14* (2013.01); *C07K 5/06034* (2013.01); *C07K 5/06052* (2013.01)

(58) Field of Classification Search

CPC .................................................... C07D 417/14

See application file for complete search history.

(56) References Cited

U.S. PATENT DOCUMENTS

| | | | | |
|---|---|---|---|---|
| 5,492,922 | A | 2/1996 | Palkowitz et al. | |
| 5,681,835 | A | 10/1997 | Willson | |
| 5,877,219 | A | 3/1999 | Willson | |
| 6,207,716 | B1 | 3/2001 | Willson | |
| 6,306,663 | B1 | 10/2001 | Kenten et al. | |
| 6,670,348 | B1 | 12/2003 | Rosen et al. | |
| 7,030,141 | B2 | 4/2006 | Bigge et al. | |
| 7,041,298 | B2 | 5/2006 | Deshaies et al. | |
| 7,208,157 | B2 | 4/2007 | Sakamoto et al. | |
| 9,500,653 | B2 | 11/2016 | Crews et al. | |
| 9,632,089 | B2 | 4/2017 | Crews et al. | |
| 10,865,202 | B2 * | 12/2020 | Crew | C07D 403/14 |
| 2008/0214501 | A1 | 9/2008 | Zhengying et al. | |
| 2012/0270800 | A1 | 10/2012 | Verdine et al. | |
| 2014/0302523 | A1 | 10/2014 | Crews et al. | |
| 2014/0356322 | A1 | 12/2014 | Crews et al. | |
| 2015/0119435 | A1 | 4/2015 | Crews et al. | |
| 2015/0291562 | A1 | 10/2015 | Crew et al. | |
| 2015/0344473 | A1 | 10/2015 | Du et al. | |
| 2016/0022642 | A1 | 1/2016 | Crews et al. | |
| 2016/0045607 | A1 | 2/2016 | Crew et al. | |
| 2016/0058872 | A1 | 3/2016 | Crew et al. | |
| 2016/0136230 | A1 | 5/2016 | Campos et al. | |
| 2016/0214972 | A1 | 7/2016 | Jin et al. | |
| 2016/0243247 | A1 | 8/2016 | Bradner et al. | |
| 2016/0272639 | A1 | 9/2016 | Crew et al. | |
| 2016/0368911 | A1 | 12/2016 | Campos et al. | |
| 2017/0008904 | A1 | 1/2017 | Crew et al. | |
| 2017/0037004 | A1 | 2/2017 | Crew et al. | |
| 2017/0065719 | A1 | 3/2017 | Qian et al. | |
| 2017/0121321 | A1 | 5/2017 | Crews et al. | |
| 2017/0281784 | A1 | 10/2017 | Wang et al. | |
| 2017/0307614 | A1 | 10/2017 | Crews et al. | |
| 2017/0327469 | A1 | 11/2017 | Crew et al. | |
| 2018/0015087 | A1 | 1/2018 | Liu et al. | |
| 2018/0072711 | A1 | 3/2018 | Crew et al. | |
| 2018/0099940 | A1 | 4/2018 | Crew et al. | |
| 2018/0125821 | A1 | 5/2018 | Crew et al. | |

(Continued)

FOREIGN PATENT DOCUMENTS

| | | |
|---|---|---|
| CN | 102477033 | 5/2012 |
| EP | 2985285 | 2/2016 |

(Continued)

OTHER PUBLICATIONS

Trogden et al (2009): STN International CAPLUS database, (Columbus, Ohio), Accession No. 2009: 6217.*
Von Angerer et al (1987): STN International CAPLUS database, (Columbus, Ohio), Accession No. 1987: 32768.*
Abraham, R.T., "Phosphatidylinositol 3-kinase related kinases", (1996), Current Opinion in Immunology. 8 (3) 412-418.
Ahn, et al., "HIF-1alpha peptide derivatives with modifications at the hydroxyproline residue as activators of HIF-1alpha", Bioorg Med Chem Lett. 19(15), 2009, 4403-4405.
Ali, S. et al. Molecular mechanisms and mode of tamoxifen resistance in breast cancer. Bioinformation 12, 135-139 (2016).

(Continued)

*Primary Examiner* — Golam M Shameem
(74) *Attorney, Agent, or Firm* — McCarter & English, LLP; Michael J. DeGrazia; James M. Alburger

(57) ABSTRACT

The present disclosure relates to compounds and a pharmaceutically acceptable salt thereof, compositions, combinations and medicaments containing the compounds, and processes for their preparation. The disclosure also relates to the use of the compounds, combinations, compositions and medicaments, for example as inhibitors of the activity of the estrogen receptor, including degrading the estrogen receptor, the treatment of diseases and conditions mediated by the estrogen receptor.

19 Claims, 1 Drawing Sheet

(56) References Cited

U.S. PATENT DOCUMENTS

| | | | |
|---|---|---|---|
| 2018/0147202 | A1 | 5/2018 | Crew et al. |
| 2018/0155322 | A1 | 6/2018 | Crew et al. |
| 2018/0177750 | A1 | 6/2018 | Crew et al. |
| 2018/0179183 | A1 | 6/2018 | Crew et al. |
| 2018/0193470 | A1 | 7/2018 | Crew et al. |
| 2018/0215731 | A1 | 8/2018 | Crew et al. |
| 2018/0228907 | A1 | 8/2018 | Crew et al. |
| 2018/0237418 | A1 | 8/2018 | Crew et al. |
| 2018/0256586 | A1 | 9/2018 | Crew et al. |

FOREIGN PATENT DOCUMENTS

| | | |
|---|---|---|
| WO | WO 1998/045287 | 10/1998 |
| WO | WO 1999/015521 | 4/1999 |
| WO | WO 2000/066119 | 11/2000 |
| WO | WO 2002/066512 | 8/2002 |
| WO | WO 2002/100845 | 12/2002 |
| WO | WO 2006/113942 | 10/2006 |
| WO | WO 2007/106670 | 9/2007 |
| WO | WO 2008/011392 | 1/2008 |
| WO | WO 2009/015254 | 1/2009 |
| WO | WO 2010/141805 | 12/2010 |
| WO | WO 2011/008260 | 1/2011 |
| WO | WO 2012/003281 | 1/2012 |
| WO | WO 2012/040527 | 3/2012 |
| WO | WO 2012/078559 | 6/2012 |
| WO | WO 2012/090104 | 7/2012 |
| WO | WO 2013/106643 | 7/2013 |
| WO | WO 2013/106646 | 7/2013 |
| WO | WO 2013/170147 | 11/2013 |
| WO | WO 2014/108452 | 7/2014 |
| WO | WO 2014/123418 | 8/2014 |
| WO | WO 2015/000867 | 1/2015 |
| WO | WO 2015/000868 | 1/2015 |
| WO | WO 2015/160845 | 10/2015 |
| WO | WO 2016/105518 | 6/2016 |
| WO | WO 2016/118666 | 7/2016 |
| WO | WO 2016/146985 | 9/2016 |
| WO | WO 2016/169989 | 10/2016 |
| WO | WO 2016/172134 | 10/2016 |
| WO | WO 2016/197114 | 12/2016 |
| WO | WO 2017/011590 | 1/2017 |
| WO | WO 2017/024318 A1 | 2/2017 |
| WO | WO 2017/024319 A1 | 2/2017 |
| WO | WO 2017/030814 | 2/2017 |
| WO | WO 2017/079267 | 5/2017 |
| WO | WO 2017/161119 | 9/2017 |
| WO | WO 2017/185036 | 10/2017 |

OTHER PUBLICATIONS

Bargagna-Mohan, et al., "Use of PROTACS as molecular probes of angiogenesis", Bioorg Med Chem Left. 15(11) 2005, 2724-2727.

Battista, M. J. & Schmidt, M. Fulvestrant for the treatment of endometrial cancer. Expert Opin Investig Drugs 25, 475-483 (2016).

Bondeson, et al., (2017) "Targeted Protein Degradation by Small Molecules." *Annu Rev Pharmacol Toxicol* 57:107-123.

Bondeson, et al., "Catalytic in vivo protein knockdown by small-molecule PROTACS", National Chem Biol. 11(8) Aug. 2015, 611-617.

Buckley, et al., "HaloPROTACS: use of small molecule PROTACS to induce degradation of HaloTag fusion proteins", ACS Chem Biol. 10(8), 2015, 1831-1837.

Buckley, et al., "Small-molecule inhibitors of the interaction between the E3 ligase VHL and HIF1a", Angew Chem Int Ed Engl.51(46), Oct. 12, 2012, 11463-11467.

Buckley, et al., "Targeting the von Hippel-Lindau E3 ubiquitin ligase using small molecules to disrupt the VHL/HIF-1α interaction", Journal of the American Chemical Society, Feb. 27, 2012, 134(10): 4465-4468.

Burke, et al., "Design, Synthesis and Biological Evaluation of Doxorubicin-Formaldehyde Conjugates Targeted to Breast Cancer Cells", Journal of Medicinal Chemistry, Jan. 24, 2004, vol. 47, No. 5, pp. 1193-1206.

Burslem, et al., (2017) "Small-Molecule Modulation of Protein Homeostasis." *Chem Rev* 117(17):11269-11301.

Carmony, KC, et al., "PROTAC-Induced Proteolytic Targeting", Methods Mol. Biol., 2012, vol. 832, pp. 627-638.

CAS Registry No. 1004933-70-3, which entered STN on Feb. 21, 2008.

CAS Registry No. 871986-52-6 entered STN Jan. 16, 2006.

Cheng-Gen, Feng, et al., "Progress in Antiestrogens for the Treatment of Breast Cancer", Chinese Journal of New Drugs, vol. 15., No. 13, pp. 1051-1057, Dec. 31, 2006 (With Abstract).

Connor, C.E., et al., "Circumventing tamoxifen resistance in breast cancers using antiestrogens that induce unique conformational changes in the estrogen receptor", Cancer Res. 61: 2917-2922 (2001).

Corson, et al., "Design and applications of bifunctional small molecules: why two heads are better than one", ACS Chemical Biology vol. 3 No. 11, pp. 677-692; Nov. 21, 2008.

Crews, C. M., "Targeting the undruggable proteome: the small molecules of my dreams", *Chem Biol* 17, 551-555, doi:S1074-5521(10)00196-1 [pii] 10.1016/j.chembiol.2010.05.011 (2010).

Cromm, et al., (2017) "Targeted Protein Degradation: from Chemical Biology to Drug Discovery." *Cell Chem Biol* 24(9):1181-1190.

Cyrus, et al., "Jostling for position: optimizing linker location in the design of estrogen receptor-targeting PROTACs", Chem Med Chem. 5(7), Jul. 5, 2010, 979-985.

Cyrus, K. et al., "Impact of Linker Length on the Activity of PROTACs," Mol. Biosyst., 2011, vol. 7, No. 2, pp. 359-364.

Cyrus, K. et al., "Two-Headed PROTAC: An Effective New Tool for Targeted Protein Degradation," Chembiochem., 2010, vol. 11, pp. 1531-1534.

Deroo, B.J., et al., "Estrogen receptors and human disease", Journal of Clinical Investigation, (2006), vol. 116(3), pp. 561-570.

Gadd, M.S., et al., "Structural basis of PROTAC cooperative recognition for selective protein degradation", Nat Chem Biol 13, 514-521 (2017).

Galdeano, et al., "Structure-guided design and optimization of small molecules targeting the protein-protein interaction between the von hippel-lindau (VHL) E3 ubiquitin ligase and the Hypoxia inducible factor (HIF) alpha subunit with in vitro nanomolar affinities", Journal Med Chem, Aug. 2014, vol. 57, pp. 8657-8663.

Garner, F., Shomali, M., Paquin, D., Lyttle, C. R. & Hattersley, G. RAD1901: a novel, orally bioavailable selective estrogen receptor degrader that demonstrates antitumor activity in breast cancer xenograft models. Anticancer Drugs 26, 948-956 (2015).

Golub, et al., "Molecular classification of cancer: class discovery and class prediction by gene expression monitoring", Science 286 531-537 (1991).

Gosink, M et al., "Redirecting the specificity of ubiquitination by modifying ubiquitin-conjugating enzymes", Pro. Natl. Acad Sci, vol. 92, pp. 9117-9121, 1995.

Heldring, et al., "Estrogen Receptors: How Do They Signal and What are Their Targets", Physiological Reviews (2007), vol. 87, pp. 905-931.

Hines, J., et al., "Posttranslational protein knockdown coupled to receptor tyrosine kinase activation with phosphoPROTACs", Proc Natl Acad Sci USA 110, 8942-8947 (2013).

Hoffmann, J. et al. Characterization of New Estrogen Receptor Destabilizing Compounds: Effects on Estrogen-Sensitive and Tamoxifen-Resistant Breast Cancer. JNCI Journal of the National Cancer Institute 96, 210-218 (2004).

Hon, et al., "Structural basis for the recognition of hydroxyproline in HIf-1 alpha by pVHL", Nature 417, Jun. 27, 2002, 975-978.

Huang, et al., (2016) "Drugging the undruggables: exploring the ubiquitin system for drug development." *Cell Res* 26(4):484-498.

Hughes, et al., (2017) "Molecular recognition of ternary complexes: a new dimension in the structure-guided design of chemical degraders." *Essays Biochem* 61(5):505-516.

Ivan, M., et al., "HIFa Targeted for VHL-Mediated Destruction by Proline Hydroxylation: Implications for O2 Sensing", Science, vol. 292, No. 5516, pp. 464-468, 2001.

(56) References Cited

OTHER PUBLICATIONS

Jang, E.R. et al., "Targeted Degradation of Proteins by PROTACs," Curr. Protoc. Chem. Biol., 2010, vol. 2, No. 2, pp. 71-87.
Jiang, et al., "Synthesis of 7alpha-substituted derivatives of 17beta-estradiol", Steroids 71(5), May 2006, 334-342 (Abstract).
Jordan, V.C. et al., "A monohydroxylated metabolite of tamoxifen with potent antioestrogenic activity", Endocrinol 75: 305-316 (1977).
Knott, Edward (1955). "Compounds containing sulphur chromophores. Part I. The action of bases on heterocyclic sulphide quarternary salts", Journal of The Chemical Society (resumed). 10.1039/jr9550000916. 949-954) (USPTO summary attached).
Lai, A. et al. Identification of GDC-0810 (ARN-810), an Orally Bioavailable Selective Estrogen Receptor Degrader (SERD) that Demonstrates Robust Activity in Tamoxifen-Resistant Breast Cancer Xenografts. J. Med. Chem. 58, 4888-4904 (2015).
Lai, A.C., et al., "Modular PROTAC Design for the Degradation of Oncogenic BCR-ABL", Angew Chem Int Ed Engl 55, 807-810 (2016).
Lai, et al., (2017) "Induced protein degradation: an emerging drug discovery paradigm." *Nat Rev Drug Discov* 16(2):101-114.
Lala, et al., "Role of nitric oxide in tumor progression: Lessons from experimental tumors", Cancer and Metastasis Reviews 17:91-106 (1998).
Lebraud, H., et al., "Protein Degradation by In-Cell Self-Assembly of Proteolysis Targeting Chimeras", ACS Central Science, 2, 927-934 (2016).
Lee, et al., "Targeted Degradation of the Aryl Hydrocarbon Receptor by the PROTAC Approach: A Useful Chemical Genetic Tool", ChemBioChem vol. 8, Issue 17, pp. 2058-2062, Nov. 23, 2007.
Lelais, G. et al., "Discovery of (R,E)-N-(7-Chloro-1-(1-[4-(dimethylamino)but-2-enoyl]azepan-3-yl)-1H-benzo[d]imidazol-2-yl)-2-methylisonicotinamide (EGF816), a novel, potent, and WT sparing covalent inhibitor of oncogenic (L858R, ex19del) and resistent (T790M) EGFR mutants for the treatment of EGFR mutant non-small-cell lung cancers", Journal of Medicinal Chemistry 2016, 59(14), 6671-6689.
Levine, et al., Targeting the androgen receptor with steroid conjugates, J. Med. Chem., vol. 57., No. 20. pp. 8224-8237, (2014).
Li, Yan, et al., "Single polymer-drug conjugate carrying two drugs for fixed-dose co-delivery", Medicinal Chemistry, 2014, vol. 4(10): 676-683.
Liu, Hong, et al., "Bioactivation of the selective estrogen receptor modulator desmethylated arzoxifene to quinoids: 4'-fluoro substitution prevents quinoid formation", Chem. Res. Toxicol. 2005, 18, 162-173.
Lu, et al., "Hijacking the E3 ubiquitin ligase cereblon to efficiently target BRD4", Chem Biol 22(6), 2015, 755-763.
Mahalingam, D., et al., "Targeting HSP90 for cancer therapy", Br J Cancer 100, 1523-1529 (2009).
Maniaci C, et al. (2017) "Homo-PROTACs: bivalent small-molecule dimerizers of the VHL E3 ubiquitin ligase to induce self-degradation." *Nat Commun* 8(1):830 1-13.
McGuire, et al., "Taxol: A unique antineoplastic agent with significant activity in advanced ovarian epithelial neoplasms", Ann. Intem, Med., 111:273, 1989.
MedlinePlus Trusted Health Information for You, www.nlm.nih.gov/medlineplus/cancer.html pp. 1-10, (2007).
Min, Jung-hyun, et al., "Structure of an HIV-1-alpha—pVHL complex: hydroxyproline recognition in signaling", Jun. 7, 2002, 296: 1886-1889.
Nathan, M. R. & Schmid, P. A Review of Fulvestrant in Breast Cancer. Oncol Ther 5, 17-29 (2017).
Neklesa, T.K., et al., "Chemical biology: Greasy tags for protein removal", Nature 487, 308-309 (2012).
Nektesa, Targeted protein degradation by PROTACs. Pharmacology & Therapeutics 174, 138-144 (2017).
Ohoka, N. et al. SNIPER(TACC3) induces cytoplasmic vacuolization and sensitizes cancer cells to Bortezomib. Cancer Sci. 108, 1032-1041 (2017).
Ottis P, et al. (2017) "Assessing Different E3 Ligases for Small Molecule Induced Protein Ubiquitination and Degradation." *ACS Chem Biol* 12(10):2570-2578.
Ottis, et al., (2017) "Proteolysis-Targeting Chimeras: Induced Protein Degradation as a Therapeutic Strategy." *ACS Chem Biol* 12(4):892-898.
Poutiainen, PK, et al., "Design, synthesis, and biological evaluation of nonsteroidal cycloalkane[d]isoxazole-containing androgen receptor modulators", J. Med. Chem. 55, 6316-6327 (2012).
Powell, C. E. et al. Chemically Induced Degradation of Anaplastic Lymphoma Kinase (ALK). J. Med. Chem. 61, 4249-4255 (2018).
Puppala, D. et al., "Development of an Aryl Hydrocarbon Receptor Antagonist Using the Proteolysis-Targeting chimeric Molecules Approach: A Potential Tool for Chemoprevention," Mol. Pharmacol., 2008, vol. 73, No. 4, pp. 1064-1071.
Qin, Zhihui, et al., "Benzothiophene selective estrogen receptor modulators with modulated oxidative activity and receptor affinity", J. Med Chem 2007, 50, 2682-2692.
Raina, et al., (2017) "Targeted protein knockdown using small molecule degraders." *Curr Opin Chem Biol* 39:46-53.
Raina, K., et al., "PROTAC-induced BET protein degradation as a therapy for castration-resistant prostate cancer", Proc Natl Acad Sci USA 113, 7124-7129 (2016).
Remillard D, et al. (2017) "Degradation of the BAF Complex Factor BRD9 by Heterobifunctional Ligands." *Angew Chem Int Ed Engl* 56(21):5738-5743.
Robertson, J. F. R. Fulvestrant (Faslodex)—how to make a good drug better. Oncologist 12, 774-784 (2007).
Rodriguez-Gonzalez, et al., "Targeting steroid hormone receptors for ubiquitination and degradation in breast and prostate cancer", Oncogene. 27(57), Dec. 4, 2008, 7201-7211.
Rotili, D., et al., "Photoactivable peptides for identifying enzyme-substrate and protein-protein interactions", Chem Commun (Carob) 47(5), Feb. 2011, 1488-1490.
Sakamoto, et al., "Development of Protacs to target cancer-promoting proteins for ubiquitination and degradation", Mol Cell Proteomics. 2(12), Dec. 2003, 1350-1358.
Sakamoto, et al., "Protacs: chimeric molecules that target proteins to the Skp 1-Cullin-F box complex for ubiquitination and degradation", Proc Natl Acad Sci U S A.98(15), Jul. 17, 2001, 8554-8559.
Salami, J. & Crews, C. M. Waste disposal—An attractive strategy for cancer therapy. Science 355, 1163-1167 (2017).
Schiedel, M., et al., "Chemically Induced Degradation of Sirtuin 2 (Sirt2) by a Proteolysis Targeting Chimera (PROTAC) Based on Sirtuin Rearranging Ligands (SirReals)", J Med Chem. (2017), 61:482-491.
Schneekloth, et al., "Chemical Genetic Control of Protein Levels: Selective in Vivo Targeted Degradation", J Am Chem Soc. 126(12), Mar. 31, 2004, 3748-3754.
Schneekloth, et al., Targeted intracellular protein degradation induced by a small molecule: En route to chemical proteomics, Bioorg. Med. Chem. Lett. 18 (2008) 5904-5908.
Smith, et al., "Targeted Intracellular Protein Degradation Induced by a Small Molecule: En Route to Chemical Proteomics", Bioorg Med Chem Lett. 18(22), Nov. 15, 2008, 5904-5908.
Stoppler, Melissa Conrad., Endometriosis [online], "Endometriosis Definition and Facts" URL http://www.medicinenet.com/endometriosis/article.htm, retrieved on Apr. 5, 2017.
Stoppler, Melissa Conrad., Endometriosis [online], "What about surgery for Endometriosis?" URL http://www.medicinenet.com/endometriosis/article.htm, retrieved on Apr. 5, 2017.
Suh, N. et al. Arzoxifene, a new selective estrogen receptor modulator for chemoprevention of experimental breast cancer. Cancer Res. 61, 8412-8415 (2001).
Toure, et al., (2016) "Small-Molecule PROTACS: New Approaches to Protein Degradation." *Angew Chem Int Ed Engl* 55(6):1966-1973.
Trewartha D, Carter K. "Advances in prostate cancer treatment", Nat Rev Drug Discov. Nov. 2013;12(11):823-824. doi: 10.1038/nrd4068. PubMed PMID: 24172327.
Van Molle, et al., "Dissecting fragment-based lead discovery at the von Hippel-Lindau protein:hypoxia inducible factor 1a protein-protein interface", Chem Biol. 19(10), Oct. 26, 2012, 1300-1312.

(56) References Cited

OTHER PUBLICATIONS

Wang, C. et al. Estrogen induces c-myc gene expression via an upstream enhancer activated by the estrogen receptor and the AP-1 transcription factor. Mol. Endocrinol. 25, 1527-1538 (2011).
Weir, H. M. et al. AZD9496: An Oral Estrogen Receptor Inhibitor That Blocks the Growth of ER-Positive and ESR1-Mutant Breast Tumors in Preclinical Models. Cancer Res. 76, 3307-3318 (2016).
Willson, T.M. et al., "3-[4-(1,2-Diphenylbut-1-Enyl)Phenyl] Acrylic Acid: A non-steroidal estrogen with functional selectivity for bone over uterus in rats", Journal of Medicinal Chemistry, American Chemical Society, US May 25, 1994, vol. 37 No. 11, pp. 1550-1552.
Winter, et al., "Phthalimide Conjugation as a strategy for in vivo target protein degradation", Science, 2015 vol. 348 (6241), pp. 1376-1381 [Pub online: May 21, 2015].
Yu, F. & Bender, W. The mechanism of tamoxifen in breast cancer prevention. Breast Cancer Research 3, A74 (2001).
Zengerle, et al., "Selective Small Molecule Induced Degradation of the BET Bromodomain Protein BRD4" Acs Chemical Biology, Jun. 2, 2015, vol. 10, pp. 1770-1777.
Zhang, D. et al., "Targeted Degradation of Proteins by Small Molecules: A Novel Tool for Functional Proteomics," comb Chem. High Throughput Screen., 2004, vol. 7, No. 7, pp. 689-697.
Zhong, H. et al., "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics", Cancer res, (2000) 60(6), 1541-1545.
Zhou, B., et al. "Discovery of a Small-Molecule Degrader of Bromodomain and Extra-Terminal (BET) Proteins with Picomolar Cellular Potencies and Capable of Achieving Tumor Regression", J Med Chem. 61(2), 462-481 (2018) (DOI:10.1021/acs.jmedchem.6b01816) (2017).
U.S. Office Action dated Nov. 5, 2019 for U.S. Appl. No. 15/074,820.
Response to U.S. Office Action for U.S. Appl. No. 15/740,820, filed Mar. 5, 2020.
U.S. Office Action dated Jan. 21, 2020 for U.S. Appl. No. 14/371,956.
U.S. Appl. No. 15/706,064, filed Sep. 15, 2017, US 2018-0072711 A1.
U.S. Appl. No. 16/376,225, filed Apr. 5, 2019, US 2019-0233408 A1.

* cited by examiner

INDOLE DERIVATIVES AS ESTROGEN RECEPTOR DEGRADERS

CROSS-REFERENCE TO RELATED APPLICATIONS

This application is a continuation of U.S. Non-Provisional patent application Ser. No. 16/376,225, filed on 5 Apr. 2019, which is a continuation of U.S. Non-Provisional patent application Ser. No. 15/706,064, filed on 15 Sep. 2017 and titled: Indole Derivatives as Estrogen Receptor Degraders, which claims the benefit of U.S. Provisional Patent Application 62/395,228; filed on 15 Sep. 2016 and titled: Indole Derivatives as Estrogen Receptor Degraders, all of which are incorporated herein by reference in their entirety for all purposes.

BACKGROUND

1. Field of the Discovery

Embodiments of the present disclosure relate to compounds, compositions, and medicaments including the compounds and processes for the preparation thereof. The present disclosure also relates to the use of the compounds, compositions and medicaments, for example, as inhibitors of the activity of the estrogen receptor, including degrading the estrogen receptor, the treatment of diseases and conditions mediated by the estrogen receptor, e.g. the treatment of breast cancer.

2. Background Information

The estrogen receptor (ER) is a member of the nuclear hormone receptor family and functions as a ligand-activated transcription factor involved with the up and down regulation of gene expression. The natural hormone for the estrogen receptor is 17-beta-estradiol (E2) and closely related metabolites. Binding of estradiol to the estrogen receptor causes a dimerization of the receptor and the dimer in turn binds to estrogen response elements (ERE's) on DNA. The ER-DNA complex recruits other transcription factors responsible for the transcription of DNA downstream from the ERE into mRNA which is eventually translated into protein. Alternatively, the interaction of ER with DNA may be indirect through the intermediacy of other transcription factors, most notably Fos and Jun.

Because the expression of a large number of genes is regulated by the estrogen receptor and because the estrogen receptor is expressed in many cell types, modulation of the estrogen receptor through binding of either natural hormones or synthetic ER ligands can have profound effects on the physiology and pathophysiology of the organism.

There are two different forms of the estrogen receptor, usually referred to as $\alpha$ and $\beta$, each encoded by a separate gene (ESR1 and ESR2, respectively). Both ERs are widely expressed in different tissue types, but there are some notable differences in their expression patterns. The ER$\alpha$ is found in endometrium, breast cancer cells, ovarian stroma cells, and the hypothalamus. In males, ER$\alpha$ protein is found in the epithelium of the efferent ducts. The expression of the ER$\beta$ protein has been documented in kidney, brain, bone, heart, lungs, intestinal mucosa, prostate, and endothelial cells. Development therefore of selective ligands may therefore preserve the beneficial aspects of estrogen.

The estrogen receptor mediates the etiology and/or pathology of a variety of diseases. Collectively, these diseases are called estrogen-dependent diseases. For example, estrogens are critical for sexual development in females. In addition, estrogens play an important role in maintaining bone density, regulation of blood lipid levels, and appear to have neuroprotective effects. Consequently, decreased estrogen production in post-menopausal women is associated with a number of diseases such as osteoporosis, atherosclerosis, depression and cognitive disorders. Conversely, certain types of proliferative diseases such as breast and uterine cancer and endometriosis are stimulated by estrogens and therefore antiestrogens (i.e. estrogen antagonists) have utility in the prevention and treatment of these types of disorders.

Breast cancer is the most common malignancy to affect women and worldwide, the incidence of the disease is increasing. Estrogens, in particular, act as endocrine growth factors for at least one-third of breast cancers, and depriving the tumor of this stimulus is a recognized therapy for advanced disease in premenopausal women, this is achieved by the ablation of ovarian function through surgical, radiotherapeutic, or medical means and, in postmenopausal women, by the use of aromatase inhibitors.

An alternative approach to estrogen withdrawal is to antagonise estrogen with antiestrogens. These are drugs that bind to and compete for estrogen receptors (ER) present in estrogen-responsive tissue. Conventional nonsteroidal antiestrogens, such as tamoxifen, compete efficiently for ER binding but their effectiveness is often limited by the partial agonism they display, which results in an incomplete blockade of estrogen-mediated activity. A specific or "pure" antiestrogen with high affinity for ER and without any agonist effect may have advantages over conventional nonsteroidal anti-estrogens in the treatment of estrogen-dependent disease. For example, Fulvestrant® is the first of a new class of potent pure anti-estrogens and is completely free of the partial agonist, estrogen-like activity, associated with currently available antiestrogens like tamoxifen.

An ongoing need exists for the development of new approaches to antagonize the ER receptor for the treatment of estrogen-related diseases. For example, a potentially powerful approach is to develop selective ER down regulators or degraders that reduce ER expression at either the transcript or protein level.

SUMMARY

The present disclosure describes bifunctional compounds which function to recruit endogenous proteins to an E3 Ubiquitin Ligase for degradation, and methods of using the same. In particular, the present disclosure provides bifunctional or proteolysis targeting chimeric (PROTAC) compounds, which find utility as modulators of targeted ubiquitination of a variety of polypeptides and other proteins, which are then degraded and/or otherwise inhibited by the bifunctional compounds as described herein. An advantage of the compounds provided herein is that a broad range of pharmacological activities is possible, consistent with the degradation/inhibition of targeted polypeptides from virtually any protein class or family. In addition, the description provides methods of using an effective amount of the compounds as described herein for the treatment or amelioration of a disease condition, such as cancer.

In one aspect of the present disclosure there is provided a compound of formula (I):

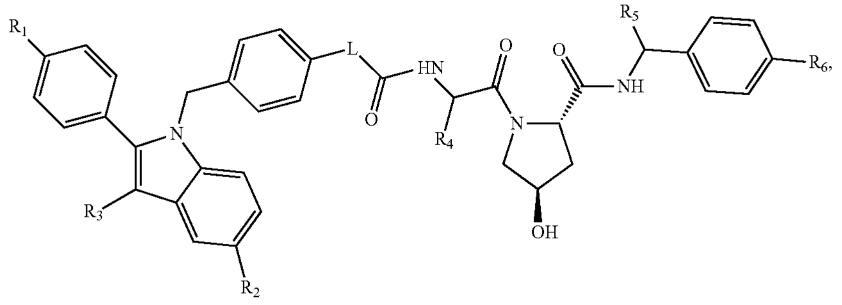

(I)

wherein:

$R_1$ is absent or OH, $OC_{1-3}$alkyl, halogen, or H;

$R_2$ is OH or $OC_{1-3}$alkyl;

$R_3$ is H or a lower alkyl, for example optionally substituted C1-C4 alkyl;

L is a group comprising one or more covalently connected structural units of A (e.g., $-A_q-$), wherein q is an integer greater than or equal to 0 (i.e., a bond);

$R_4$ is a straight chain or branched $C_{1-6}$alkyl or $C_{3-6}$ cycloalkyl;

$R_5$ is H or a an optionally substituted lower alkyl, e.g., C1-C4 alkyl, hydroxylaklyl, or alkylamino substituted lower alkyl;

$R_6$ is 4-methylthiazol-5-yl, oxazol-5-yl, substituted imidazole, substituted pyrazole, substituted oxadiazole, substituted triazole, halogen, or cyano group; when R6 is 4-methylthiazol-5-yl, the methyl group can be substituted with lower alkyl or hydroxyl group or a pharmaceutically acceptable salt thereof.

In another aspect of the present disclosure, there is provided a compound of formula (I), or a pharmaceutically acceptable salt thereof for use in therapy, for example the treatment of diseases and conditions mediated by the estrogen receptor.

In a further aspect of the present disclosure, there is provided a pharmaceutical composition comprising a compound of formula (I) or a pharmaceutically acceptable salt thereof and one or more of pharmaceutically acceptable carriers, diluents and excipients.

In an additional aspect of the present disclosure, there is provided a method of treating diseases and conditions mediated by the estrogen receptor in a subject comprising administering a therapeutically effective amount of a compound of formula (I) or a pharmaceutically acceptable salt thereof.

In a further aspect of the present disclosure, there is provided the use of a compound of formula (I), or a pharmaceutically acceptable salt thereof in the manufacture of a medicament for use in treating diseases and conditions mediated by the estrogen receptor.

In a particular aspect of the present disclosure, there is provided a combination comprising a compound of formula (I) or a pharmaceutically acceptable salt thereof and at least one further therapeutic agent.

In an aspect of the present disclosure, there is provided a combination comprising a compound of formula (I) or a pharmaceutically acceptable salt thereof and at least one further therapeutic agent for use in therapy, particularly for treating diseases and conditions mediated by the estrogen receptor.

In a further aspect of the present disclosure, there is provided a combination comprising compound of formula (I) or a pharmaceutically acceptable salt thereof and at least one further therapeutic agent for use in treating diseases and conditions mediated by the estrogen receptor.

In another aspect of the present disclosure, there is provided a method of treating diseases and conditions mediated by the estrogen receptor comprising administering to a human in need thereof a therapeutically effective amount of a combination comprising compound of formula (I) or a pharmaceutically acceptable salt thereof, and at least one further therapeutic agent.

In an additional aspect of the present disclosure, there is provided the use of a combination comprising compound of formula (I) or a pharmaceutically acceptable salt thereof and at least one further therapeutic agent in the manufacture of a medicament for treating diseases and conditions mediated by the estrogen receptor.

In a further aspect of the present disclosure, there is provided a combination comprising a compound of formula (I) or a pharmaceutically acceptable salt thereof and at least one anti-neoplastic agent.

In a particular aspect of the present disclosure, there is provided a combination comprising a compound of formula (I) or a pharmaceutically acceptable salt thereof and at least one anti-neoplastic agent, for use in therapy, in particular for diseases and conditions mediated by the estrogen receptor.

In a further aspect of the present disclosure, there is provided the use of a combination comprising a compound of formula (I) or a pharmaceutically acceptable salt thereof and at least one anti-neoplastic agent, in the manufacture of a medicament for treating diseases and conditions mediated by the estrogen receptor.

In an aspect of the present disclosure, there is provided a method of treating diseases and conditions mediated by the estrogen receptor, comprising administering to a human in need thereof a therapeutically effective amount of a combination comprising a compound of formula (I) or a pharmaceutically acceptable salt thereof and at least one anti-neoplastic agent.

In another aspect of the present disclosure, there is provided a pharmaceutical composition comprising a combination comprising a compound of formula (I) or a pharmaceutically acceptable salt thereof and at least one further therapeutic agent, for example at least one anti-neoplastic agent and/or one or more of pharmaceutically acceptable carriers, diluents and excipients.

In a further aspect of the present disclosure, there is provided a method of degrading the estrogen receptor comprising administration comprising administering to a human in need thereof a therapeutically effective amount of a compound of Formula (I) or a pharmaceutically acceptable salt thereof.

BRIEF DESCRIPTION OF THE DRAWINGS

The accompanying drawings, which are incorporated into and form a part of the specification, illustrate several embodiments of the present invention and, together with the description, serve to explain the principles of the invention. The drawings are only for the purpose of illustrating an embodiment of the invention and are not to be construed as limiting the invention. Further objects, features and advantages of the invention will become apparent from the following detailed description taken in conjunction with the accompanying figures showing illustrative embodiments of the invention, in which.

DETAILED DESCRIPTION

Figure 1:
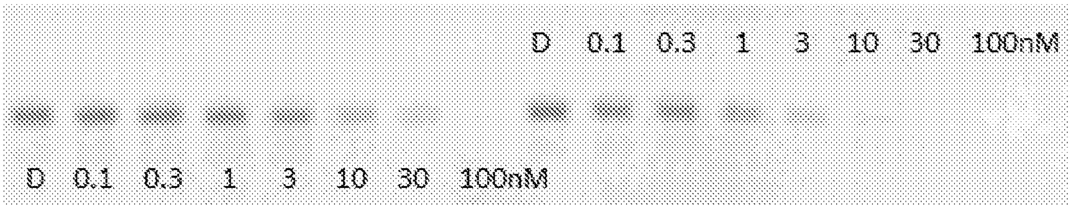
FIG. 1: Western blot analysis of ERα level in MCF-7 cells. Cells were treated with ERα degraders (in the presence of 10% FBS) according the described assay procedure. Left panel: effect of Example #1 on degrading ERα; Right panel: effect of Example #2 on degrading ERα. D: DMSO, compound concentration 0.1 nM to 100 nM.

The following is a detailed description provided to aid those skilled in the art in practicing the present invention. Those of ordinary skill in the art may make modifications and variations in the embodiments described herein without departing from the spirit or scope of the present disclosure. All publications, patent applications, patents, figures and other references mentioned herein are expressly incorporated by reference in their entirety.

Presently described are compositions and methods that relate to the surprising and unexpected discovery that an E3 ubiquitin ligase protein (e.g., inhibitors of apoptosis proteins (IAP), a Von Hippel-Lindau E3 ubiquitin ligase (VHL), or a mouse double minute 2 homolog (MDM2) E3 ubiquitin ligase) ubiquitinates a target protein once it and the target protein are placed in proximity by a bifunctional or chimeric construct that binds the E3 ubiquitin ligase protein and the target protein. Accordingly the present disclosure provides such compounds and compositions comprising an E3 ubiquintin ligase binding moiety ("ULM") coupled to a protein target binding moiety ("PTM"), which result in the ubiquitination of a chosen target protein (e.g., estrogen receptor [ER]), which leads to degradation of the target protein by the proteasome (see FIGS. 1 and 2). The present disclosure also provides a library of compositions and the use thereof.

In certain aspects, the present disclosure provides compounds which comprise a ligand, e.g., a small molecule ligand (i.e., having a molecular weight of below 2,000, 1,000, 500, or 200 Daltons), which is capable of binding to a E3 ubiquitin ligase, such as IAP, VHL, or MDM2, and a moiety that is capable of binding to target protein, in such a way that a target protein (such as ER) is placed in proximity to the E3 ubiquitin ligase to effect degradation (and/or inhibition) of that protein. Small molecule can mean, in addition to the above, that the molecule is non-peptidyl, that is, it is not generally considered a peptide, e.g., comprises fewer than 4, 3, or 2 amino acids. In accordance with the present description, the PTM, ULM or PROTAC molecule can be a small molecule.

As used herein, "a compound of the invention", "a compound of the disclosure", and "a compound of the present disclosure" includes all solvates, complexes, polymorphs, radiolabelled derivatives, stereoisomers and optical isomers of the compounds of formula (I) and salts thereof.

Unless otherwise defined, all technical and scientific terms used herein have the same meaning as commonly understood by one of ordinary skill in the art to which this invention belongs. The terminology used in the description is for describing particular embodiments only and is not intended to be limiting of the invention.

Where a range of values is provided, it is understood that each intervening value, to the tenth of the unit of the lower limit unless the context clearly dictates otherwise (such as in the case of a group containing a number of carbon atoms in which case each carbon atom number falling within the range is provided), between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

The following terms are used to describe the present invention. In instances where a term is not specifically defined herein, that term is given an art-recognized meaning by those of ordinary skill applying that term in context to its use in describing the present invention.

The articles "a" and "an" as used herein and in the appended claims are used herein to refer to one or to more than one (i.e., to at least one) of the grammatical object of the article unless the context clearly indicates otherwise. By way of example, "an element" means one element or more than one element.

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of."

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

As used herein in the specification and in the claims, the phrase "at least one," in reference to a list of one or more elements, should be understood to mean at least one element selected from anyone or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a nonlimiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, in certain methods described herein that include more than one step or act, the order of the steps or acts of the method is not necessarily limited to the order in which the steps or acts of the method are recited unless the context indicates otherwise.

The terms "co-administration" and "co-administering" or "combination therapy" refer to both concurrent administration (administration of two or more therapeutic agents at the same time) and time varied administration (administration of one or more therapeutic agents at a time different from that of the administration of an additional therapeutic agent or agents), as long as the therapeutic agents are present in the patient to some extent, preferably at effective amounts, at the same time. In certain preferred aspects, one or more of the present compounds described herein, are co-administered in combination with at least one additional bioactive agent, especially including an anticancer agent. In particularly preferred aspects, the co-administration of compounds results in synergistic activity and/or therapy, including anticancer activity.

The term "compound", as used herein, unless otherwise indicated, refers to any specific chemical compound disclosed herein and includes tautomers, regioisomers, geometric isomers, and where applicable, stereoisomers, including optical isomers (enantiomers) and other steroisomers (diastereomers) thereof, as well as pharmaceutically acceptable salts and derivatives (including prodrug forms) thereof where applicable, in context. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds. The term also refers, in context to prodrug forms of compounds which have been modified to facilitate the administration and delivery of compounds to a site of activity. It is noted that in describing the present compounds, numerous substituents and variables associated with same, among others, are described. It is understood by those of ordinary skill that molecules which are described herein are stable compounds as generally described hereunder. When the bond is shown, both a double bond and single bond are represented within the context of the compound shown.

The term "Ubiquitin Ligase" refers to a family of proteins that facilitate the transfer of ubiquitin to a specific substrate protein, targeting the substrate protein for degradation. For example, cereblon is an E3 Ubiquitin Ligase protein that alone or in combination with an E2 ubiquitin-conjugating enzyme causes the attachment of ubiquitin to a lysine on a target protein, and subsequently targets the specific protein substrates for degradation by the proteasome. Thus, E3 ubiquitin ligase alone or in complex with an E2 ubiquitin conjugating enzyme is responsible for the transfer of ubiquitin to targeted proteins. In general, the ubiquitin ligase is involved in polyubiquitination such that a second ubiquitin is attached to the first; a third is attached to the second, and so forth. Polyubiquitination marks proteins for degradation by the proteasome. However, there are some ubiquitination events that are limited to mono-ubiquitination, in which only a single ubiquitin is added by the ubiquitin ligase to a substrate molecule. Mono-ubiquitinated proteins are not targeted to the proteasome for degradation, but may instead be altered in their cellular location or function, for example, via binding other proteins that have domains capable of binding ubiquitin. Further complicating matters, different lysines on ubiquitin can be targeted by an E3 to make chains. The most common lysine is Lys48 on the ubiquitin chain. This is the lysine used to make polyubiquitin, which is recognized by the proteasome.

The term "patient" or "subject" is used throughout the specification to describe an animal, preferably a human or a domesticated animal, to whom treatment, including prophylactic treatment, with the compositions according to the present disclosure is provided. For treatment of those infections, conditions or disease states which are specific for a specific animal such as a human patient, the term patient refers to that specific animal, including a domesticated animal such as a dog or cat or a farm animal such as a horse, cow, sheep, etc. In general, in the present disclosure, the term patient refers to a human patient unless otherwise stated or implied from the context of the use of the term.

As used herein "halo" means fluoro (—F), chloro (—Cl), bromo (—Br) or iodo (—I).

As used herein, the term "effective amount" means that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, or amelioration of a disease, disorder, or side effect, or a decrease in the rate of advancement of a disease or disorder. The term also includes within its scope amounts effective to enhance normal physiological function.

As used herein, the term "pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein, the term "alkylene" when used, refers to a —$(CH_2)_n$— group (n is an integer generally from 6 and 20), which may be optionally substituted.

The compounds of the present disclosure may exist in solid or liquid form. In solid form, compound of the present disclosure may exist in a continuum of solid states ranging from fully amorphous to fully crystalline. The term "amorphous" refers to a state in which the material lacks long range order at the molecular level and, depending upon the temperature, may exhibit the physical properties of a solid or a liquid. Generally, such materials do not give distinctive X-ray diffraction patterns and, while exhibiting the properties of a solid, are more formally described as a liquid. Upon heating, a change from solid to liquid properties occurs, which is characterized by a change of state, typically second order ("glass transition"). The term "crystalline" refers to a solid phase in which the material has a regular ordered internal structure at the molecular level and gives a distinctive X-ray diffraction pattern with defined peaks. Such materials when heated sufficiently will also exhibit the properties of a liquid, but the change from solid to liquid is characterized by a phase change, typically first order ("melting point").

The compound of formula (I) may exist in solvated and unsolvated forms. As used herein, the term "solvate" refers to a complex of variable stoichiometry formed by a solute (in this invention, a compound of formula (I) or a salt) and a solvent. Such solvents for the purpose of the invention may not interfere with the biological activity of the solute. The skilled artisan will appreciate that pharmaceutically acceptable solvates may be formed for crystalline compounds wherein solvent molecules are incorporated into the crystalline lattice during crystallization. The incorporated solvent molecules may be water molecules or non-aqueous such as ethanol, isopropanol, DMSO, acetic acid, ethanolamine, and ethyl acetate molecules. Crystalline lattice incorporated with water molecules are typically referred to as "hydrates". Hydrates include stoichiometric hydrates, as well as compositions containing variable amounts of water. The present disclosure includes all such solvates.

The compounds of the disclosure may have the ability to crystallize in more than one form, a characteristic, which is known as polymorphism, and it is understood that such polymorphic forms ("polymorphs") are within the scope of the invention. Polymorphism generally can occur as a response to changes in temperature or pressure or both and can also result from variations in the crystallization process.

Polymorphs can be distinguished by various physical characteristics known in the art such as x-ray diffraction patterns, solubility and melting point.

As used herein, the term "estrogen receptor inhibitor" refers to any compound or treatment capable of inhibiting or reducing the expression or activity of the estrogen receptor. The inhibitor is preferably selective.

Exemplary Compounds

Described herein are bifunctional compounds capable of binding an estrogen receptor protein and a ubiquitin ligase enzyme, thereby effectuating ubiquitination and degradation of the estrogen receptor.

In one aspect of the present disclosure there is provided a compound of formula (I):

(I)

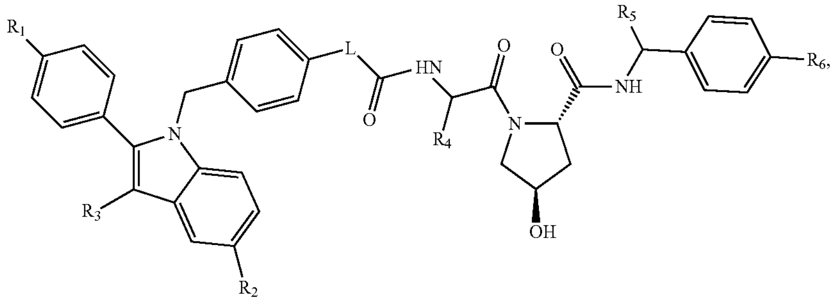

wherein:

$R_1$ is H, OH, $OC_{1-3}$alkyl, or a halogen, e.g., Br, F, Cl;

$R_2$ is OH or $OC_{1-3}$alkyl;

$R_3$ is H or a lower alkyl, for example optionally substituted C1-C4 alkyl, e.g., an optionally substituted methyl;

L is a group comprising one or more covalently connected structural units represented by: $-(A)_q-$, wherein q is an integer greater than or equal to 0 (i.e., a bond);

$R_4$ is a straight chain or branched $C_{1-6}$alkyl or $C_{3-6}$ cycloalkyl;

$R_5$ is H or a an optionally substituted lower alkyl, e.g., optionally substituted C1-C4 alkyl, optionally substituted hydroxylaklyl, or alkylamino substituted lower alkyl;

$R_6$ is 4-methylthiazol-5-yl, oxazol-5-yl, optionally substituted imidazole, optionally substituted pyrazole, optionally substituted oxadiazole, optionally substituted triazole, halogen, or cyano group, or a pharmaceutically acceptable salt thereof.

In certain embodiments, when R6 is 4-methylthiazol-5-yl, the methyl group can be substituted with lower alkyl or hydroxyl group.

In one aspect $R_6$ is 4-methylthiazol-5-yl, oxazol-5-yl, or 4-methyloxazole-5-yl.

In a further aspect, $R_6$ is 4-methylthiazol-5-yl.

In an aspect $R_6$ is chloro.

In one aspect $R_6$ is —CN.

In one aspect $R_1$ is OH, F, Br, Cl, $OCH_3$ or H.

In a further aspect $R_1$ is OH.

In one aspect $R_2$ is OH or $OCH_3$.

In a further aspect $R_2$ is OH.

In one aspect, $R_3$ is H, methyl, or ethyl.

In a further aspect, $R_3$ is methyl.

In one aspect $R_4$ is iso-propyl or tert-butyl.

In a further aspect, $R_4$ is tert-butyl.

In one aspect, $R_5$ is H, methyl, ethyl, $CH_2F$, or $CH_2NHCH_3$.

In a further aspect, $R_5$ is H.

In another aspect, $R_5$ is methyl.

It is also noted that the compounds of formula (I) may form tautomers. It is understood that all tautomers and mixtures of tautomers of the compounds of the present disclosure are included within the scope of the compounds of the present disclosure.

Exemplary Linkers

In an aspect, the linker group "L" is a group comprising one or more covalently connected structural units of A, e.g., $-(A)_q-$, wherein q is an integer greater than or equal to 0. In certain embodiments, q is an integer greater than or equal to 1. In certain embodiments, e.g., where q is greater than 2, $A_1$ and $A_q$ are coupled via structural units of A (number of such structural units of A: q-2). In certain additional embodiments, e. g., where q is 1, the structure of the linker group L is $-A_1-$.

In additional embodiments, q is an integer from 1 to 100, 1 to 90, 1 to 80, 1 to 70, 1 to 60, 1 to 50, 1 to 40, 1 to 30, 1 to 20, or 1 to 10.

In certain embodiments, each A is independently selected from the group consisting of, a bond, $CR^{L1}R^{L2}$, O, S, SO, $SO_2$, $NR^{L3}$, $SO_2NR^{L3}$, $SONR^{L3}$, $CONR^{L3}$, $NR^{L3}CONR^{L3}$, $NR^{L3}SO_2NR^{L4}$, CO, $CR^{L1}{=}CR^{L2}$, C≡C, $SiR^{L1}R^{L2}$, $P(O)R^{L1}$, $P(O)OR^{L1}$, $NR^{L3}C({=}NCN)NR^{L4}$, $NR^{L3}C({=}NCN)$, $NR^{L3}C({=}CNO_2)NR^{L4}$, $C_{3-11}$cycloalkyl optionally substituted with 0-6 $R^{L1}$ and/or $R^{L2}$ groups, $C_{5-13}$ spirocycloalkyl optionally substituted with 0-9 $R^{L1}$ and/or $R^{L2}$ groups, $C_{3-11}$heterocyclyl optionally substituted with 0-6 $R^{L1}$ and/or $R^{L2}$ groups, $C_{5-13}$ spiroheterocycloalkyl optionally substituted with 0-8 $R^{L1}$ and/or $R^{L2}$ groups, aryl optionally substituted with 0-6 $R^{L1}$ and/or $R^{L2}$ groups, heteroaryl optionally substituted with 0-6 $R^{L1}$ and/or $R^{L2}$ groups, where $R^{L1}$ or $R^{L2}$, each independently are optionally linked to other groups to form cycloalkyl and/or heterocyclyl moiety, optionally substituted with 0-4 $R^{L5}$ groups;

$R^{L1}$, $R^{L2}$, $R^{L3}$, $R^{L4}$ and $R^{L5}$ are, each independently, H, halo, $C_{1-8}$alkyl, $OC_{1-8}$alkyl, $SC_{1-8}$alkyl, $NHC_{1-8}$alkyl, $N(C_{1-8}alkyl)_2$, $C_{3-11}$cycloalkyl, aryl, heteroaryl, $C_{3-11}$heterocyclyl, $OC_{1-8}$cycloalkyl, $SC_{1-8}$cycloalkyl, $NHC_{1-8}$cycloalkyl, $N(C_{1-8}cycloalkyl)_2$, $N(C_{1-8}cycloalkyl)(C_{1-8}alkyl)$, OH, $NH_2$, SH, $SO_2C_{1-8}$alkyl, $P(O)(OC_{1-8}alkyl)(C_{1-8}alkyl)$, $P(O)(OC_{1-8}alkyl)_2$, $CC—C_{1-8}$alkyl, CCH, $CH{=}CH(C_{1-8}alkyl)$, $C(C_{1-8}alkyl){=}CH(C_{1-8}alkyl)$, $C(C_{1-8}alkyl){=}C(C_{1-8}alkyl)_2$, $Si(OH)_3$, $Si(C_{1-8}alkyl)_3$, $Si(OH)(C_{1-8}alkyl)_2$, $COC_{1-8}$alkyl, $CO_2H$, halogen, CN, $CF_3$, $CHF_2$, $CH_2F$, $NO^2$, $SF_5$, $SO_2NHC_{1-8}$alkyl, $SO_2N(C_{1-8}alkyl)_2$, $SONHC_{1-8}$alkyl, $SON(C_{1-8}alkyl)_2$, $CONHC_{1-8}$alkyl, $CON(C_{1-8}\ alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)\ SO_2N(C_{1-8}alkyl)_2$, $NH\ SO_2NH(C_{1-8}alkyl)$, $NH\ SO_2N(C_{1-8}alkyl)_2$, $NH\ SO_2NH_2$.

In certain embodiments, q of the linker is an integer greater than or equal to 0. In certain embodiments, q is an integer greater than or equal to 1.

In certain embodiments, e.g., where q of the linker is greater than 2, $A_q$ is a group which is connected to ULM, and $A_1$ and $A_q$ are connected via structural units of the linker (L).

In certain embodiments, e.g., where q of the linker is 2, $A_q$ is a group which is connected to $A_1$ and to a ULM.

In certain embodiments, e.g., where q of the linker is 1, the structure of the linker group L is $-A_1-$, and $A_1$ is a group which is connected to a ULM moiety and a PTM moiety.

In certain embodiments, the linker (L) comprises a group represented by a general structure selected from the group consisting of: $—NR(CH_2)_n$-(lower alkyl)-, $—NR(CH_2)_n$-(lower alkoxyl)-, $—NR(CH_2)_n$-(lower alkoxyl)-$OCH_2—$, $—NR(CH_2)_n$-(lower alkoxyl)-(lower alkyl)-$OCH_2—$, $—NR(CH_2)_n$-(cycloalkyl)-(lower alkyl)-$OCH_2—$, $—NR(CH_2)_n$-(hetero cycloalkyl)-, $—NR(CH_2CH_2O)_n$-(lower alkyl)-$O—CH_2—$, $—NR(CH_2CH_2O)_n$-(hetero cycloalkyl)-$O—CH_2—$, $—NR(CH_2CH_2O)_n$-Aryl-$O—CH_2—$, $—NR(CH_2CH_2O)_n$-(hetero aryl)-$O—CH_2—$, $—NR(CH_2CH_2O)_n$-(cyclo alkyl)-O-(hetero aryl)-$O—CH_2—$, $—NR(CH_2CH_2O)_n$-(cyclo alkyl)-O-Aryl-$O—CH_2—$, $—NR(CH_2CH_2O)_n$-(lower alkyl)-NH-Aryl-$O—CH_2—$, $—NR(CH_2CH_2O)_n$-(lower alkyl)-O-Aryl-$CH_2$, $—NR(CH_2CH_2O)_n$-cycloalkyl-O-Aryl-, $—NR(CH_2CH_2O)_n$-cycloalkyl-O-(heteroaryl)l-, $—NR(CH_2CH_2)_n$-(cycloalkyl)-O-(heterocycle)-$CH_2$, $—NR(CH_2CH_2)_n$-(heterocycle)-(heterocycle)-$CH_2$, —N(R1R2)-(heterocycle)-$CH_2$; wherein n of the linker can be 0 to 10;

R of the linker can be H, lower alkyl;

R1 and R2 of the linker can form a ring with the connecting N.

In certain embodiments, the linker (L) comprises a group represented by a general structure selected from the group consisting of: $—N(R)—(CH2)_m$-$O(CH2)_n$-$O(CH2)_o$-$O(CH2)_p$-$O(CH2)_q$-$O(CH2)_r$-OCH2-; $—O—(CH2)_m$-$O(CH2)_n$-$O(CH2)_o$-$O(CH2)_p$-$O(CH2)_q$-$O(CH2)_r$-OCH2-; $—O—(CH2)_m$-$O(CH2)_n$-$O(CH2)_o$-$O(CH2)_p$-$O(CH2)_q$-$O(CH2)_r$-O—; $—N(R)—(CH2)_m$-$O(CH2)_n$-$O(CH2)_o$-$O(CH2)_p$-$O(CH2)_q$-$O(CH2)_r$-O—; $—(CH2)_m$-$O(CH2)_n$-$O(CH2)_o$-$O(CH2)_p$-$O(CH2)_q$-$O(CH2)_r$-O—; $—(CH2)_m$-$O(CH2)_n$-$O(CH2)_o$-$O(CH2)_p$-$O(CH2)_q$-$O(CH2)_r$-OCH2-;

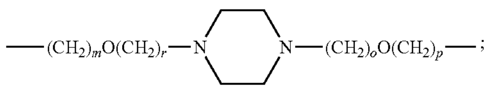

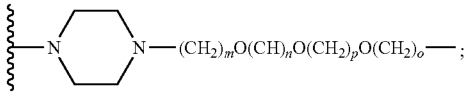

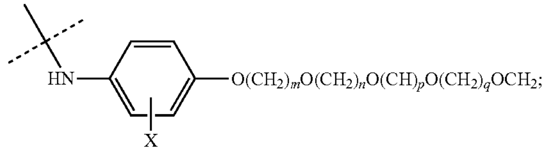

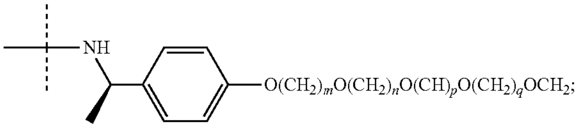

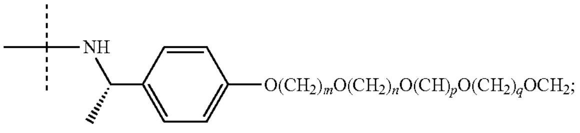

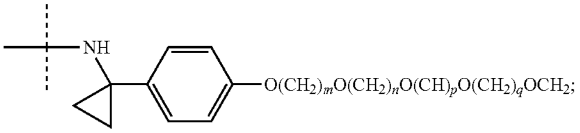

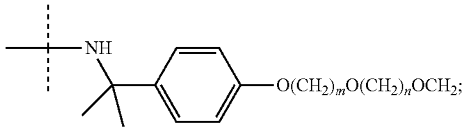

-continued
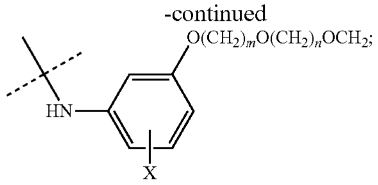
and
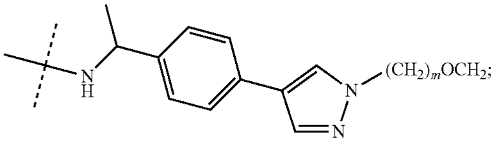
wherein
m, n, o, p, q, and r of the linker are independently 0, 1, 2, 3, 4, 5, 6;
when the number is zero, there is no N—O or O—O bond
R of the linker is H, methyl and ethyl;
X of the linker is H and F
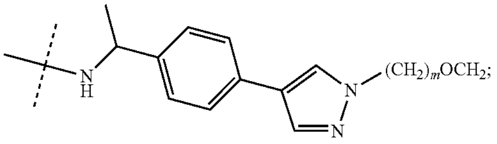
where m of the linker can be 2, 3, 4, 5
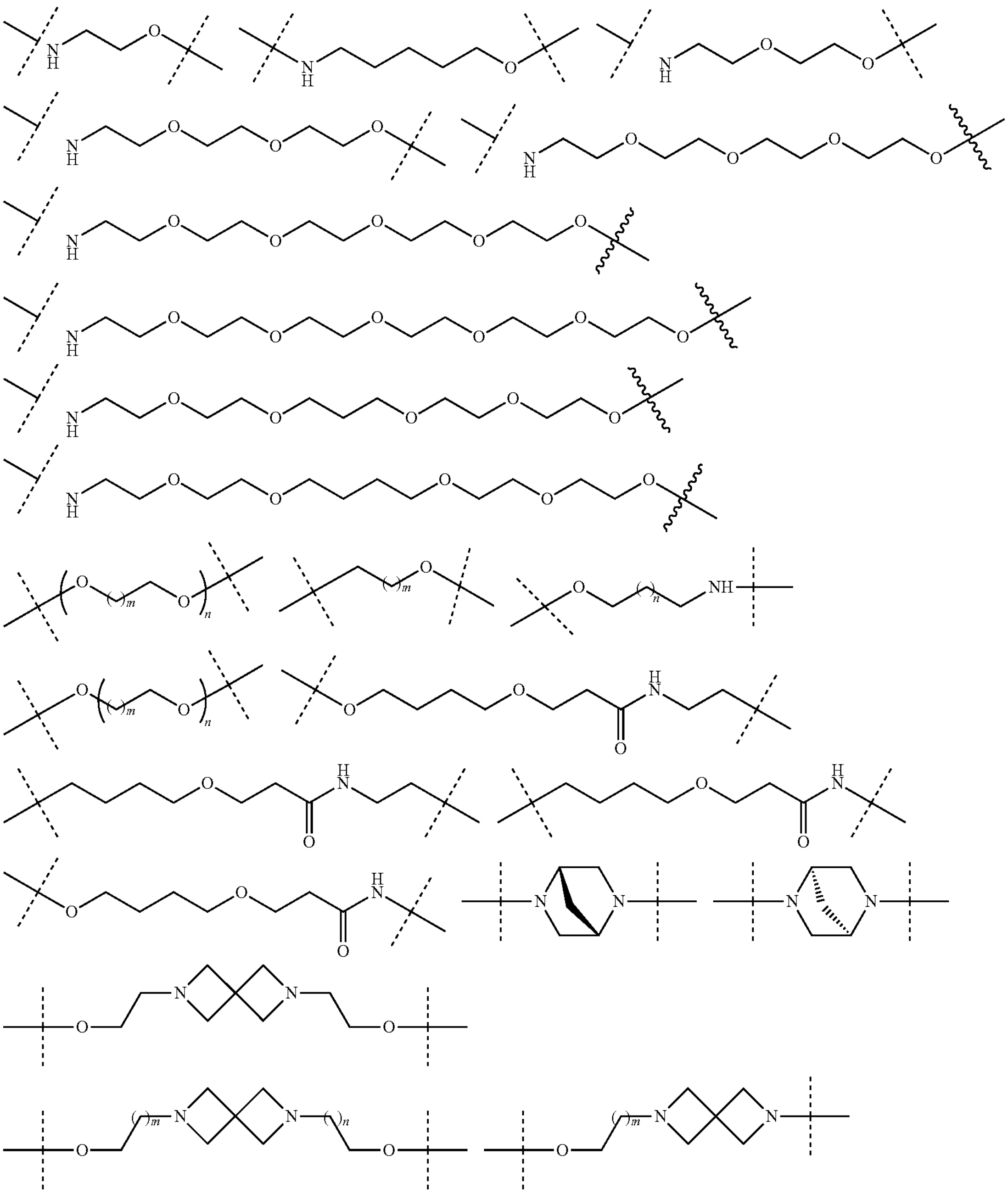

-continued
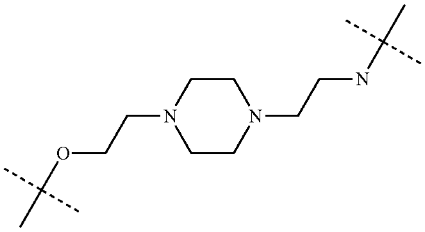
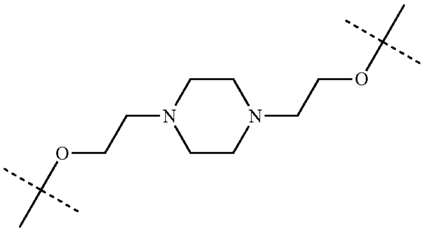
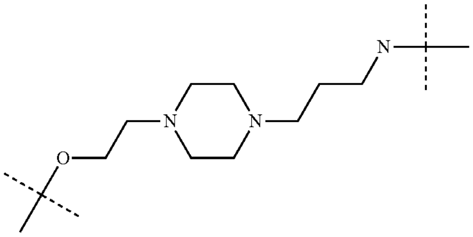
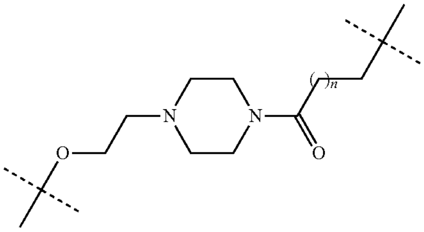
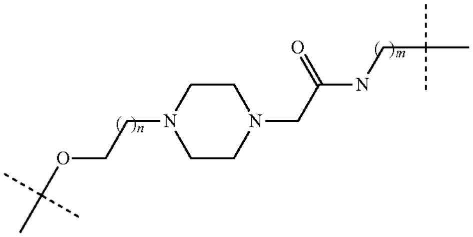
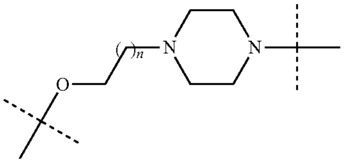
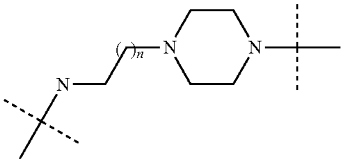
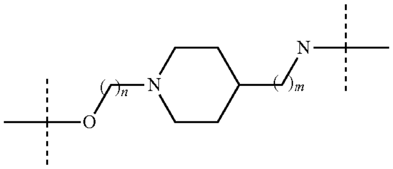
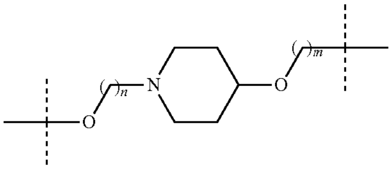
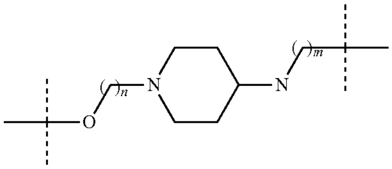
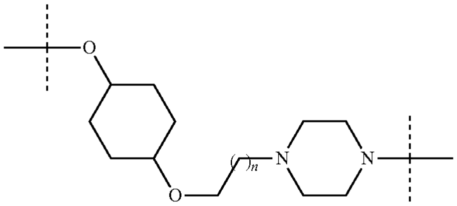
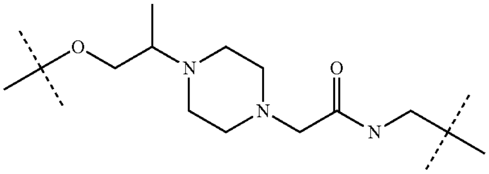
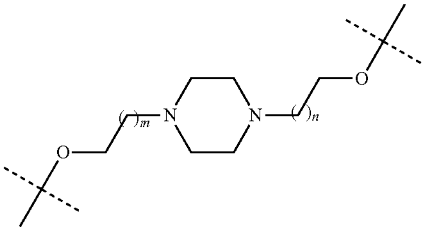
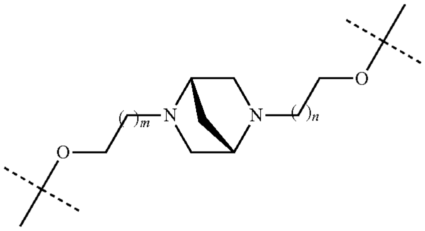
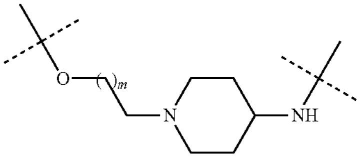
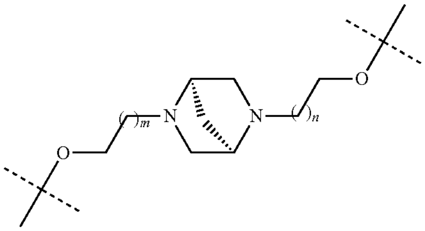
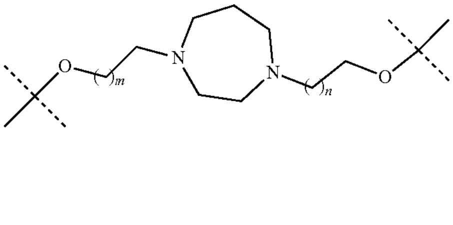
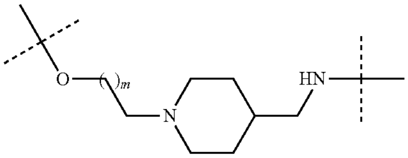

-continued
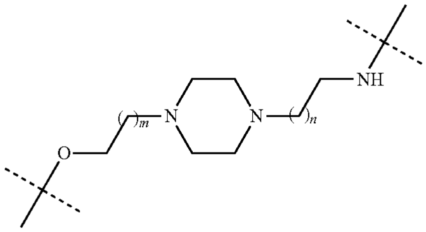
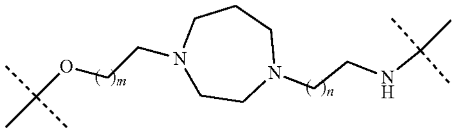
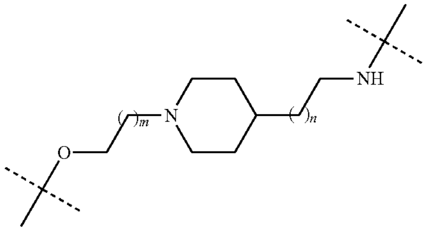
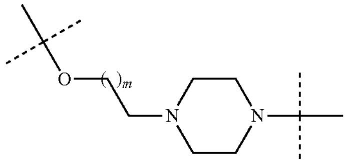
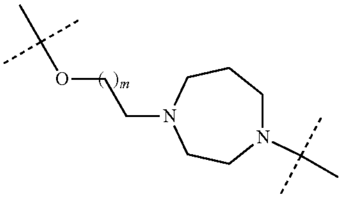
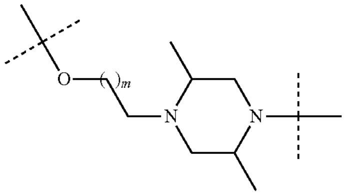
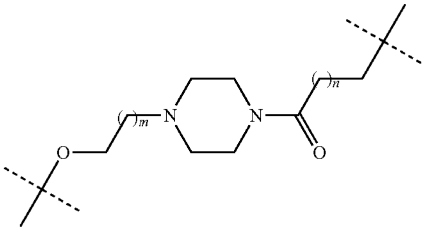
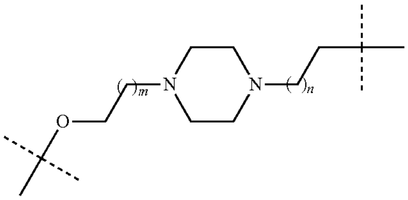
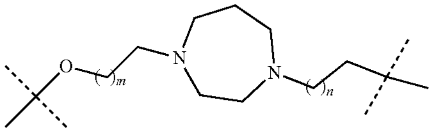
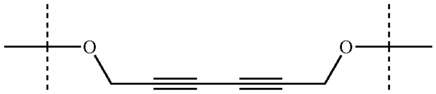
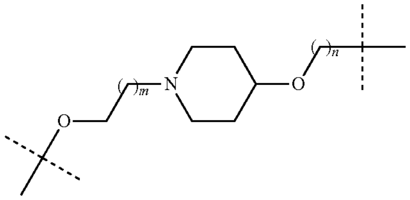
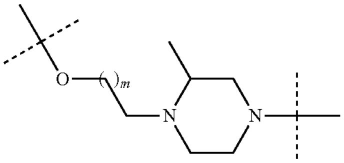
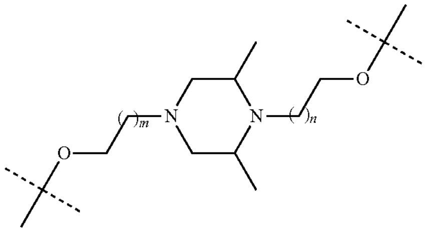
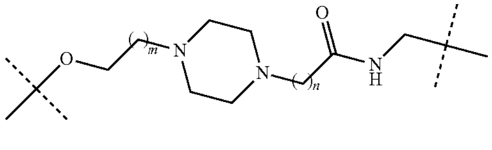
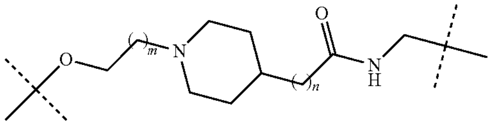
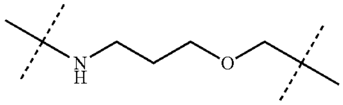
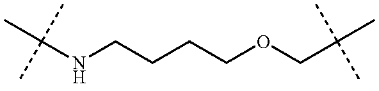
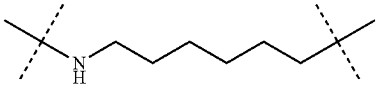
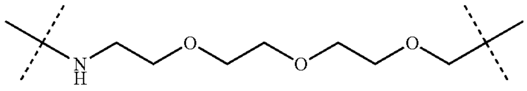
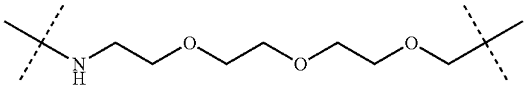
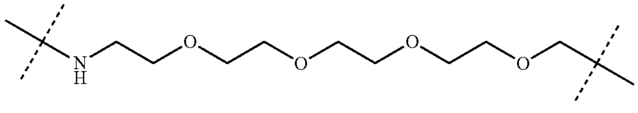
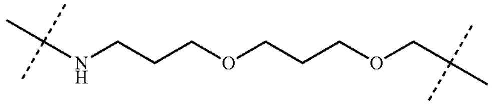

-continued
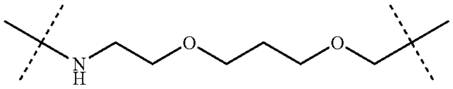
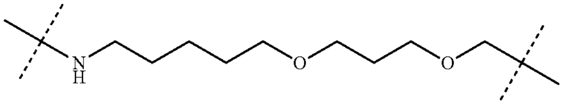
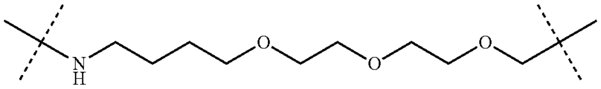
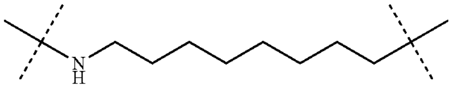
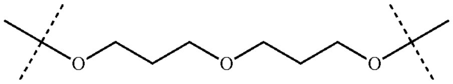
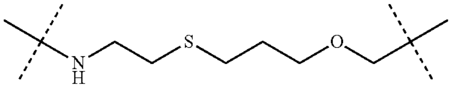
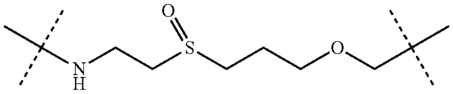
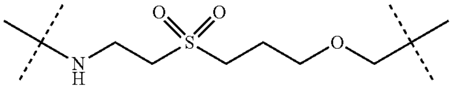
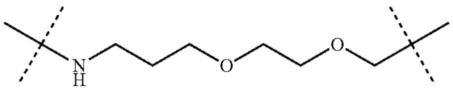
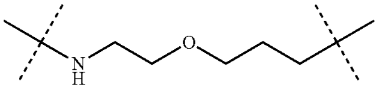
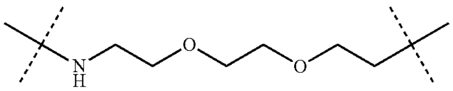
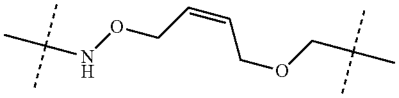
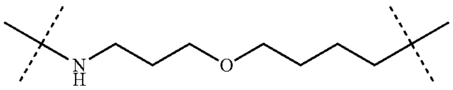
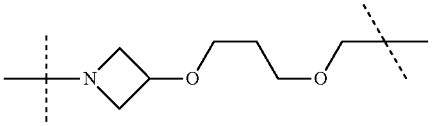
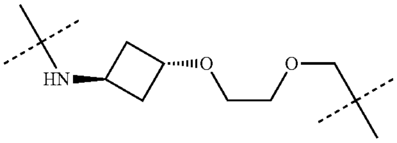
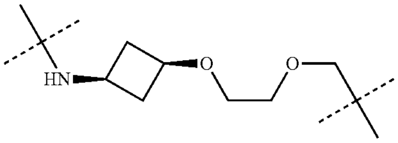
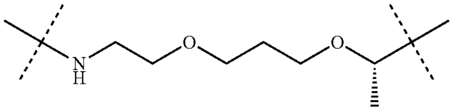
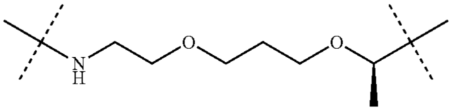
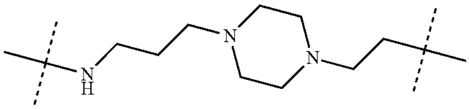
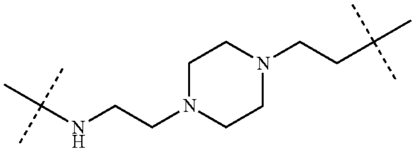
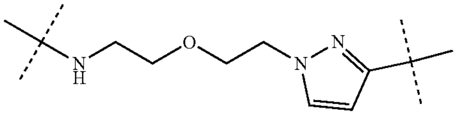
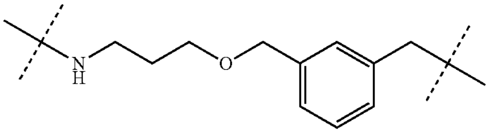
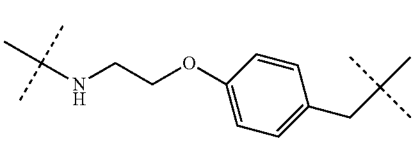
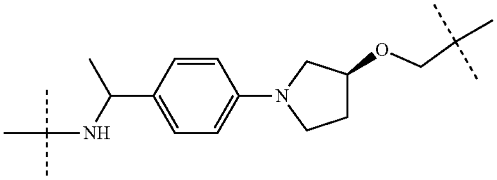
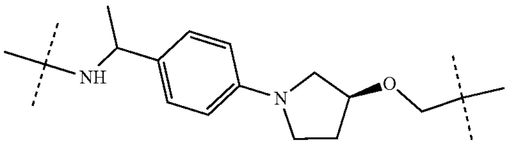
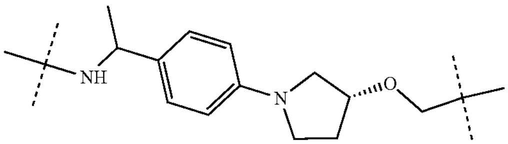

-continued
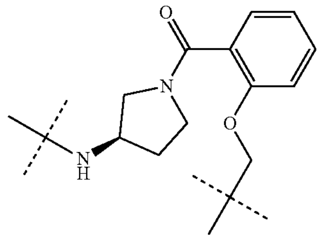
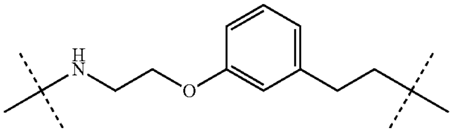
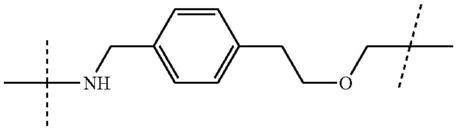
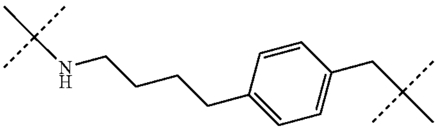
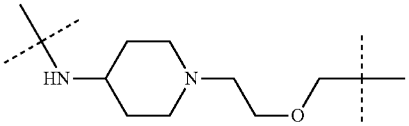
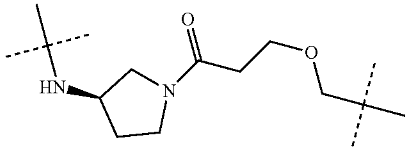
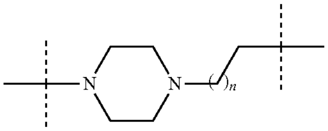
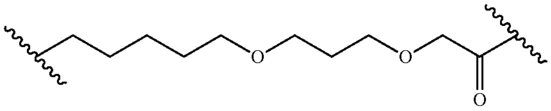 ;
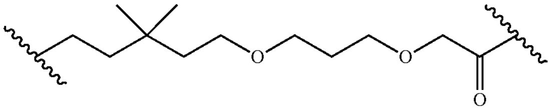 ;
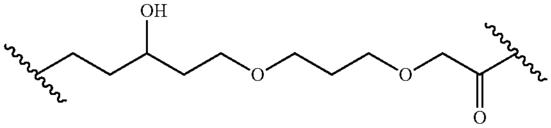 ;
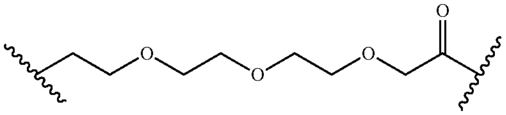 ;
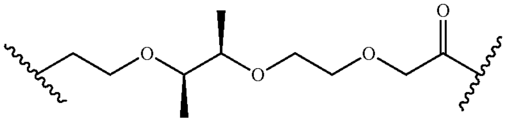 ;
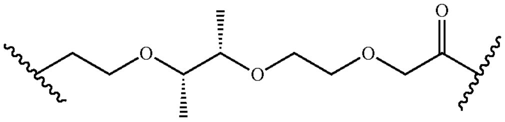 ;
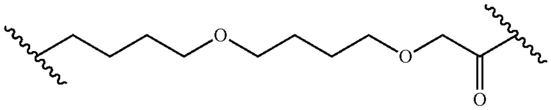 ;
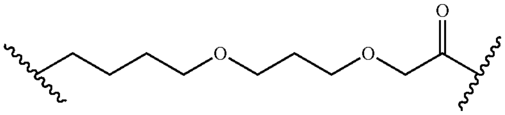 ;
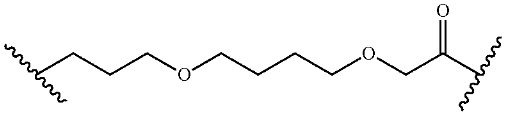 ;
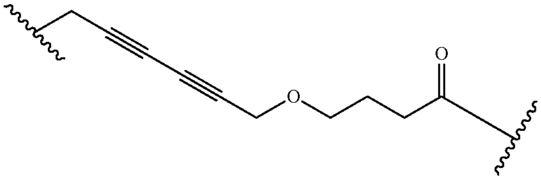 ;
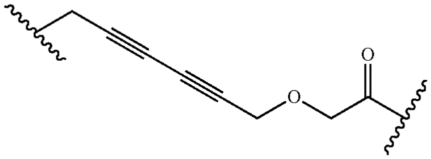 ;
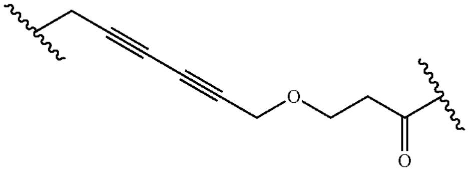 ;
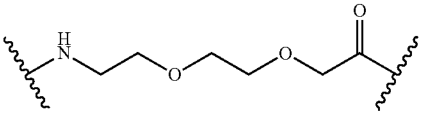 ;
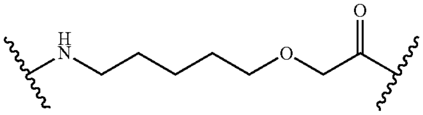 ;
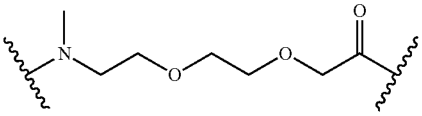 ;
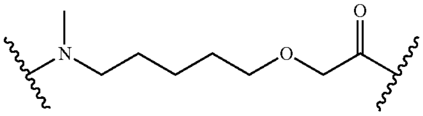 ;

-continued
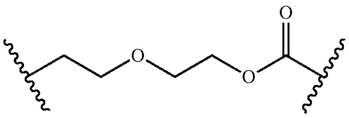 ; 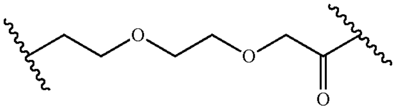 ;
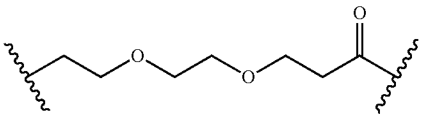 ; 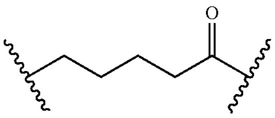 ; 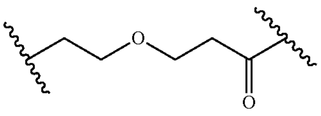 ;
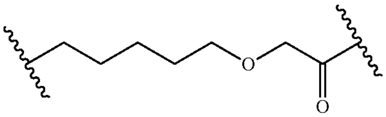 ; 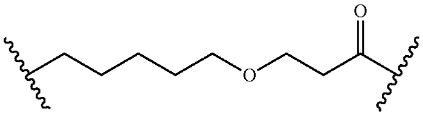 ;
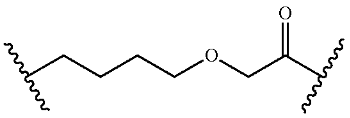 ; 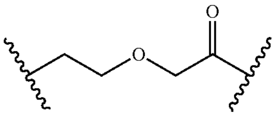 ; 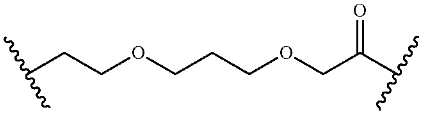 ;
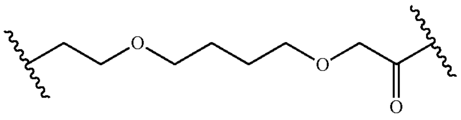 ; 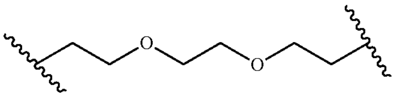 ;
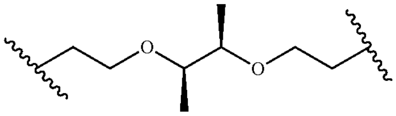 ;
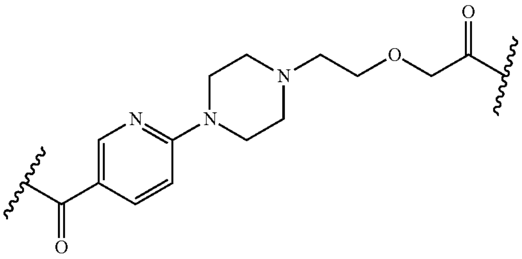 ;
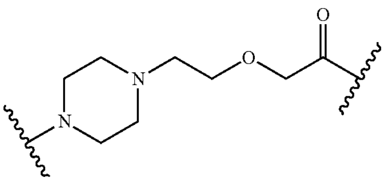 ; 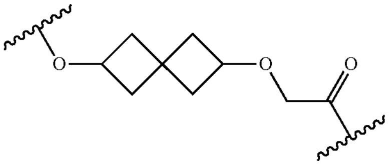 ;
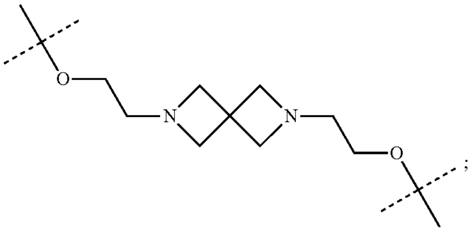 ; 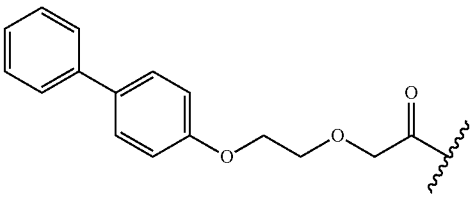 ;
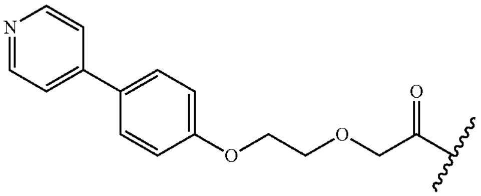 ; 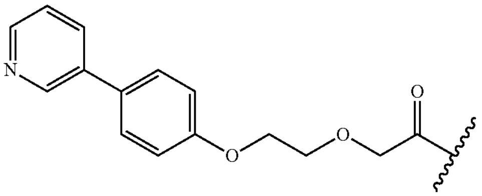 ;

-continued
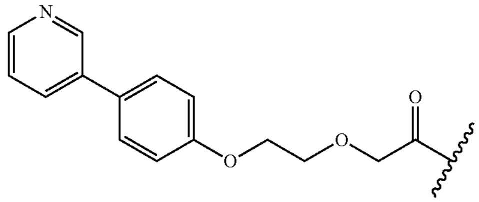
;
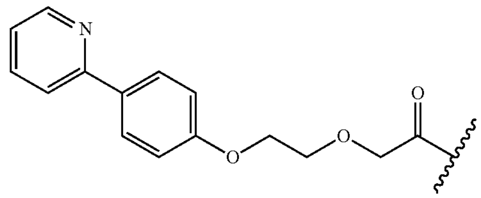
;
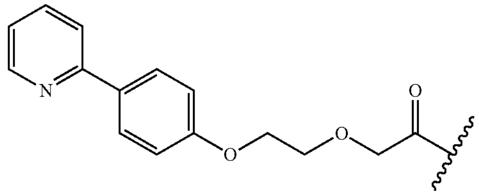
;
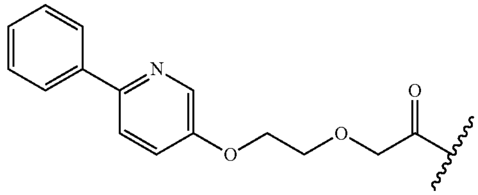
;
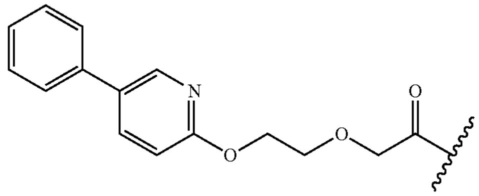
;
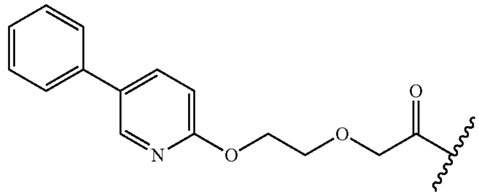
;
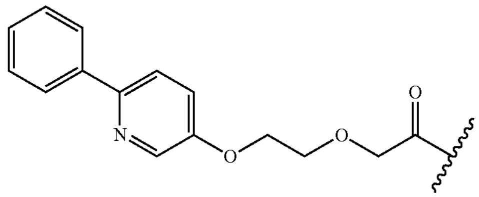
;
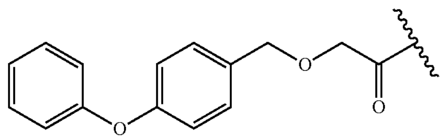
;
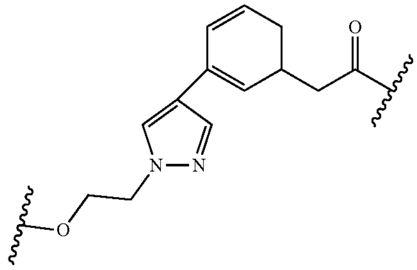
;
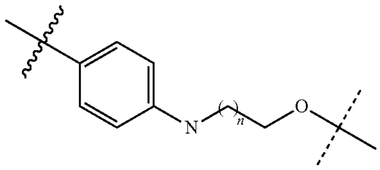
;
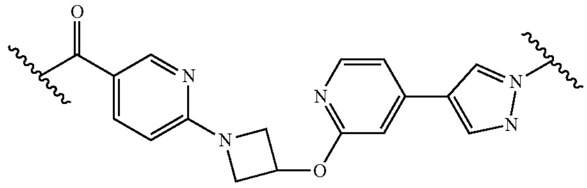
;
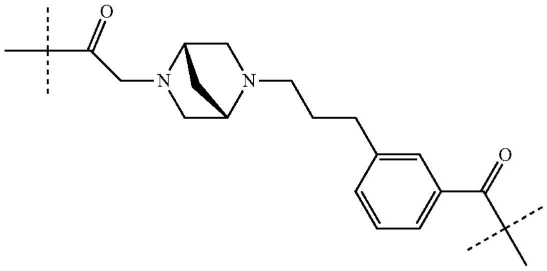
;
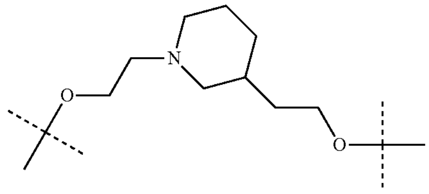
;
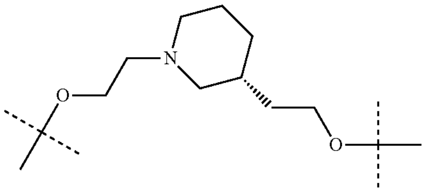
;
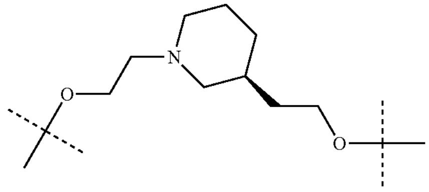
;
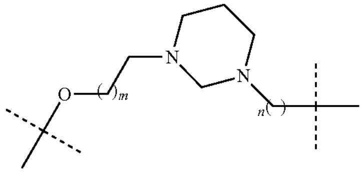

-continued
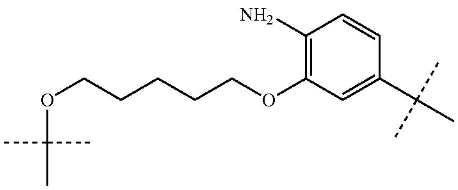
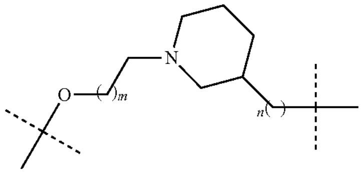
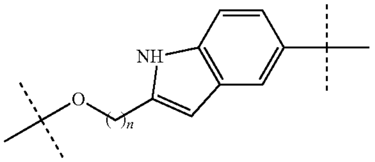
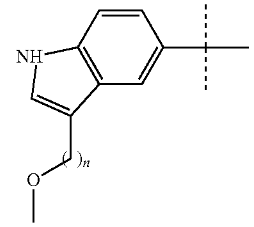
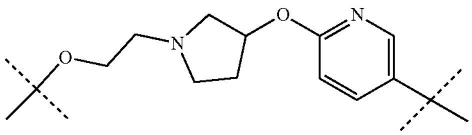
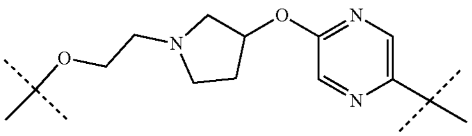
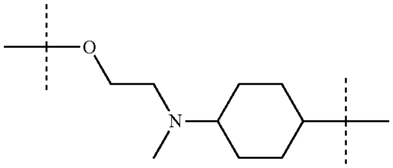
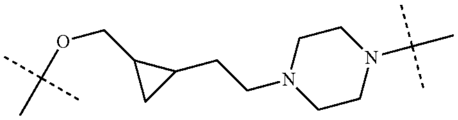
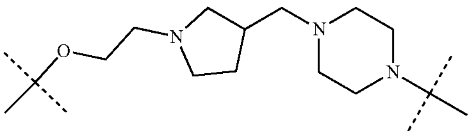
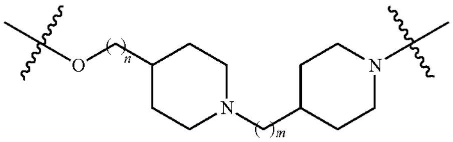
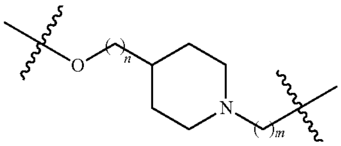
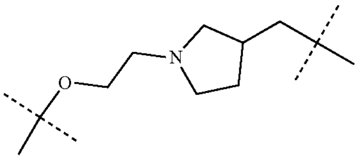
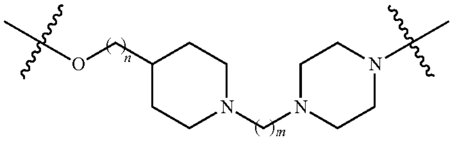
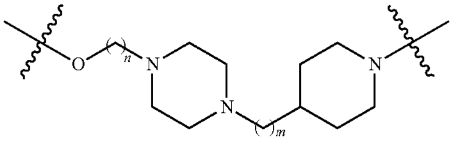
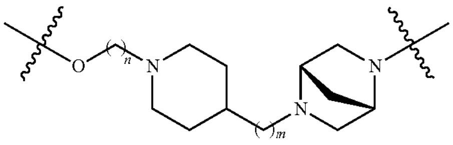
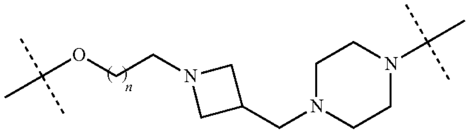
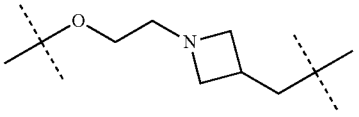
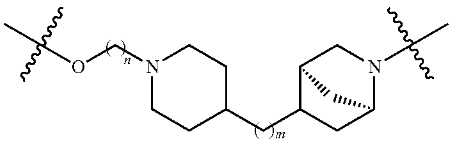
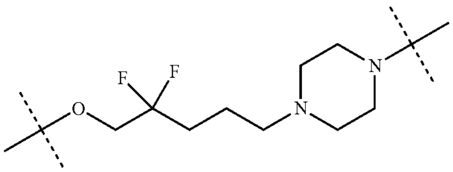
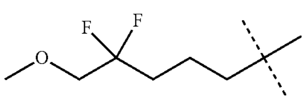
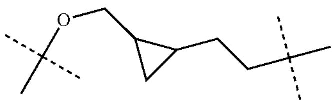
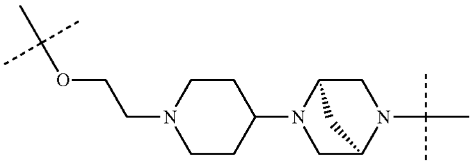
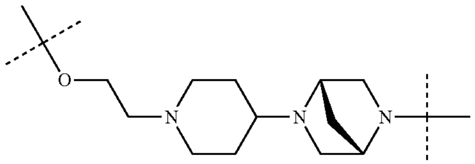

-continued
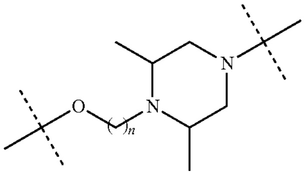
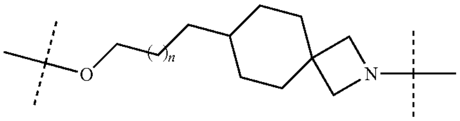
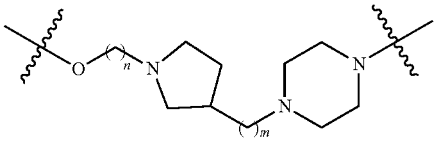
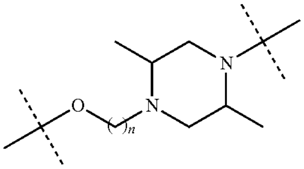
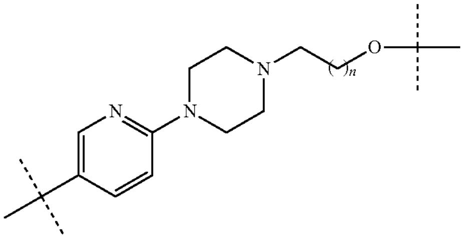
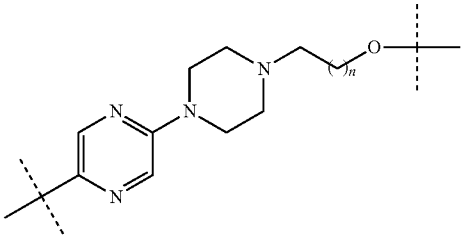
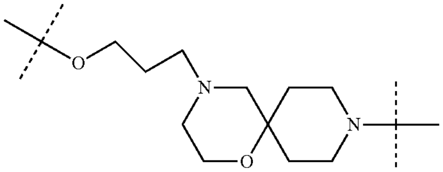
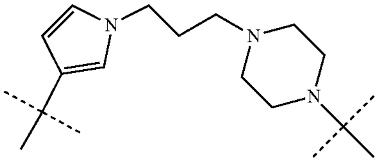
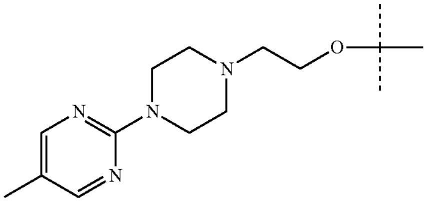
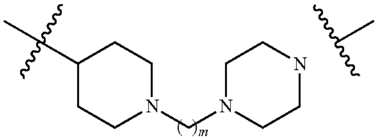
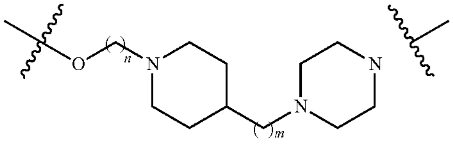
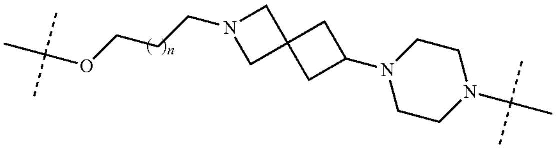
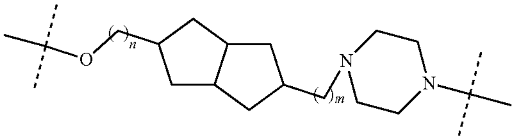
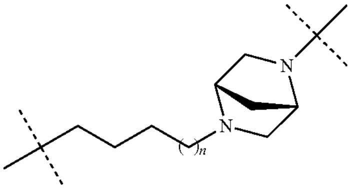
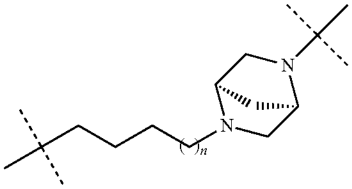
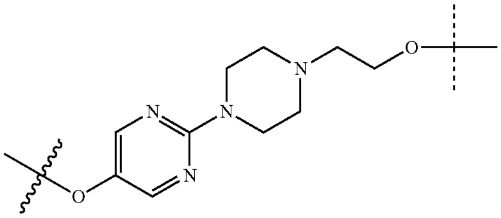
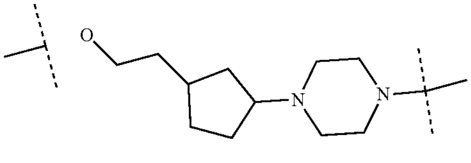
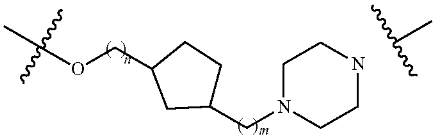

-continued
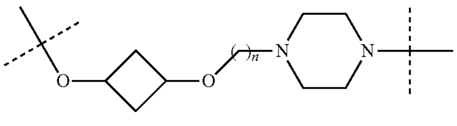
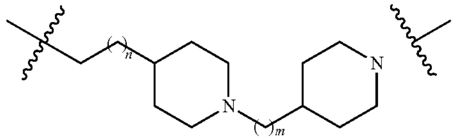
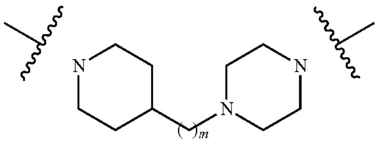
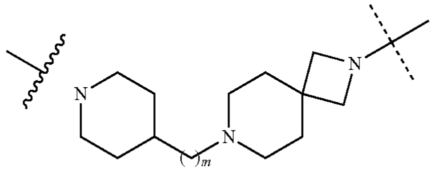
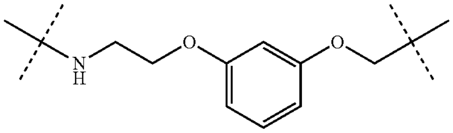
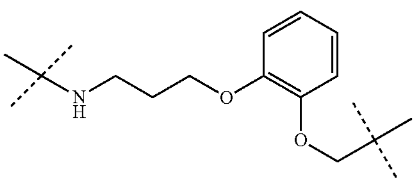
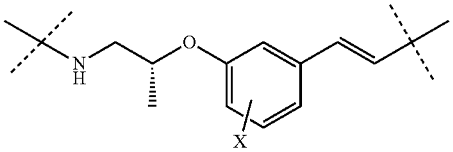
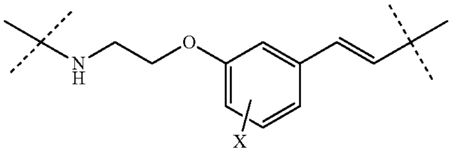
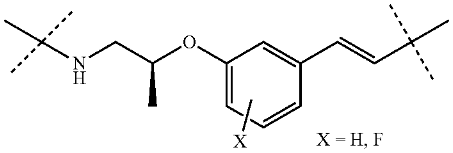
X = H, F
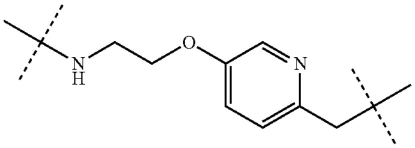
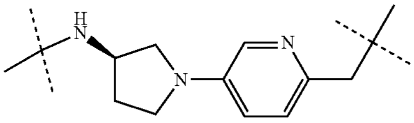
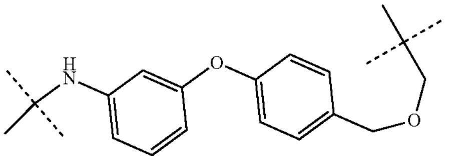
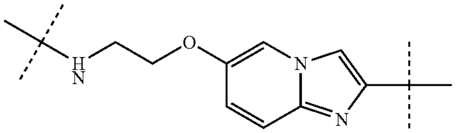
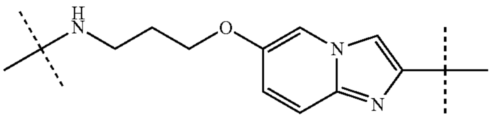
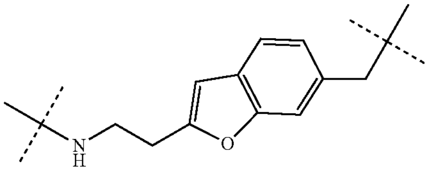
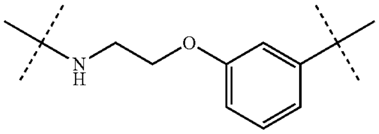
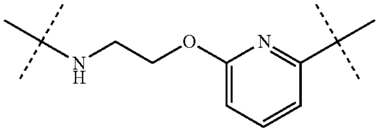
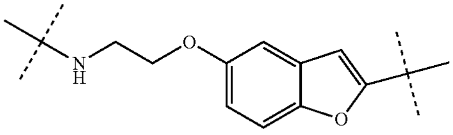
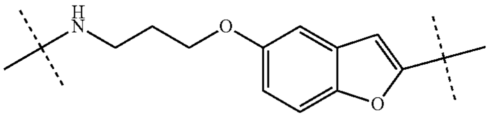
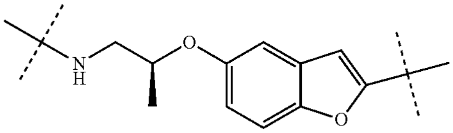
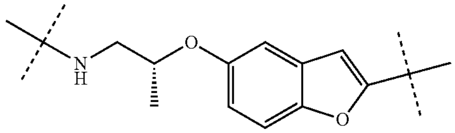
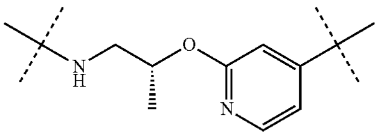
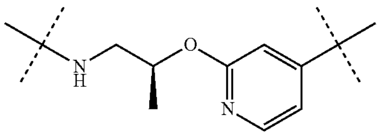

-continued
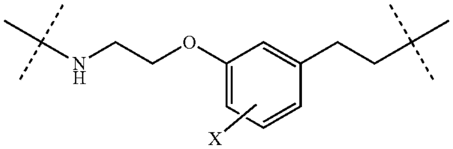
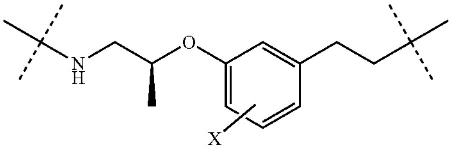
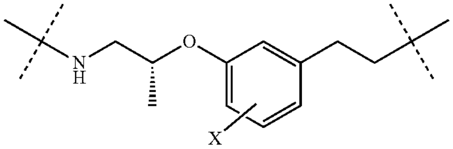
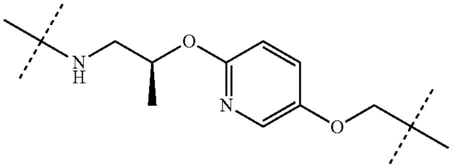
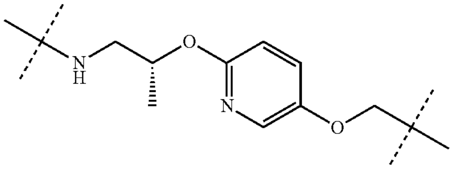
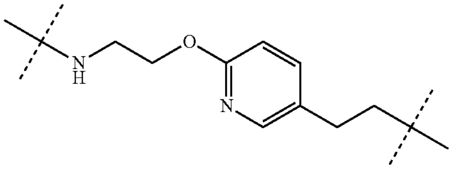
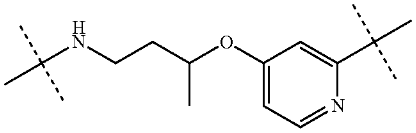
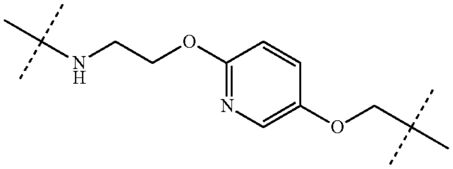
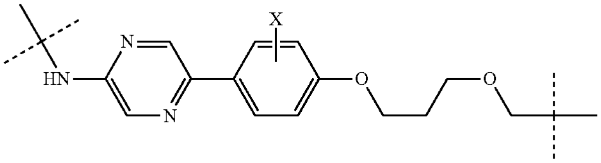
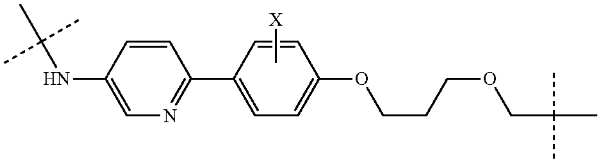
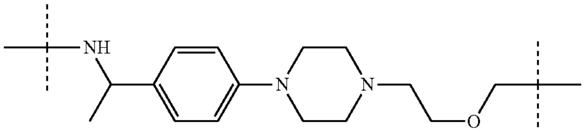
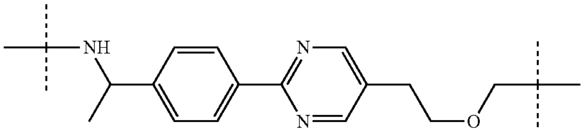
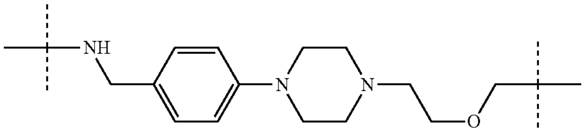
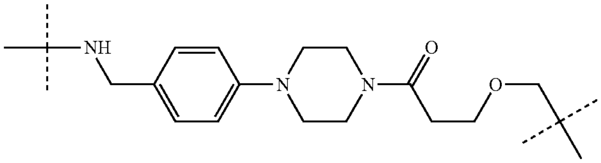
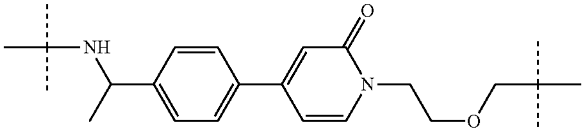
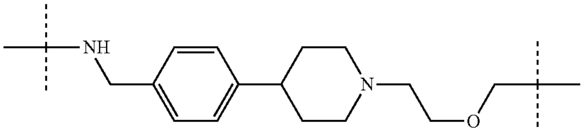
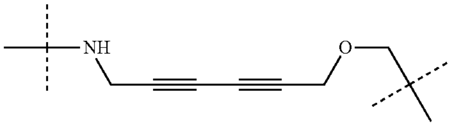
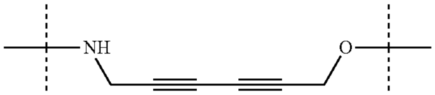
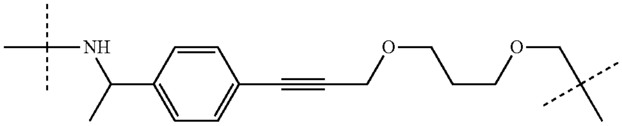

-continued
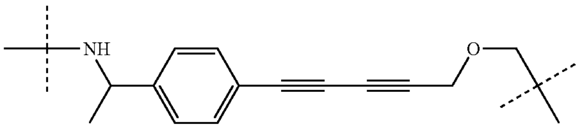
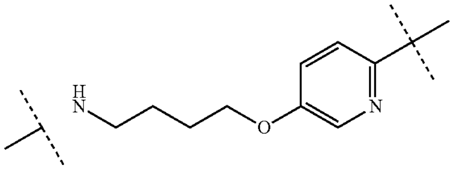
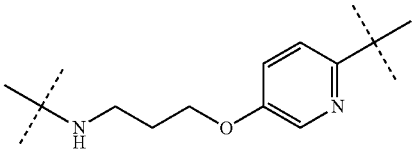
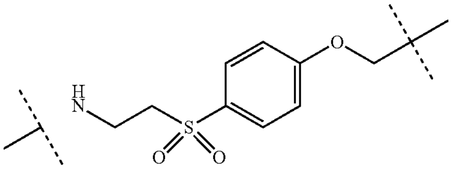
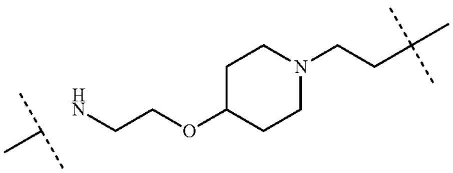
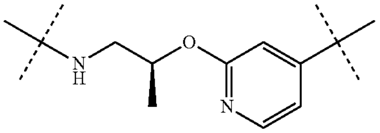
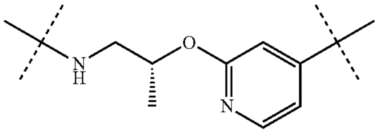
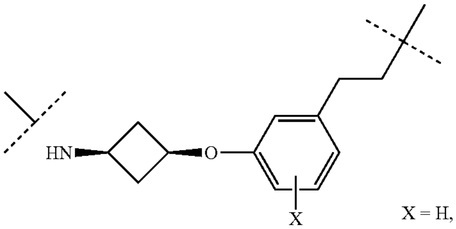
X = H, F
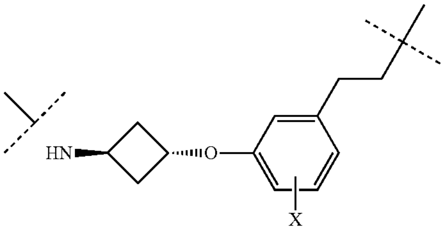
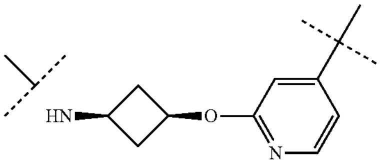
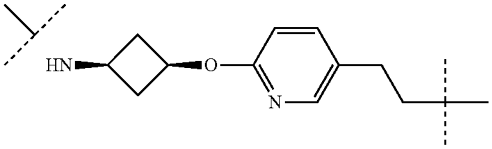
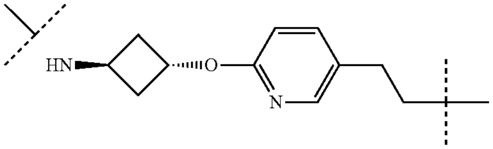
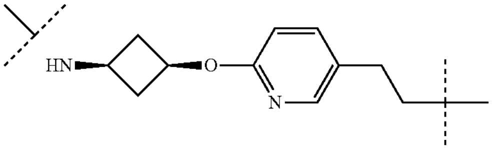
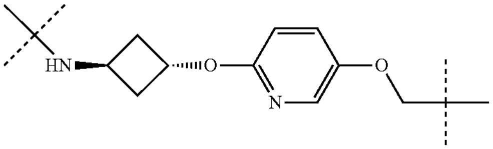
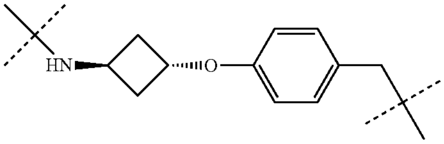
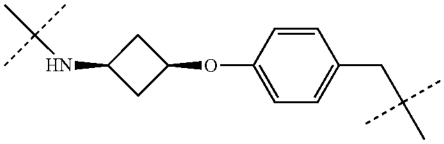
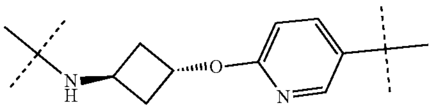
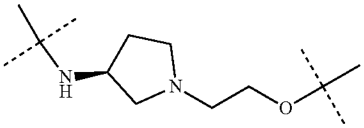
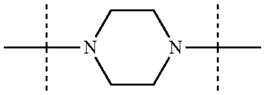
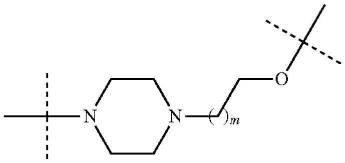
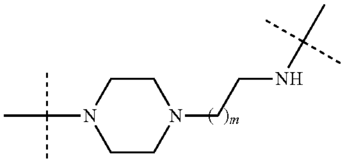

-continued
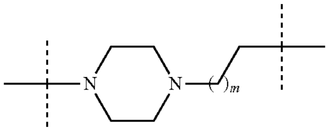
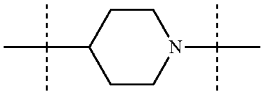
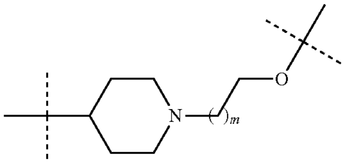
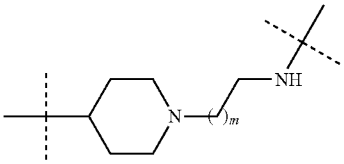
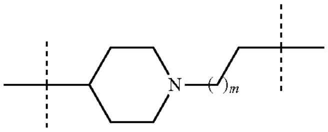
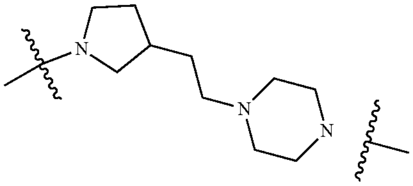
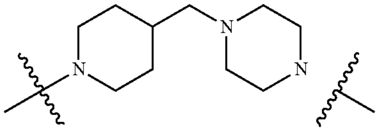
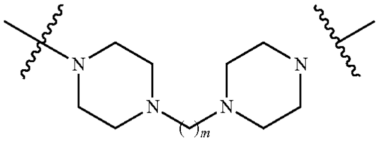
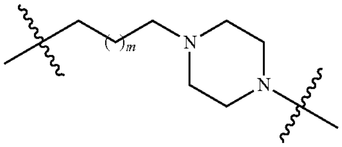
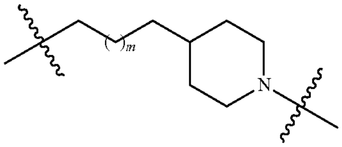
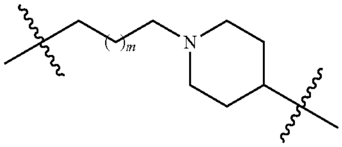
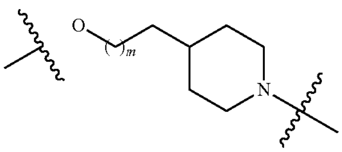
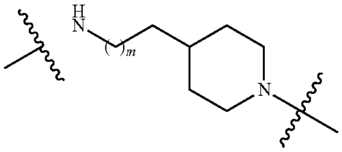
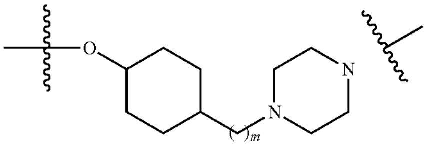
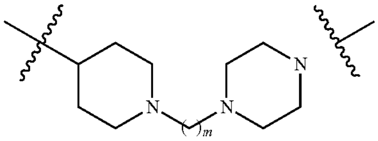
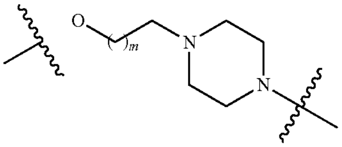
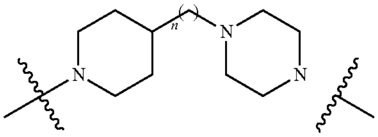
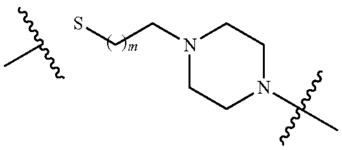
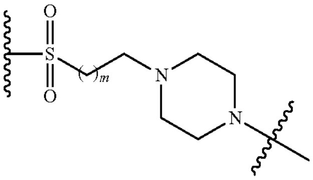
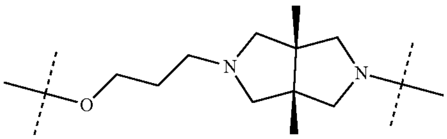
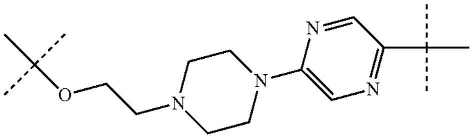
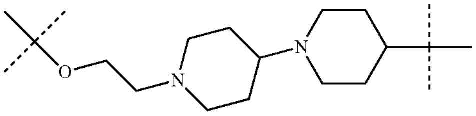
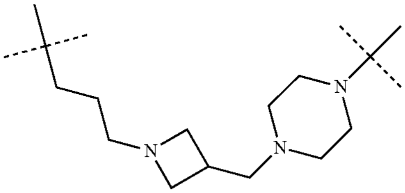
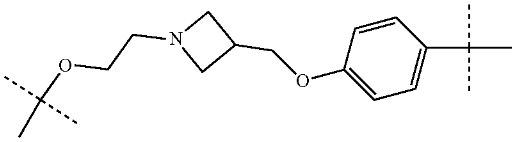
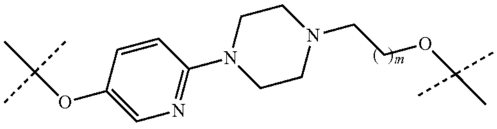
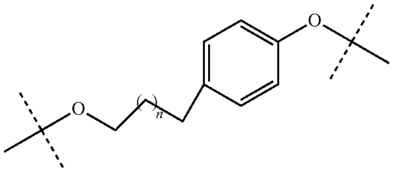

-continued
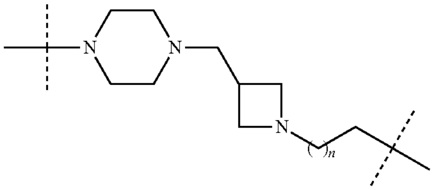
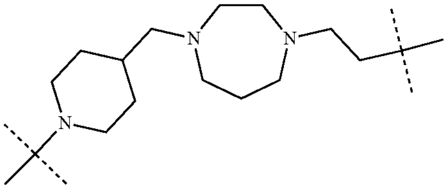
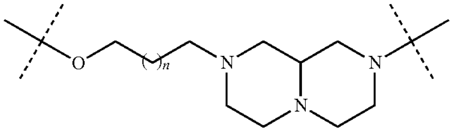
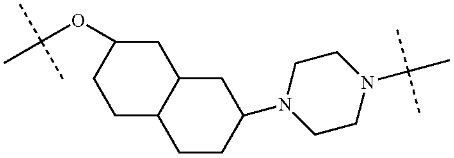
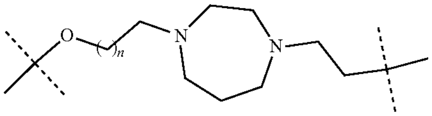
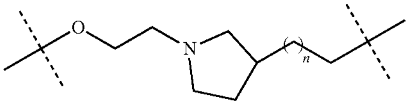
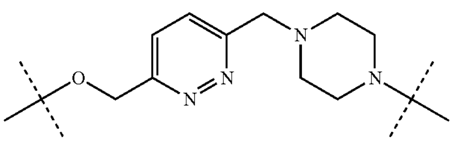
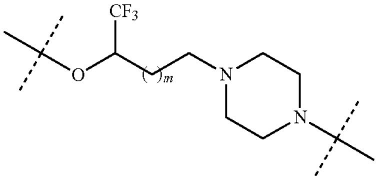
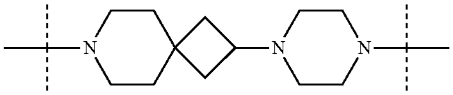
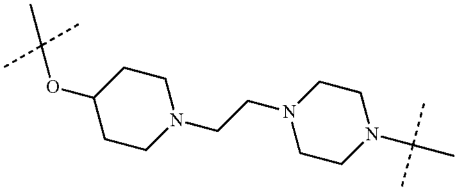
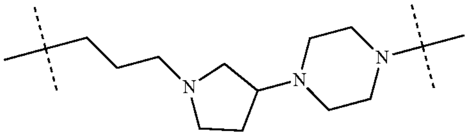
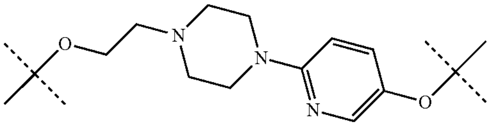
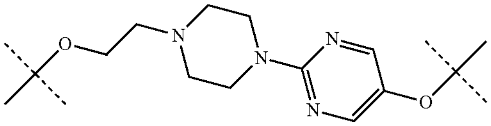
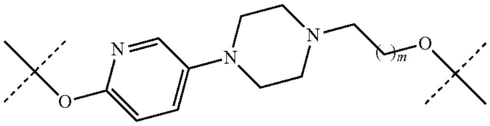
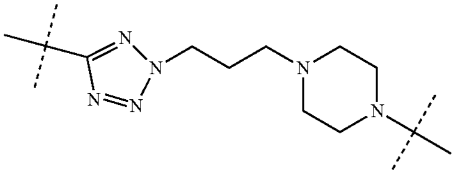
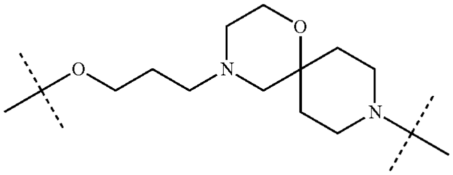
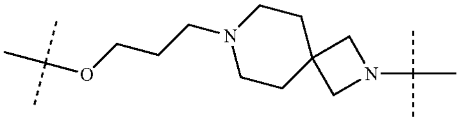
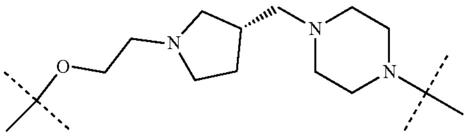
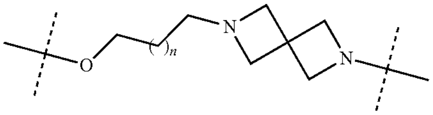
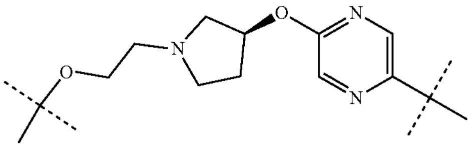
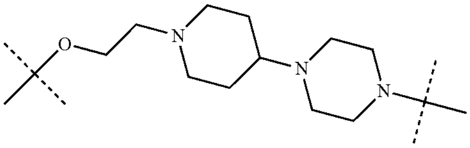

-continued
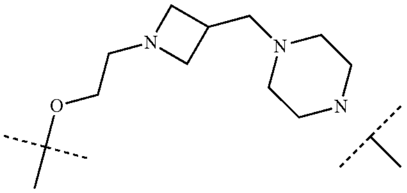
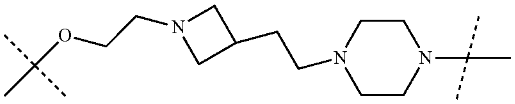
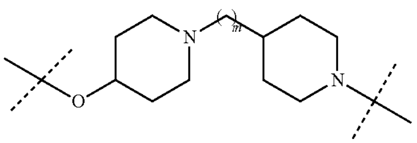
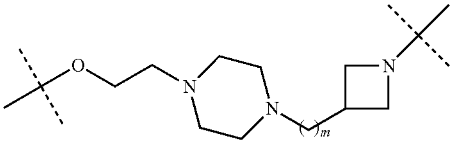
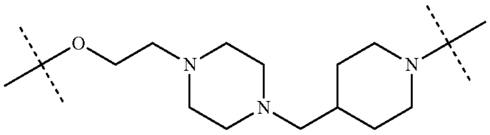
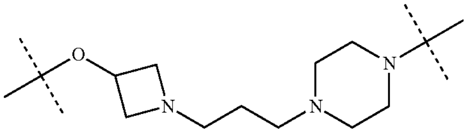
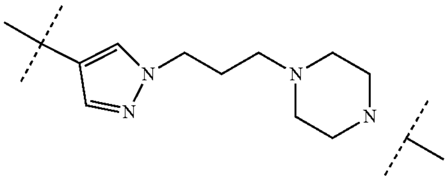
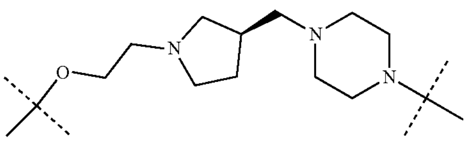
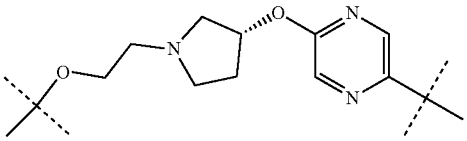
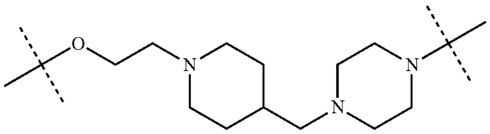
m = 1, 2; n = 0, 1
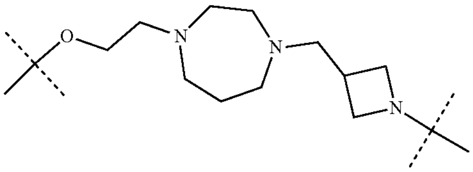
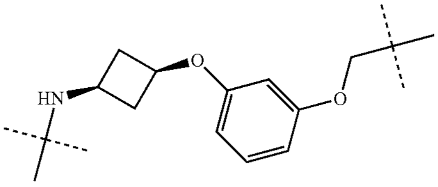
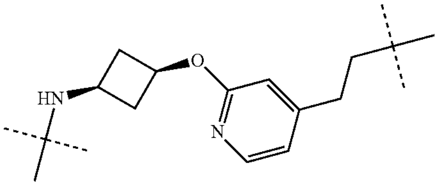
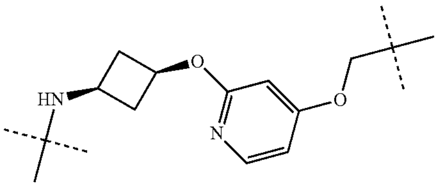
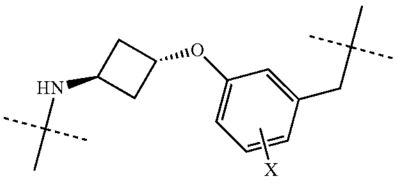
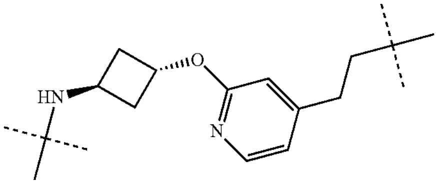
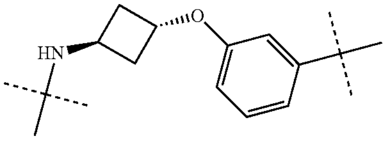
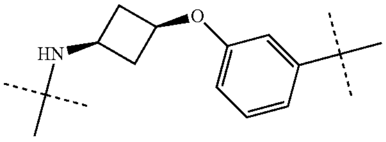
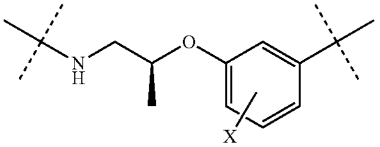
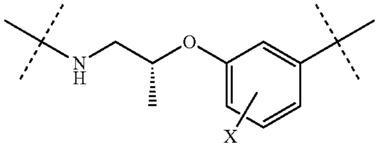

-continued
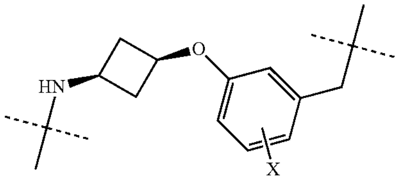
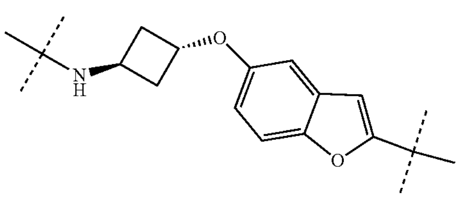
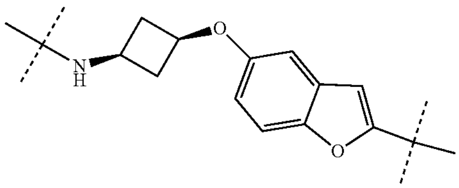
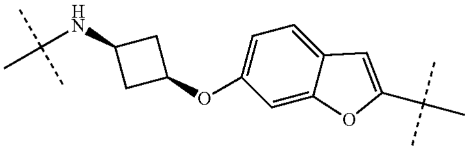
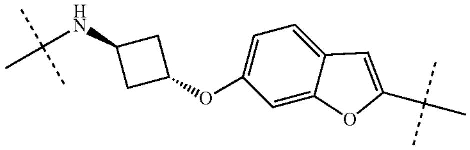
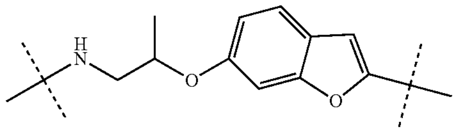
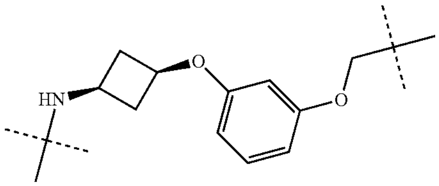
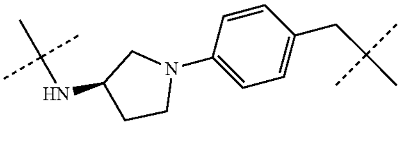
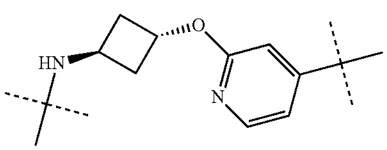
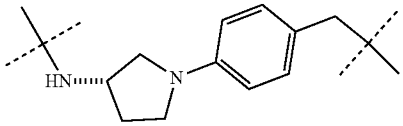
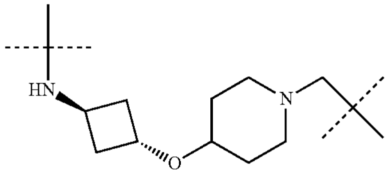
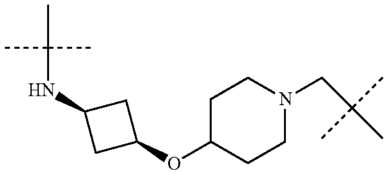
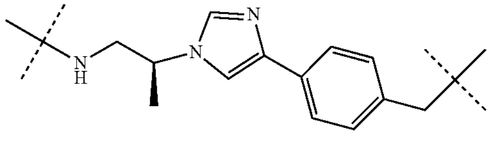
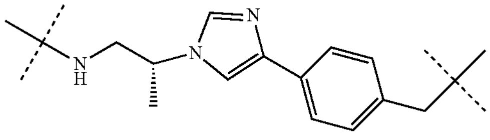
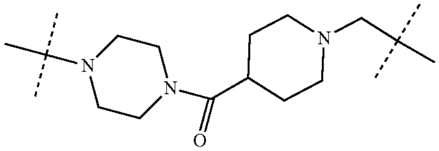
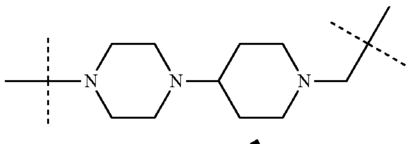
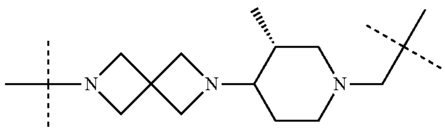
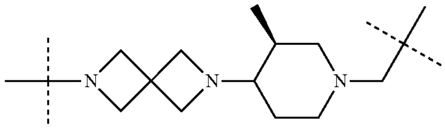
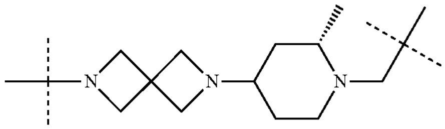
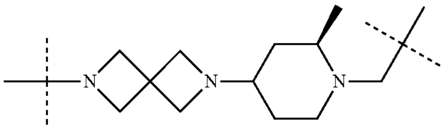

-continued
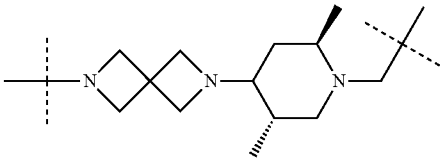
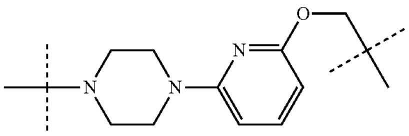
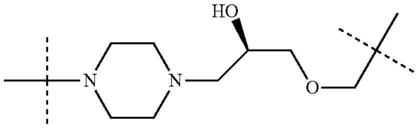
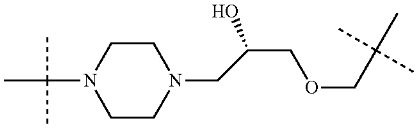
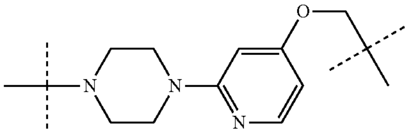
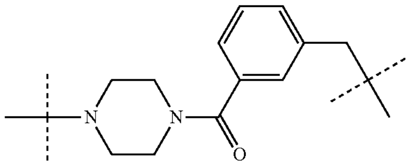
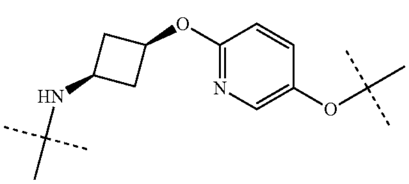
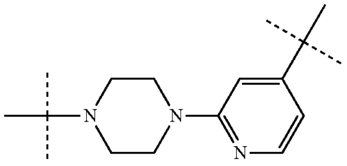
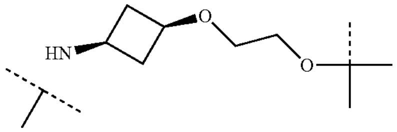
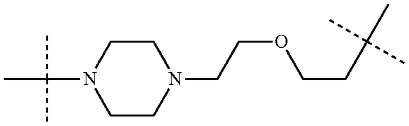
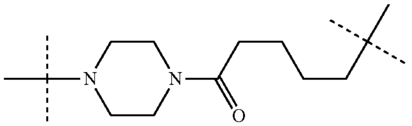
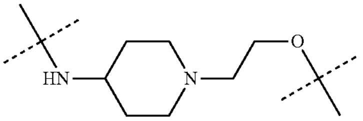
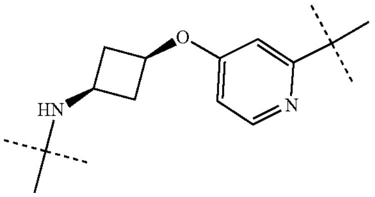
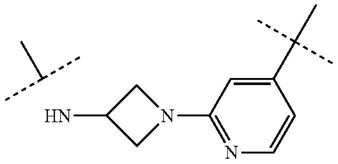
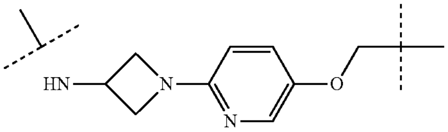
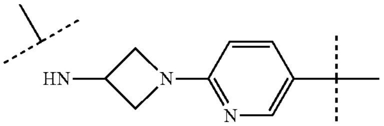
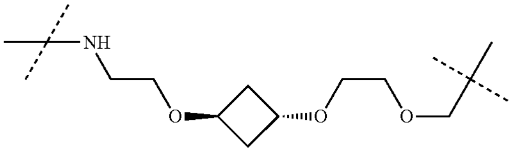
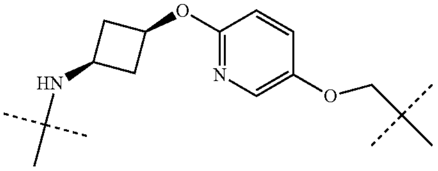
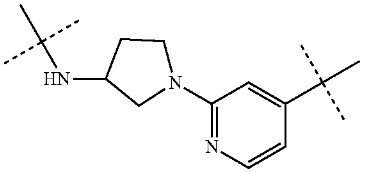
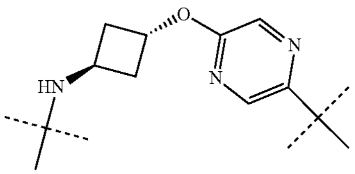
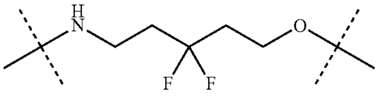
where n and m of the linker can be 0, 1, 2, 3, 4, 5, 6.
In additional embodiments, the linker (L) comprises a structure selected from, but not limited to the structure shown below, where a dashed line indicates the attachment point to the PTM or ULM moieties.
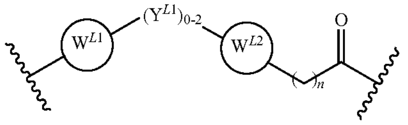

wherein:

$W^{L1}$ and $W^{L2}$ are each independently a 4-8 membered ring with 0-4 heteroatoms, optionally substituted with $R^Q$, each $R^Q$ is independently a H, halo, OH, CN, $CF_3$, $NH_2$, carboxyl, $C_1$-$C_6$ alkyl (linear, branched, optionally substituted), $C_1$-$C_6$ alkoxy (linear, branched, optionally substituted), or 2 $R^Q$ groups taken together with the atom they are attached to, form a 4-8 membered ring system containing 0-4 heteroatoms; and $Y^{L1}$ is each independently a bond, $C_1$-$C_6$ alkyl (linear, branched, optionally substituted) and optionally one or more C atoms are replaced with O; or $C_1$-$C_6$ alkoxy (linear, branched, optionally substituted).

In additional embodiments, the linker (L) comprises a structure selected from, but not limited to the structure shown below, where a dashed line indicates the attachment point to the PTM or ULM moieties.

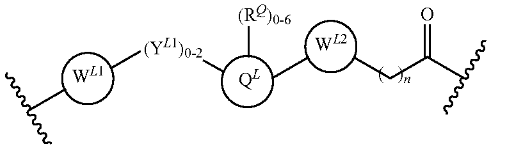

wherein:

$W^{L1}$ and $W^{L2}$ are each independently aryl, heteroaryl, cyclic, heterocyclic, $C_{1-6}$ alkyl (linear, branched, optionally substituted), C1-C6 alkoxy (linear, branched, optionally substituted), bicyclic, biaryl, biheteroaryl, or biheterocyclic, each optionally substituted with $R^Q$, each $R^Q$ is independently a H, halo, OH, CN, $CF_3$, $NH_2$, carboxyl, hydroxyl, nitro, C≡CH, $C_{2-6}$ alkenyl, $C_{2-6}$ alkynyl, $C_1$-$C_6$ alkyl (linear, branched, optionally substituted), $C_1$-$C_6$ alkoxy (linear, branched, optionally substituted), $OC_{1-3}$alkyl (optionally substituted by 1 or more —F), OH, $NH_2$, $NR^{Y1}R^{Y2}$, CN, or 2 $R^Q$ groups taken together with the atom they are attached to, form a 4-8 membered ring system containing 0-4 heteroatoms;

$Y^{L1}$ is each independently a bond, $NR^{YL1}$, O, S, $NR^{YL2}$, $CR^{YL1}RY^{YL2}$, C═O, C═S, SO, $SO_2$, $C_1$-$C_6$alkyl (linear, branched, optionally substituted) and optionally one or more C atoms are replaced with O; $C_1$-$C_6$ alkoxy (linear, branched, optionally substituted);

$Q^L$ is a 3-6 membered alicyclic or aromatic ring with 0-4 heteroatoms, biheterocyclic, or bicyclic, optionally bridged, optionally substituted with 0-6 $R^Q$, each $R^Q$ is independently H, $C_{1-6}$ alkyl (linear, branched, optionally substituted by 1 or more halo, $C_{1-6}$ alkoxyl), or 2 $R^Q$ groups taken together with the atom they are attached to, form a 3-8 membered ring system containing 0-2 heteroatoms);

$R^{YL1}$, $R^{YL2}$ are each independently H, OH, $C_{1-6}$ alkyl (linear, branched, optionally substituted by 1 or more halo, $C_{1-6}$ alkoxyl), or $R^1$, $R^2$ together with the atom they are attached to, form a 3-8 membered ring system containing 0-2 heteroatoms); and n is 0-10.

In additional embodiments, the linker group is optionally substituted (poly)ethyleneglycol having between 1 and about 100 ethylene glycol units, between about 1 and about 50 ethylene glycol units, between 1 and about 25 ethylene glycol units, between about 1 and 10 ethylene glycol units, between 1 and about 8 ethylene glycol units and 1 and 6 ethylene glycol units, between 2 and 4 ethylene glycol units, or optionally substituted alkyl groups interdispersed with optionally substituted, O, N, S, P or Si atoms. In certain embodiments, the linker is substituted with an aryl, phenyl, benzyl, alkyl, alkylene, or heterocycle group. In certain embodiments, the linker may be asymmetric or symmetrical.

In any of the embodiments of the compounds described herein, the linker group may be any suitable moiety as described herein. In one embodiment, the linker is a substituted or unsubstituted polyethylene glycol group ranging in size from about 1 to about 12 ethylene glycol units, between 1 and about 10 ethylene glycol units, about 2 about 6 ethylene glycol units, between about 2 and 5 ethylene glycol units, between about 2 and 4 ethylene glycol units.

In another embodiment, the present disclosure is directed to a compound which comprises a PTM group as described above, which binds to a target protein (e.g., ER) or polypeptide, which is ubiquitinated by an ubiquitin ligase and is chemically linked directly to the ULM group or through a linker moiety L, or PTM is alternatively a ULM' group which is also an E3 ubiquitin ligase binding moiety, which may be the same or different than the ULM group as described above and is linked directly to the ULM group directly or through the linker moiety; and L is a linker moiety as described above which may be present or absent and which chemically (covalently) links ULM to PTM, or a pharmaceutically acceptable salt, enantiomer, stereoisomer, solvate or polymorph thereof.

In certain embodiments, the linker group L is a group comprising one or more covalently connected structural units independently selected from the group consisting of:

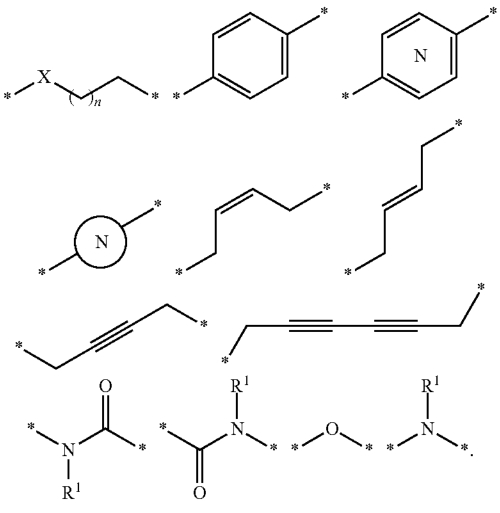

The X is selected from the group consisting of O, N, S, S(O) and $SO_2$; n is integer from 1 to 5; $R^{L1}$ is hydrogen or alkyl,

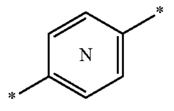

is a mono- or bicyclic aryl or heteroaryl optionally substituted with 1-3 substituents selected from alkyl, halogen, haloalkyl, hydroxy, alkoxy or cyano;

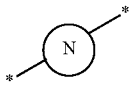

is a mono- or bicyclic cycloalkyl or a heterocycloalkyl optionally substituted with 1-3 substituents selected from alkyl, halogen, haloalkyl, hydroxy, alkoxy or cyano; and the phenyl ring fragment can be optionally substituted with 1, 2 or 3 substituents selected from the group consisting of alkyl, halogen, haloalkyl, hydroxy, alkoxy and cyano. In an embodiment, the linker group L comprises up to 10 covalently connected structural units, as described above.

Although the ULM group and PTM group may be covalently linked to the linker group through any group which is appropriate and stable to the chemistry of the linker, in preferred aspects of the present disclosure, the linker is independently covalently bonded to the ULM group and the PTM group preferably through an amide, ester, thioester, keto group, carbamate (urethane), carbon or ether, each of which groups may be inserted anywhere on the ULM group and PTM group to provide maximum binding of the ULM group on the ubiquitin ligase and the PTM group on the target protein to be degraded. (It is noted that in certain aspects where the PTM group is a ULM group, the target protein for degradation may be the ubiquitin ligase itself). In certain preferred aspects, the linker may be linked to an optionally substituted alkyl, alkylene, alkene or alkyne group, an aryl group or a heterocyclic group on the ULM and/or PTM groups.

While aspects for each variable have generally been listed above separately for each variable embodiments of the present disclosure includes those compounds in which several or each aspect in formula (I) is selected from each of the aspects listed above. Therefore, this invention is intended to include all combinations of aspects for each variable.

Examples of compounds of the present disclosure include the following:

(2S,4R)-1-[(2S)-2-[1-(4-{[2-(4-fluorophenyl)-5-hydroxy-3-methyl-1H-indol-1-yl]methyl}phenyl)-1,4,7,10-tetraoxadodecan-12-amido]-3,3-dimethylbutanoyl]-4-hydroxy-N-{[4-(4-methyl-1,3-thiazol-5-yl)phenyl]methyl}pyrrolidine-2-carboxamide;

(2S,4R)-1-[(2S)-2-[1-(4-{[2-(4-fluorophenyl)-5-hydroxy-3-methyl-1H-indol-1-yl]methyl}phenyl)-1,4,7,10-tetraoxadodecan-12-amido]-3,3-dimethylbutanoyl]-4-hydroxy-N-[(1S)-1-[4-(4-methyl-1,3-thiazol-5-yl)phenyl]ethyl]pyrrolidine-2-carboxamide;

(2S,4R)-4-hydroxy-1-[(2S)-2-[1-(4-{[5-hydroxy-2-(4-hydroxyphenyl)-3-methyl-1H-indol-1-yl]methyl}phenyl)-1,4,7,10-tetraoxadodecan-12-amido]-3,3-dimethylbutanoyl]-N-{[4-(4-methyl-1,3-thiazol-5-yl)phenyl]methyl}pyrrolidine-2-carboxamide;

(2S,4R)-4-hydroxy-1-[(2S)-2-[1-(4-{[5-hydroxy-2-(4-hydroxyphenyl)-3-methyl-1H-indol-1-yl]methyl}phenyl)-1,4,7,10-tetraoxadodecan-12-amido]-3,3-dimethylbutanoyl]-N—[(S)-1-[4-(4-methyl-1,3-thiazol-5-yl)phenyl]ethyl]pyrrolidine-2-carboxamide;

(2S,4R)-4-hydroxy-1-[(2S)-2-(1-{4-[(5-hydroxy-3-methyl-2-phenyl-1H-indol-1-yl)methyl]phenyl}-1,4,7,10-tetraoxadodecan-12-amido)-3,3-dimethylbutanoyl]-N-{[4-(4-methyl-1,3-thiazol-5-yl)phenyl]methyl}pyrrolidine-2-carboxamide;

(2S,4R)-1-[(2S)-2-{2-[2-({1-[2-(4-{[2-(4-fluorophenyl)-5-hydroxy-3-methyl-1H-indol-1-yl]methyl}phenoxy)ethyl]piperidin-4-yl}oxy)ethoxy]acetamido}-3,3-dimethylbutanoyl]-4-hydroxy-N-{[4-(4-methyl-1,3-thiazol-5-yl)phenyl]methyl}pyrrolidine-2-carboxamide;

(2S,4R)-1-[(2S)-2-[1-(4-{[2-(4-chlorophenyl)-5-hydroxy-3-methyl-1H-indol-1-yl]methyl}phenyl)-1,4,7,10-tetraoxadodecan-12-amido]-3,3-dimethylbutanoyl]-4-hydroxy-N-{[4-(4-methyl-1,3-thiazol-5-yl)phenyl]methyl}pyrrolidine-2-carboxamide;

(2S,4R)-1-[(2S)-2-[1-(4-{[2-(4-bromophenyl)-5-hydroxy-3-methyl-1H-indol-1-yl]methyl}phenyl)-1,4,7,10-tetraoxadodecan-12-amido]-3,3-dimethylbutanoyl]-4-hydroxy-N-{[4-(4-methyl-1,3-thiazol-5-yl)phenyl]methyl}pyrrolidine-2-carboxamide;

(2S,4R)-4-hydroxy-1-[(2S)-2-{2-[2-({1-[2-(4-{[5-hydroxy-2-(4-hydroxyphenyl)-3-methyl-1H-indol-1-yl]methyl}phenoxy)ethyl]piperidin-4-yl}oxy)ethoxy]acetamido}-3,3-dimethylbutanoyl]-N-{[4-(4-methyl-1,3-thiazol-5-yl)phenyl]methyl}pyrrolidine-2-carboxamide;

and pharmaceutically acceptable salt thereof.

Therapeutic/Pharmaceutical Compositions

In an additional aspect, the disclosure provides a use of a compound of the invention in the manufacture of a medicament for treating diseases, disorders or conditions mediated by the estrogen receptor. Pharmaceutical compositions comprising combinations of an effective amount of at least one bifunctional compound as described herein, and optionally with one or more of the compounds otherwise described herein, all in effective amounts, in combination with a pharmaceutically acceptable amount of a carrier, additive or excipient, represents a further aspect of the present disclosure. The carrier(s), diluents(s) or excipient(s) must be acceptable in the sense of being compatible with the other ingredients of the composition and not deleterious to the recipient thereof.

In accordance with another aspect of the present disclosure there is also provided a process for the preparation of a pharmaceutical composition including the agent, or pharmaceutically acceptable salts thereof, with one or more pharmaceutically acceptable carriers, diluents or excipients. The pharmaceutical composition can be for use in the treatment and/or prophylaxis of any of the conditions described herein.

For example, the compounds of Formula (I) may be in the form of a salt. Typically, the salts of the present disclosure are pharmaceutically acceptable salts. Salts encompassed within the term "pharmaceutically acceptable salts" refer to non-toxic salts of the compounds of this invention. For a review on suitable salts see Berge et al, J. Pharm. Sci. 1977, 66, 1-19.

The present disclosure includes, where applicable, the compositions comprising the pharmaceutically acceptable salts, in particular, acid or base addition salts of compounds as described herein. The acids which are used to prepare the pharmaceutically acceptable acid addition salts of the aforementioned base compounds useful according to this aspect are those which form non-toxic acid addition salts, i.e., salts containing pharmacologically acceptable anions, such as the hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate [i.e., 1,1'-methylene-bis-(2-hydroxy-3 naphthoate)]salts, among numerous others.

A pharmaceutically acceptable acid addition salt can be formed by reaction of a compound of formula (I) with a suitable inorganic or organic acid (such as hydrobromic, hydrochloric, sulfuric, nitric, phosphoric, p-toluenesulfonic, benzenesulfonic, methanesulfonic, ethanesulfonic, naphthalenesulfonic such as 2-naphthalenesulfonic), optionally in a suitable solvent such as an organic solvent, to give the salt which is usually isolated for example by crystallisation and filtration. A pharmaceutically acceptable acid addition salt of a compound of formula (I) can comprise or be, for example, a hydrobromide, hydrochloride, sulfate, nitrate, phosphate, p-toluenesulfonate, benzenesulfonate, methanesulfonate, ethanesulfonate, or naphthalenesulfonate (e.g. 2-naphthalenesulfonate) salt.

Other non-pharmaceutically acceptable salts, e.g. trifluoroacetates, may be used, for example, in the isolation of compounds of the invention, and are included within the scope of the present disclosure.

Pharmaceutically acceptable base addition salts may also be used to produce pharmaceutically acceptable salt forms of the compounds or derivatives according to the present disclosure. The chemical bases that may be used as reagents to prepare pharmaceutically acceptable base salts of the present compounds that are acidic in nature are those that form non-toxic base salts with such compounds. Such non-toxic base salts include, but are not limited to those derived from such pharmacologically acceptable cations such as alkali metal cations (eg., potassium and sodium) and alkaline earth metal cations (eg, calcium, zinc and magnesium), ammonium or water-soluble amine addition salts such as N-methylglucamine-(meglumine), and the lower alkanolammonium and other base salts of pharmaceutically acceptable organic amines, among others.

The compounds and compositions as described herein may, in accordance with the disclosure, be administered in single or divided unit dosage forms by the oral, parenteral or topical routes. Preferred unit dosage compositions are those containing a daily dose or sub-dose, or an appropriate fraction thereof, of an active ingredient. Such unit doses may therefore be administered once or more than once a day. Such pharmaceutical compositions may be prepared by any of the methods well known in the pharmacy art.

Administration of the active compound may range from continuous (intravenous drip) to several oral administrations per day (for example, Q.I.D.) and may include oral, topical, parenteral, intramuscular, intravenous, sub-cutaneous, transdermal (which may include a penetration enhancement agent), buccal, sublingual and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Administration of compounds according to the present disclosure as sprays, mists, or aerosols for intra-nasal, intra-tracheal or pulmonary administration may also be used.

The present disclosure therefore also is directed to pharmaceutical compositions comprising an effective amount of compound as described herein, optionally in combination with a pharmaceutically acceptable carrier, additive or excipient. Compounds according to the present disclosure may be administered in immediate release, intermediate release or sustained or controlled release forms. Sustained or controlled release forms are preferably administered orally, but also in suppository and transdermal or other topical forms. Intramuscular injections in liposomal form may also be used to control or sustain the release of compound at an injection site.

The compositions as described herein may be formulated in a conventional manner using one or more pharmaceutically acceptable carriers and may also be administered in controlled-release formulations. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions as described herein may be administered orally, parenterally, by inhalation spray, topically, rectally, nasally, buccally, vaginally or via an implanted reservoir. The term “parenteral” as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously.

Sterile injectable forms of the compositions as described herein may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer’s solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

Pharmaceutical compositions adapted for parental administration can include aqueous and non-aqueous sterile injection solutions, which may contain anti-oxidants, buffers, bacteriostats and solutes which render the composition isotonic with the blood of the intended recipient; and/or aqueous and non-aqueous sterile suspensions, which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water, for injections, immediately prior to use. Extemporaneous injection solutions and suspensions may be prepared from sterile powders, granules and tablets.

The pharmaceutical compositions as described herein may be orally administered in any orally acceptable dosage form including, but not limited to, capsules, tablets, aqueous solutions or suspensions in aqueous or non-aqueous liquids, edible foams or whips, oil-in-water liquid emulsions, or water-in-oil liquid emulsions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Oral compositions will generally include an inert diluent or an edible carrier. They may be enclosed in gelatin capsules or compressed into tablets. For the purpose of oral therapeutic administration, the active compound or its prodrug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

For instance, for oral administration in the form of a tablet or capsule, the active drug component can be combined with an oral, non-toxic pharmaceutically acceptable inert carrier, such as ethanol, glycerol, water and the like. Powders are prepared by reducing the compound to a suitable fine size and mixing with a similarly prepared pharmaceutical carrier, such as an edible carbohydrate, for example starch or mannitol. Flavouring, preservative, dispersing and colouring agent can also be present.

Capsules are made by preparing a powder mixture, as described above, and filling formed gelatin sheaths. Glidants and lubricants, such as colloidal silica, talc, magnesium stearate, calcium stearate, or solid polyethylene glycol, can be added to the powder mixture before the filling operation. A disintegrating or solubilizing agent, such as agar-agar, calcium carbonate, or sodium carbonate, can also be added to improve the availability of the medicament when the capsule is ingested.

Moreover, when desired or necessary, suitable binders, glidants, lubricants, sweetening agents, flavours, disintegrating agents, and/or colouring agents can also be incorporated into the therapeutic composition mixture. Suitable binders include starch, gelatin, natural sugars, such as glucose or beta-lactose, corn sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch, methyl cellulose, agar, bentonite, xanthan gum and the like. Tablets are formulated, for example, by preparing a powder mixture, granulating or slugging, adding a lubricant and disintegrant and pressing into tablets. A powder mixture is prepared by mixing the compound, suitably comminuted, with a diluent or base as described above, and optionally, with a binder (such as carboxymethylcellulose, an aliginate, gelatin, or polyvinyl pyrrolidone), a solution retardant such as paraffin, a resorption accelerator such as a quaternary salt and/or an absorption agent (such as bentonite, kaolin or dicalcium phosphate). The powder mixture can be granulated by wetting with a binder such as syrup, starch paste, acadia mucilage or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material and a polish coating of wax can be provided. Dyestuffs can be added to these coatings to distinguish different unit dosages.

Oral fluids, such as solution, syrups, and elixirs, can be prepared in dosage unit form so that a given quantity contains a predetermined amount of the compound. Syrups can be prepared by dissolving the compound in a suitably flavoured aqueous solution, while elixirs are prepared through the use of a non-toxic alcoholic vehicle. Suspensions can be formulated by dispersing the compound in a non-toxic vehicle. Solubilizers and emulsifiers (such as ethoxylated isostearyl alcohols and polyoxy ethylene sorbitol ethers), preservatives, flavor additive (such as peppermint oil or natural sweeteners or saccharin or other artificial sweeteners), and the like can also be added.

Where appropriate, dosage unit compositions for oral administration can be microencapsulated. The composition can also be prepared to prolong or sustain the release, for example, by coating or embedding particulate material in polymers, wax or the like.

The compounds of the disclosure may also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Pharmaceutical compositions adapted for transdermal administration may be presented as discrete patches intended to remain in intimate contact with the epidermis of the recipient for a prolonged period of time.

The pharmaceutical compositions as described herein may also be administered topically. Pharmaceutical compositions adapted for topical administration may be formulated as ointments, creams, suspensions, lotions, powders, solutions, pastes, gels, sprays, aerosols, or oils. Suitable topical formulations are readily prepared for each of these areas or organs. Topical application for the lower intestinal tract can be effected in a rectal suppository formulation (see above) or in a suitable enema formulation. Topically-acceptable transdermal patches may also be used.

For topical applications, the pharmaceutical compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax, sorbitan monostearate, polysorbate 60, cetyl esters wax, cetearyl alcohol, 2-octyldodecanol, benzyl alcohol, and water. In certain preferred aspects of the disclosure, the compounds may be coated onto a stent which is to be surgically implanted into a patient in order to inhibit or reduce the likelihood of occlusion occurring in the stent in the patient.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum. Pharmaceutical compositions adapted for topical administrations to the eye include eye drops wherein the active ingredient is dissolved or suspended in a suitable carrier, especially an aqueous solvent.

Alternatively, the pharmaceutical compositions as described herein may be administered in the form of suppositories or enemas for rectal administration. These can be prepared by mixing the agent with a suitable non-irritating excipient, which is solid at room temperature but liquid at rectal temperature and therefore will melt in the rectum to release the drug. Such materials include cocoa butter, beeswax and polyethylene glycols.

The pharmaceutical compositions as described herein may also be administered by nasal aerosol or inhalation. Dosage forms for nasal or inhaled administration may conveniently be formulated as aerosols, solutions, suspensions drops, gels, or dry powders. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Pharmaceutical compositions adapted for vaginal administration may be presented as pessaries, tampons, creams, gels, pastes, foams, or spray formulations.

It should be understood that in addition to the ingredients particularly mentioned above, the compositions may include other agents conventional in the art having regard to the type of formulation in question, for example those suitable for oral administration may include flavouring agents.

The amount of compound in a pharmaceutical composition as described herein that may be combined with the carrier materials to produce a single dosage form will vary depending upon the host and disease treated, the particular mode of administration. Preferably, the compositions should be formulated to contain between about 0.05 milligram to about 750 milligrams or more, more preferably about 1 milligram to about 600 milligrams, and even more preferably about 10 milligrams to about 500 milligrams of active ingredient, alone or in combination with at least one other compound according to the present disclosure.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known therapeutic agents as otherwise identified herein.

A therapeutically effective amount of the agent will depend upon a number of factors including, for example, the age and weight of the subject, the precise condition requiring treatment and its severity, the nature of the formulation, and the route of administration, and will ultimately be at the discretion of the attendant physician or veterinarian. In particular, the subject to be treated is a mammal, particularly a human.

The agent may be administered in a daily dose. This amount may be given in a single dose per day or in a number (such as two, three, four, five or six) of sub-doses per day such that the total daily dose is the same.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient/patient per day. A typical topical dosage will range from 0.01-5% wt/wt in a suitable carrier.

In certain embodiments, the amount of the compound as described herein is administered in an amount selected from 0.001 mg to 3 g per day (calculated as the free or unsalted compound). In certain embodiments, the amount of the compound as described herein is administered in any suitable unit dosage form, including but not limited to one containing less than 1 mg, 1 mg to 3000 mg, preferably 5 to 500 mg of active ingredient per unit dosage form. An oral dosage of about 25-250 mg is often convenient.

The active ingredient is preferably administered to achieve peak plasma concentrations of the active compound of about 0.00001-30 mM, preferably about 0.1-30 μM. This may be achieved, for example, by the intravenous injection of a solution or formulation of the active ingredient, optionally in saline, or an aqueous medium or administered as a bolus of the active ingredient. Oral administration is also appropriate to generate effective plasma concentrations of active agent.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as anti-cancer agents, among others. In certain preferred aspects of the disclosure, one or more compounds according to the present disclosure are coadministered with another bioactive agent, such as an anti-cancer agent or a would healing agent, including an antibiotic, as otherwise described herein.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Combination Therapies

The compounds of the present disclosure may be used in combination with or include one or more additional therapeutic or bioactive agents and may be administered either sequentially or simultaneously by any convenient route in separate or combined pharmaceutical compositions.

The term "additional therapeutic or bioactive agent" is used to describe an agent, other than a compound according to the present disclosure, which is used in combination with the present compounds as an agent with biological activity to assist in effecting an intended therapy, inhibition and/or prevention/prophylaxis for which the present compounds are used. Preferred bioactive agents for use herein include those agents which have pharmacological activity similar to that for which the present compounds are used or administered and include for example, anti-cancer agents, antiviral agents, especially including anti-HIV agents and anti-HCV agents, antimicrobial agents, antifungal agents, etc.

The therapeutically effective amount of the further therapeutic agents of the present disclosure will depend upon a number of factors including, for example the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected in order to achieve the desired combined therapeutic effect.

The compounds of the present disclosure and further therapeutic agent(s) may be employed in combination by administration simultaneously in a unitary pharmaceutical composition including both compounds. Alternatively, the combination may be administered separately in separate pharmaceutical compositions, each including one of the compounds in a sequential manner wherein, for example, the compound of the disclosure is administered first and the other second and vice versa. Such sequential administration may be close in time (e.g. simultaneously) or remote in time. Furthermore, it does not matter if the compounds are administered in the same dosage form, for example one compound may be administered topically and the other compound may be administered orally. Suitably, both compounds can be administered orally.

The combinations may be presented as a combination kit. By the term "combination kit" "or kit of parts" as used herein is meant the pharmaceutical composition or compositions that are used to administer the combination according to the disclosure. When both compounds are administered simultaneously, the combination kit can contain both compounds in a single pharmaceutical composition, such as a tablet, or in separate pharmaceutical compositions. When the compounds are not administered simultaneously, the combination kit will contain each compound in separate pharmaceutical compositions either in a single package or in separate pharmaceutical compositions in separate packages.

The combination kit can also be provided with instructions, such as dosage and administration instructions. Such dosage and administration instructions can be of the kind that are provided to a doctor, for example by a drug product label, or they can be of the kind that are provided by a doctor, such as instructions to a patient.

When the combination is administered separately in a sequential manner wherein one is administered first and the other second, or vice versa, such sequential administration may be close in time or remote in time. For example, administration of the other agent several minutes to several dozen minutes after the administration of the first agent, and administration of the other agent several hours to several days after the administration of the first agent are included, wherein the lapse of time is not limited, for example, one agent may be administered once a day, and the other agent may be administered 2 or 3 times a day, or one agent may be administered once a week, and the other agent may be administered once a day and the like.

It will be clear to a person skilled in the art that, where appropriate, the other therapeutic ingredients(s) may be used in the form of salts, for example as alkali metal or amine salts, or as acid addition salts, or prodrugs, or as esters, for example lower alkyl esters, or as solvates, for example hydrates, to optimise the activity and/or stability and/or physical characteristics, such as solubility, of the therapeutic ingredient. It will be clear also that, where appropriate, the therapeutic ingredients may be used in optically pure form.

When combined in the same composition it will be appreciated that the two compounds must be stable and compatible with each other and the other components of the composition and may be formulated for administration. When formulated separately they may be provided in any convenient composition, conveniently, in such a manner as known for such compounds in the art.

When the compound of formula (I) is used in combination with a second therapeutic agent active against the same disease, condition or disorder, the dose of each compound may differ from that when the compound is used alone. Appropriate doses will be readily appreciated by those skilled in the art.

In the embodiment, the compound of formula (I) or a pharmaceutically acceptable salt thereof may be employed with other therapeutic methods of cancer treatment. In particular, an anti-neoplastic therapy, combination therapy with other chemotherapeutic, hormonal, antibody agents as well as surgical and/or radiation treatments other than those mentioned above are envisaged.

As indicated, therapeutically effective amounts of the compound of formula (I) or a pharmaceutically acceptable salt thereof are discussed above. The therapeutically effective amount of the additional therapeutic or bioactive agent of the present disclosure will depend upon a number of factors including, for example the age and weight of the mammal, the precise condition requiring treatment, the severity of the condition, the nature of the formulation, and the route of administration. Ultimately, the therapeutically effective amount will be at the discretion of the attendant physician or veterinarian. The relative timings of administration will be selected in order to achieve the desired combined therapeutic effect.

In one embodiment, the additional anti-cancer therapy is surgical and/or radiotherapy.

In certain embodiments, the disclosure provides a composition comprising a compound as described herein in combination with an additional anti-cancer agent.

In certain embodiments, the additional anti-cancer agent is an anti-cancer agent, which may be combined with compounds according to the present disclosure to treat cancer. These agents include, for example, everolimus, trabectedin, abraxane, TLK 286, AV-299, DN-101, pazopanib, GSK690693, RTA 744, ON 0910.Na, AZD 6244 (ARRY-142886), AMN-107, TKI-258, GSK461364, AZD 1152, enzastaurin, vandetanib, ARQ-197, MK-0457, MLN8054, PHA-739358, R-763, AT-9263, a FLT-3 inhibitor, a VEGFR inhibitor, an EGFR TK inhibitor, an aurora kinase inhibitor, a PIK-1 modulator, a Bcl-2 inhibitor, an HDAC inhibitor, a c-MET inhibitor, a PARP inhibitor, a Cdk inhibitor, an EGFR TK inhibitor, an IGFR-TK inhibitor, an anti-HGF antibody, a PI3 kinase inhibitor, an AKT inhibitor, an mTORC1/2 inhibitor, a JAK/STAT inhibitor, a checkpoint-1 or 2 inhibitor, a focal adhesion kinase inhibitor, a Map kinase kinase (mek) inhibitor, a VEGF trap antibody, pemetrexed, erlotinib, dasatanib, nilotinib, decatanib, panitumumab, amrubicin, oregovomab, Lep-etu, nolatrexed, azd2171, batabulin, ofatumumab, zanolimumab, edotecarin, tetrandrine, rubitecan, tesmilifene, oblimersen, ticilimumab, ipilimumab, gossypol, Bio 111, 131-I-TM-601, ALT-110, BIO 140, CC 8490, cilengitide, gimatecan, IL13-PE38QQR, INO 1001, IPdR1 KRX-0402, lucanthone, LY317615, neuradiab, vitespan, Rta 744, Sdx 102, talampanel, atrasentan, Xr 311, romidepsin, ADS-100380, sunitinib, 5-fluorouracil, vorinostat, etoposide, gemcitabine, doxorubicin, liposomal doxorubicin, 5'-deoxy-5-fluorouridine, vincristine, temozolomide, ZK-304709, seliciclib; PD0325901, AZD-6244, capecitabine, L-Glutamic acid, N-[4-[2-(2-amino-4,7-dihydro-4-oxo-1H-pyrrolo[2,3-d]pyrimidin-5-yl)ethyl]benzoyl]-, disodium salt, heptahydrate, camptothecin, PEG-labeled irinotecan, tamoxifen, toremifene citrate, anastrazole, exemestane, letrozole, DES (diethylstilbestrol), estradiol, estrogen, conjugated estrogen, bevacizumab, IMC-1C11, CHIR-258); 3-[5-(methylsulfonylpiperadinemethyl)-indolyl-quinolone, vatalanib, AG-013736, AVE-0005, goserelin acetate, leuprolide acetate, triptorelin pamoate, medroxyprogesterone acetate, hydroxyprogesterone caproate, megestrol acetate, raloxifene, bicalutamide, flutamide, nilutamide, megestrol acetate, CP-724714; TAK-165, HKI-272, erlotinib, lapatanib, canertinib, ABX-EGF antibody, erbitux, EKB-569, PKI-166, GW-572016, Ionafarnib, BMS-214662, tipifarnib; amifostine, NVP-LAQ824, suberoyl analide hydroxamic acid, valproic acid, trichostatin A, FK-228, SU11248, sorafenib, KRN951, aminoglutethimide, arnsacrine, anagrelide, L-asparaginase, Bacillus Calmette-Guerin (BCG) vaccine, adriamycin, bleomycin, buserelin, busulfan, carboplatin, carmustine, chlorambucil, cisplatin, cladribine, clodronate, cyproterone, cytarabine, dacarbazine, dactinomycin, daunorubicin, diethylstilbestrol, epirubicin, fludarabine, fludrocortisone, fluoxymesterone, flutamide, gleevec, gemcitabine, hydroxyurea, idarubicin, ifosfamide, imatinib, leuprolide, levamisole, lomustine, mechlorethamine, melphalan, 6-mercaptopurine, mesna, methotrexate, mitomycin, mitotane, mitoxantrone, nilutamide, octreotide, oxaliplatin, pamidronate, pentostatin, plicamycin, porfimer, procarbazine, raltitrexed, rituximab, streptozocin, teniposide, testosterone, thalidomide, thioguanine, thiotepa, tretinoin, vindesine, 13-cis-retinoic acid, phenylalanine mustard, uracil mustard, estramustine, altretamine, floxuridine, 5-deooxyuridine, cytosine arabinoside, 6-mecaptopurine, deoxycoformycin, calcitriol, valrubicin, mithramycin, vinblastine, vinorelbine, topotecan, razoxin, marimastat, COL-3, neovastat, BMS-275291, squalamine, endostatin, SU5416, SU6668, EMD121974, interleukin-12, IM862, angiostatin, vitaxin, droloxifene, idoxyfene, spironolactone, finasteride, cimitidine, trastuzumab, denileukin diftitox, gefitinib, bortezimib, paclitaxel, cremophor-free paclitaxel, docetaxel, epithilone B, BMS-247550, BMS-310705, droloxifene, 4-hydroxytamoxifen, pipendoxifene, ERA-923, arzoxifene, fulvestrant, acolbifene, lasofoxifene, idoxifene, TSE-424, HMR-3339, ZK186619, topotecan, PTK787/ZK 222584, VX-745, PD 184352, rapamycin, 40-O-(2-hydroxyethyl)-rapamycin, temsirolimus, AP-23573, RAD001, ABT-578, BC-210, LY294002, LY292223, LY292696, LY293684, LY293646, wortmannin, ZM336372, L-779, 450, PEG-filgrastim, darbepoetin, erythropoietin, granulocyte colony-stimulating factor, zolendronate, prednisone, cetuximab, granulocyte macrophage colony-stimulating factor, histrelin, pegylated interferon alfa-2a, interferon alfa-2a, pegylated interferon alfa-2b, interferon alfa-2b, azacitidine, PEG-L-asparaginase, lenalidomide, gemtuzumab, hydrocortisone, interleukin-11, dexrazoxane, alemtuzumab, all-transretinoic acid, ketoconazole, interleukin-2, megestrol, immune globulin, nitrogen mustard, methylprednisolone, ibritgumomab tiuxetan, androgens, decitabine, hexamethylmelamine, bexarotene, tositumomab, arsenic trioxide, cortisone, editronate, mitotane, cyclosporine, liposomal daunorubicin, Edwina-asparaginase, strontium 89, casopitant, netupitant, an NK-1 receptor antagonist, palonosetron, aprepitant, diphenhydramine, hydroxyzine, metoclopramide, lorazepam, alprazolam, haloperidol, droperidol, dronabinol, dexamethasone, methylprednisolone, prochlorperazine, granisetron, ondansetron, dolasetron, tropisetron, pegfilgrastim, erythropoietin, epoetin alfa, darbepoetin alfa and mixtures thereof.

In one embodiment, the additional anti-cancer agent is at least one additional anti-neoplastic agent.

Any anti-neoplastic agent that has activity versus a susceptible tumor being treated may be utilized in the combination. Typical anti-neoplastic agents useful include, but are not limited to: anti-microtubule agents, such as diterpenoids and vinca alkaloids; platinum coordination complexes; alkylating agents, such as nitrogen mustards, oxazaphosphorines, alkylsulfonates, nitrosoureas, and triazenes; antibiotic agents, such as anthracyclins, actinomycins and bleomycins; topoisomerase II inhibitors, such as epipodophyllotoxins; antimetabolites, such as purine and pyrimidine analogues and anti-folate compounds; topoisomerase I inhibitors, such as camptothecins; hormones and hormonal analogues; signal transduction pathway inhibitors; non-receptor tyrosine angiogenesis inhibitors; immunotherapeutic agents; proapoptotic agents; and cell cycle signaling inhibitors.

Anti-Microtubule or Anti-Mitotic Agents:

Anti-microtubule or anti-mitotic agents are phase specific agents active against the microtubules of tumor cells during M or the mitosis phase of the cell cycle. Examples of anti-microtubule agents include, but are not limited to, diterpenoids and *vinca* alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine, is a natural diterpene product isolated from the Pacific yew tree *Taxus brevifolia* and is commercially available as an injectable solution TAXOL®. It is a member of the taxane family of terpenes. Paclitaxel has been approved for clinical use in the treatment of refractory ovarian cancer in the United States (Markman et al., Yale Journal of Biology and Medicine, 64:583, 1991; McGuire et al., Ann. Intem, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate, is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate. is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine [R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum Coordination Complexes:

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, oxaliplatin, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer.

Carboplatin, platinum, diammine [1,1-cyclobutane-dicarboxylate(2-)— O,O'], is commercially available as PARAPLATIN® as an injectable solution. Carboplatin is primarily indicated in the first and second line treatment of advanced ovarian carcinoma.

Alkylating Agents:

Alkylating agents are non-phase anti-cancer specific agents and strong electrophiles. Generally, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to: nitrogen mustards, such as cyclophosphamide, melphalan, and chlorambucil; alkyl sulfonates, such as busulfan; nitrosoureas, such as carmustine; and triazenes, such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas, such as lymphosarcoma, giant follicular lymphoma, and Hodgkin's disease.

Busulfan, 1,4-butanediol dimethanesulfonate, is commercially available as MYLERAN® TABLETS. Busulfan is indicated for the palliative treatment of chronic myelogenous leukemia.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease.

Antibiotic Anti-Neoplastics:

Antibiotic anti-neoplastics are non-phase specific agents, which bind or intercalate with DNA. Generally, such action results in stable DNA complexes or strand breakage, which disrupts ordinary function of the nucleic acids leading to cell death. Examples of antibiotic anti-neoplastic agents include, but are not limited to: actinomycins, such as dactinomycin; anthrocyclins, such as daunorubicin and doxorubicin; and bleomycins.

Dactinomycin, also known as Actinomycin D, is commercially available in injectable form as COSMEGEN®. Dactinomycin is indicated for the treatment of Wilm's tumor and rhabdomyosarcoma.

Daunorubicin, (8S-cis-)-8-acetyl-10-[(3-amino-2,3,6-trideoxy-α-L-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma.

Doxorubicin, (8S, 10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas.

Topoisomerase II Inhibitors:

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA, thereby causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers.

Teniposide, 4'-demethyl-epipodophyllotoxin 9[4,6-0-(R)-thenylidene-R-D-glucopyranoside], is commercially available as an injectable solution as VUMON® and is commonly known as VM-26. Teniposide is indicated as a single agent or in combination with other chemotherapy agents in the treatment of acute leukemia in children.

Antimetabolite Neoplastic Agents:

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result is generally cell death. 5-fluorouracil is indicated as a single agent or in combination with other chemotherapy agents in the treatment of carcinomas of the breast, colon, rectum, stomach and pancreas. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine).

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Other purine analogs include pentostatin, erythrohydroxynonyladenine, fludarabine phosphate, and cladribine.

Gemcitabine, 2'-deoxy-2', 2'-difluorocytidine monohydrochloride (β-isomer), is commercially available as GEMZAR®. Gemcitabine exhibits cell phase specificity at S-phase and by blocking progression of cells through the GUS boundary. Gemcitabine is indicated in combination with cisplatin in the treatment of locally advanced non-small cell lung cancer and alone in the treatment of locally advanced pancreatic cancer.

Methotrexate, N-[4[[(2,4-diamino-6-pteridinyl) methyl] methylamino] benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder.

Topoisomerase I Inhibitors:

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®. Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum.

Topotecan HCl, (S)-10-[(dimethylamino)methyl]-4-ethyl-4,9-dihydroxy-1H-pyrano[3',4',6,7]indolizino[1,2-b] quinoline-3,14-(4H,12H)-dione monohydrochloride, is commercially available as the injectable solution HYCAMTIN. Topotecan is a derivative of camptothecin, which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer.

Hormones and Hormonal Analogues:

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to: adrenocorticosteroids, such as prednisone and prednisolone which are useful in the treatment of malignant lymphoma and acute leukemia in children; aminoglutethimide and other aromatase inhibitors, such as anastrozole, letrazole, vorazole, and exemestane useful in the treatment of adrenocortical carcinoma and hormone dependent breast carcinoma containing estrogen receptors; progestrins, such as megestrol acetate useful in the treatment of hormone dependent breast cancer and endometrial carcinoma; estrogens, and anti-estrogens, such as fulvestrant, flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment of prostatic carcinoma, for instance, LHRH agonists and antagagonists such as goserelin acetate and luprolide.

Signal Transduction Pathway Inhibitors:

Signal transduction pathway inhibitors are those inhibitors, which block or inhibit a chemical process which evokes an intracellular change. As used herein this change is cell proliferation or differentiation. Signal transduction inhibitors useful in the present invention include inhibitors of receptor tyrosine kinases, non-receptor tyrosine kinases, SH2/SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, ret, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases useful in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (She, Crk, Nck, Grb2) and Ras-GAP. Smithgall, T. E. (1995), Journal of Pharmacological and Toxicological Methods. 34(3) 125-32, discusses SH2/SH3 domains as targets for anti-cancer drugs.

Inhibitors of Serine/Threonine Kinases include MAP kinase cascade blockers which include blockers of Raf kinases (rafk), Mitogen or Extracellular Regulated Kinase (MEKs), and Extracellular Regulated Kinases (ERKs); and Protein kinase C family member blockers include blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members, including blockers of PI3-kinase, ATM, DNA-PK, and Ku, are also useful in embodiments of the present disclosure. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also useful in embodiments of the present disclosure are Myo-inositol signaling inhibitors, such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases, as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example, Imclone C225 EGFR specific antibody (see Green, M. C. et al, Monoclonal Antibody Therapy for Solid Tumors, Cancer Treat. Rev., (2000), 26(4), 269-286), Herceptin® erbB2 antibody (see Tyrosine Kinase Signalling in Breast cancer:erbB Family Receptor Tyrosine Kinases, Breast cancer Res., 2000, 2(3), 176-183), and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Anti-Angiogenic Agents:

Anti-angiogenic agents including non-receptor MEK angiogenesis inhibitors may also be useful. Anti-angiogenic agents such as those which inhibit the effects of vascular edothelial growth factor, (for example, the anti-vascular endothelial cell growth factor antibody bevacizumab [Avastin™]), and compounds that work by other mechanisms (for example, linomide, inhibitors of integrin $\alpha v\beta 3$ function, endostatin and angiostatin).

Immunotherapeutic Agents:

Agents used in immunotherapeutic regimens may also be useful in combination with the compounds of formula (I). Immunotherapy approaches include, for example: ex-vivo and in-vivo approaches to increase the immunogenecity of patient tumour cells, such as transfection with cytokines such as interleukin 2, interleukin 4 or granulocyte-macrophage colony stimulating factor; approaches to decrease T-cell anergy; approaches using transfected immune cells, such as cytokine-transfected dendritic cells; approaches using cytokine-transfected tumour cell lines; and approaches using anti-idiotypic antibodies.

Proapoptotic Agents:

Agents used in proapoptotic regimens (e.g., bcl-2 antisense oligonucleotides) may also be used in the combination of the present disclosure.

Cell Cycle Signalling Inhibitors

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4 and CDK6, and inhibitors for the same are described in, for instance, Rosania et al, Exp. Opin. Ther. Patents (2000) 10(2):215-230.

In an embodiment, the combination of the present disclosure comprises a compound of formula I or a salt or solvate thereof and at least one anti-neoplastic agent selected from anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine MEK angiogenesis inhibitors, immunotherapeutic agents, proapoptotic agents, and cell cycle signaling inhibitors.

In another embodiment, the combination of the present disclosure comprises a compound of formula I or a salt or solvate thereof, and at least one anti-neoplastic agent, which is an anti-microtubule agent selected from diterpenoids and vinca alkaloids.

In a further embodiment, at least one anti-neoplastic agent is a diterpenoid.

In a further embodiment, at least one anti-neoplastic agent is a vinca alkaloid.

In some embodiment, the combination of the present disclosure comprises a compound of formula I or a salt or solvate thereof, and at least one anti-neoplastic agent, which is a platinum coordination complex.

In an embodiment, at least one anti-neoplastic agent is paclitaxel, carboplatin, or vinorelbine.

In a further embodiment, at least one anti-neoplastic agent is carboplatin.

In another embodiment, at least one anti-neoplastic agent is vinorelbine.

In a particular embodiment, at least one anti-neoplastic agent is paclitaxel.

In some embodiment, the combination of the present disclosure comprises a compound of formula I and salts or solvates thereof, and at least one anti-neoplastic agent, which is a signal transduction pathway inhibitor.

In a further embodiment, the signal transduction pathway inhibitor is an inhibitor of a growth factor receptor kinase VEGFR2, TIE2, PDGFR, BTK, erbB2, EGFr, IGFR-1, TrkA, TrkB, TrkC, or c-fms.

In another embodiment, the signal transduction pathway inhibitor is an inhibitor of a serine/threonine kinase rafk, akt, or PKC-zeta.

In an embodiment, the signal transduction pathway inhibitor is an inhibitor of a non-receptor tyrosine kinase selected from the src family of kinases.

In yet another embodiment, the signal transduction pathway inhibitor is an inhibitor of c-src.

In a further embodiment, the signal transduction pathway inhibitor is an inhibitor of Ras oncogene selected from inhibitors of farnesyl transferase and geranylgeranyl transferase.

In another embodiment, embodiment the signal transduction pathway inhibitor is an inhibitor of a serine/threonine kinase selected from the group consisting of PI3K.

In some embodiment, the signal transduction pathway inhibitor is a dual EGFr/erbB2 inhibitor, for example N-{3-Chloro-4-[(3-fluorobenzyl) oxy]phenyl}-6-[5-({[2-(methanesulphonyl) ethyl]amino}methyl)-2-furyl]-4-quinazolinamine (structure below):

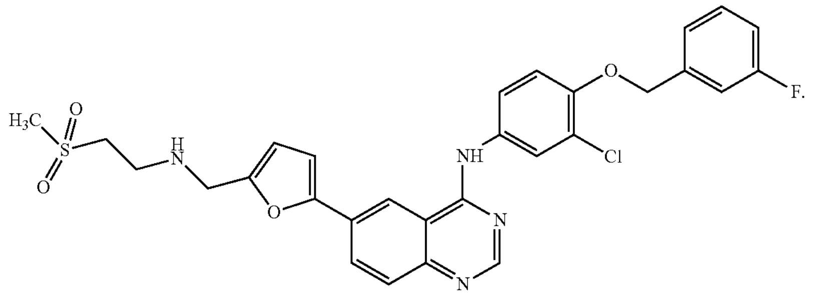 [SMILES: CS(=O)(=O)CCNCc1ccc(-c2ccc3ncnc(Nc4ccc(OCc5cccc(F)c5)c(Cl)c4)c3c2)o1]

In one embodiment, the combination of the present disclosure comprises a compound of formula I or a salt or solvate thereof, and at least one anti-neoplastic agent, which is a cell cycle signaling inhibitor.

In further embodiment, the cell cycle signaling inhibitor is an inhibitor of CDK2, CDK4, or CDK6.

In the case of CDK4/6 inhibitors, Palbociclib (PD-0332991) and other chemotypes (such as LY2835219) can be combined with the described estrogen receptor degraders.

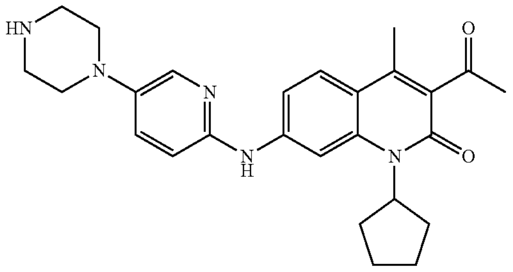 [SMILES: CC(=O)c1c(C)c2ccc(Nc3ccc(N4CCNCC4)cn3)cc2n(C2CCCC2)c1=O]

Particular components of combination therapy include combinations with other anti-estrogens, including tamoxifen and/or fulvestrant.

Therapeutic Methods

The compounds of the disclosure are useful in the treatment of estrogen receptor associated conditions. An “estrogen receptor-associated condition,” as used herein, denotes a condition or disorder, e.g., cancer, which can be treated by modulating the function or activity of an estrogen receptor in a subject, wherein treatment comprises prevention, partial alleviation or cure of the condition or disorder. Modulation may occur locally, for example within certain tissues of the subject, or more extensively throughout a subject being treated for such a condition or disorder.

The terms “treat”, “treating”, and “treatment”, etc., as used herein, refer to any action providing a benefit to a patient for which the present compounds may be administered, including the treatment of any disease state or condition which is modulated through the protein to which the present compounds bind. Disease states or conditions, including cancer, which may be treated using compounds according to the present disclosure are set forth hereinabove.

As such, in another aspect, the description provides a method of ubiquitinating/degrading a target protein in a cell. In certain embodiments, the method comprises administering a bifunctional compound as described herein comprising, e.g., ULM and a PTM, preferably linked through a linker moiety, as otherwise described herein, wherein the ULM is coupled to the PTM and wherein the ULM recognizes a ubiquitin pathway protein (e.g., an ubiquitin ligase, preferably an E3 ubiquitin ligase) and the PTM recognizes the target protein (e.g., ER) such that degradation of the target protein will occur when the target protein is placed in proximity to the ubiquitin ligase, thus resulting in degradation/inhibition of the effects of the target protein and the control of protein levels. The control of protein levels afforded by the present disclosure provides treatment of a disease state or condition (e.g., an estrogen receptor-mediated disease or disorder), which is modulated through the target protein by lowering the level of that protein in the cell, e.g., cell of a patient. In certain embodiments, the method comprises administering an effective amount of a compound as described herein, optionally including a pharamaceutically acceptable excipient, carrier, adjuvant, another bioactive agent or combination thereof. In certain embodiments, the estrogen mediated disease or disorder is breast cancer.

In additional embodiments, the description provides methods for treating or emeliorating a disease, disorder or symptom thereof in a subject or a patient, e.g., an animal such as a human, comprising administering to a subject in need thereof a composition comprising an effective amount, e.g., a therapeutically effective amount, of a compound as described herein or salt form thereof, and a pharmaceutically acceptable excipient, carrier, adjuvant, another bioactive agent or combination thereof, wherein the composition is effective for treating or ameliorating the disease or disorder or symptom thereof in the subject.

In one embodiment, the subject to be treated in the methods and uses described herein is a mammal, e.g., a human.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

A patient or subject in need of therapy using compounds according to the methods described herein can be treated by administering to the patient (subject) an effective amount of the compound according to the present disclosure including pharmaceutically acceptable salts, solvates or polymorphs, thereof optionally in a pharmaceutically acceptable carrier or diluent, either alone, or in combination with other known erythopoiesis stimulating agents as otherwise identified herein.

In another aspect, the description provides methods for identifying the effects of the degradation of proteins of interest in a biological system using compounds according to the present disclosure.

In another embodiment, the present disclosure is directed to a method of treating a human patient in need for a disease state or condition modulated through a protein where the degradation of that protein will produce a therapeutic effect in that patient, the method comprising administering to a patient in need an effective amount of a compound according to the present disclosure, optionally in combination with another bioactive agent. The disease state or condition may be a disease caused by overexpression of a protein, which leads to a disease state and/or condition.

The term "disease state or condition" is used to describe any disease state or condition wherein protein dysregulation (i.e., the amount of protein expressed in a patient is elevated) occurs and where degradation of one or more proteins in a patient may provide beneficial therapy or relief of symptoms to a patient in need thereof. In certain instances, the disease state or condition may be cured.

Disease states of conditions which may be treated using compounds according to the present disclosure include, for example, asthma, autoimmune diseases such as multiple sclerosis, various cancers, ciliopathies, cleft palate, diabetes, heart disease, hypertension, inflammatory bowel disease, mental retardation, mood disorder, obesity, refractive error, infertility, Angelman syndrome, Canavan disease, Coeliac disease, Charcot-Marie-Tooth disease, Cystic fibrosis, Duchenne muscular dystrophy, Haemochromatosis, Haemophilia, Klinefelter's syndrome, Neurofibromatosis, Phenylketonuria, Polycystic kidney disease, (PKD1) or 4 (PKD2) Prader-Willi syndrome, Sickle-cell disease, Tay-Sachs disease, Turner syndrome.

Further disease states or conditions which may be treated by compounds according to the present disclosure include Alzheimer's disease, Amyotrophic lateral sclerosis (Lou Gehrig's disease), Anorexia nervosa, Anxiety disorder, Atherosclerosis, Attention deficit hyperactivity disorder, Autism, Bipolar disorder, Chronic fatigue syndrome, Chronic obstructive pulmonary disease, Crohn's disease, Coronary heart disease, Dementia, Depression, Diabetes mellitus type 1, Diabetes mellitus type 2, Epilepsy, Guillain-Barré syndrome, Irritable bowel syndrome, Lupus, Metabolic syndrome, Multiple sclerosis, Myocardial infarction, Obesity, Obsessive-compulsive disorder, Panic disorder, Parkinson's disease, Psoriasis, Rheumatoid arthritis, Sarcoidosis, Schizophrenia, Stroke, Thromboangiitis obliterans, Tourette syndrome, Vasculitis.

Still additional disease states or conditions which can be treated by compounds according to the present disclosure include aceruloplasminemia, Achondrogenesis type II, achondroplasia, Acrocephaly, Gaucher disease type 2, acute intermittent porphyria, Canavan disease, Adenomatous Polyposis Coli, ALA dehydratase deficiency, adenylosuccinate lyase deficiency, Adrenogenital syndrome, Adrenoleukodystrophy, ALA-D porphyria, ALA dehydratase deficiency, Alkaptonuria, Alexander disease, Alkaptonuric ochronosis, alpha 1-antitrypsin deficiency, alpha-1 proteinase inhibitor, emphysema, amyotrophic lateral sclerosis Alström syndrome, Alexander disease, Amelogenesis imperfecta, ALA dehydratase deficiency, Anderson-Fabry disease, androgen insensitivity syndrome, Anemia Angiokeratoma Corporis Diffusum, Angiomatosis retinae (von Hippel-Lindau disease) Apert syndrome, Arachnodactyly (Marfan syndrome), Stickler syndrome, Arthrochalasis multiplex congenital (Ehlers-Danlos syndrome #arthrochalasia type) ataxia telangiectasia, Rett syndrome, primary pulmonary hypertension, Sandhoff disease, neurofibromatosis type II, Beare-Stevenson cutis gyrata syndrome, Mediterranean fever, familial, Benjamin syndrome, beta-thalassemia, Bilateral Acoustic Neurofibromatosis (neurofibromatosis type II), factor V Leiden thrombophilia, Bloch-Sulzberger syndrome (incontinentia pigmenti), Bloom syndrome, X-linked sideroblastic anemia, Bonnevie-Ullrich syndrome (Turner syndrome), Bourneville disease (tuberous sclerosis), prion disease, Birt-Hogg-Dubé syndrome, Brittle bone disease (osteogenesis imperfecta), Broad Thumb-Hallux syndrome (Rubinstein-Taybi syndrome), Bronze Diabetes/Bronzed Cirrhosis (hemochromatosis), Bulbospinal muscular atrophy (Kennedy's disease), Burger-Grutz syndrome (lipoprotein lipase deficiency), CGD Chronic granulomatous disorder, Campomelic dysplasia, biotinidase deficiency, Cardiomyopathy (Noonan syndrome), Cri du chat, CAVD (congenital absence of the vas deferens), Caylor cardiofacial syndrome (CBAVD), CEP (congenital erythropoietic porphyria), cystic fibrosis, congenital hypothyroidism, Chondrodystrophy syndrome (achondroplasia), otospondylomegaepiphyseal dysplasia, Lesch-Nyhan syndrome, galactosemia, Ehlers-Danlos syndrome, Thanatophoric dysplasia, Coffin-Lowry syndrome, Cockayne syndrome, (familial adenomatous polyposis), Congenital erythropoietic porphyria, Congenital heart disease, Methemoglobinemia/ Congenital methaemoglobinaemia, achondroplasia, X-linked sideroblastic anemia, Connective tissue disease, Conotruncal anomaly face syndrome, Cooley's Anemia (beta-thalassemia), Copper storage disease (Wilson's disease), Copper transport disease (Menkes disease), hereditary coproporphyria, Cowden syndrome, Craniofacial dysarthrosis (Crouzon syndrome), Creutzfeldt-Jakob disease (prion disease), Cockayne syndrome, Cowden syndrome, Curschmann-Batten-Steinert syndrome (myotonic dystrophy), Beare-Stevenson cutis gyrata syndrome, primary hyperoxaluria, spondyloepimetaphyseal dysplasia (Strudwick type), muscular dystrophy, Duchenne and Becker types (DBMD), Usher syndrome, Degenerative nerve diseases including de Grouchy syndrome and Dejerine-Sottas syndrome, developmental disabilities, distal spinal muscular atrophy, type V, androgen insensitivity syndrome, Diffuse Globoid Body Sclerosis (Krabbe disease), Di George's syndrome, Dihydrotestosterone receptor deficiency, androgen insensitivity syndrome, Down syndrome, Dwarfism, erythropoietic protoporphyria Erythroid 5-aminolevulinate synthetase deficiency, Erythropoietic porphyria, erythropoietic protoporphyria, erythropoietic uroporphyria, Friedreich's ataxia, familial paroxysmal polyserositis, porphyria cutanea tarda, familial pressure sensitive neuropathy, primary pulmonary hypertension (PPH), Fibrocystic disease of the pancreas, fragile X syndrome, galactosemia, genetic brain disorders, Giant cell hepatitis (Neonatal hemochromatosis), Gronblad-Strandberg syndrome (pseudoxanthoma elasticum), Gunther disease (congenital erythropoietic porphyria), haemochromatosis, Hallgren syndrome, sickle cell anemia, hemophilia, hepatoerythropoietic porphyria (HEP), Hippel-Lindau disease (von Hippel-Lindau disease), Huntington's disease, Hutchinson-Gilford progeria syndrome (progeria), Hyperandrogenism, Hypochondroplasia, Hypochromic anemia, Immune system disorders, including X-linked severe combined immunodeficiency, Insley-Astley syndrome, Jackson-Weiss syndrome, Joubert syndrome, Lesch-Nyhan syndrome, Jackson-Weiss syndrome, Kidney diseases, including hyperoxaluria, Klinefelter's syndrome, Kniest dysplasia, Lacunar dementia, Langer-Saldino achondrogenesis, ataxia telangiectasia, Lynch syndrome, Lysylhydroxylase deficiency, Machado-Joseph disease, Metabolic disorders, including Kniest dysplasia, Marfan syndrome, Movement disorders, Mowat-Wilson syndrome, cystic fibrosis, Muenke syndrome, Multiple neurofibromatosis, Nance-Insley syndrome, Nance-Sweeney chondrodysplasia, Niemann-Pick disease, Noack syndrome (Pfeiffer syndrome), Osler-Weber-Rendu disease, Peutz-Jeghers syndrome, Polycystic kidney disease, polyostotic fibrous dysplasia (McCune-Albright syndrome), Peutz-Jeghers syndrome, Prader-Labhart-Willi syndrome, hemochromatosis, primary hyperuricemia syndrome (Lesch-Nyhan syndrome), primary pulmonary hypertension, primary senile degenerative dementia, prion disease, progeria (Hutchinson Gilford Progeria Syndrome), progressive chorea, chronic hereditary (Huntington) (Huntington's disease), progressive muscular atrophy, spinal muscular atrophy, propionic acidemia, protoporphyria, proximal myotonic dystrophy, pulmonary arterial hypertension, PXE (pseudoxanthoma elasticum), Rb (retinoblastoma), Recklinghausen disease (neurofibromatosis type I), Recurrent polyserositis, Retinal disorders, Retinoblastoma, Rett syndrome, RFALS type 3, Ricker syndrome, Riley-Day syndrome, Roussy-Levy syndrome, severe achondroplasia with developmental delay and acanthosis nigricans (SADDAN), Li-Fraumeni syndrome, sarcoma, breast, leukemia, and adrenal gland (SBLA) syndrome, sclerosis tuberose (tuberous sclerosis), SDAT, SED congenital (spondyloepiphyseal dysplasia congenita), SED Strudwick (spondyloepimetaphyseal dysplasia, Strudwick type), SEDc (spondyloepiphyseal dysplasia congenita) SEMD, Strudwick type (spondyloepimetaphyseal dysplasia, Strudwick type), Shprintzen syndrome, Skin pigmentation disorders, Smith-Lemli-Opitz syndrome, South-African genetic porphyria (variegate porphyria), infantile-onset ascending hereditary spastic paralysis, Speech and communication disorders, sphingolipidosis, Tay-Sachs disease, spinocerebellar ataxia, Stickler syndrome, stroke, androgen insensitivity syndrome, tetrahydrobiopterin deficiency, beta-thalassemia, Thyroid disease, Tomaculous neuropathy (hereditary neuropathy with liability to pressure palsies), Treacher Collins syndrome, Triplo X syndrome (triple X syndrome), Trisomy 21 (Down syndrome), Trisomy X, VHL syndrome (von Hippel-Lindau disease), Vision impairment and blindness (Alström syndrome), Vrolik disease, Waardenburg syndrome, Warburg Sjo Fledelius Syndrome, Weissenbacher-Zweymuller syndrome, Wolf-Hirschhorn syndrome, Wolff Periodic disease, Weissenbacher-Zweymuller syndrome and Xeroderma pigmentosum, among others.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Exemplary cancers which may be treated by the present compounds either alone or in combination with at least one additional anti-cancer agent include squamous-cell carcinoma, basal cell carcinoma, adenocarcinoma, hepatocellular carcinomas, and renal cell carcinomas, cancer of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, including Ewing's sarcoma, hemangiosarcoma, Kaposi's sarcoma, liposarcoma, myosarcomas, peripheral neuroepithelioma, synovial sarcoma, gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas; bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, melanoma; carcinosarcoma, Hodgkin's disease, Wilms' tumor and teratocarcinomas. Additional cancers which may be treated using compounds according to the present disclosure include, for example, T-lineage Acute lymphoblastic Leukemia (T-ALL), T-lineage lymphoblastic Lymphoma (T-LL), Peripheral T-cell lymphoma, Adult T-cell Leukemia, Pre-B ALL, Pre-B Lymphomas, Large B-cell Lymphoma, Burkitts Lymphoma, B-cell ALL, Philadelphia chromosome positive ALL and Philadelphia chromosome positive chronic myelogenous leukemia (CML).

The term "pharmaceutically acceptable salt" is used throughout the specification to describe, where applicable, a salt form of one or more of the compounds described herein which are presented to increase the solubility of the compound in the gastic juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art. Sodium and potassium salts are particularly preferred as neutralization salts of the phosphates according to the present disclosure.

The term "pharmaceutically acceptable derivative" is used throughout the specification to describe any pharmaceutically acceptable prodrug form (such as an ester, amide other prodrug group), which, upon administration to a patient, provides directly or indirectly the present compound or an active metabolite of the present compound.

General Synthetic Methods

Compounds of general formula (I) may be prepared by methods known in the art of organic synthesis as set forth in the specific Examples described below. In all of the methods, it is well understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3$^{rd}$ edition, John Wiley & Sons). These groups are removed at a convenient stage of the compound synthesis using methods that are readily apparent to those skilled in the art. The selection of processes as well as the reaction conditions and order of their execution shall be consistent with the preparation of compounds of Formula (I).

Methods in the literature to construct indole ring can be used to prepare the required indole fragment in formula (I). Procedures described in the selected examples are the only representative methods for indole synthesis.

Abbreviations:

BOP: (Benzotriazole-1-yloxy)tris(dimethylanino)phosphonium hexafluorophosphate
DCM: dichloromethane.
DEAD: diethyl azodicarboxylate
DIEA or DIPEA: N,N-diisopropylethylamine.
DMF: N,N-dimethylformamide.
ES$^+$: electron spary with positive charge
h: hour.
HATU: 2-(7-aza-1H-benzotriazole-1-yl)-1,1,3,3-tetramethyluronium hexafluorophosphate.
HPLC: high-performance liquid chromatography.
LC-MS: liquid chromatography-mass spectrometry
Min: minutes.
NMR: Nuclear magnetic resonance.
RT or $t_R$: retention time.
TBAC: tetrabutylammonium chloride
TFA: trifluoroacetic acid.
THF: tetrahydrofuran.

General Synthetic Approach

The synthetic realization and optimization of the bifunctional molecules as described herein may be approached in a step-wise or modular fashion. For example, identification of compounds that bind to the target molecules can involve high or medium throughput screening campaigns if no suitable ligands are immediately available. It is not unusual for initial ligands to require iterative design and optimization cycles to improve suboptimal aspects as identified by data from suitable in vitro and pharmacological and/or ADMET assays. Part of the optimization/SAR campaign would be to probe positions of the ligand that are tolerant of substitution and that might be suitable places on which to attach the linker chemistry previously referred to herein. Where crystallographic or NMR structural data are available, these can be used to focus such a synthetic effort.

In a very analogous way one can identify and optimize ligands for an E3 Ligase, i.e. ULMs.

With PTMs and ULMs in hand, one skilled in the art can use known synthetic methods for their combination with or without a linker moiety. Linker moieties can be synthesized with a range of compositions, lengths and flexibility and functionalized such that the PTM and ULM groups can be attached sequentially to distal ends of the linker. Thus a library of bifunctional molecules can be realized and profiled in in vitro and in vivo pharmacological and ADMET/PK studies. As with the PTM and ULM groups, the final bifunctional molecules can be subject to iterative design and optimization cycles in order to identify molecules with desirable properties.

In some instances, protecting group strategies and/or functional group interconversions (FGIs) may be required to facilitate the preparation of the desired materials. Such chemical processes are well known to the synthetic organic chemist and many of these may be found in texts such as "Greene's Protective Groups in Organic Synthesis" Peter G. M. Wuts and Theodora W. Greene (Wiley), and "Organic Synthesis: The Disconnection Approach" Stuart Warren and Paul Wyatt (Wiley).

Protein Level Control

This description also provides methods for the control of protein levels with a cell. This is based on the use of compounds as described herein, which are known to interact with a specific target protein such that degradation of a target protein in vivo will result in the control of the amount of protein in a biological system, preferably to a particular therapeutic benefit.

The following examples are used to assist in describing the present invention, but should not be seen as limiting the present invention in any way.

Exemplary Conditions and Analytical Methods

All solvents used were commercially available and were used without further purification. Reactions were typically run using anhydrous solvents under an inert atmosphere of nitrogen. Flash column chromatography was generally carried out using Silica gel 60 (0.035-0.070 mm particle size).

All NMR experiments were recorded either on Bruker Mercury Plus 400 NMR Spectrometer equipped with a Bruker 400 BBFO probe at 400 MHz for proton NMR or on Bruker Mercury Plus 300 NMR Spectrometer equipped with a Bruker 300 BBFO probe at 300 MHz for proton NMR. All deuterated solvents contained typically 0.03% to 0.05% v/v tetramethylsilane, which was used as the reference signal (set at δ 0.00 for both $^1H$ and $^{13}C$).

LC-MS analyses were performed on a SHIMADZU LC-MS machine consisting of an UFLC 20-AD system and LCMS 2020 MS detector. The column used was a Shim-pack XR-ODS, 2.2 μm, 3.0×50 mm. A linear gradient was applied, starting at 95% A (A: 0.05% TFA in water) and ending at 100% B (B: 0.05% TFA in acetonitrile) over 2.2 min with a total run time of 3.6 min. The column temperature was at 40° C. with the flow rate at 1.0 mL/min. The Diode Array detector was scanned from 200-400 nm. The mass spectrometer was equipped with an electro spray ion source (ES) operated in a positive or negative mode. The mass spectrometer was scanned between m/z 90-900 with a scan time of 0.6 s.

Preparation of Intermediates

Intermediate 1: (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride

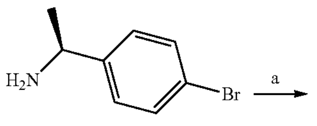

1

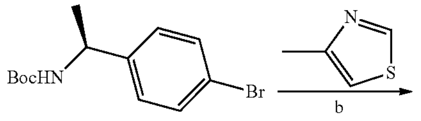

2

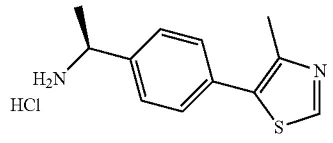

3

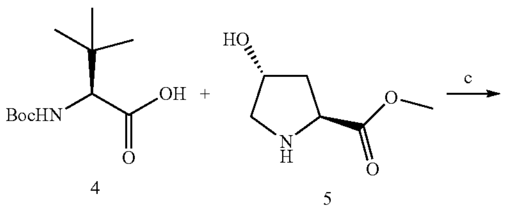

4

5

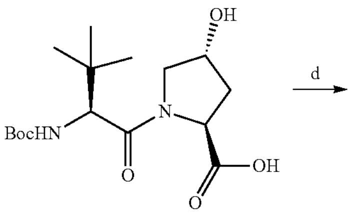

6

-continued

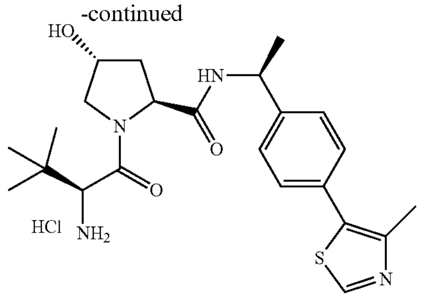

7

Reagents and conditions: (a) $(Boc)_2O$, $NaHCO_3$, $EtOAc/H_2O$; (b) (1) $Pd(OAc)_2$, KOAc, 90° C.; (2) 4N HCl in MeOH; (c) (1) HATU, DIPEA, DMF; (2) LiOH, THF, $H_2O$; (d) (1) compound 3, HATU, DIPEA, THF; (2) 4N HCl in MeOH

Step 1: Preparation of (S)-tert-butyl-1-(4-bromophenyl)-ethyl carbamate (2)

To a mixture of (S)-1-(4-bromophenyl)ethanamine (3.98 g, 19.9 mmol) and $NaHCO_3$(1.24 g, 14.8 mmol) in $H_2O$ (10 mL) and ethyl acetate (10 mL) was added $(Boc)_2O$ (5.20 g, 23.8 mmol) at 5° C. The reaction was continued to react for 2 h. TLC showed reaction was complete. The reaction mixture was filtered. The solid was collected and suspended in a mixture of hexane (10 mL) and $H_2O$ (10 mL) for 0.5 h. The mixture was filtered and the solid was collected and dried in oven at 50° C. to afford the title compound as white solid (5.9 g, 98.7%). $^1$HNMR (400 MHz, DMSO-$d_6$): δ1.28 (d, J=7.2 Hz, 3H), 1.36 (s, 9H), 4.55-4.60 (m, 1H), 7.25 (d, J=8.4 Hz, 2H), 7.39 (br, 1H), 7.49 (d, J=8.4 Hz, 2H).

Step 2: Preparation of (S)-1-(4-(4-methylthiazol-5-yl)phenyl)ethanamine hydrochloride (3)

A mixture of compound 2 (4.0 g, 13.3 mmol), 4-methylthiazole (2.64 g, 26.6 mmol), palladium (II) acetate (29.6 mg, 0.13 mmol) and potassium acetate (2.61 g, 26.6 mmol) in N,N-dimethylacetamide (10 mL) was stirred at 90° C. under $N_2$ for 18 h. After cooling to ambient temperature, the reaction mixture was filtered. To the filtrate was added $H_2O$ (50 mL) and the resulting mixture was stirred at ambient temperature for 4 h. The reaction mixture was filtered. The solid was collected by filtration and dried in oven at 50° C. to afford (S)-tert-butyl 1-(4-(4-methylthiazol-5-yl)phenyl) ethylcarbamate (3.48 g, 82.3%) as gray solid. $^1$HNMR (400 MHz, DMSO-$d_6$): δ 1.33 (d, J=7.2 Hz, 3H), 1.38 (s, 9H), 2.46 (s, 3H), 4.64-4.68 (m, 1H), 7.23 (br d, 0.5H), 7.39 (d, J=8 Hz, 2H), 7.44 (d, J=8.4 Hz, 2H), 7.50 (br d, 0.5H), 8.99 (s, 1H); LC-MS $[M+1]^+$: 319.5

This solid material (1.9 g, 6.0 mmol) was dissolved in 4N hydrochloride in methanol (5 mL, 20 mmol, prepared from acetyl chloride and methanol) and the mixture was stirred at ambient temperature for 3 h. the mixture was filtered and the solid was collected and dried in oven at 60° C. to afford (S)-1-(4-(4-methylthiazol-5-yl)phenyl)ethanamine hydrochloride (1.3 g, 85%) as a light green solid. $^1$HNMR (400 MHz, DMSO-d6): δ 1.56 (d, J=6.8 Hz, 3H), 2.48 (s, 3H), 4.41-4.47 (m, 1H), 7.57 (d, J=8.4 Hz, 2H), 7.67 (d, J=8.4 Hz), 8.75 (s, 3H), 9.17 (s, 1H); LC-MS $[M+1]^+$: 219.2

Step 3: Preparation of (2S, 4R)-1-{(S)-2-[(tert-butoxycarbonyl)amino]-3,3-dimethylbutanoyl}-4-hydroxypyrrolidine-2-carboxylicacid (6)

HATU (2.15 g, 5.7 mmol) was added to a solution of (S)-2-(tert-butoxycarbonyl)amino-3,3-dimethylbutanoic acid (1.25 g, 5.4 mol), (2S,4R)-methyl 4-hydroxypyrrolidine-2-carboxylate hydrochloride (0.98 g, 5.4 mmol) and DIPEA (2.43 g, 18.9 mmol) in DMF (10 mL) at 0° C. under nitrogen. The mixture was stirred at ambient temperature for 18 h. TLC showed the reaction complete. The reaction mixture was quenched with water (30 mL) and extracted with ethyl acetate (15 mL×4). The combined organic layer was washed with the 5% citric acid (10 mL×2), saturated $NaHCO_3$ solution (10 mL×2), brine (10 mL×2) and dried over $Na_2SO_4$. The organic solution was filtered and concentrated to afford (2S, 4R)-methyl 1-{(S)-2-[(tert-butoxycarbonyl)amino]-3,3-dimethylbutanoyl}-4-hydroxypyrrolidine-2-carboxylate as pale yellow oil (1.93 g, 100% yield). This crude product (1.93 g) and lithium hydroxide hydrate (2.2 g, 54 mmol) were taken into THF (20 mL) and $H_2O$ (10 mL). The resulting mixture was stirred at ambient temperature for 18 h. THF was removed by concentration. The residue was diluted with ice-water (10 mL) and slowly adjusted to pH 2-3 with 3N HCl. The resulting suspension was filtered, washed with $H_2O$ (6 mL×2). The solid was collected by filtration and dried in oven at 50° C. to afford the title compound as a white solid (1.4 g, 75% for two steps). $^1$HNMR (400 MHz, DMSO-$d_6$): δ 6.50 (d, J=9.6 Hz, 1H), 5.19 (br s, 1H), 4.32 (br s, 1H), 4.25 (t, J=8.4 Hz, 1H), 4.16 (d, J=9.2 Hz, 1H), 3.57-3.66 (m, 2H), 2.08-2.13 (m, 1H), 1.85-1.91 (m, 1H), 1.38 (s, 9H), 0.94 (s, 9H).

Step 4: Preparation of (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide hydrochloride (7)

HATU (1.6 g, 4.2 mmol) was added to a stirred solution of compound 6 (1.21 g, 3.5 mmol), compound 3 (0.9 g, 3.5 mmol), and DIPEA (1.36 g, 10.5 mmol) in anhydrous THF (15 mL) at 0° C. The resulting mixture was allowed to warm up to ambient temperature and continued to stir for 2 h. TLC showed reaction complete. THF was removed by concentration. To the residue was added water (15 mL) and the resulting mixture was stirred for 4 h. The resulting mixture was filtered. The solid was collected and dried in oven at 50° C. to give a white solid. This solid was taken into methanol (10 mL) and activated carbon (150 mg) was added. The resulting mixture was heated at 80° C. and stirred for 1 h. The mixture was filtered while it was hot. Water (5 mL) was added to the filtrate at 80° C. The resulting mixture was cooled to ambient temperature and continued to stir for 18 h. The suspension was filtered. The solid was collected and dried in oven at 50° C. to afford tert-butyl-{(S)-1-[(2S,4R)-4-hydroxy]-2-[(S)-1-(4-(4-methylthiazol-5-yl)phenyl)ethylcarbamoyl]pyrrolidin-1-yl}-3,3-dimethyl-1-oxobutan-2-ylcarbamate (1.41 g, 74.2%) as white solid. $^1$H NMR (400 MHz, $CDCl_3$): δ 1.05 (s, 9H), 1.42 (s, 9H), 1.47 (d, J=7.2 Hz, 3H), 2.04-2.10 (m, 1H), 2.53 (s, 3H), 2.58-2.64 (m, 1H), 3.23 (s, 1H), 3.58 (dd, J=11.2 Hz, 3.2 Hz, 1H), 4.11 (d, J=11.6 Hz, 1H), 4.22 (d, J=9.2 Hz, 1H), 4.51 (br, 1H), 4.79 (t, J=8.0 Hz, 1H), 5.04-5.11 (m, 1H), 5.22 (d, J=8.8 Hz, 1H), 7.36-7.42 (m, 4H), 7.61 (d, J=7.6 Hz 1H), 8.68 (s, 1H). This solid (1.04 g, 1.9 mmol) was dissolved in 4N hydrogen chloride in methanol (3.0 mL) and the mixture was stirred at ambient temperature for 3 h. TLC showed reaction complete. The reaction mixture was concentrated to remove all volatiles under reduced pressure to give a light yellow solid. The solid was added to TBME (5 mL) and the resulting mixture was stirred at ambient temperature for 4 h. The reaction mixture was filtered and the solid was collected and dried in oven at 50° C. to afford compound 7 (0.92 g, 100%). $^1$H NMR (400 MHz, DMSO-d6): δ 1.03 (s, 9H), 1.38 (d, J=7.2 Hz, 3H), 1.72-1.79 (m, 1H), 2.09-2.14 (m, 1H), 2.49 (s, 3H), 3.48-3.52 (m, 1H), 3.75-3.79 (m, 1H), 3.88-3.90 (m, 1H), 4.31 (br, 1H), 4.56 (t, J=8.4 Hz, 1H), 4.89-4.95 (m, 1H), 7.41 (d, J=8.4 Hz, 2H), 7.47 (d, J=8.4 Hz, 2H), 8.20 (br, 3H), 8.67 (d, J=7.6 Hz, 1H), 9.22 (s, 1H); $^{13}$C NMR (400 MHz, DMSO-d6): δ 170.7, 167.1, 153.0, 146.5, 145.7, 132.5, 129.4, 129.3, 126.9, 69.4, 59.3, 58.5, 56.9, 48.3, 38.4, 34.8, 26.6, 23.0, 15.7; LC-MS $[M+1]^+$: 445.6

Intermediate 2: (2S,4R)-1-[(2S)-2-amino-3,3-dimethylbutanoyl]-4-hydroxy-N-{[4-(4-methyl-1,3-thiazol-5-yl)phenyl]methyl}pyrrolidine-2-carboxamide hydrochloride

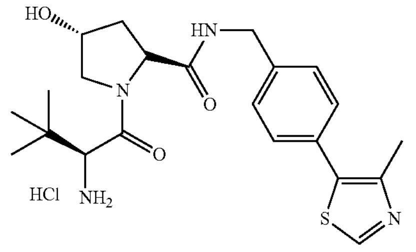

Intermediate 2 was prepared using exactly the same method as described in the preparation of Intermediate 1.

Synthesis of Linkers, L

L-1: 2-(3-(5-(tosyloxy)pentyloxy)propoxy)acetic acid

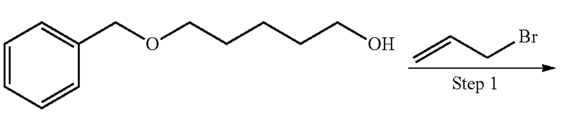

W

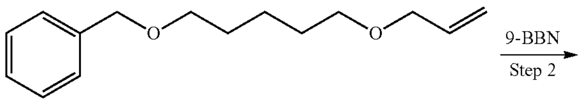

X

-continued

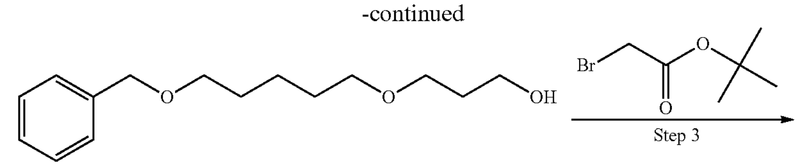

Y

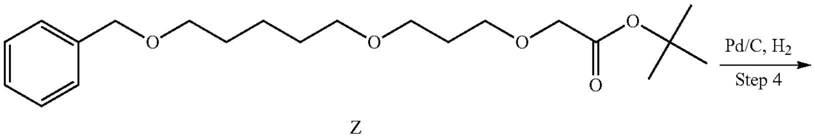

Z

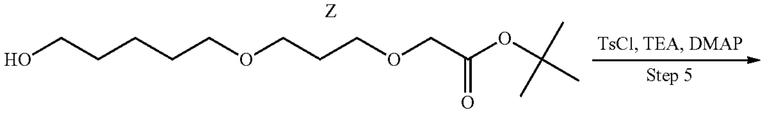

AA

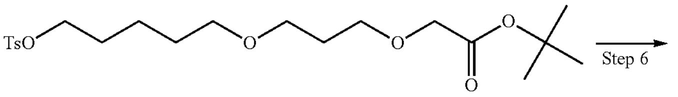

AB

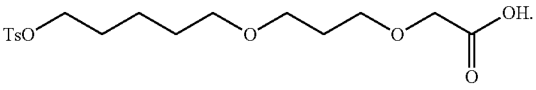

L-1

Step 1: Synthesis of ({[5-(prop-2-en-1-yloxy)pentyl]oxy}methyl)benzene

To a stirred solution of 5-(benzyloxy)pentan-1-ol (W, 4.0 g, 20.59 mmol) in N,N-dimethylformamide (50 mL) was added sodium hydride (1.24 g, 51.67 mmol) in portions at 0° C. under an atmosphere of nitrogen. The resulting mixture was then stirred at rt for 1 h. To this mixture was added 3-bromoprop-1-ene (3.71 g, 30.67 mmol), the reaction mixture was stirred overnight at 60° C. in an oil bath. LC-MS indicated formation of the desired product. The reaction mixture was cooled to 0° C. and then quenched by water (100 mL), the resulting mixture was extracted with ethyl acetate (200 mL×2). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:40)) to give 4.57 g of X. $^1$H NMR (300 MHz, $CDCl_3$): δ 7.36 (s, 4H), 7.32 (m, 1H), 5.98 (m, 1H), 5.33 (m, 1H), 5.21 (m, 1H), 4.53 (s, 2H), 3.99 (m, 2H), 3.53 (m, 4H), 1.72 (m, 4H), 1.52 (m, 2H). LC-MS ($ES^+$): m/z 235.00 [$MH^+$], $t_R$=1.18 min (2.0 minute run).

Step 2: Synthesis of 3-{[5-(benzyloxy)pentyl]oxy}propan-1-ol (Y)

To a 250-mL round-bottom flask with 9-BBN (0.5 M in THF, 77 mL) was added a solution of ({[5-(prop-2-en-1-yloxy)pentyl]oxy}methyl)benzene (X, 3.0 g, 12.80 mmol) in anhydrous tetrahydrofuran (20 mL) with stirring at 0° C. under an atmosphere of nitrogen. The resulting solution was stirred overnight at rt. LC-MS indicated formation of the desired product. Methanol (15 mL, with 30% sodium hydroxide and 30% $H_2O_2$) was added to the reaction and the resulting mixture was stirred at rt for 2 h. This mixture was then extracted with ethyl acetate (20 mL×3). The organic layers were combined, washed with saturated aqueous solution of sodium chloride (100 mL), dried over anhydrous sodium sulfate and then concentrated under reduced pressure to give a crude residue. The residue was purified by a flash silica gel chromatography (eluent: ethyl acetate/petroleum ether (v:v=1:1)) to provide 1.96 g of Y as light yellow oil. $^1$H NMR (300 MHz, $CDCl_3$): δ 7.34 (m, 5H), 4.49 (s, 2H), 3.75 (m, 2H), 3.59 (m, 2H), 3.49 (m, 4H), 2.65 (bs, 1H), 1.84 (m, 2H), 1.68 (m, 4H), 1.50 (m, 2H). LC-MS ($ES^+$): m/z 253.17 [$MH^+$], $t_R$=1.44 min (2.6 minute run).

Step 3: Synthesis of tert-butyl 2-(3-{[5-(benzyloxy)pentyl]oxy}propoxy)acetate (Z)

To a stirred solution of 3-{[5-(benzyloxy)pentyl]oxy}propan-1-ol (Y, 3.7 g, 14.66 mmol) in dichloromethane (30 mL) was added a solution of NaOH in water (37%, 30 mL) followed by tert-butyl 2-bromoacetate (11.39 g, 58.39 mmol) and TBACl (4.17 g). The resulting mixture was stirred at rt overnight. LC-MS indicated formation of the desired product. The reaction mixture was then extracted with ethyl acetate (50 mL×3). The organic layers were combined, washed with saturated aqueous solution of sodium chloride (60 mL), dried over anhydrous sodium sulfate and then concentrated under reduced pressure to give a crude residue. The residue was purified by a flash silica gel chromatography (eluent: ethyl acetate/petroleum ether (v:v=1:2) to give 3.2 g of Z as a yellow oil. $^1$H NMR (400 MHz, $CDCl_3$): 7.34 (s, 4H), 7.29 (m, 1H), 4.50 (s, 4H), 4.3 (m, 2H), 3.51 (m, 4H), 3.42 (m, 2H), 1.98 (m, 2H), 1.67 (m, 4H), 1.48 (s, 9H), 1.46 (m, 2H). LC-MS ($ES^+$): m/z 367.25 [$MH^+$], $t_R$=1.28 min (2.0 minute run).

Step 4: Synthesis of tert-butyl 2-[3-[(5-hydroxypentyl)oxy]propoxy]acetate (AA)

To a stirred solution of tert-butyl 2-(3-{[5-(benzyloxy)pentyl]oxy}propoxy)acetate (Z, 3.2 g, 8.73 mmol) in methanol (30 mL) was added AcOH (1.5 mL), palladium on carbon (1.5 g) under an atmosphere of nitrogen. Hydrogen was then introduced to the reaction mixture via a hydrogen balloon, and the reaction was stirred at rt for 3 h. The solid material was removed by filtration, the solution was concentrated under vacuum to provide 2.3 g of AA as light yellow oil, which was used for the next step without any further purifications. LC-MS ($ES^+$): m/z 277.10 [$MH^+$], $t_R$=0.86 min (2.0 minute run).

Step 5: Synthesis of tert-butyl 2-[3-({5-[(4-methylbenzenesulfonyl)oxy]-pentyl}oxy)propoxy]acetate (AB)

To a stirred solution of tert-butyl 2-[3-[(5-hydroxypentyl) oxy]propoxy]acetate (AA, 2.3 g, 8.32 mmol) in dichloromethane (30 mL) was added 4-methylbenzene-1-sulfonyl chloride (3.17 g, 16.63 mmol), triethylamine (2.52 g, 24.90 mmol) and 4-dimethylaminopyridine (203 mg, 1.66 mmol) at rt. The resulting mixture was stirred overnight at rt. The resulting mixture was concentrated under reduced pressure to give a crude residue, which was purified by a flash silica gel chromatography (eluent: ethyl acetate/petroleum ether (v:v=1:2) to give 2.6 g of AB as a yellow oil. $^1$H NMR (300 MHz, $CDCl_3$): δ 7.77 (d, J=8.1 Hz, 2H), 7.36 (d, J=8.1 Hz, 2H), 4.51 (s, 2H), 4.31 (m, 2H), 4.13 (m, 2H), 3.52 (m, 4H), 2.05 (s, 3H), 1.97 (m, 2H), 1.69 (m, 4H), 1.48 (s, 9H), 1.46 (m, 2H). LC-MS ($ES^+$): m/z 431.20 [$MH^+$], $t_R$=1.21 min (2.0 minute run).

Step 6: Synthesis of 2-[3-({5-[(4-methylbenzenesulfonyl)oxy]pentyl}oxy)-propoxy]acetic acid (L-1)

To a stirred solution of tert-butyl 2-[3-({5-[(4-methylbenzenesulfonyl)oxy]pentyl}oxy)-propoxy]acetate (AB, 1.3 g, 3.02 mmol) in dichloromethane (10 mL) was added trifluoroacetic acid (10 mL) at rt. The resulting solution was stirred at rt for 3 h. The reaction mixture was then concentrated under vacuum to give 1.5 g (crude) of L-1, which was used for next step without any further purification. LC-MS ($ES^+$): m/z 375.34 [$MH^+$], $t_R$=1.39 min (2.6 minute run).

The following Linkers (L) were prepared in a similar manner as for the preparation of L-1.

L-2:2-(3-(3,3-dimethyl-5-(tosyloxy)pentyloxy) propoxy)acetic acid

L-2

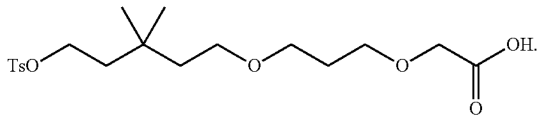

L-3:2-(3-(3-hydroxy-5-(tosyloxy)pentyloxy) propoxy)acetic acid

L-3

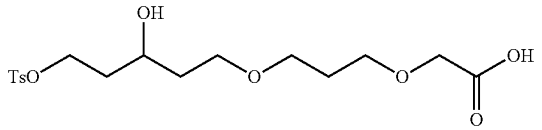

L-4:2-(2-(2-(2-(tosyloxy)ethoxy)ethoxy)ethoxy)acetic acid

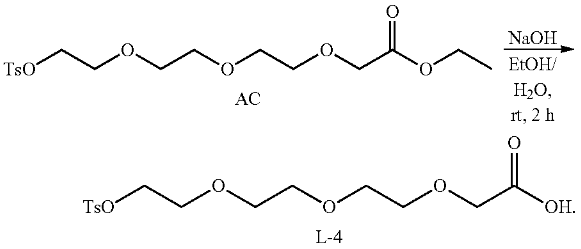

To a stirred solution of ethyl 2-[2-(2-{2-[(4-methylbenzenesulfonyl)oxy]ethoxy}ethoxy)-ethoxy]acetate (AC, 2 g, 5.12 mmol, 1.00 equiv) in methanol (20 mL) was added a solution of NaOH (500 mg, 12.50 mmol) in water (4 mL), and the resulting mixture was stirred at rt for 2 h. Aqueous hydrogen chloride (1 M) was then added to the reaction mixture to adjust pH to ~5. Solids precipitated were collected by filtration to give L-4 (yield: 98%). Mass (ES+): m/z 363, [MH+].

The following Linkers (L) were prepared in a similar manner as for the preparation of L-4.

L-5: 2-(2-((2R,3R)-3-(2-(tosyloxy)ethoxy)butan-2-yloxy)ethoxy)acetic acid

L-5

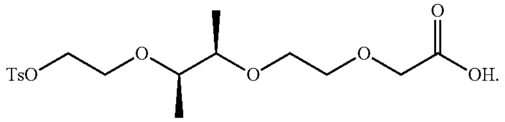

L-6: 2-(2-((2S,3S)-3-(2-(tosyloxy)ethoxy)butan-2-yloxy)ethoxy)acetic acid

L-6

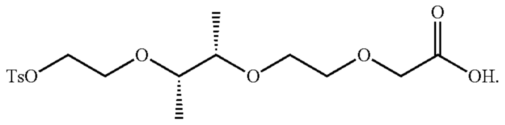

L-7: 2-(4-(4-(tosyloxy)butoxy)butoxy)acetic acid

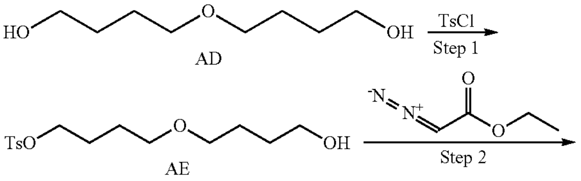

-continued

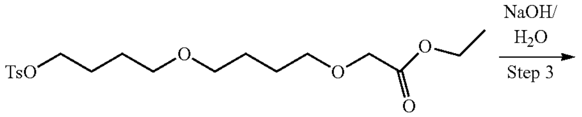

AF

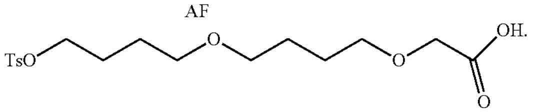

L-7

Step 1: Synthesis of 4-{4-[(4-methylbenzenesulfonyl)oxy]butoxy}butan-1-ol (AE)

To a stirred solution of 4-(4-hydroxybutoxy)butan-1-ol (AD, 2 g, 12.33 mmol) in dichloromethane (20 mL) was added $Ag_2O$ (4.25 g, 18.49 mmol), KI (409 mg, 2.46 mmol) and TsCl (2.345 g, 12.30 mmol). The resulting mixture was stirred at rt for 12 h. The inorganic salt formed was removed by filtration and the organic solution was concentrated under reduced pressure to give a crude residue. The residue was purified by flash silica gel chromatography (eluent: ethyl acetate/petroleum ether (v:v=1:1)) to give AE (yield: 28%) as a colorless oil.

Step 2: Synthesis of ethyl 2-(4-{4-[(4-methylbenzenesulfonyl)oxy]-butoxy}butoxy)acetate (AF)

To a stirred solution of 4-{4-[(4-methylbenzenesulfonyl)oxy]butoxy}butan-1-ol (AE, 1.1 g, 3.48 mmol) in dichloromethane (10 mL) was slowly added $BF_3.Et_2O$ (49.4 mg, 0.35 mmol) followed by ethyl 2-diazoacetate (794 mg, 6.96 mmol) at 0° C. The resulting mixture was stirred overnight at rt. The reaction was then quenched by water (2.0 mL). The resulting mixture was extracted with dichloromethane (50 mLx3), the organic layers were combined, dried over anhydrous sodium sulfate and then concentrated under reduced pressure to give a crude residue. The residue was purified by flash silica gel chromatography (eluent: ethyl acetate/petroleum ether (v:v=1:4) to give AF (yield: 93 as light yellow oil. Mass ($ES^+$): m/z 403.10 [$MH^+$].

Step 3: Synthesis of 2-(4-{4-[(4-methylbenzenesulfonyl)oxy]-butoxy}butoxy)acetic acid (L-7)

To a stirred solution of ethyl 2-(4-{4-[(4-methylbenzenesulfonyl)oxy]butoxy}butoxy)acetate (AF, 1.3 g, 3.23 mmol) in methanol (25 mL) was added a solution of NaOH (388 mg, 9.70 mmol) in water (6 mL) at rt. The resulting solution was stirred at rt for 4 h. The bulk of organic solvent was removed under reduced pressure, to the resulting mixture was added aqueous hydrogen chloride (1.0 M) to adjust the pH=~5. The solution was then extracted with ethyl acetate (250 mLx3), the organic layers were combined and dried over anhydrous sodium sulfate, concentrated under reduced pressure to give L-7 (yield: 93%) as light yellow oil. Mass ($ES^+$): m/z 375.05 [$MH^+$].

L-8: tert-butyl 2-(3-(4-(tosyloxy)butoxy)propoxy)acetate

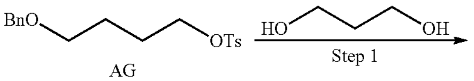

AG

-continued

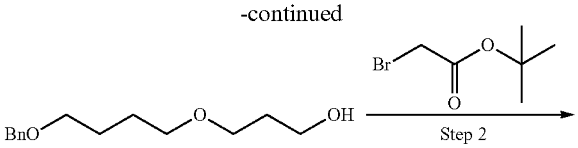

AH

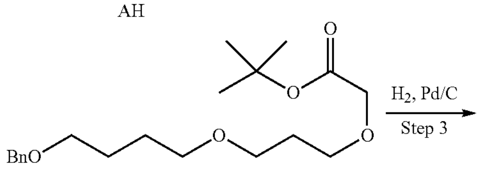

AI

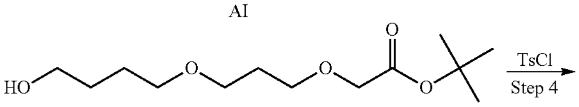

AJ

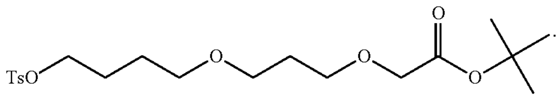

L-8

Step 1. Synthesis of 3-[4-(benzyloxy)butoxy]propan-1-ol (AH)

To a stirred solution of propane-1, 3-diol (1.52 g, 19.98 mmol) in N, N-dimethylformamide (20 mL) was added sodium hydride (840 mg, 35.00 mmol) at rt, the resulting mixture was stirred at rt for 30 min. Then to the mixture was added 4-(benzyloxy) butyl 4-methylbenzene-1-sulfonate (AG, 6.68 g, 19.97 mmol) and the reaction was stirred overnight at 50° C. TLC indicated formation of the desired product, at this time the reaction was allowed to cool down to rt. Water (10 mL) was added slowly to quench the reaction; the resulting mixture was then extracted with ethyl acetate (80 mLx2). The organic layers were combined, washed with saturated aqueous solution of sodium chloride (20 mL), dried over anhydrous sodium sulfate and then concentrated under reduced pressure to give a crude residue, which was purified by flash silica gel chromatography (eluent: ethyl acetate/petroleum ether (v:v=1:2)) to give AH (yield: 67%) as a light yellow oil. $^1H$ NMR (300 MHz, $CDCl_3$) δ 7.38-7.29 (m, 5H), 4.52 (m, 2H), 3.80 (m, 2H), 3.61 (m, 2H), 3.49-3.46 (m, 4H), 2.04 (m, 2H), 1.82 (m, 2H), 1.68 (m, 2H); Mass ($ES^+$): m/z 239.05 [$MH^+$].

Step 2. Synthesis of tert-butyl 2-[3-[4-(benzyloxy)butoxy]propoxy]acetate (AI)

To a stirred solution of 3-[4-(benzyloxy)butoxy]propan-1-ol (AH, 2.38 g, 9.99 mmol) in dichloromethane (15 mL) was added tert-butyl 2-bromoacetate (7.76 g, 39.78 mmol), TBAC (2.78 g, 10.00 mmol) followed by aqueous sodium hydroxide (37%, 15 mL). The resulting mixture was stirred overnight at rt. The reaction mixture was then extracted with dichloromethane (100 mLx3), the organic layers were combined, washed with saturated aqueous solution of sodium chloride (20 mL), dried over anhydrous sodium sulfate and then concentrated under reduced pressure to give a crude residue. The residue was purified by flash silica gel chromatography (eluent: ethyl acetate/petroleum ether (v:v=1:5)) to give AI (yield 57%) as a yellow oil. Mass ($ES^+$): m/z 353.10 [$MH^+$].

Step 3. Synthesis of tert-butyl 2-[3-(4-hydroxybutoxy)propoxy]acetate (AJ)

To a stirred mixture of tert-butyl 2-[3-[4-(benzyloxy)butoxy]propoxy]acetate (AI, 1 g, 2.84 mmol), palladium on carbon (10%, 200 mg) in methanol (20 mL) was added acetic acid (0.05 mL) under a nitrogen atmosphere. Hydrogen was then introduced to the reaction mixture via a balloon, the reaction was then stirred overnight at rt. The insoluble solids were removed by filtration and the solution phase was concentrated under reduced pressure to give the desired product (yield: 94%) as a yellow oil. Mass ($ES^+$): m/z 263.05 [$MH^+$].

Step 4. Synthesis of tert-butyl 2-(3-{4-[(4-methylbenzenesulfonyl)oxy]butoxy}propoxy)acetate (L-8)

To a stirred solution of tert-butyl 2-[3-(4-hydroxybutoxy)propoxy]acetate (AJ, 700 mg, 2.67 mmol) in dichloromethane (10 mL) was added 4-methylbenzene-1-sulfonyl chloride (558.4 mg, 2.93 mmol), TEA (539.5 mg, 5.33 mmol) and 4-dimethylaminopyridine (32.6 mg, 0.27 mmol). The resulting mixture was stirred overnight at rt. The bulk of solvent was removed under reduced pressure to give a crude residue, which was purified by flash silica gel chromatography (eluent: ethyl acetate/petroleum ether (v:v=1:2)) to give titled product (yield: 52%) as a yellow oil. $^1H$ NMR (300 MHz, $CDCl_3$) δ7.79 (d, J=8.4 Hz, 2H), 7.35 (d, J=8.0 Hz, 2H), 4.05 (m, 2H), 3.95 (s, 2H), 3.59 (m, 2H), 3.48 (m, 2H), 3.38 (m, 2H), 2.46 (s, 3H), 1.82 (m, 2H), 1.70 (m, 2H), 1.57 (m, 2H), 1.50 (s, 9H); Mass ($ES^+$): m/z 417.05 [$MH^+$].

L-9: tert-butyl 2-(4-(3-(tosyloxy)propoxy)butoxy)acetate

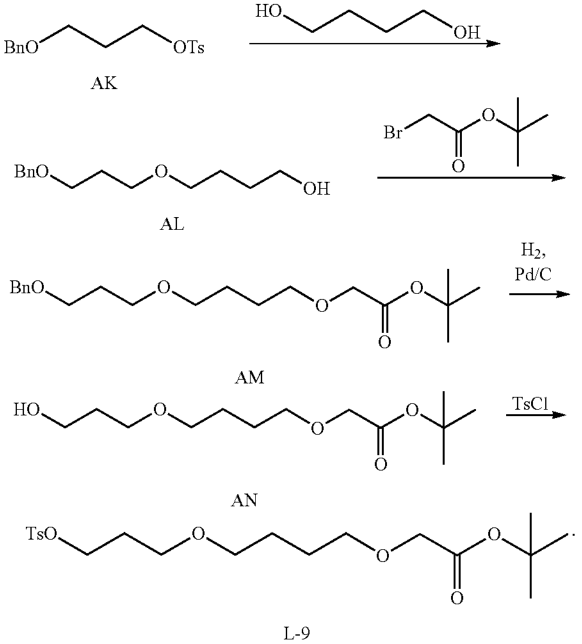

L-9 was prepared in a similar manner as that used to prepare L-8, except that AK was used in place of AG. Mass ($ES^+$): m/z 439.15 [$MNa^+$].

L-10: tert-butyl 2-(6-(tosyloxy)hexa-2,4-diynyloxy)acetate

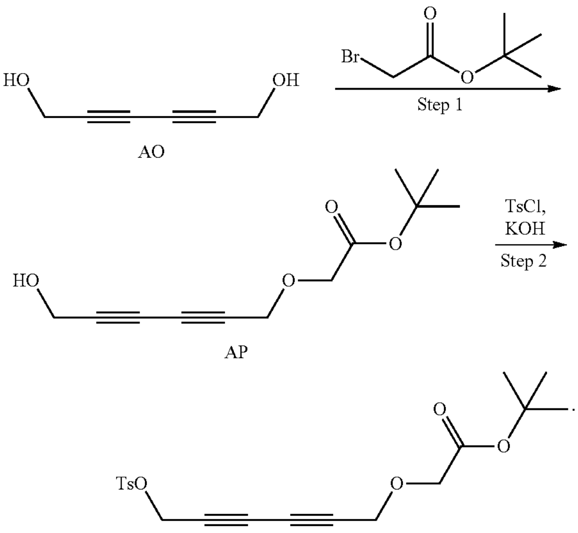

Step 1: Synthesis of tert-butyl 2-[(6-hydroxyhexa-2,4-diyn-1-yl)oxy]acetate (AP)

To a stirred solution of hexa-2, 4-diyne-1, 6-diol (AO, 100 mg, 0.91 mmol) in N, N-dimethylformamide (5 mL) was added sodium hydride (32 mg, 1.33 mmol) at 0° C. The resulting mixture was then warmed up to rt and stirred at rt for 30 min. The reaction mixture was cooled to 0° C. followed by addition of tert-butyl 2-bromoacetate (176 mg, 0.90 mmol), and the resulting mixture was stirred at 0° C. for 2 h. LC-MS indicated formation of the desired product. The reaction was then quenched by water (10 mL, added slowly) at 0° C., and was extracted with ethyl acetate (20×2 mL). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give AP (yield: 49%) as a yellow oil.

Step 2. Synthesis of tert-butyl 2-({6-[(4-methylbenzenesulfonyl)oxy]hexa-2,4-diyn-1-yl}oxy)acetate (L-10)

To a stirred solution of tert-butyl 2-[(6-hydroxyhexa-2, 4-diyn-1-yl) oxy] acetate (AP, 50 mg, 0.22 mmol) in ether (2 mL) was added 4-toluenesulfonyl chloride (51 mg, 0.27 mmol) at 0° C., followed by potassium hydroxide (125 mg, 2.23 mmol) in several batches at 0° C. The resulting mixture was stirred at 0° C. for 4 h. LC-MS indicated formation of the desired product. Water (10 mL) was added to the reaction, and the resulting mixture was extracted with ethyl acetate (20 mL×2). The organic layers were combined, dried over anhydrous sodium sulfate and then concentrated under reduced pressure to give a crude residue, which was purified by flash silica gel chromatography (eluent: ethyl acetate/petroleum ether (v:v=1:2)) to give L-10 (yield: 71%) as a yellow oil. $^1H$ NMR (300 MHz, $CDCl_3$): δ 7.83 (d, J=6.0 Hz, 2H), 7.39 (d, J=6.0 Hz, 2H), 4.79 (s, 2H), 4.37 (s, 2H), 4.05 (s, 2H), 2.48 (s, 3H), 1.51 (s, 9H); LC-MS ($ES^+$): m/z 401.05 [$MNa^+$], $t_R$=1.71 min (2.6 minute run).

The following Linkers (L) were prepared in a similar manner as for the preparation of L-10.

L-11: tert-butyl 3-(6-(tosyloxy)hexa-2,4-diynyloxy)propanoate

L-11

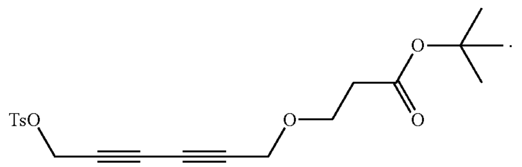

L-12: tert-butyl 4-(6-(tosyloxy)hexa-2,4-diynyloxy)butanoate

L-12

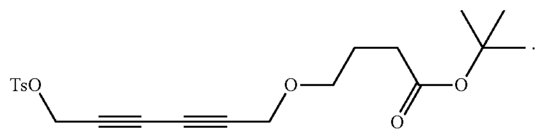

L-13: ethyl 2-(2-(2-aminoethoxy)ethoxy)acetate hydrochloride

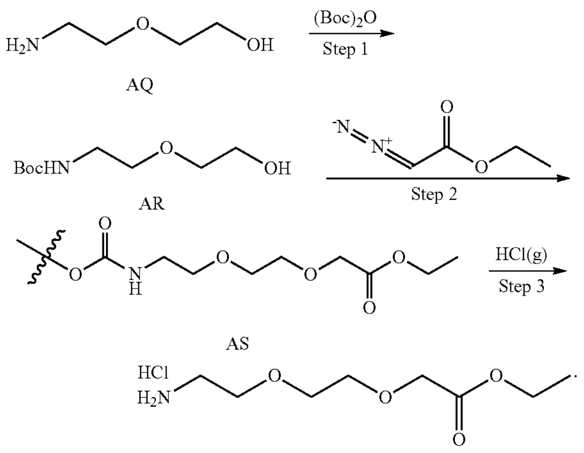

L-13

Step 1: Synthesis of tert-butyl N-[2-(2-hydroxyethoxy)ethyl]carbamate (AR)

To a stirred solution of 2-(2-aminoethoxy)ethan-1-ol (AQ, 5.25 g, 49.94 mmol) in tetrahydrofuran (100 mL) was added aqueous solution of sodium bicarbonate (20% (w/w), 40 ml) and $(Boc)_2O$ (11.4 g, 52.23 mmol, added in several batches) at 0° C. The resulting mixture was then warmed up slowly to rt and stirred at rt for 5 h. The bulk of organic solvent was removed under reduced pressure and the resulting residue was diluted with water (300 mL), extracted with of ethyl acetate (100 mL×3). The organic layers were combined, washed with saturated aqueous solution of sodium chloride (20 mL×2), dried over anhydrous sodium sulfate and then concentrated under reduced pressure to give AR (yield: 98%) as colorless oil.

Step 2: Synthesis of ethyl 2-[2-(2-{[(tert-butoxy)carbonyl]amino}ethoxy)ethoxy]-acetate (AS)

To a stirred solution of tert-butyl N-[2-(2-hydroxyethoxy)ethyl]carbamate (AR, 4.0 g, 19.49 mmol) in dichloromethane (30 mL) was added 1-diazo-3-methoxypropan-2-one (3.34 g, 29.27 mmol) and $BF_3$-$Et_2O$ (0.2 mL) at rt. The resulting solution was stirred at rt for 2 h. Water (20 mL) was added to the reaction mixture, organic layer was separated and washed with brine (20 mL), dried over anhydrous sodium sulfate and concentrated under reduced pressure to give a crude residue. The residue was purified by flash silica gel chromatography (eluent: ethyl acetate/petroleum ether (v:v=1:2)) to give AS (yield: 18%) as yellow solid. $^1$H NMR (400 MHz, $CDCl_3$): δ 4.25-4.22 (q, J=7.2 Hz, 2H), 4.14 (s, 2H), 3.74 (b, 2H), 3.72 (b, 1H), 3.67-3.32 (m, 4H), 1.414 (s, 9H), 1.31 (t, J=7.2 Hz, 3H).

Step 3: Synthesis of ethyl 2-[2-(2-aminoethoxy)ethoxy]acetate hydrochloride (L-13)

To a stirred solution of ethyl 2-[2-(2-{[(tert-butoxy)carbonyl]amino}ethoxy)ethoxy]acetate (AS, 500 mg, 1.72 mmol) in 1,4-dioxane (10 mL) was introduced hydrogen chloride (gas) via bubbling at rt for 2 h. The solvent was then removed under vacuum to give L-13 (yield: 99%). LC-MS ($ES^+$): m/z 192.00 [$MH^+$], $t_R$=0.41 min (2.0 minute run).

L-14: ethyl 2-(5-aminopentyloxy)acetate

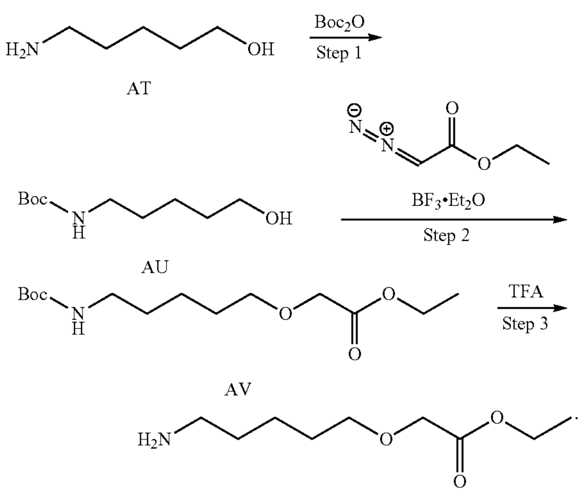

L-14

Step 1: Synthesis of tert-butyl 5-hydroxypentylcarbamate (AU)

To a stirred solution of 5-aminopentan-1-ol (AT, 3.1 g, 30.05 mmol) in dichloromethane (30 mL) was added di-tertbutyl dicarbonate (6.56 g, 30.06 mmol) at 0° C. The resulting mixture was then stirred at rt for 4 h. The solvent was removed under reduced pressure to give a crude residue which was purified by flash silica gel chromatography (eluent: ethyl acetate/petroleum ether (v:v=1:2)) to give AU (yield: 98%) as a colorless oil. LC-MS ($ES^+$): m/z 204.00 [$MH^+$], $t_R$=1.29 min (2.6 minute run).

Step 2: Synthesis of ethyl 2-[(5-{[(tert-butoxy)carbonyl]amino}pentyl)oxy]acetate (AV)

To a stirred solution of tert-butyl N-(5-hydroxypentyl) carbamate (AU, 1.5 g, 7.38 mmol) in dichloromethane (10 mL) was added $BF_3.Et_2O$ (0.1 mL) at 0° C. To this mixture was then added a solution of ethyl 2-diazoacetate (850 mg, 7.45 mmol) in dichloromethane (2 mL) at 0° C. The resulting mixture was allowed to warm up to rt and stirred at rt for 2 h. Saturated aqueous sodium bicarbonate (30 mL) was added to the reaction, the resulting mixture was extracted with ethyl acetate (150 mL×3). The organic layers were combined, dried over anhydrous sodium sulfate and then concentrated under reduced pressure to give a crude residue, which was purified by flash silica gel chromatography (eluent: ethyl acetate/petroleum ether (v:v=1:7)) to give AV (yield: 15%) as a colorless oil. LC-MS ($ES^+$): m/z 290.05 [$MH^+$], $t_R$=1.55 min (2.6 minute run).

Step 3: Synthesis of ethyl 2-(5-aminopentyloxy)acetate (L-14)

To a stirred solution of ethyl ethyl 2-[(5-{[(tert-butoxy) carbonyl]amino}pentyl)oxy]acetate (AV, 400 mg, 1.38 mmol) in dichloromethane (5 mL) was added trifluoroacetic acid (5 mL) at rt. The resulting solution was stirred at rt for 2 h. The reaction mixture was then concentrated under vacuum to give L-14 (yield: 84%) as a yellow oil. LC-MS ($ES^+$): m/z 190.00 [$MH^+$], $t_R$=1.01 min (2.6 minute run).

L-15: methyl 2-(2-(2-(methylamino)ethoxy)ethoxy)acetate

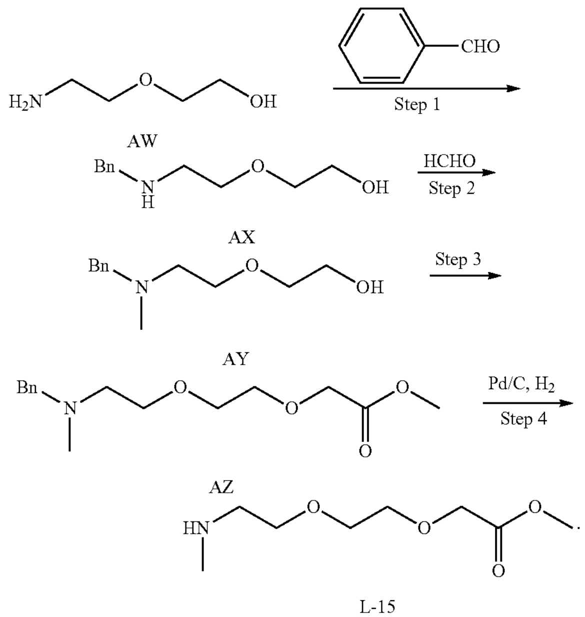

L-15

Step 1: Synthesis of 2-[2-(benzylamino)ethoxy]ethan-1-ol (AX)

To a stirred solution of 2-(2-aminoethoxy)ethan-1-ol (AW, 5.0 g) and benzaldehyde (5.0 g) in THF (50 mL) was added sodium triacetoxyborohydride (15.8 g, 74.5 mmol) at 0° C. The resulting solution was then stirred at rt for 4 h. Water (50 mL) was added to the reaction and the resulting mixture was extracted with ethyl acetate (50 mL×2). The organic layers were combined, dried over anhydrous sodium sulfate and then concentrated under reduced pressure to give a crude residue, which was purified by flash silica gel chromatography (eluent: dichloromethane/methanol (v:v=3:1) to give AX (yield: 85%) as a white solid. LC-MS ($ES^+$): m/z 195.95[$MH^+$], $t_R$=0.22 min (2.0 minute run).

Step 2: Synthesis of 2-{2-[benzyl(methyl)amino] ethoxy}ethan-1-ol (AY)

To a stirred solution of 2-[2-(benzylamino)ethoxy]ethan-1-ol (AX, 10.0 g) in methanol (200 mL) was added formaldehyde (38% in water) (4.9 mL) and triacetoxyborohydride (17.0 g) at rt. The resulting solution was stirred at rt for 2 h. Saturated aq. sodium bicarbonate (100 mL) was added to the reaction, and bulk of organic solvent was then removed under reduced pressure. The resulting mixture was extracted with ethyl acetate (200 mL×3). The organic layers were combined, dried over anhydrous sodium sulfate and then concentrated under reduced pressure followed by high vacuum pump to give AY (yield: 33%) as a yellow oil. LC-MS ($ES^+$): m/z 210.00 [$MH^+$], $t_R$=0.43 min (2.0 minute run).

Step 3: Synthesis of methyl 2-(2-{2-[benzyl (methyl)amino]ethoxy}ethoxy)acetate (AZ)

To a stirred solution of 2-{2-[benzyl(methyl)amino] ethoxy}ethan-1-ol (AY, 2 g) in dichloromethane (20 mL) was added a solution of sodium hydroxide (37%) in water (20 mL) followed by tert-butyl 2-bromoacetate (7.76 g) and TBAC (2.78 g) at rt. The resulting mixture was stirred at rt for 15 h. The aqueous layer was separated, and to which aq. hydrogen chloride (4N) was added to adjust the pH to ~3 before it was concentrated under reduced pressure to give a crude residue. Methanol (20 mL) was then added to this residue and insoluble salts were filtered out. The solution was concentrated under vacuum to give 2-(2-[2-[benzyl (methyl)amino]ethoxy]ethoxy)acetic acid (yield: 78%) as a yellow oil. To a stirred solution of 2-(2-{2-[benzyl(methyl) amino]ethoxy}ethoxy)acetic acid (2 g, 7.48 mmol, 1.00 equiv) prepare above in methanol (50 mL) was slowly added sulfuric acid (2 mL) at rt. The resulting solution was stirred at 70° C. in an oil bath for 3 h. The bulk of solvent was removed under reduced pressure to give a residue, which was diluted with $H_2O$ (30 mL). Sodium carbonate was then added to the mixture to adjust the pH to ~8. The mixture was then extracted with ethyl acetate (50 mL×2), the organic layers were combined, dried over anhydrous sodium sulfate and then concentrated under reduced pressure followed by high vacuum pump to give AZ (yield: 29%) as a yellow oil. LC-MS ($ES^+$): m/z 281.95 [$MH^+$], $t_R$=0.30 min (2.0 minute run).

Step 4: Synthesis of methyl 2-{2-[2-(methylamino) ethoxy]ethoxy}acetate (L-15)

To a stirred mixture of methyl 2-(2-{2-[benzyl(methyl) amino]ethoxy}ethoxy)acetate (AZ, 600 mg, 2.13 mmol) and palladium on carbon (300 mg) in methanol (30 mL) under a nitrogen atmosphere was charged with hydrogen gas via a balloon. The resulting mixture was stirred at rt for 15 h. The solid material was removed by filtration and the solution was concentrated under vacuum to give L-15 (400 mg) as yellow oil, which was used for next step without any further purifications. LC-MS ($ES^+$): m/z 191.95 [$MH^+$], $t_R$=0.31 min (2.0 minute run).

L-16: ethyl 2-(5-(methylamino)pentyloxy)acetate

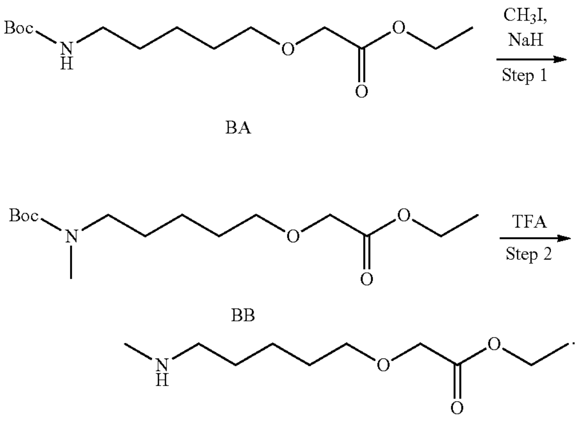

BA

BB

L-16

Step 1: Synthesis of ethyl 2-[(5-{[(tert-butoxy)carbonyl](methyl)amino}pentyl)oxy]acetate (BB)

To a stirred solution of ethyl 2-[(5-{[(tert-butoxy)carbonyl]amino}pentyl)oxy]acetate (BA, 1.1 g, 3.8 mmol) in N,N-dimethylformamide (10 mL) was added $CH_3I$ (0.71 mL, 11.4 mmol) at 0° C., followed by sodium hydride (304 mg, 7.60 mmol, 60% in mineral oil) in several portions at 0° C. The resulting mixture was stirred at rt for 16 h. Water (1.0 mL) was added and the resulting mixture was extracted with ethyl acetate (50 mLx2). The organic layers were combined, washed with saturated aqueous solution of sodium chloride (100 mL), dried over anhydrous sodium sulfate and then concentrated under reduced pressure to give a crude residue which was purified by a flash silica gel chromatography (eluent: ethyl acetate/petroleum ether (v:v=1:10)) to give BB (yield: 21%) as a yellow oil. LC-MS ($ES^+$): m/z 326.20 [$MNa^+$], $t_R$=1.55 min (2.6 minute run).

Step 2: Synthesis of ethyl 2-{[5-(methylamino)pentyl]oxy}acetate (L-16)

To a stirred solution of ethyl 2-[(5-{[(tert-butoxy)carbonyl](methyl)amino}pentyl)oxy]acetate (BB, 240 mg, 0.79 mmol) in dichloromethane (5 mL) was added trifluoroacetic acid (0.5 mL). The resulting solution was stirred at rt for 16 h. The solvents were removed under recued pressure followed by high vacuum pump to give L-16 (yield: 99%) as a yellow oil. LC-MS ($ES^+$): m/z 204.20 [$MH^+$], $t_R$=0.56 min (2.0 minute run).

L-17: 2-(3-(2-(tosyloxy)ethoxy)propoxy)acetic acid

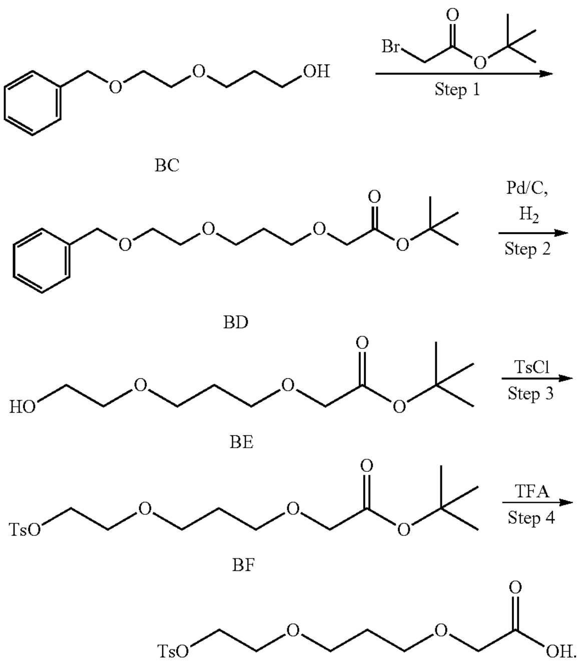

BC

BD

BE

BF

L-17

Step 1: Synthesis of tert-butyl 2-{3-[2-(benzyloxy)ethoxy]propoxy}acetate (BD)

To a stirred solution of 3-[2-(benzyloxy)ethoxy]propan-1-ol (BC, 1.8 g, 8.56 mmol) and tert-butyl 2-bromoacetate (6.6 g, 33.84 mmol, 4.00 equiv) in dichloromethane (40 mL) was added TBAC (2.4 g) and aq. Solution of sodium hydroxide (37%, 40 mL). The resulting mixture was stirred at rt overnight. LC-MS indicated formation of the desired product. The reaction mixture was then extracted with ethyl acetate (150x3 mL), the organic layers combined, dried over anhydrous sodium sulfate and concentrated under reduced pressure to give a crude residue, which was purified by a flash silica gel chromatography (eluent: ethyl acetate/petroleum ether (v:v=1:2) to give BD (yield: 90%) as a colorless oil. $^1H$ NMR (300 MHz, $CDCl_3$): δ 7.35-7.27 (m, 5H), 4.57 (s, 2H), 3.94 (s, 2H), 3.63-3.57 (m, 8H), 1.96-1.87 (m, 2H), 1.47 (s, 9H); LC-MS ($ES^+$): m/z 347.10 [$MNa^+$], $t_R$=1.72 min (2.6 minute run).

Step 2: Synthesis of tert-butyl 2-[3-(2-hydroxyethoxy)propoxy]acetate (BE)

To a stirred mixture of tert-butyl 2-{3-[2-(benzyloxy)ethoxy]propoxy}acetate (BD, 2.5 g, 7.71 mmol) and palladium on carbon (2.0 g) in methanol (20 mL) under a nitrogen atmosphere was introduced hydrogen gas via a balloon. The resulting mixture was stirred overnight at rt under hydrogen gas atmosphere. LC-MS indicated completion of the reaction. The solids were removed by filtration, the solution was concentrated under vacuum to give BE (yield: 99%) as a colorless oil. LC-MS ($ES^+$): m/z 257.10 [$MNa^+$], $t_R$=1.21 min (2.6 minute run).

Step 3: Synthesis of tert-butyl 2-(3-{2-[(4-methylbenzenesulfonyl)oxy]ethoxy}propoxy)acetate (BF)

To a stirred solution of tert-butyl 2-[3-(2-hydroxyethoxy)propoxy]acetate (BE, 1.8 g, 7.68 mmol) in dichloromethane (50 mL) was added 4-toluenesulfonyl chloride (2.2 g, 11.54 mmol), triethylamine (2.33 g, 23.03 mmol) and 4-dimethylaminopyridine (95 mg, 0.78 mmol). The resulting mixture was stirred overnight at rt. LC-MS indicated formation of the desired product. The reaction mixture was concentrated under reduced pressure to give a crude residue, which was purified by a flash silica gel chromatography (eluent:ethyl acetate/petroleum ether (v:v=1:2) to give BF (yield: 80%) as a yellow oil. $^1$H NMR (400 MHz, $CDCl_3$): δ 7.80 (d, J=8.0 Hz, 2H), 7.34 (d, J=8.4 Hz, 2H), 4.15 (t, J=3.6 Hz, 2H), 3.93 (s, 2H), 3.61 (t, J=3.6 Hz, 2H), 3.55-3.49 (m, 4H), 2.45 (s, 3H), 1.85-1.78 (m, 2H), 1.48 (s, 9H); LC-MS ($ES^+$): m/z 411.00 [$MNa^+$], $t_R$=1.12 min (2.0 minute run).

Step 4: Synthesis of 2-(3-{2-[(4-methylbenzenesulfonyl)oxy]ethoxy}propoxy)acetic acid (L-17)

To a stirred solution of tert-butyl 2-(3-{2-[(4-methylbenzenesulfonyl)oxy]ethoxy}propoxy)-acetate (BF, 400 mg, 1.03 mmol) in dichloromethane (3 mL) was added trifluoroacetic acid (1 mL) at rt. The resulting solution was stirred at rt for 1 h. LC-MS indicated completion of the reaction. The reaction mixture was concentrated under reduced pressure to give L-17 (350 mg) as a yellow oil, which was used for next step without further purifications. LC-MS ($ES^+$): m/z 332.90 [$MH^+$], $t_R$=0.81 min (2.0 minute run).

Unless otherwise noted, the following intermediates and their analogs (for examples, but not limited to, analogs with substitutions such as halogens) were synthesized according to similar procedures described above for the synthesis of L-17, by utilizing corresponding starting materials and reagents.

L-18:2-(2-hydroxyethoxy)ethyl 4-methylbenzenesulfonate

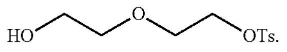 [SMILES: Cc1ccc(S(=O)(=O)OCCOCCO)cc1]

L-19: ethyl 2-(2-(2-(tosyloxy)ethoxy)ethoxy)acetate

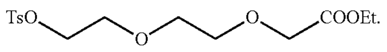 [SMILES: CCOC(=O)COCCOCCOS(=O)(=O)c1ccc(C)cc1]

L-20: ethyl 3-(2-(2-(tosyloxy)ethoxy)ethoxy)propanoate

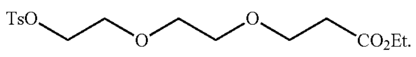

L-21: ethyl 5-(tosyloxy)pentanoate

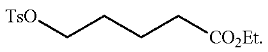

L-22: ethyl 3-(2-(tosyloxy)ethoxy)propanoate

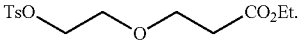 [SMILES: CCOC(=O)CCOCCOS(=O)(=O)c1ccc(C)cc1]

L-23: ethyl 2-(5-(tosyloxy)pentyloxy)acetate

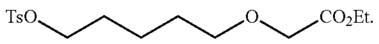

L-24: ethyl 3-(5-(tosyloxy)pentyloxy)propanoate

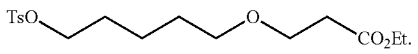

L-25: 5-hydroxypentyl 4-methylbenzenesulfonate

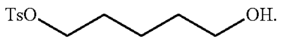 [SMILES: Cc1ccc(S(=O)(=O)OCCCCCO)cc1]

L-26: ethyl 2-(5-(tosyloxy)pentyloxy)acetate

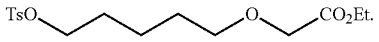

L-27: ethyl 2-(3-(tosyloxy)propoxy)acetate

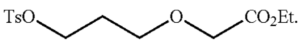

L-28: ethyl 2-(2-(tosyloxy)ethoxy)acetate

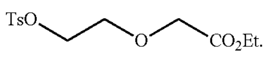

L-29: ethyl 2-(4-(2-(tosyloxy)ethoxy)butoxy)acetate

L-29

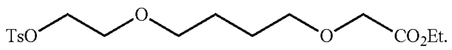

L-30:2-(2-(2-hydroxyethoxy)ethoxy)ethyl 4-methylbenzenesulfonate

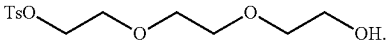 [SMILES: Cc1ccc(S(=O)(=O)OCCOCCOCCO)cc1]

L-31: 2-((2R,3R)-3-(2-hydroxyethoxy)butan-2-yloxy)ethyl 4-methylbenzenesulfonate

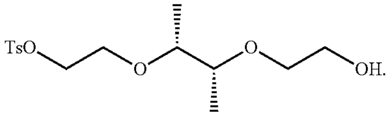 [SMILES: Cc1ccc(S(=O)(=O)OCCO[C@H](C)[C@@H](C)OCCO)cc1]

Synthesis of Exemplary PROTACs

Example #1: (2S,4R)-1-[(2S)-2-[1-(4-[[2-(4-fluoro-phenyl)-5-hydroxy-3-methyl-1H-indol-1-yl] methyl] phenyl)-1,4,7,10-tetraoxadodecan-12-amido]-3, 3-dimethylbutanoyl]-4-hydroxy-N-[[4-(4-methyl-1, 3-thiazol-5-yl)phenyl]methyl]pyrrolidine-2-carboxamide

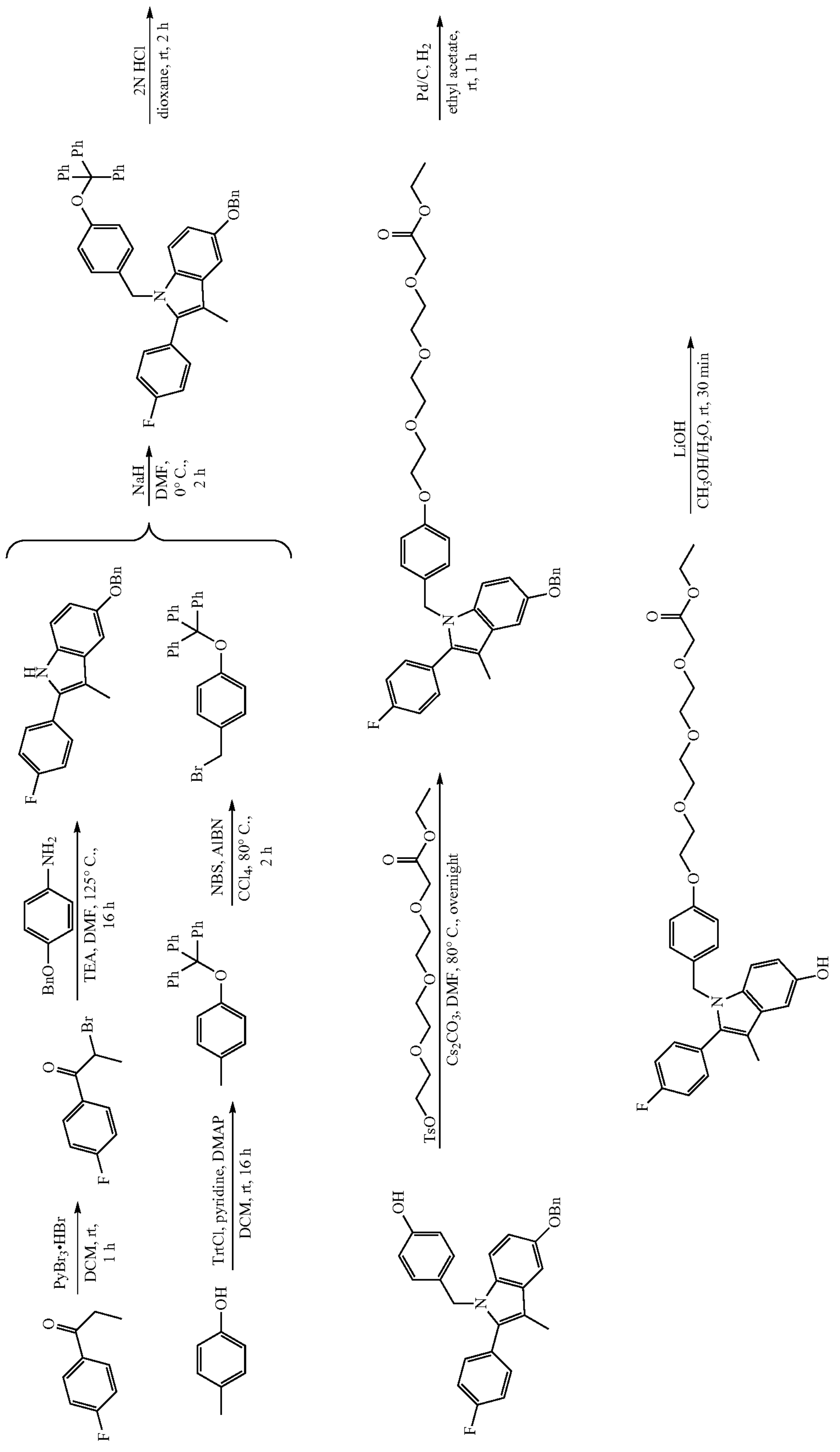
PyBr$_3$•HBr
DCM, rt, 1 h
TEA, DMF, 125° C., 16 h
TrtCl, pyridine, DMAP
DCM, rt, 16 h
NBS, AIBN
CCl$_4$, 80° C., 2 h
NaH
DMF, 0° C., 2 h
2N HCl
dioxane, rt, 2 h
Cs$_2$CO$_3$, DMF, 80° C., overnight
Pd/C, H$_2$
ethyl acetate, rt, 1 h
LiOH
CH$_3$OH/H$_2$O, rt, 30 min -continued
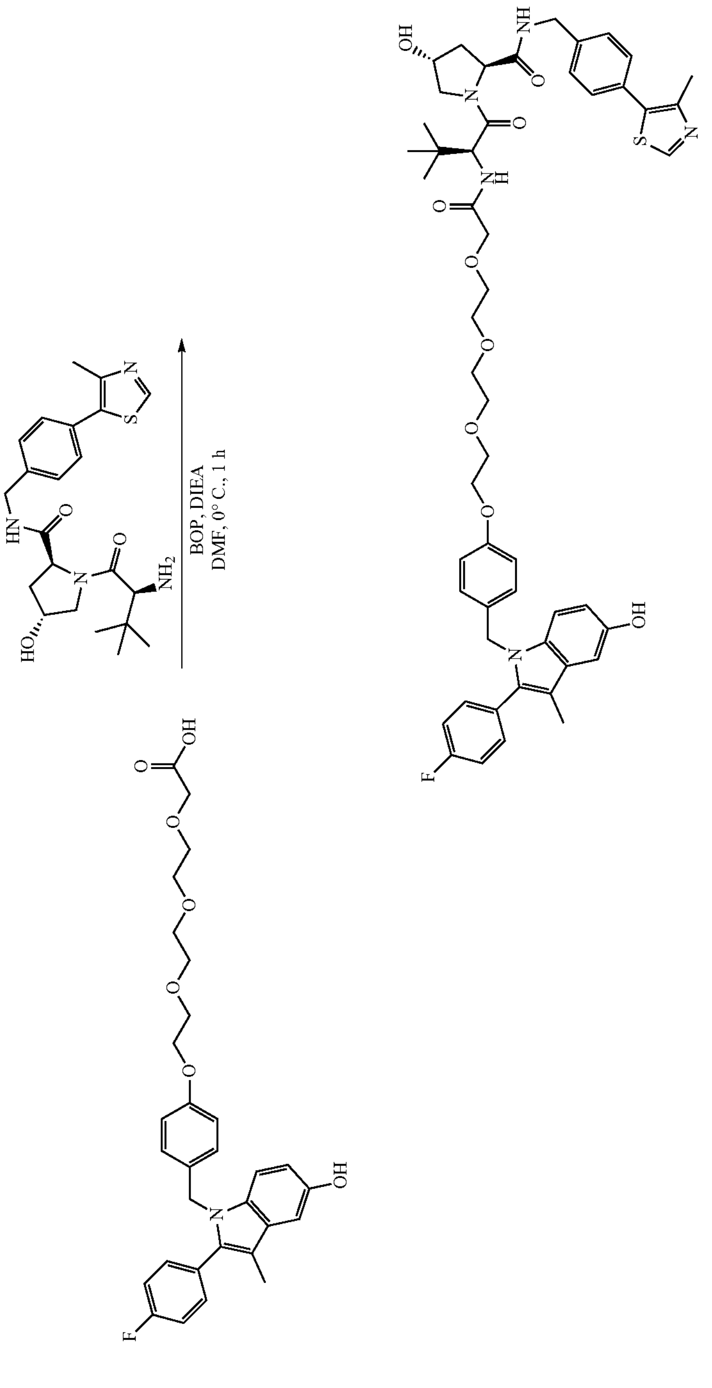

Step 1: Preparation of 2-bromo-1-(4-fluorophenyl) propan-1-one

In a 250 mL round bottom flask, 1-(4-fluorophenyl) propan-1-one (5.0 g, 32.86 mmol, 1.00 equiv) and $PyBr_3$.HBr (11.5 g, 35.96 mmol, 1.10 equiv) were dissolved in dichloromethane (50 mL) at room temperature. The resulting solution was stirred for 1 hour at room temperature. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure. This resulted in 5.0 g (66%) of 2-bromo-1-(4-fluorophenyl)propan-1-one as light yellow oil.

Step 2: Preparation of 5-(benzyloxy)-2-(4-fluorophenyl)-3-methyl-1H-indole

In a 100 mL round bottom flask, 2-bromo-1-(4-fluorophenyl) propan-1-one (2.0 g, 8.66 mmol, 1.00 equiv) and triethylamine (2 mL) were dissolved in N, N-dimethylformamide (20 mL) at room temperature. Then 4-(benzyloxy) aniline (2.6 g, 13.05 mmol, 1.5 equiv) was added. The resulting solution was stirred for 16 hours at 125° C. in an oil bath. The mixture was cooled to room temperature and was quenched by the addition of AcOH (5%, 50 mL). The resulting mixture was extracted with ethyl acetate (100 mL×2) and the organic layers were combined, washed with brine and dried over anhydrous sodium sulfate. The organic solvent was removed under reduced pressure and the residue was applied onto a silica gel column eluting with ethyl acetate/petroleum ether (v:v=1:10). This resulted in 1.2 g (42%) of 5-(benzyloxy)-2-(4-fluorophenyl)-3-methyl-1H-indole as a yellow solid. $^1$H NMR (400 MHz, DMSO-$d_6$ ppm): δ 11.01 (s, 1H), 7.68 (m, 2H), 7.48 (m, 2H), 7.38 (m, 5H), 7.27 (m, 1H), 7.11 (s, 1H), 6.84 (d, J=8.0 Hz, 1H), 5.12 (s, 2H), 2.35 (s, 3H); LC-MS (ES$^+$): m/z 332.15 [M+H]$^+$; $t_R$=2.51 min (3.60 minute run).

Step 3: Preparation of 1-methyl-4-(triphenylmethoxy)benzene

In a 500 mL round-bottom flask, 4-methylphenol (10.8 g, 99.87 mmol, 1.00 equiv), (chlorodiphenylmethyl)benzene (25.1 g, 89.96 mmol, 0.90 equiv), pyridine (10 mL) and 4-dimethylaminopyridine (1.2 g, 9.82 mmol, 0.10 equiv) were dissolved in dichloromethane (200 mL) at room temperature. The resulting solution was stirred for 16 hours at room temperature. The reaction mixture was then concentrated under reduced pressure and the residue was applied onto a silica gel column eluting with dichloromethane/petroleum ether (v:v=1:20). This resulted in 21.0 g (60%) of 1-methyl-4-(triphenylmethoxy)benzene as colorless oil.

Step 4: Preparation of 1-(bromomethyl)-4-(triphenylmethoxy)benzene

In a 100 mL round bottom flask, 1-methyl-4-(triphenylmethoxy) benzene (2.0 g, 5.71 mmol, 1.00 equiv), 2,2'-azobis-isobutyronitrile (200.0 mg, 1.22 mmol, 0.21 equiv) and N-bromo succinimide (1.0 g, 5.62 mmol, 1.00 equiv) were dissolved in carbon tetrachloride (30 mL) at room temperature. The resulting solution was stirred for 2 hours at 80° C. in an oil bath. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure. This resulted in 2.3 g (94%) of 1-(bromomethyl)-4-(triphenylmethoxy)benzene as white solid.

Step 5: Preparation of 5-(benzyloxy)-2-(4-fluorophenyl)-3-methyl-1-{[4-(triphenylmethoxy)phenyl] methyl}-1H-indole In a 250 mL round bottom flask, sodium hydride (362.0 mg, 15.08 mmol, 1.50 equiv) was added to a solution of 5-(benzyloxy)-2-(4-fluorophenyl)-3-methyl-1H-indole (2.0 g, 6.04 mmol, 1.00 equiv) in N,N-dimethylformamide (50 mL) at 0° C. The resulting mixture was stirred for 10 min at 0° C., and then was added 1-(bromomethyl)-4-(triphenylmethoxy)benzene (2.6 g, 6.06 mmol, 1.00 equiv). The resulting mixture was stirred for 2 hours at 0° C. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure and the residue was applied onto a silica gel column eluting with ethyl acetate/petroleum ether (v:v=1:3). This resulted in 1.0 g (24%) of 5-(benzyloxy)-2-(4-fluorophenyl)-3-methyl-1-[[4-(triphenylmethoxy)phenyl]methyl]-1H-indole as a yellow solid.

Step 6: Preparation of 4-{[5-(benzyloxy)-2-(4-fluorophenyl)-3-methyl-1H-indol-1-yl]methyl}phenol In a 100 mL round bottom flask, hydrogen chloride (2 N in water, 0.5 mL) was added to a solution of 5-(benzyloxy)-2-(4-fluorophenyl)-3-methyl-1-[[4-(triphenylmethoxy)phenyl] methyl]-1H-indole (1.0 g, 1.47 mmol, 1.00 equiv) in dioxane (10 mL) at room temperature. The resulting solution was stirred for 2 hours at room temperature. The mixture was extracted with ethyl acetate (20 mL×2) and the organic layers were combined, washed with brine and dried over anhydrous sodium sulfate. The organic solvent was removed under reduced pressure and the residue was applied onto a silica gel column eluting with ethyl acetate/petroleum ether (v:v=1:3). This resulted in 400.0 mg (62%) of 4-{[5-(benzyloxy)-2-(4-fluorophenyl)-3-methyl-H-indol-1-yl] methyl}phenol as yellow solid. $^1$H NMR (400 MHz, $CD_3OD$, ppm): δ 7.53 (m, 2H), 7.46 (m, 2H), 7.40 (m, 2H), 7.30 (m, 1H), 7.15 (m, 4H), 6.95 (m, 1H), 6.83 (d, J=8.0 Hz, 2H), 6.68 (d, J=8.0 Hz, 2H), 5.16 (s, 2H), 5.11 (s, 2H), 2.25 (s, 3H); LC-MS (ES$^+$): m/z 438.00 [M+H]$^+$; $t_R$=1.19 min (1.90 minute run).

Step 7: Preparation of ethyl 1-(4-{[5-(benzyloxy)-2-(4-fluorophenyl)-3-methyl-1H-indol-1-yl] methyl}phenyl)-1,4,7,10-tetraoxadodecan-12-oate In a 100 mL round bottom flask, 4-{[5-(benzyloxy)-2-(4-fluorophenyl)-3-methyl-1H-indol-1-yl]methyl}phenol (200.0 mg, 0.46 mmol, 1.00 equiv), ethyl 2-[2-[2-(2-[[(4-methylbenzene)sulfonyl]oxy]ethoxy)ethoxy]ethoxy]acetate (178.0 mg, 0.46 mmol, 1.00 equiv) and potassium carbonate (190.0 mg, 1.37 mmol, 3.00 equiv) were mixed in N,N-dimethylformamide (10 mL) at room temperature. The resulting solution was stirred overnight at 80° C. The reaction was then quenched by the addition of water. The resulting mixture was extracted with ethyl acetate (20 mL×2) and the organic layers were combined, washed with brine and dried over anhydrous sodium sulfate. The organic solvent was removed under reduced pressure and the residue was applied onto a silica gel column eluting with ethyl acetate/petroleum ether (v:v=1:1). This resulted in 180.0 mg (70%) of ethyl 1-(4-{[5-(benzyloxy)-2-(4-fluorophenyl)-3-methyl-1H-indol-1-yl]methyl}phenyl)-1,4,7,10-tetraoxadodecan-12-oate as a yellow oil. LC-MS ($ES^+$): m/z 656.35 $[M+H]^+$; $t_R$=1.42 min (1.90 minute run).

Step 8: Preparation of ethyl 1-(4-[[2-(4-fluorophenyl)-5-hydroxy-3-methyl-1H-indol-1-yl] methyl] phenyl)-1, 4, 7, 10-tetraoxadodecan-12-oate In a 100 mL round bottom flask, 10% of palladium on carbon (100.0 mg) was added to a solution of ethyl 1-(4-[[5-(benzyloxy)-2-(4-fluorophenyl)-3-methyl-1H-indol-1-yl]methyl]phenyl)-1, 4, 7, 10-tetraoxadodecan-12-oate (180.0 mg, 0.27 mmol, 1.00 equiv) in ethyl acetate (10 mL) at room temperature under nitrogen atmosphere. The reaction flask was vacuumed and charged with a hydrogen balloon. The resulting solution was then stirred for 1 hour at room temperature under hydrogen atmosphere. The reaction mixture was then filtered through a Celite pad and the filtrate was concentrated under reduced pressure. This resulted in 150.0 mg (97%) of ethyl 1-(4-[[2-(4-fluorophenyl)-5-hydroxy-3-methyl-1H-indol-1-yl]methyl]phenyl)-1,4,7,10-tetraoxadodecan-12-oate as yellow oil. LC-MS ($ES^+$): m/z 566.05 $[M+H]^+$; $t_R$=1.05 min (1.90 minute run).

Step 9: Preparation of 1-(4-{[2-(4-fluorophenyl)-5-hydroxy-3-methyl-1H-indol-1-yl]methyl}phenyl)-1, 4, 7, 10-tetraoxadodecan-12-oic acid In a 50 mL round bottom flask, ethyl 1-(4-{[2-(4-fluorophenyl)-5-hydroxy-3-methyl-1H-indol-1-yl] methyl}phenyl)-1,4,7,10-tetraoxadodecan-12-oate (150.0 mg, 0.27 mmol, 1.00 equiv) was added to a suspension of lithium hydroxide (1 mol/L, 0.5 mL) in methanol (5 mL) at room temperature. The resulting mixture was stirred for 30 minutes at room temperature. After the reaction was done, the pH value of the mixture was adjusted to 1 with hydrogen chloride solution (2 M). The resulting mixture was extracted with ethyl acetate (20 mL×2) and the organic layers were combined, washed with brine and dried over anhydrous sodium sulfate. The organic solvent was removed under reduced pressure. This resulted in 140.0 mg (98%) of 1-(4-{[2-(4-fluorophenyl)-5-hydroxy-3-methyl-1H-indol-1-yl]methyl}phenyl)-1,4,7,10-tetraoxadodecan-12-oic acid as a yellow oil. LC-MS ($ES^+$): m/z 538.05 $[M+H]^+$; $t_R$=0.94 min (1.90 minute run).

Step 10: Preparation of (2S,4R)-1-[(2S)-2-[1-(4-[[2-(4-fluorophenyl)-5-hydroxy-3-methyl-1H-indol-1-yl] methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide In a 50 mL round bottom flask, 1-(4-[[2-(4-fluorophenyl)-5-hydroxy-3-methyl-1H-indol-1-yl]methyl]phenyl)-1,4,7,10-tetraoxadodecan-12-oic acid (60.0 mg, 0.11 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl] pyrrolidine-2-carboxamide (48.0 mg, 0.11 mmol, 1.00 equiv), (benzotriazole-1-yloxy)-tris-(dimethylamino)phosphonium hexafluorophosphate (59.0 mg, 1.20 equiv) and N,N-diisopropylethylamine (43.0 mg, 0.33 mmol, 3.00 equiv) were dissolved in N,N-dimethylformamide (2 mL) at 0° C. The resulting solution was stirred for 1 hour at 0° C. The reaction was then quenched by the addition of water. The resulting mixture was extracted with ethyl acetate (20 mL×2) and the organic layers were combined, washed with brine and dried over anhydrous sodium sulfate. The organic solvent was removed under reduced pressure and the residue was purified by prep-HPLC with the following conditions: column, X Bridge C18, 19×250 mm, 5 um; mobile phase A, water with ammonium bicarbonate (10 mM), mobile phase B, acetonitrile; flow rate: 20 mL/min; gradient, 10% B to 80% B in 12 min; detector: UV 254 nm. This resulted in 25.0 mg of (24%) of (2S,4R)-1-[(2S)-2-[1-(4-[[2-(4-fluorophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl] methyl]pyrrolidine-2-carboxamide as white solid. $^1H$ NMR (400 MHz, $CD_3OD$): δ 8.83 (s, 1H), 7.48-7.30 (m, 6H), 7.20-7.12 (m, 2H), 7.09 (d, J=8.8 Hz, 1H), 6.95 (s, 1H), 6.78-6.66 (m, 5H), 5.12 (s, 2H), 4.69 (s, 1H), 4.60-4.46 (m, 3H), 4.33 (m, 1H), 4.05-3.95 (m, 4H), 3.86-3.73 (m, 4H), 3.71-3.63 (m, 8H), 2.48 (s, 3H), 2.28-2.15 (m, 4H), 2.12-2.02 (m, 1H), 1.01 (s, 9H); [M/Z] calculated for $C_2H_{60}FN_5O_9S$: 949.41; Observed from LC-MS ($ES^+$): m/z 950.50 $[M+H]^+$; $t_R$=1.61 min (2.90 minute run).

Example #2: (2S,4R)-1-[(2S)-2-[1-(4-[[2-(4-fluorophenyl)-5-hydroxy-3-methyl-1H-indol-1-yl] methyl] phenyl)-1,4,7,10-tetraoxadodecan-12-amido]-3,3-dimethylbutanoyl]-4-hydroxy-N-[(1S)-1-[4-(4-methyl-1,3-thiazol-5-yl)phenyl]ethyl]pyrrolidine-2-carboxamide

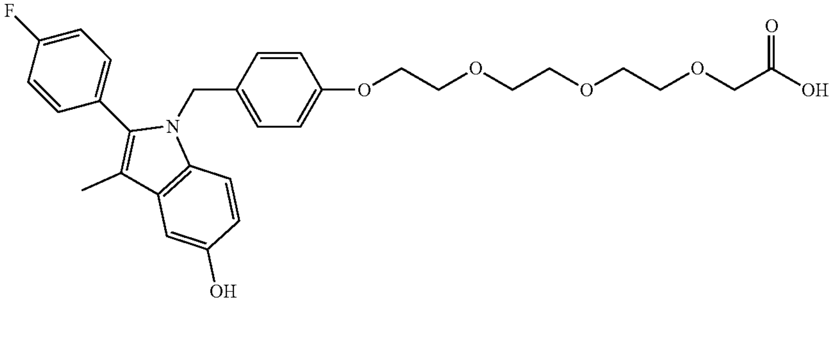

+

-continued

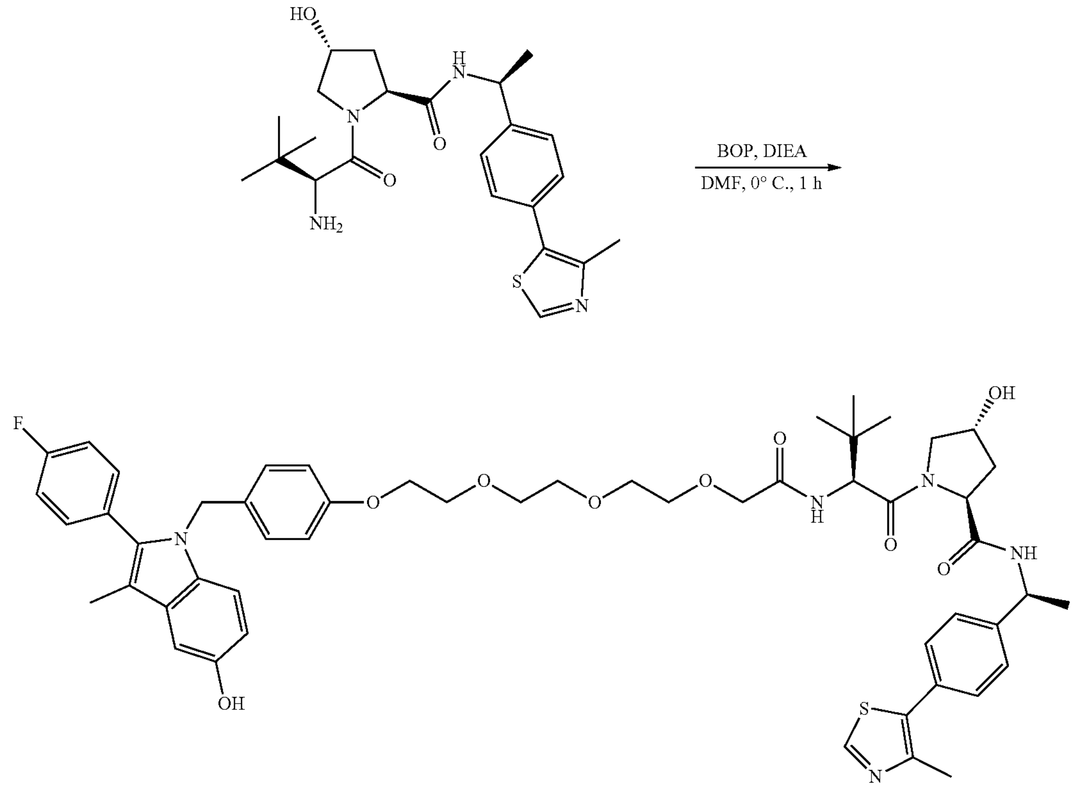

In a 50 mL round-bottom flask, 1-(4-[[2-(4-fluorophenyl)-5-hydroxy-3-methyl-1H-indol-1-yl]methyl]phenyl)-1,4,7,10-tetraoxadodecan-12-oic acid (80.0 mg, 0.15 mmol, 1.00 equiv), (2S,4R)-1-[(2S)-2-amino-3,3-dimethylbutanoyl]-4-hydroxy-N-[(1S)-1-[4-(4-methyl-1,3-thiazol-5-yl)phenyl]ethyl]pyrrolidine-2-carboxamide (66.0 mg, 0.15 mmol, 1.00 equiv), (benzotriazole-1-yloxy)-tris-(dimethylamino)phosphonium hexafluorophosphate (79.0 mg, 1.20 equiv) and N,N-diisopropylethylamine (58.0 mg, 0.45 mmol, 3.00 equiv) were dissolved in N,N-dimethylformamide (2 mL) at 0° C. The resulting solution was stirred for 1 hour at 0° C. The reaction was then quenched by the addition of water. The resulting mixture was extracted with ethyl acetate (20 mL×2) and the organic layers were combined, washed with brine and dried over anhydrous sodium sulfate. The organic solvent was removed under reduced pressure and the residue was purified by prep-HPLC using the following conditions: column: X Bridge C18, 19×250 mm, 5 um; mobile phase A, water with ammonium bicarbonate (10 mM), mobile phase B, acetonitrile; flow rate, 20 mL/min; gradient, 10% B to 80% B in 12 min; detector, UV 254 nm. This resulted in 31.0 mg (22%) of (2S,4R)-1-[(2S)-2-[1-(4-[[2-(4-fluorophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[(1S)-1-[4-(4-methyl-1,3-thiazol-5-yl)phenyl]ethyl]pyrrolidine-2-carboxamide as white solid. $^1$H NMR (400 MHz, $CD_3OD$, ppm): δ 8.87 (s, 1H), 7.48-7.37 (m, 4H), 7.33 (m, 2H), 7.17 (m, 2H), 7.07 (m, 1H), 6.95 (s, 1H), 6.78-6.72 (m, 4H), 6.68 (m, 1H), 5.15 (s, 2H), 5.00 (m, 1H), 4.69 (s, 1H), 4.57 (m, 1H), 4.44 (m, 1H), 4.08-4.01 (m, 4H), 3.88-3.65 (m, 12H), 2.48 (s, 3H), 2.25-2.15 (m, 4H), 1.97 (m, 1H), 1.57-1.47 (m, 3H), 1.02 (s, 9H); [M/Z] calculated for $C_{53}H_{62}FN_5O_9S$: 963.43; Observed from LC-MS ($ES^+$): m/z 964.30 $[M+H]^+$; $t_R$ 1.55 min (3.00 minute run).

Example #3: (2S,4R)-1-[(2S)-2-[2-[2-([1-[2-(4-[[2-(4-fluorophenyl)-5-hydroxy-3-methyl-1H-indol-1-yl]methyl]phenoxy)ethyl]piperidin-4-yl]oxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide

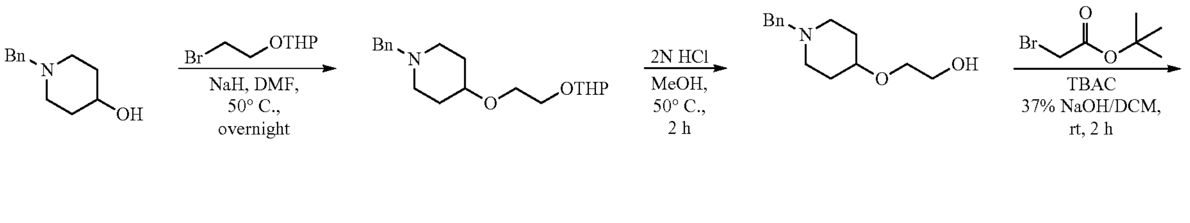

-continued
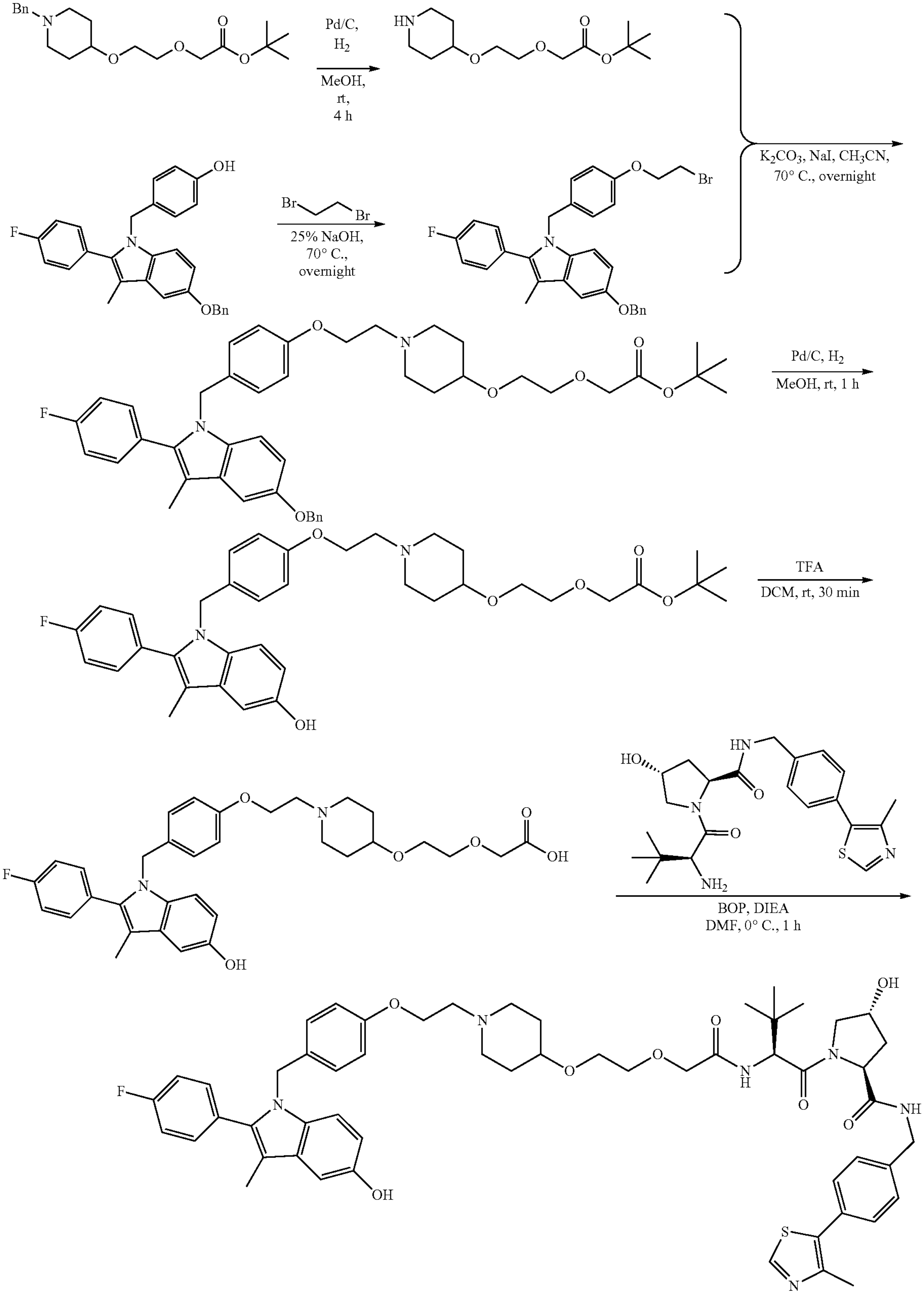

Step 1: Preparation of 1-benzyl-4-[2-(oxan-2-yloxy) ethoxy]piperidine

In 250 mL round bottom flask, sodium hydride (5.0 g, 208.33 mmol, 4.00 equiv) was added to a solution of 1-benzylpiperidin-4-ol (9.0 g, 47.05 mmol, 1.50 equiv) in N, N-dimethylformamide (150 mL) at room temperature. The resulting mixture was stirred for 20 minutes at room temperature. Then 2-(2-bromoethoxy)oxane (6.5 g, 31.09 mmol, 1.00 equiv) was added and the reaction mixture was heated to 50° C. and stirred overnight. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure and the residue was applied onto a silica gel column eluting with dichloromethane/methanol (v:v=10:1). This resulted in 8.0 g (81%) of 1-benzyl-4-[2-(oxan-2-yloxy)ethoxy] piperidine as yellow oil. LC-MS ($ES^+$): m/z 320.05 $[M+H]^+$; $t_R$=1.14 min (2.60 minute run).

Step 2: Preparation of 2-[(1-benzylpiperidin-4-yl) oxy]ethan-1-ol

In a 250 mL round bottom flask, hydrogen chloride (2 N in water, 10 mL) was added to a solution of 1-benzyl-4-[2-(oxan-2-yloxy)ethoxy] piperidine (8.0 g, 25.04 mmol, 1.00 equiv) in methanol (100 mL) at room temperature. The resulting solution was stirred for 2 hours at 50° C. The reaction mixture was cooled to room temperature and was concentrated under reduced pressure. The residue was extracted with methylene chloride and sodium hydroxide solution. The organic layer was dried and solvent was removed. This resulted in 5.5 g (93%) of 2-[(1-benzylpiperidin-4-yl)oxy]ethan-1-ol as yellow oil. LC-MS ($ES^+$): m/z 236.00 $[MH^+]$; $t_R$=0.42 min (1.90 minute run).

Step 3: Preparation of tert-butyl 2-[2-[(1-benzylpiperidin-4-yl)oxy]ethoxy]acetate In a 500 mL round bottom flask, 2-[(1-benzylpiperidin-4-yl) oxy] ethan-1-ol (5.5 g, 23.37 mmol, 1.00 equiv), tert-butyl 2-bromoacetate (13.6 g, 69.72 mmol, 3.00 equiv), tetrabutylammonium chloride (6.5 g, 1.00 equiv) were dissolved in dichloromethane (100 mL) at room temperature, to which was added a aqueous solution of sodium hydroxide (37%, 100 mL). The resulting mixture was stirred for 2 hours at room temperature. After the reaction was done, the reaction mixture was extracted with ethyl acetate (100 mL×2) and the organic layers were combined, washed with brine and dried over anhydrous sodium sulfate. The organic solvent was removed under reduced pressure and the residue was applied onto a silica gel column eluting with dichloromethane/methanol (v:v=10:1). This resulted in 3.0 g (37%) of tert-butyl 2-[2-[(1-benzylpiperidin-4-yl)oxy] ethoxy]acetate as a yellow oil. LC-MS ($ES^+$): m/z 350.05 $[M+H]^+$; $t_R$=0.64 min (1.90 minute run).

Step 4: Preparation of tert-butyl 2-[2-(piperidin-4-yloxy)ethoxy]acetate

In a 500 mL round bottom flask, 10% of palladium on carbon (1.0 g) was added to a solution of tert-butyl 2-[2-[(1-benzylpiperidin-4-yl)oxy]ethoxy] acetate (3.0 g, 8.58 mmol, 1.00 equiv) in methanol (30 mL) at room temperature under nitrogen atmosphere. The reaction flask was vacuumed and charged with a hydrogen balloon. The resulting mixture was stirred for 4 hours at room temperature under hydrogen atmosphere. After the reaction was done, the reaction mixture was filtered through a Celite pad and the filtrate was concentrated under reduced pressure. This resulted in 2.0 g (90%) of tert-butyl 2-[2-(piperidin-4-yloxy) ethoxy]acetate as a yellow oil. LC-MS ($ES^+$): m/z 260.15 $[M+H]^+$; $t_R$=0.69 min (1.90 minute run).

Step 5: Preparation of 5-(benzyloxy)-1-[[4-(2-bromoethoxy)phenyl]methyl]-2-(4-fluorophenyl)-3-methyl-1H-indole In a 100 mL round bottom flask, 4-[[5-(benzyloxy)-2-(4-fluorophenyl)-3-methyl-H-indol-1-yl]methyl] phenol (200.0 mg, 0.46 mmol, 1.00 equiv, from Example 1) and 1, 2-dibromoethane (1.7 g, 9.05 mmol, 20.00 equiv) were mixed in an aqueous solution of sodium hydroxide (25%, 10 mL) at room temperature. The resulting mixture was stirred overnight at 70° C. The reaction mixture was cooled to room temperature and was extracted with ethyl acetate (100 mL×2). The organic layers were combined, washed with brine and dried over anhydrous sodium sulfate. The organic solvent was removed under reduced pressure and the residue was applied onto a silica gel column eluting with ethyl acetate/petroleum ether (v:v=1:3). This resulted in 190.0 mg (76%) of 5-(benzyloxy)-1-[[4-(2-bromoethoxy)phenyl] methyl]-2-(4-fluorophenyl)-3-methyl-H-indole as a white solid. LC-MS ($ES^+$): m/z 543.95 $[M+H]^+$; $t_R$=1.33 min (1.90 minute run).

Step 6: Preparation of tert-butyl 2-[2-([1-[2-(4-[[5-(benzyloxy)-2-(4-fluorophenyl)-3-methyl-1H-indol-1-yl]methyl] phenoxy)ethyl]piperidin-4-yl]oxy) ethoxy]acetate In a 100 mL round bottom flask, 5-(benzyloxy)-1-[[4-(2-bromoethoxy)phenyl]methyl]-2-(4-fluorophenyl)-3-methyl-1H-indole (200.0 mg, 0.37 mmol, 1.00 equiv), tert-butyl 2-[2-(piperidin-4-yloxy)ethoxy]acetate (143.0 mg, 0.55 mmol, 1.50 equiv), potassium carbonate (152.0 mg, 1.10 mmol, 3.00 equiv) and sodium iodide (55.0 mg, 0.10 equiv) were mixed in acetonitrile (10 mL) at room temperature. The resulting mixture was stirred overnight at 70° C. The reaction mixture was cooled to room temperature and was extracted with ethyl acetate (20 mL×2). The organic layers were combined, washed with brine and dried over anhydrous sodium sulfate. The organic solvent was removed under reduced pressure and the residue was applied onto a silica gel column eluting with dichloromethane/methanol (v:v=10:1). This resulted in 170.0 mg (64%) of tert-butyl 2-[2-([1-[2-(4-[[5-(benzyloxy)-2-(4-fluorophenyl)-3-methyl-1H-indol-1-yl]methyl]phenoxy)ethyl]piperidin-4-yl]oxy)ethoxy]acetate as a yellow oil. LC-MS ($ES^+$): m/z 723.15 $[M+H]^+$; $t_R$=1.28 min (2.00 minute run).

Step 7: Preparation of tert-butyl 2-[2-([1-[2-(4-[[2-(4-fluorophenyl)-5-hydroxy-3-methyl-1H-indol-1-yl] methyl] phenoxy)ethyl]piperidin-4-yl]oxy)ethoxy] acetate In a 100 mL round bottom flask, palladium carbon (20.0 mg) was added to a solution of tert-butyl 2-[2-([1-[2-(4-[[5-(benzyloxy)-2-(4-fluorophenyl)-3-methyl-1H-indol-1-yl] methyl]-phenoxy)ethyl]piperidin-4-yl]oxy)ethoxy]acetate (40.0 mg, 0.06 mmol, 1.00 equiv) in methanol (5 mL) at room temperature under nitrogen atmosphere. The reaction flask was vacuumed and charged with a hydrogen balloon.

The resulting solution was stirred for 1 hour at room temperature under hydrogen atmosphere. After the reaction was completed, the mixture was filtered through a Celite pad and the filtrate was concentrated under reduced pressure. This resulted in 30.0 mg (86%) of tert-butyl 2-[2-([1-[2-(4-[[2-(4-fluorophenyl)-5-hydroxy-3-methyl-1H-indol-1-yl]methyl]phenoxy)ethyl]piperidin-4-yl]oxy)ethoxy]acetate as a yellow oil. LC-MS ($ES^+$): m/z 633.30 $[M+H]^+$; $t_R$=0.99 min (1.90 minute run).

Step 8: Preparation of 2-[2-([1-[2-(4-[[2-(4-fluorophenyl)-5-hydroxy-3-methyl-1H-indol-1-yl]methyl]phenoxy)ethyl]piperidin-4-yl]oxy)ethoxy]acetic acid In a 50 mL round bottom flask, trifluoroacetic acid (1 mL) was added to a solution of tert-butyl 2-[2-([1-[2-(4-[[2-(4-fluorophenyl)-5-hydroxy-3-methyl-1H-indol-1-yl]methyl]phenoxy)ethyl]piperidin-4-yl]oxy)ethoxy] acetate (30.0 mg, 0.05 mmol, 1.00 equiv) in dichloromethane (2 mL) at room temperature. The resulting solution was stirred for 30 minutes at room temperature. The reaction mixture was concentrated under reduced pressure. This resulted in 25.0 mg (91%) of 2-[2-([1-[2-(4-[[2-(4-fluorophenyl)-5-hydroxy-3-methyl-1H-indol-1-yl]methyl] phenoxy)ethyl]piperidin-4-yl]oxy)ethoxy]acetic acid as a yellow oil. LC-MS ($ES^+$): m/z 577.30 $[M+H]^+$, $t_R$=0.86 min (1.90 minute run).

Step 9: Preparation of (2S,4R)-1-[(2S)-2-[2-[2-([1-[2-(4-[[2-(4-fluorophenyl)-5-hydroxy-3-methyl-1H-indol-1-yl]methyl]phenoxy)ethyl]piperidin-4-yl]oxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide Into a 50 mL round bottom flask, was placed a solution of 2-[2-([1-[2-(4-[[2-(4-fluorophenyl)-5-hydroxy-3-methyl-1H-indol-1-yl]methyl]phenoxy)ethyl]piperidin-4-yl]oxy)ethoxy]acetic acid (25.0 mg, 0.04 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (19.0 mg, 0.04 mmol, 1.00 equiv), (benzotriazole-1-yloxy)-tris-(dimethylamino)phosphonium hexafluorophosphate (23.0 mg, 1.20 equiv) and N,N-diisopropylethylamine (17.0 mg, 0.13 mmol, 3.00 equiv) in N,N-dimethylformamide (2 mL) at 0° C. The resulting solution was stirred for 1 hour at 0° C. The reaction was then quenched by the addition of water. The resulting mixture was extracted with ethyl acetate (20 mL×2) and the organic layers were combined, washed with brine and dried over anhydrous sodium sulfate. The organic solvent was removed under reduced pressure and the residue was purified by prep-HPLC using the following conditions: column, X Bridge C18, 19×250 mm, 5 um; mobile phase A: water with ammonium bicarbonate (10 mM), mobile phase B: acetonitrile; flow rate: 20 mL/min; gradient: 27% B to 79% B in 12 min; detector: UV 220 & 254 nm. This resulted in 14.0 mg (33%) of (2S,4R)-1-[(2S)-2-[2-[2-([1-([2-(4-[[2-(4-fluorophenyl)-5-hydroxy-3-methyl-1H-indol-1-yl]methyl]phenoxy)ethyl]piperidin-4-yl]oxy)ethoxy]acetamido]-3,3-dimethylbutanoyl]-4-hydroxy-N-[[4-(4-methyl-1,3-thiazol-5-yl)phenyl]methyl]pyrrolidine-2-carboxamide as a white solid. $^1$H NMR (400 MHz, $CD_3OD$, ppm): δ 8.83 (s, 1H), 7.48-7.29 (m, 6H), 7.21-7.12 (m, 2H), 7.09 (d, J=8.8 Hz, 1H), 6.93 (s, 1H), 6.78-6.66 (m, 5H), 5.12 (s, 2H), 4.71 (s, 1H), 4.61-4.49 (m, 3H), 4.33 (m, 1H), 4.08-3.95 (m, 4H), 3.92-3.78 (m, 2H), 3.75-3.66 (m, 4H), 3.45 (m, 1H), 2.85 (m, 2H), 2.75 (m, 2H), 2.47 (s, 3H), 2.42-2.31 (m, 2H), 2.28-2.19 (m, 4H), 2.13-2.05 (m, 1H), 1.95 (m, 2H), 1.70 (m, 2H), 1.05 (s, 9H); [M/Z] calculated for $C_{55}H_{65}FN_6O_8S$: 988.46; Observed from LC-MS ($ES^+$): m/z 989.50 $[M+H]^+$; $t_R$=1.32 min (2.90 minute run).

Example #4: Preparation of (2S,4R)-4-hydroxy-1-[(2S)-2-[1-(4-{[5-hydroxy-2-(4-hydroxyphenyl)-3-methyl-1H-indol-1-yl]methyl}phenyl)-1,4,7,10-tetraoxadodecan-12-amido]-3,3-dimethylbutanoyl]-N-{[4-(4-methyl-1,3-thiazol-5-yl)phenyl]methyl}pyrrolidine-2-carboxamide

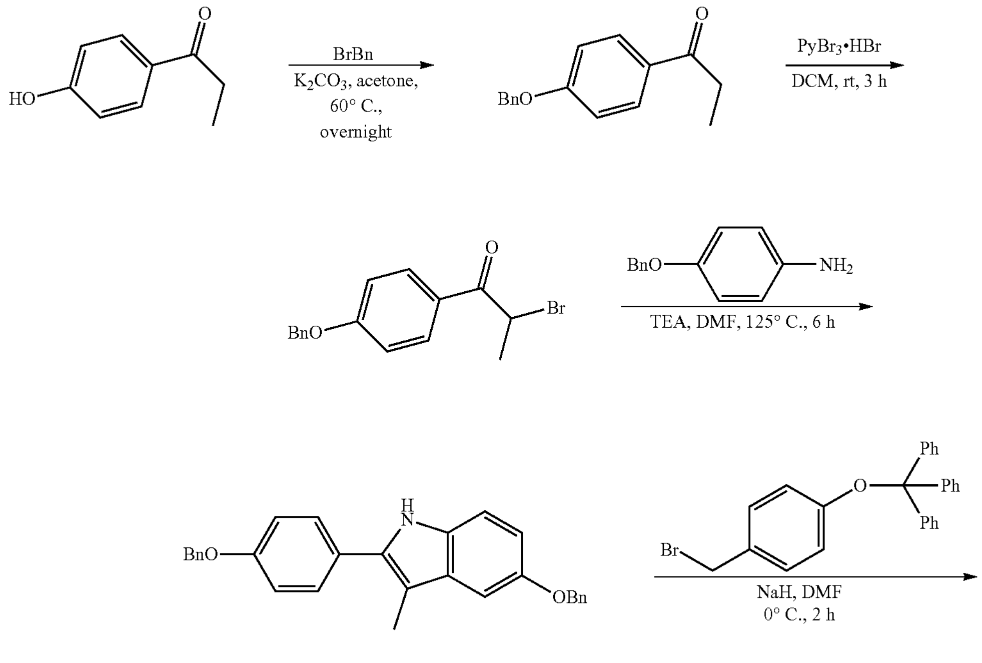

-continued
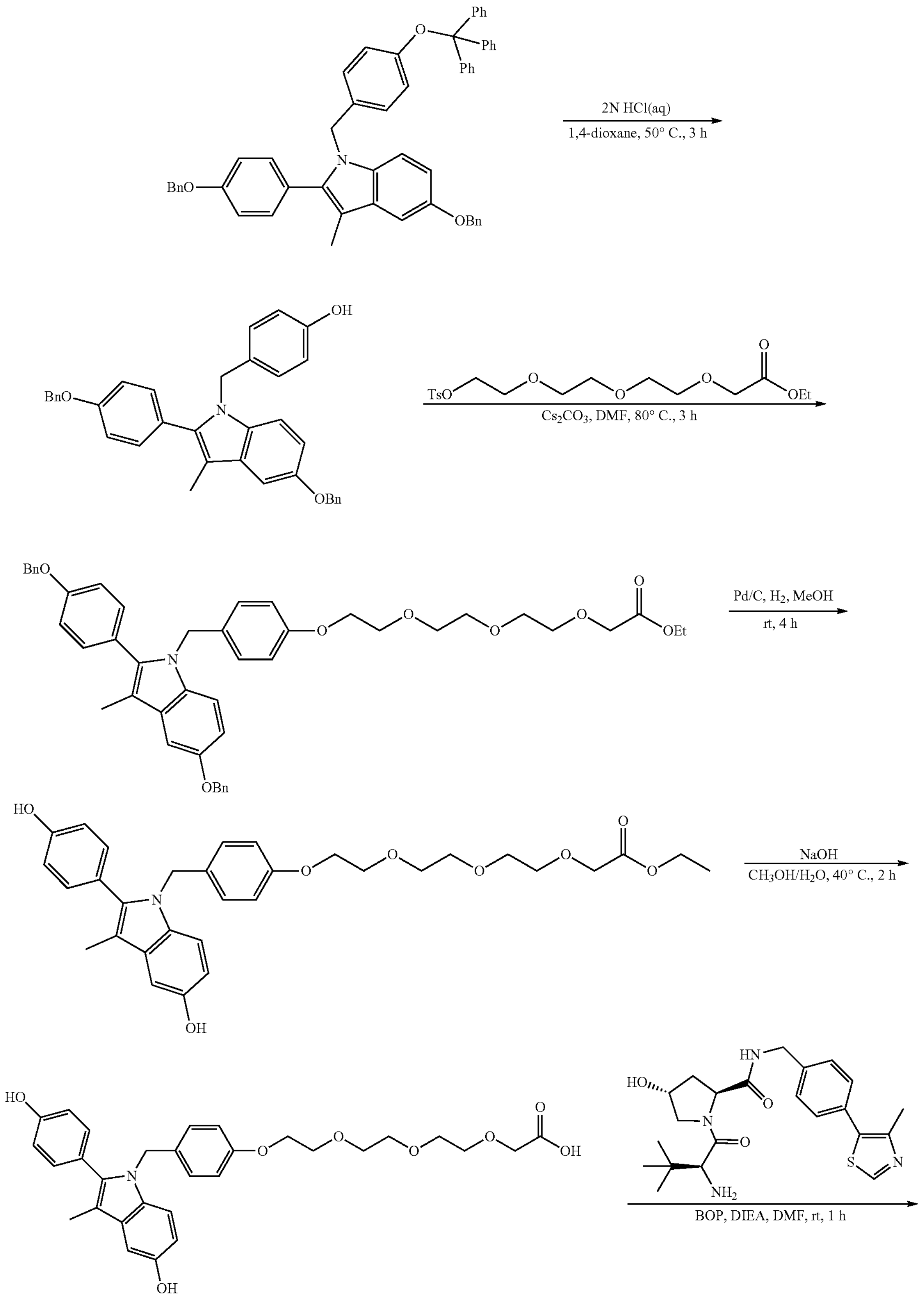

-continued

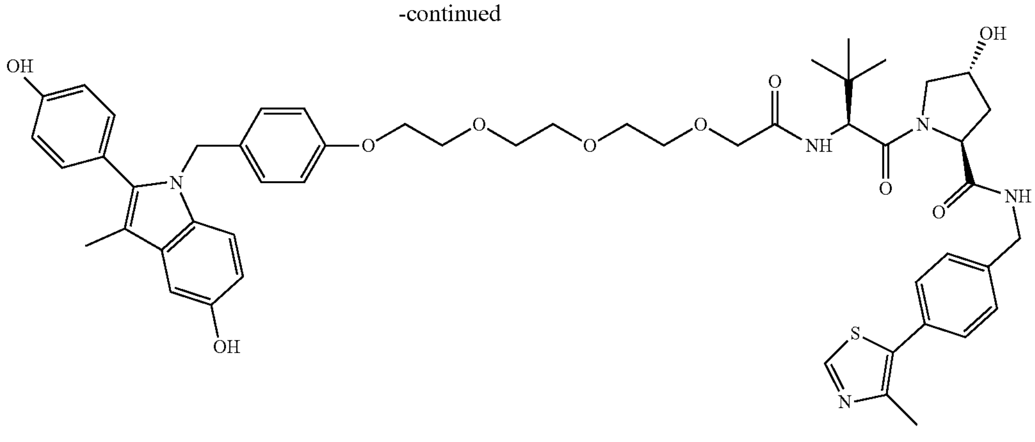

Step 1: Preparation of 1-[4-(benzyloxy)phenyl]propan-1-one

In a 250 mL round bottom flask, 1-(4-hydroxyphenyl) propan-1-one (20.0 g, 133.18 mmol, 1.00 equiv), (bromomethyl)benzene (23.0 g, 134.48 mmol, 1.00 equiv) and potassium carbonate (30.0 g, 2.00 equiv) were mixed in acetone (100 mL) at room temperature. The resulting solution was stirred overnight at 60° C. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure. This resulted in 25.0 g (78%) of 1-[4-(benzyloxy)phenyl]propan-1-one as white solid.

Step 2: Preparation 1-[4-(benzyloxy)phenyl]-2-bromopropan-1-one

In a 100 mL round bottom flask, $PyBr_3$.HBr (7.3 g, 22.88 mmol, 1.10 equiv) was added to a solution of 1-[4-(benzyloxy)phenyl]propan-1-one (5.0 g, 20.81 mmol, 1.00 equiv) in dichloromethane (40 mL) at room temperature. The resulting solution was stirred for 3 h at room temperature in an oil bath. The reaction was then quenched by the addition of water. The resulting mixture was extracted with dichloromethane (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:5). This resulted in 4.3 g (65%) of 1-[4-(benzyloxy)phenyl]-2-bromopropan-1-one as light yellow oil.

Step 3: Preparation of 5-(benzyloxy)-2-[4-(benzyloxy)phenyl]-3-methyl-1H-indole

In a 250 mL round bottom flask, 4-(benzyloxy)aniline (8.8 g, 44.34 mmol, 3.00 equiv) was added to a solution of 1-[4-(benzyloxy)phenyl]propan-1-one (4.3 g, 17.89 mmol, 1.00 equiv) in DMF/TEA (40/4.3 mL). The resulting solution was stirred for 6 hours at 125° C. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:5). This resulted in 1.7 g (23%) of 5-(benzyloxy)-2-[4-(benzyloxy)phenyl]-3-methyl-1H-indole as a light brown solid.

Step 4: Preparation of 5-(benzyloxy)-2-[4-(benzyloxy)phenyl]-3-methyl-1-[[4-(triphenylmethoxy)phenyl]methyl]-1H-indole In a 50 mL round bottom flask, sodium hydride (105.0 mg, 4.38 mmol, 1.10 equiv) was added to a solution of 5-(benzyloxy)-2-[4-(benzyloxy)phenyl]-3-methyl-H-indole (1.0 g, 2.38 mmol, 1.00 equiv) in N,N-dimethylformamide (20 mL) at 0° C. in a water/ice bath. The resulting mixture was stirred for 10 min at 0° C., and then was added by 1-(bromomethyl)-4-(triphenylmethoxy)benzene (1.3 g, 3.03 mmol, 1.30 equiv). The resulting mixture was stirred for 2 h at 0° C. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:5). This resulted in 1.2 g (66%) of 5-(benzyloxy)-2-[4-(benzyloxy)phenyl]-3-methyl-1-[[4-(triphenylmethoxy)phenyl]methyl]-1H-indole as brown solid.

Step 5: Preparation of 4-[[5-(benzyloxy)-2-[4-(benzyloxy)phenyl]-3-methyl-1H-indol-1-yl]methyl]phenol In a 50-mL round-bottom flask, HCl (2 M in water, 5 mL) was added to a solution of 5-(benzyloxy)-2-[4-(benzyloxy)phenyl]-3-methyl-1-[[4-(triphenylmethoxy) phenyl]methyl]-1H-indole (690.0 mg, 0.90 mmol, 1.00 equiv) in 1,4-dioxane (10 mL) at room temperature. The resulting solution was stirred for 3 h at 50° C. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:1). This resulted in 400.0 mg (85%) of 4-[[5-(benzyloxy)-2-[4-(benzyloxy)phenyl]-3-methyl-H-indol-1-yl]methyl]phenol as light yellow oil.

Step 6: Preparation of Ethyl 1-(4-[[5-(benzyloxy)-2-[4-(benzyloxy)phenyl]-3-methyl-1H-indol-1-yl]methyl]phenyl)-1,4,7,10-tetraoxadodecan-12-oate In a 50-mL round-bottom flask, 4-[[5-(benzyloxy)-2-[4-(benzyloxy)phenyl]-3-methyl-1H-indol-1-yl]methyl]phenol (300.0 mg, 0.57 mmol, 1.00 equiv), ethyl 2-(2-(2-(2-(tosyloxy)ethoxy)ethoxy)ethoxy)acetate (267.0 mg, 0.68 mmol, 1.20 equiv) and $Cs_2CO_3$ (372.0 mg, 1.14 mmol, 2.00 equiv) were mixed in N,N-dimethylformamide (10 mL) at room temperature. The resulting solution was stirred for 3 h at 80° C. The reaction was then quenched by the addition of water. The resulting solution was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:1). This resulted in 320.0 mg (75%) of ethyl 1-(4-[[5-(benzyloxy)-2-[4-(benzyloxy)phenyl]-3-methyl-1H-indol-1-yl]methyl]phenyl)-1,4,7,10-tetraoxadodecan-12-oate as light yellow liquid.

Step 7: Preparation of ethyl 1-(4-[[5-hydroxy-2-(4-hydroxyphenyl)-3-methyl-1H-indol-1-yl]methyl]phenyl)-1,4,7,10-tetraoxadodecan-12-oate In a 25-mL round-bottom flask, palladium (10%) on carbon (600 mg) was added to a solution of ethyl 1-(4-[[5-(benzyloxy)-2-[4-(benzyloxy)phenyl]-3-methyl-1H-indol-1-yl]methyl]phenyl)-1,4,7,10-tetraoxadodecan-12-oate (320.0 mg, 0.43 mmol, 1.00 equiv) in methanol (10 mL) at room temperature under nitrogen atmosphere. The reaction flask was vacuumed and charged with a hydrogen balloon. The resulting mixture was stirred for 4 hours at room temperature under hydrogen atmosphere. After the reaction was completed, the reaction mixture was filtered through a Celite pad and the filtrate was concentrated under reduced pressure and the residue was applied onto a silica gel column with ethyl acetate/petroleum ether (1:1). This resulted in 124.0 mg (51%) of ethyl 1-(4-[[5-hydroxy-2-(4-hydroxyphenyl)-3-methyl-1H-indol-1-yl]methyl]phenyl)-1,4,7,10-tetraoxadodecan-12-oate as light yellow oil.

Step 8: Preparation of 1-(4-[[5-hydroxy-2-(4-hydroxyphenyl)-3-methyl-1H-indol-1-yl]methyl]phenyl)-1,4,7,10-tetraoxadodecan-12-oic acid In a 25-mL round-bottom flask, sodium hydroxide (30.0 mg, 0.75 mmol, 3.00 equiv) was added to a solution of ethyl 1-(4-[[5-hydroxy-2-(4-hydroxyphenyl)-3-methyl-1H-indol-1-yl]methyl]phenyl)-1,4,7,10-tetraoxadodecan-12-oate (124.0 mg, 0.22 mmol, 1.00 equiv) in methanol/$H_2O$ (10/2 mL) at room temperature. The resulting solution was stirred for 2 h at 40° C. The reaction mixture was cooled to room temperature and was concentrated under reduced pressure. The remaining mixture was diluted with water (20 mL). The pH value of the resulting solution was adjusted to 4-5 with hydrogen chloride solution (1 M). The resulting mixture was extracted with ethyl acetate (20 mL×3) and the organic layers were combined, washed with brine and dried over anhydrous sodium sulfate. The organic solvent was removed under reduced pressure. This resulted in 115.0 mg (98%) of 1-(4-[[5-hydroxy-2-(4-hydroxyphenyl)-3-methyl-1H-indol-1-yl]methyl]phenyl)-1,4,7,10-tetraoxadodecan-12-oic acid as brown oil.

Step 9: Preparation of (2S,4R)-4-hydroxy-1-[(2S)-2-[1-(4-[[5-hydroxy-2-(4-hydroxyphenyl)-3-methyl-1H-indol-1-yl]methyl]phenyl)-1,4,7,10-tetraoxadodecan-12-amido]-3,3-dimethylbutanoyl]-N-[[4-(4-methyl-1,3-thiazol-5-yl)phenyl]methyl]pyrrolidine-2-carboxamide In a 25-mL round-bottom flask, 1-(4-[[5-hydroxy-2-(4-hydroxyphenyl)-3-methyl-H-indol-1-yl]methyl]phenyl)-1,4,7,10-tetraoxadodecan-12-oic acid (60.0 mg, 0.11 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (63.0 mg, 0.14 mmol, 1.20 equiv), BOP (60.0 mg, 0.14 mmol, 1.20 equiv), DIEA (0.3 mL, 5.00 equiv) were mixed in N,N-dimethylformamide (10 mL) at room temperature. The resulting solution was stirred for 1 h at room temperature. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was purified by prep-HPLC with the following conditions: column, X Bridge C18, 19×250 mm, 5 um; mobile phase A, water with ammonium bicarbonate (10 mM), mobile phase B, acetonitrile; flow rate: 20 mL/min; gradient, 10% B to 80% B in 12 min; detector: UV 254 nm. This resulted in 45.5 mg (43%) of (2S,4R)-4-hydroxy-1-[(2S)-2-[1-(4-[[5-hydroxy-2-(4-hydroxyphenyl)-3-methyl-1H-indol-1-yl]methyl]phenyl)-1,4,7,10-tetraoxadodecan-12-amido]-3,3-dimethylbutanoyl]-N-[[4-(4-methyl-1,3-thiazol-5-yl)phenyl]methyl]pyrrolidine-2-carboxamide as white solid. $^1$H NMR (300 MHz, methanol-$d_4$, ppm) δ 8.81 (s, 1H), 7.48-7.33 (m, 4H), 7.12 (d, J=8.4 Hz, 2H), 7.02 (d, J=8.7 Hz, 1H), 6.91 (s, 1H), 6.84 (m, 2H), 6.80-6.69 (m, 4H), 6.63 (m, 1H), 5.10 (s, 2H), 4.68 (s, 1H), 4.59-4.46 (m, 3H), 4.30 (d, J=15.5 Hz, 1H), 4.08-3.98 (m, 4H), 3.92-3.73 (m, 4H), 3.71-3.63 (m, 8H), 2.45 (s, 3H), 2.26-2.02 (m, 5H), 1.02 (s, 9H). [M/Z] calculated for $C_2H_{61}N_5O_{10}S$: 947.41; Observed from LC-MS ($ES^+$): m/z 948.20 $[M+H]^+$; $t_R$=1.32 min.

Example #5: (2S,4R)-4-hydroxy-1-[(2S)-2-[1-(4-[[5-hydroxy-2-(4-hydroxyphenyl)-3-methyl-1H-indol-1-yl]methyl]phenyl)-1,4,7,10-tetraoxadodecan-12-amido]-3,3-dimethylbutanoyl]-N-[(1S)-1-[4-(4-methyl-1,3-thiazol-5-yl)phenyl]ethyl]pyrrolidine-2-carboxamide

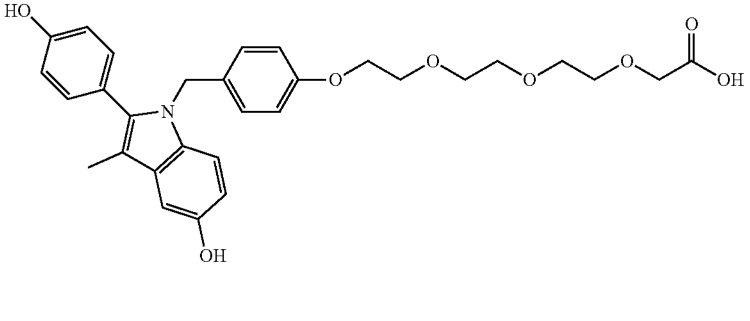

+

-continued

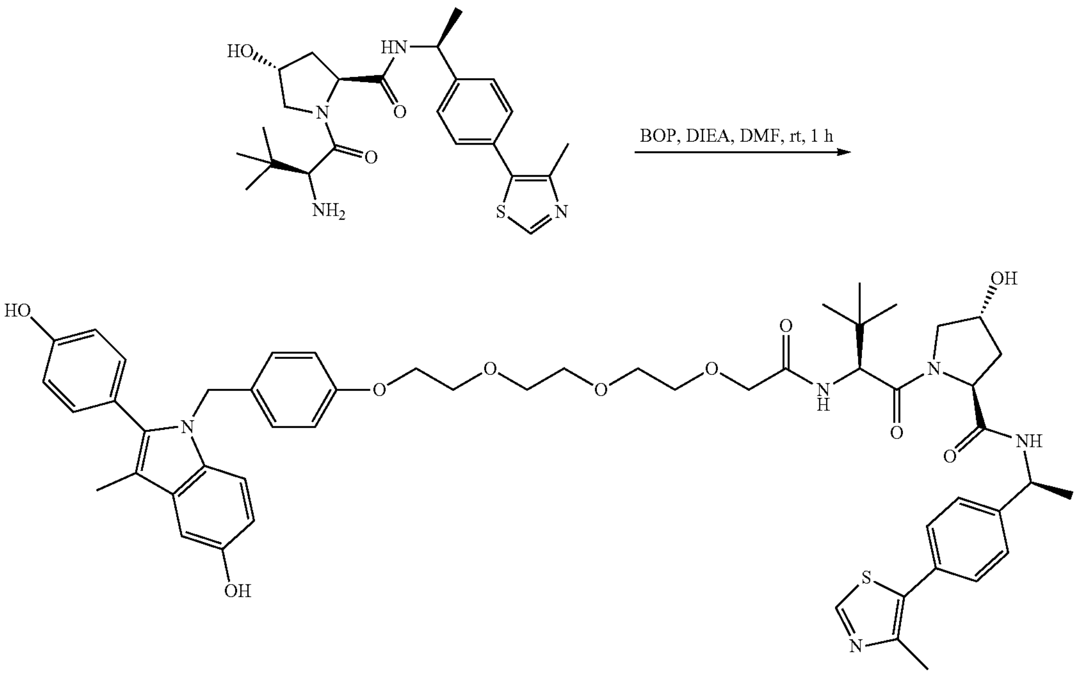

In a 25-mL round-bottom flask, 1-(4-[[5-hydroxy-2-(4-hydroxyphenyl)-3-methyl-1H-indol-1-yl]methyl]phenyl)-1,4,7,10-tetraoxadodecan-12-oic acid (60.0 mg, 0.11 mmol, 1.00 equiv), (2S,4R)-1-((S)-2-amino-3,3-dimethylbutanoyl)-4-hydroxy-N—((S)-1-(4-(4-methylthiazol-5-yl)phenyl)ethyl)pyrrolidine-2-carboxamide (65.0 mg, 0.14 mmol, 1.20 equiv), BOP (60.0 mg, 0.14 mmol, 1.20 equiv) and N,N-diisopropylethylamine (0.3 mL, 5.00 equiv) were mixed in N,N-dimethylformamide (10 mL) at room temperature. The resulting solution was stirred for 1 h at room temperature. The reaction was then quenched by the addition of water (10 mL). The resulting mixture was extracted with ethyl acetate (10 mL×3) and the organic layers were combined, washed with brine and dried over anhydrous sodium sulfate. The organic solvent was removed under reduced pressure and the residue was purified by prep-HPLC with the following conditions: column, X Bridge C18, 19×250 mm, 5 um; mobile phase A, water with ammonium bicarbonate (10 mM), mobile phase B, acetonitrile; flow rate: 20 mL/min; gradient, 10% B to 80% B in 12 min; detector: UV 254 nm. This resulted in 50.2 mg (47%) of (2S,4R)-4-hydroxy-1-[(2S)-2-[1-(4-[[5-hydroxy-2-(4-hydroxyphenyl)-3-methyl-1H-indol-1-yl]methyl]phenyl)-1,4,7,10-tetraoxadodecan-12-amido]-3,3-dimethylbutanoyl]-N-[(1S)-1-[4-(4-methyl-1,3-thiazol-5-yl)phenyl]ethyl]pyrrolidine-2-carboxamide as white solid. $^1$H NMR (300 MHz, methanol-$d_4$, ppm) δ 8.86 (s, 1H), 7.48-7.33 (m, 4H), 7.18-7.07 (m, 2H), 7.02 (d, J=8.7 Hz, 1H), 6.89 (s, 1H), 6.88-6.71 (m, 6H), 6.64 (dd, J=8.6, 2.4 Hz, 1H), 5.10 (d, J=3.7 Hz, 2H), 4.99 (q, J=7.0 Hz, 1H), 4.67 (s, 1H), 4.62-4.50 (m, 1H), 4.43 (m, 1H), 4.11-3.97 (m, 4H), 3.89-3.75 (m, 4H), 3.74-3.65 (m, 8H), 2.47 (s, 3H), 2.16 (m, 4H), 2.07-1.88 (m, 1H), 1.57-1.45 (m, 3H), 1.02 (s, 9H). [M/Z] calculated for $C_{53}H_{63}N_5O_{10}S$: 961.43; Observed from LC-MS ($ES^+$): m/z 962.20 $[M+H]^+$; $t_R$=1.32 min.

Example #6: (2S,4R)-1-[(2S)-2-[1-(4-[[2-(4-bromophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide

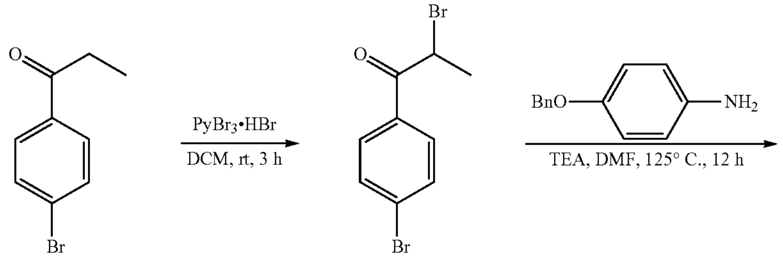

-continued
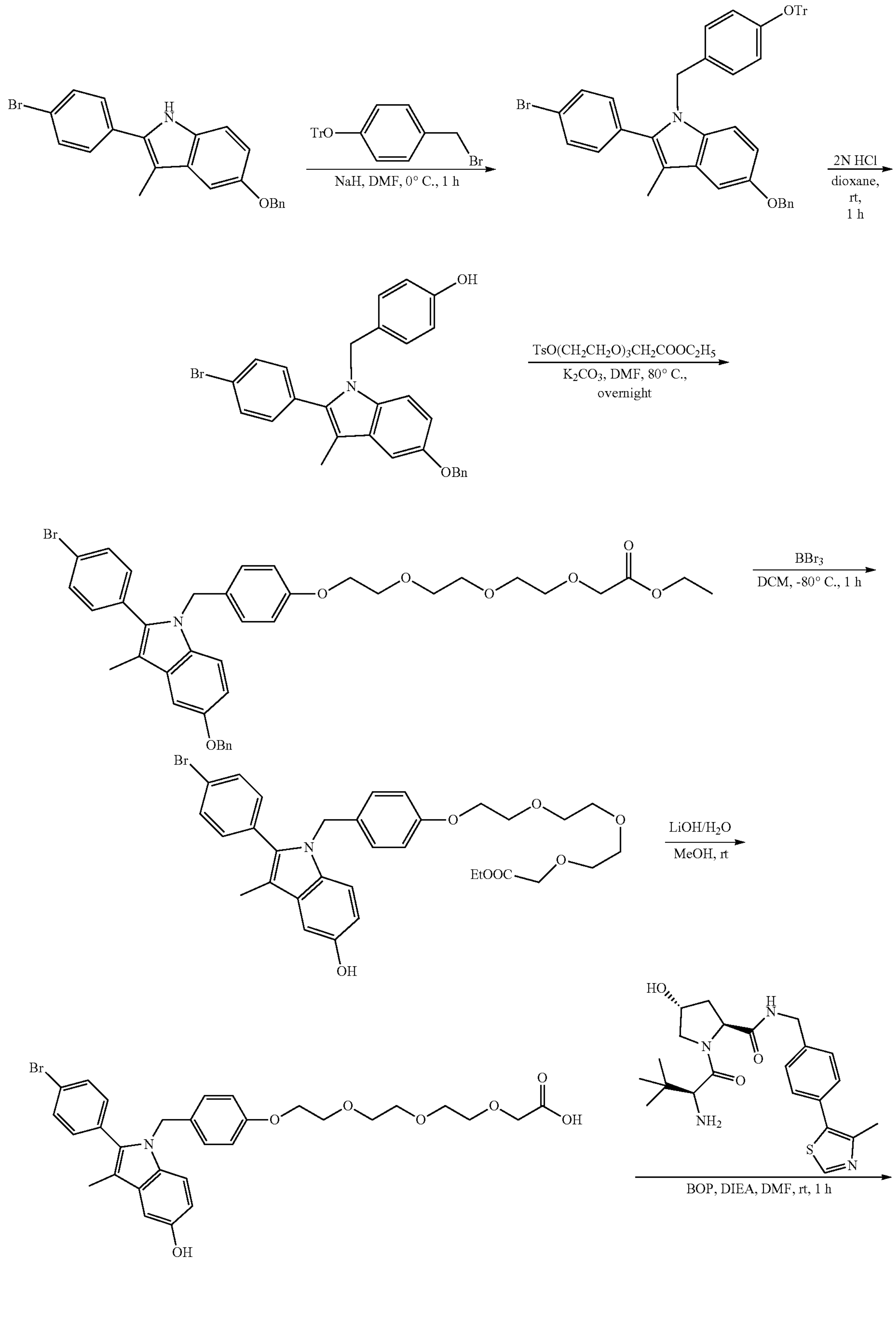

-continued

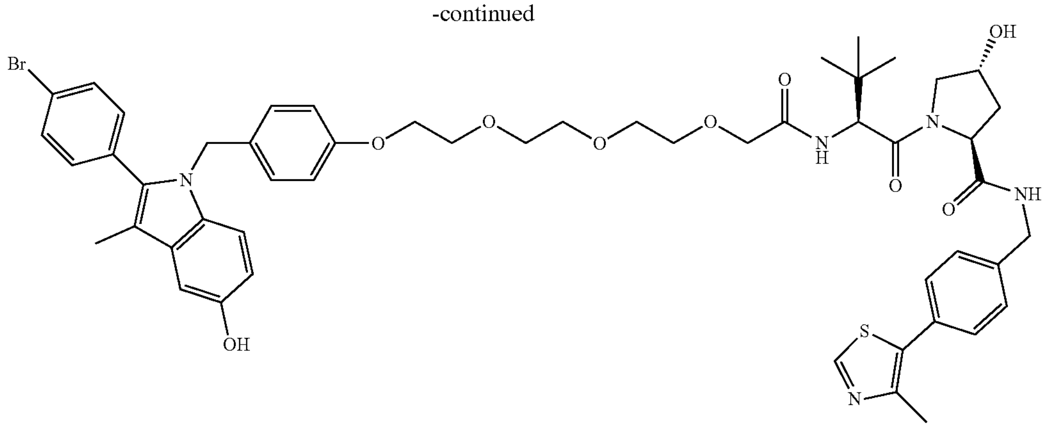

Step 1: Preparation of 2-bromo-1-(4-bromophenyl) propan-1-one

Into a 250-mL round-bottom flask, was placed a solution of 1-(4-bromophenyl) propan-1-one (5.0 g, 23.47 mmol, 1.00 equiv) and pyridinium bromide perbromide (8.3 g, 26.02 mmol, 1.10 equiv) in dichloromethane (100 mL) at room temperature. The resulting solution was stirred for 3 hours at room temperature. The reaction was then quenched by the addition of water. The resulting mixture was extracted with dichloromethane (100 mL×2) and the organic layers were combined, washed with brine and dried over anhydrous sodium sulfate. The solids were filtered out. The resulting mixture was concentrated under vacuum. The residue was applied onto a silica gel column eluting with ethyl acetate/petroleum ether (v:v=1:15). This resulted in 5.0 g (73%) of 2-bromo-1-(4-bromophenyl)propan-1-one as yellow solid.

Step 2: Preparation of 5-benzyloxy-2-(4-bromophenyl)-3-methyl-1H-indole

Into a 100-mL round-bottom flask, was placed a solution of 2-bromo-1-(4-bromophenyl) propan-1-one (2.9 g, 9.93 mmol, 1.00 equiv), 4-(benzyloxy) aniline (3.0 g, 15.06 mmol, 1.50 equiv) and triethylamine (3.0 mL) in N, N-dimethylformamide (30 mL) at room temperature. The resulting solution was stirred for 12 hours at 125° C. The reaction was then quenched by the addition of water. The resulting mixture was extracted with ethyl acetate (100 mL×2) and the organic layers were combined, washed with brine and dried over anhydrous sodium sulfate. The solids were filtered out. The resulting mixture was concentrated under vacuum. The residue was applied onto a silica gel column eluting with ethyl acetate/petroleum ether (v:v=1:2). This resulted in 1.3 g (33%) of 5-benzyloxy-2-(4-bromophenyl)-3-methyl-1H-indole as yellow solid.

Step 3: Preparation of 5-benzyloxy-2-(4-bromophenyl)-3-methyl-1-[[4-(triphenylmethoxy)phenyl] methyl]-1H-indole Into a 50 mL round-bottom flask purged and maintained with an inert atmosphere of nitrogen, NaH (60% in oil, 150.0 mg, 6.25 mmol, 1.50 equiv) was added to a solution of 5-benzyloxy-2-(4-bromophenyl)-3-methyl-1H-indole (1.0 g, 2.55 mmol, 1.00 equiv) in N, N-dimethylformamide (20 mL) at 0° C. The resulting mixture was stirred for 10 min at 0° C. and was followed by the addition of 1-(bromomethyl)-4-(triphenylmethoxy)-benzene (1.1 g, 2.56 mmol, 1.00 equiv). The reaction mixture was stirred for 1 hour at 0° C. Then the reaction was quenched by the addition of water. The resulting mixture was extracted with ethyl acetate (100 mL×2) and the organic layers were combined, washed with brine and dried over anhydrous sodium sulfate. The solids were filtered out. The resulting mixture was concentrated under vacuum. The residue was applied onto a silica gel column eluting with ethyl acetate/petroleum ether (v:v=1:3). This resulted in 720.0 mg (38%) of 5-(benzyloxy)-2-(4-bromophenyl)-3-methyl-1-[[4-(triphenylmethoxy)phenyl] methyl]-1H-indole as light yellow oil. LC-MS ($ES^+$): m/z 740.71 $[M+H]^+$; $t_R$=4.00 min (4.80 minute run).

Step 4: Preparation of 4-[[5-(benzyloxy)-2-(4-bromophenyl)-3-methyl-1H-indol-1-yl]-methyl]-phenol Into a 100 mL round-bottom flask, hydrogen chloride (2 N in water, 5 mL) was added to a solution of 5-(benzyloxy)-2-(4-bromophenyl)-3-methyl-1-[[4-(triphenylmethoxy) phenyl]methyl]-1H-indole (600.0 mg, 0.81 mmol, 1.00 equiv) in dioxane (30 mL) at room temperature. The resulting solution was stirred for 1 hour at room temperature. The reaction mixture was extracted with ethyl acetate (50 mL×2) and the organic layers were combined, washed with brine and dried over anhydrous sodium sulfate. The solids were filtered out. The resulting mixture was concentrated under vacuum. The residue was applied onto a silica gel column eluting with ethyl acetate/petroleum ether (v:v=1:2). This resulted in 320.0 mg (79%) of 4-[[5-(benzyloxy)-2-(4-bromophenyl)-3-methyl-1H-indol-1-yl]methyl]phenol as yellow oil.

Step 5: Preparation of ethyl 1-(4-[[5-(benzyloxy)-2-(4-bromophenyl)-3-methyl-1H-indol-1-yl] methyl] phenyl)-1, 4, 7, 10-tetraoxadodecan-12-oate Into a 50 mL round-bottom flask, was placed a solution of 4-[[5-(benzyloxy)-2-(4-bromophenyl)-3-methyl-1H-indol-1-yl]methyl]phenol (200.0 mg, 0.40 mmol, 1.00 equiv), ethyl 2-(2-(2-(2-(tosyloxy)ethoxy)ethoxy)ethoxy)acetate (156.0 mg, 0.40 mmol, 1.00 equiv) and potassium carbonate (110.0 mg, 0.80 mmol, 2.00 equiv) in N,N-dimethylformamide (10 mL) at room temperature. The resulting solution was stirred overnight at 80° C. The reaction was then quenched by the addition of water. The resulting mixture was extracted with ethyl acetate (50 mL×2) and the organic layers were combined, washed with brine and dried over anhydrous sodium sulfate. The solids were filtered out. The resulting mixture was concentrated under vacuum. The residue was applied onto a silica gel column eluting with ethyl acetate/petroleum ether (v:v=1:2). This resulted in 180.0 mg (63%) of ethyl 1-(4-[[5-(benzyloxy)-2-(4-bromophenyl)-3-methyl-H-indol-1-yl]methyl]phenyl)-1,4,7,10-tetraoxadodecan-12-oate as yellow oil. LC-MS ($ES^+$): m/z 716.00 $[M+H]^+$; $t_R$=1.32 min (1.90 minute run).

Step 6: Preparation of ethyl 1-(4-[[2-(4-bromophenyl)-5-hydroxy-3-methyl-1H-indol-1-yl] methyl] phenyl)-1, 4, 7, 10-tetraoxadodecan-12-oate Into a 50 mL 3-necked round-bottom flask, was placed a solution of ethyl 1-(4-[[5-(benzyloxy)-2-(4-bromophenyl)-3-methyl-H-indol-1-yl]methyl] phenyl)-1, 4, 7, 10-tetraoxadodecan-12-oate (170.0 mg, 0.24 mmol, 1.00 equiv) in dichloromethane (10 mL) at −80° C. This was followed by the addition of boron tribromide (1 M in dichloromethane) (0.16 mL, 2.00 equiv) at −80° C. The resulting solution was stirred for 1 hour at −80° C. The reaction was then quenched by the addition of water. The resulting mixture was extracted with ethyl acetate (50 mL×2) and the organic layers were combined, washed with brine and dried over anhydrous sodium sulfate. The solids were filtered out. The resulting mixture was concentrated under vacuum. This resulted in 100.0 mg (67%) of ethyl 1-(4-[[2-(4-bromophenyl)-5-hydroxy-3-methyl-1H-indol-1-yl]methyl]phenyl)-1,4,7,10-tetraoxadodecan-12-oate as brown oil.

Step 7: Preparation of 1-(4-[[2-(4-bromophenyl)-5-hydroxy-3-methyl-1H-indol-1-yl] methyl] phenyl)-1, 4, 7, 10-tetraoxadodecan-12-oic acid Into a 50 mL round-bottom flask, was placed a solution of ethyl 1-(4-[[2-(4-bromophenyl)-5-hydroxy-3-methyl-1H-indol-1-yl]methyl]phenyl)-1,4,7,10-tetraoxadodecan-12-oate (100.0 mg, 0.16 mmol, 1.00 equiv), lithium hydroxide (19.2 mg, 0.80 mmol, 5.00 equiv) in water (2 mL)/methanol (10 mL) at room temperature. The resulting solution was stirred for 1 hour at room temperature. The pH value of the solution was adjusted to 2 using hydrogen chloride solution (2 N). The resulting solution was extracted with ethyl acetate (50 mL×2) and the organic layers were combined, washed with brine and dried over anhydrous sodium sulfate. The solids were filtered out. The resulting mixture was concentrated under vacuum. This resulted in 76.0 mg (80%) of 1-(4-[[2-(4-bromophenyl)-5-hydroxy-3-methyl-1H-indol-1-yl] methyl]phenyl)-1,4,7,10-tetraoxadodecan-12-oic acid as yellow oil. LC-MS ($ES^+$): m/z 597.90 $[M+H]^+$; $t_R$=1.01 min (1.90 minute run).

Step 8: Preparation of (2S,4R)-1-[(2S)-2-[1-(4-[[2-(4-bromophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide Into a 10 mL round bottom flask, was placed a solution of 1-(4-[[2-(4-bromophenyl)-5-hydroxy-3-methyl-1H-indol-1-yl]methyl]phenyl)-1,4,7,10-tetraoxadodecan-12-oic acid (150.0 mg, 0.25 mmol, 1.00 equiv), (2S,4R)-1-[(2S)-2-amino-3,3-dimethylbutanoyl]-4-hydroxy-N-[[4-(4-methyl-1,3-thiazol-5-yl) phenyl] methyl]pyrrolidine-2-carboxamide (105.0 mg, 0.24 mmol, 1.00 equiv), (benzotriazole-1-yloxy) tris (dimethylamino) phosphonium hexafluorophosphate (111.0 mg, 0.25 mmol, 1.00 equiv) and N,N-diisopropylethylamine (65.0 mg, 0.50 mmol, 2.00 equiv) in N,N-dimethylformamide (2 mL) at room temperature. The resulting solution was stirred for 1 hour at room temperature. The reaction was then quenched by the addition of water. The resulting mixture was extracted with ethyl acetate (50 mL×2) and the organic layers were combined, washed with brine and dried over anhydrous sodium sulfate. The solids were filtered out. The resulting mixture was concentrated under vacuum. The crude product was purified by prep-HPLC using the following conditions: Column, XBridge Shield $RP_{18}$ OBD Column, Sum, 19×150 mm; mobile phase A, water with ammonium bicarbonate (10 mM), mobile phase B, acetonitrile; isocratic 57.0% B in 11 min; Detector, UV 254 nm. This resulted in 30.0 mg (12%) of (2S,4R)-1-[(2S)-2-[1-(4-[[2-(4-bromophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide as white solid. $^1H$ NMR (400 MHz, $CD_3OD$, ppm): δ 8.88 (s, 1H), 7.61-7.55 (m, 2H), 7.48-7.36 (m, 4H), 7.28-7.22 (m, 2H), 7.09 (m, 1H), 6.95 (s, 1H), 6.79-6.68 (m, 5H), 5.17 (s, 2H), 4.69 (s, 1H), 4.61-4.48 (m, 3H), 4.30 (m, 1H), 4.09-3.98 (m, 4H), 3.91-3.76 (m, 4H), 3.75-3.65 (m, 8H), 2.47 (s, 3H), 2.29-2.18 (m, 4H), 2.16-2.05 (m, 1H), 1.03 (s, 9H); [M/Z] calculated for $C_2H_{60}BrN_5O_9S$: 1011.33 ($Br^{81}$); Observed from LC-MS ($ES^+$): m/z 1012.05 $[M+H]^+$; $t_R$=1.64 min (3.00 minute run).

Example #7: (2S,4R)-1-[(2S)-2-[1-(4-[[2-(4-chlorophenyl)-5-hydroxy-3-methyl-1H-indol-1-yl] methyl] phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide

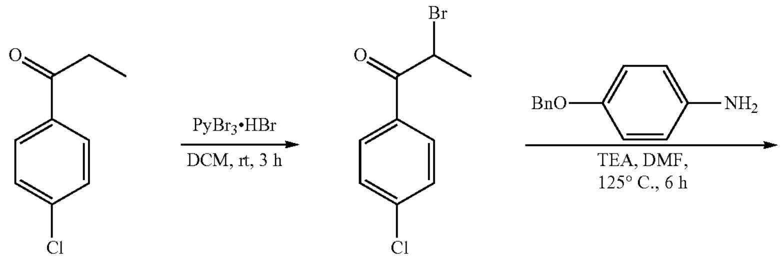

-continued
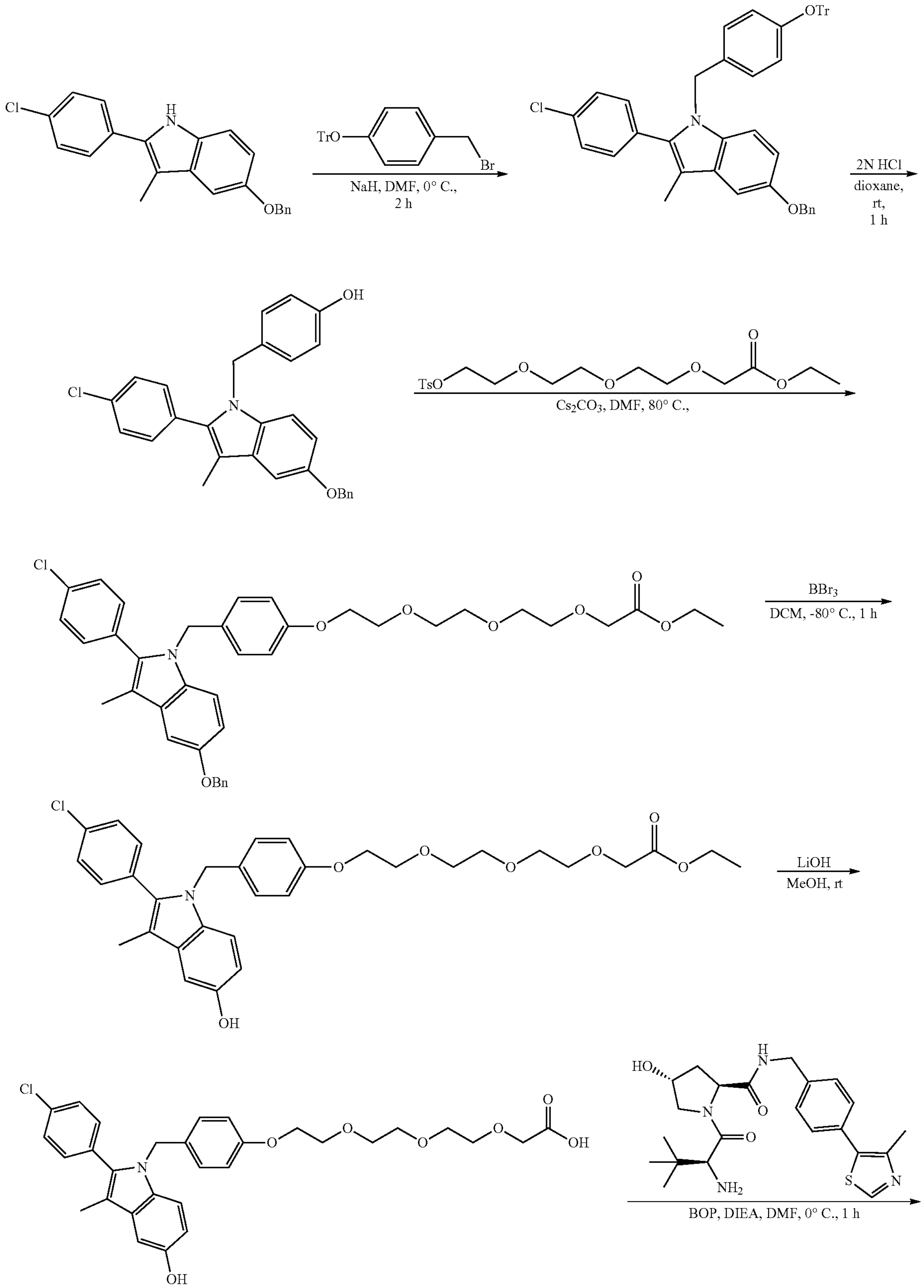

-continued

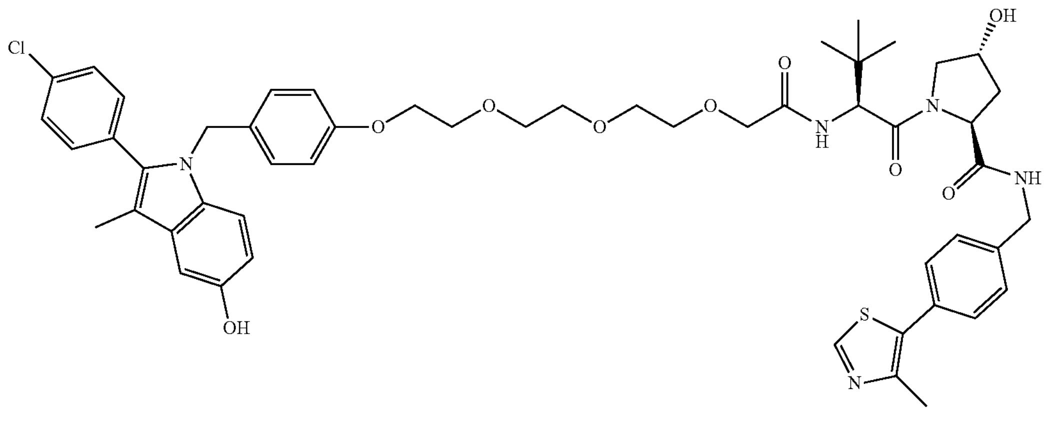

Step 1: Preparation of 2-bromo-1-(4-chlorophenyl) propan-1-one

In a 100 mL round bottom flask, $PyBr_3$.HBr (8.3 g, 26.02 mmol, 1.10 equiv) was added to a solution of 1-(4-chlorophenyl) propan-1-one (5.0 g, 23.47 mmol, 1.00 equiv) in dichloromethane (40 mL) at room temperature. The resulting solution was stirred for 3 h at room temperature. The reaction was then quenched by the addition of water. The resulting mixture was extracted with dichloromethane (100 mL×3) and the organic layers were combined, washed with brine and dried over anhydrous sodium sulfate. The organic solvent was removed under reduced pressure and the residue was applied onto a silica gel column eluting with ethyl acetate/petroleum ether (v:v=1:5). This resulted in 5.0 g (73%) of 2-bromo-1-(4-chlorophenyl)propan-1-one as a yellow solid.

Step 2: Preparation of 5-(benzyloxy)-2-(4-chlorophenyl)-3-methyl-1H-indole

In a 250 mL round bottom flask, 4-(benzyloxy)benzenamine (3.0 g, 15.06 mmol, 1.50 equiv) was added to a solution of 2-bromo-1-(4-chlorophenyl) propan-1-one (2.9 g, 9.93 mmol, 1.00 equiv) in DMF (30 mL)/TEA (3 mL). The resulting solution was stirred for 6 hours at 125° C. The reaction was then quenched by the addition of water. The resulting mixture was extracted with ethyl acetate (100 mL×3) and the organic layers were combined, washed with brine and dried over anhydrous sodium sulfate. The organic solvent was removed under reduced pressure and the residue was applied onto a silica gel column eluting with ethyl acetate/petroleum ether (v:v=1:2). This resulted in 1.3 g (33%) of 5-(benzyloxy)-2-(4-chlorophenyl)-3-methyl-1H-indole as a yellow solid. LC-MS ($ES^+$): m/z 348.10 $[M+H]^+$, $t_R$=1.40 min (1.90 minute run).

Step 3: Preparation of 5-(benzyloxy)-2-(4-chlorophenyl)-3-methyl-1-[[4-(triphenylmethoxy)phenyl] methyl]-1H-indole In a 50 mL round bottom flask, sodium hydride (190.0 mg, 7.92 mmol, 1.50 equiv) was added to a solution of 5-(benzyloxy)-2-(4-chlorophenyl)-3-methyl-1H-indole (1.1 g, 3.16 mmol, 1.00 equiv) in N,N-dimethylformamide (20 mL) at 0° C. in a water/ice bath. The resulting mixture was stirred for 10 min at 0° C., and then 1-(bromomethyl)-4-(triphenylmethoxy)benzene (1.4 g, 3.26 mmol, 1.00 equiv) was added. The resulting mixture was stirred for 2 h at 0° C. The reaction was then quenched by the addition of water. The resulting mixture was extracted with ethyl acetate (25 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:5). This resulted in 800.0 mg (36%) of 5-(benzyloxy)-2-(4-chlorophenyl)-3-methyl-1-[[4-(triphenylmethoxy)phenyl]methyl]-1H-indole as a yellow solid. LC-MS ($ES^+$): m/z 696.20 $[M+H]^+$, $t_R$=1.62 min (1.90 minute run).

Step 4: Preparation of 4-[[5-(benzyloxy)-2-(4-chlorophenyl)-3-methyl-1H-indol-1-yl]methyl]phenol In a 50 mL round bottom flask, HCl (2 M in water, 2 mL) was added to a solution of 5-(benzyloxy)-2-(4-chlorophenyl)-3-methyl-1-[[4-(triphenylmethoxy) phenyl] methyl]-1H-indole (800.0 mg, 1.15 mmol, 1.00 equiv) in 1,4-dioxane (10 mL) at room temperature. The resulting solution was stirred for 1 h at room temperature. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (1:1). This resulted in 280.0 mg (54%) of 4-[[5-(benzyloxy)-2-(4-chlorophenyl)-3-methyl-1H-indol-1-yl]methyl]phenol as yellow solid.

$^1$H NMR (400 MHz, $CDCl_3$): δ 7.51 (m, 2H), 7.44 (m, 5H), 7.24 (m, 2H), 7.15 (m, 1H), 7.10 (m, 1H), 6.91 (m, 1H), 6.78 (d, J=8.8 Hz, 2H), 6.68 (m, 2H), 5.13 (s, 2H), 5.09 (s, 2H), 2.24 (s, 3H); LC-MS ($ES^+$): m/z 453.95 $[M+H]^+$, $t_R$=1.36 min (2.00 minute run).

Step 5: Preparation of ethyl 1-(4-[[5-(benzyloxy)-2-(4-chlorophenyl)-3-methyl-1H-indol-1-yl] methyl] phenyl)-1, 4, 7, 10-tetraoxadodecan-12-oate In a 100 mL round bottom flask, was placed a solution of 4-[[5-(benzyloxy)-2-(4-chlorophenyl)-3-methyl-1H-indol-1-yl]methyl]phenol (250.0 mg, 0.55 mmol, 1.00 equiv), ethyl 2-[2-[2-(2-[[(4-methylbenzene)sulfonyl]oxy]ethoxy) ethoxy]ethoxy]acetate (258.0 mg, 0.66 mmol, 1.20 equiv) and potassium carbonate (228.0 mg, 1.65 mmol, 3.00 equiv) in N,N-dimethylformamide (10 mL) at room temperature. The resulting solution was stirred overnight at 80° C. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure and the residue was applied onto a silica gel column eluting with ethyl acetate/petroleum ether (v:v=1:2). This resulted in 200.0 mg (54%) of ethyl 1-(4-[[5-(benzyloxy)-2-(4-chlorophenyl)-3-methyl-1H-indol-1-yl]methyl]phenyl)-1,4,7,10-tetraoxadodecan-12-oate as yellow oil. LC-MS ($ES^+$): m/z 672.30 $[M+H]^+$, $t_R$=1.49 min (1.90 minute run).

Step 6: Preparation of ethyl 1-(4-[[2-(4-chlorophenyl)-5-hydroxy-3-methyl-1H-indol-1-yl] methyl] phenyl)-1, 4, 7, 10-tetraoxadodecan-12-oate Into a 50 mL 3-necked round-bottom flask, was placed a solution of ethyl 1-(4-[[5-(benzyloxy)-2-(4-chlorophenyl)-3-methyl-H-indol-1-yl] methyl] phenyl)-1, 4, 7, 10-tetraoxadodecan-12-oate (100.0 mg, 0.15 mmol, 1.00 equiv) in dichloromethane (5 mL) at −80° C. This was followed by the addition of boron tribromide (1 M in dichloromethane, 0.45 mL, 0.44 mmol, 2.98 equiv) dropwise at −80° C. The resulting solution was stirred for 1 hour at −80° C. The reaction was then quenched by the addition of water. The resulting mixture was extracted with ethyl acetate (50 mL×2) and the organic layers were combined, washed with brine and dried over anhydrous sodium sulfate. The solids were filtered out. The resulting mixture was concentrated under vacuum. This resulted in 80.0 mg (92%) of ethyl 1-(4-[[2-(4-chlorophenyl)-5-hydroxy-3-methyl-1H-indol-1-yl]methyl]phenyl)-1,4,7,10-tetraoxadodecan-12-oate as yellow oil. LC-MS ($ES^+$): m/z 582.00 $[M+H]^+$, $t_R$=1.11 min (1.90 minute run).

Step 7: Preparation of 1-(4-[[2-(4-chlorophenyl)-5-hydroxy-3-methyl-1H-indol-1-yl] methyl] phenyl)-1, 4, 7, 10-tetraoxadodecan-12-oic acid Into a 50 mL round bottom flask, was placed a solution of ethyl 1-(4-[[2-(4-chlorophenyl)-5-hydroxy-3-methyl-1H-indol-1-yl]methyl]phenyl)-1,4,7,10-tetraoxadodecan-12-oate (80.0 mg, 0.14 mmol, 1.00 equiv), lithium hydroxide (16.0 mg, 5 equiv) in methanol (5 mL)/water (0.5 mL). The resulting solution was stirred for 1 hour at room temperature. The pH value of the solution was adjusted to 1 with HCl solution (2 N). The resulting mixture was extracted with ethyl acetate (100 mL×2) and the organic layers were combined, washed with brine and dried over anhydrous sodium sulfate. The organic solvent was removed under reduced pressure. This resulted in 75.0 mg (98%) of 1-(4-[[2-(4-chlorophenyl)-5-hydroxy-3-methyl-1H-indol-1-yl] methyl]phenyl)-1,4,7,10-tetraoxadodecan-12-oic acid as yellow oil. LC-MS ($ES^+$): m/z 554.20 $[M+H]^+$, $t_R$=1.09 min (1.90 minute run).

Step 8: Preparation of (2S,4R)-1-[(2S)-2-[1-(4-[[2-(4-chlorophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl]pyrrolidine-2-carboxamide Into a 50 mL round-bottom flask, was placed a solution of 1-(4-[[2-(4-chlorophenyl)-5-hydroxy-3-methyl-1H-indol-1-yl]methyl]phenyl)-1,4,7,10-tetraoxadodecan-12-oic acid (75.0 mg, 0.14 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide (58.0 mg, 0.13 mmol, 1.00 equiv), (benzotriazole-1-yloxy) tris (dimethylamino) phosphonium hexafluorophosphate (72.0 mg, 1.20 equiv), N,N-diisopropylethylamine (52.0 mg, 0.40 mmol, 3.00 equiv) in N,N-dimethylformamide (2 mL) at 0° C. The resulting solution was stirred for 1 hour at 0° C. The reaction was then quenched by the addition of water. The reaction was then quenched by the addition of water. The resulting mixture was extracted with ethyl acetate (100 mL×2) and the organic layers were combined, washed with brine and dried over anhydrous sodium sulfate. The organic solvent was removed under reduced pressure and the residue was purified by prep-HPLC using the following conditions: column, XBridge Shield $RP_{18}$ OBD column, Sum, 19×150 mm; mobile phase A, water with ammonium bicarbonate (10 mM), mobile phase B, acetonitrile; isocratic 57.0% B in 11 min; detector, UV 254 nm. This resulted in 24.0 mg (18%) of (2S,4R)-1-[(2S)-2-[1-(4-[[2-(4-chlorophenyl)-5-hydroxy-3-methyl-1H-indol-1-yl]methyl]phenyl)-1,4,7,10-tetraoxadodecan-12-amido]-3,3-dimethylbutanoyl]-4-hydroxy-N-[[4-(4-methyl-1,3-thiazol-5-yl)phenyl]methyl] pyrrolidine-2-carboxamide as a white solid. $^1$H NMR (400 MHz, $CD_3OD$, ppm): δ 8.86 (s, 1H), 7.48-7.38 (m, 6H), 7.28 (d, J=8.0 Hz, 2H), 7.09 (d, J=8.4 Hz, 1H), 6.95 (s, 1H), 6.78-6.68 (m, 5H), 5.14 (s, 2H), 4.69 (m, 1H), 4.60-4.48 (m, 3H), 4.37-4.29 (m, 1H), 4.05-3.97 (m, 4H), 3.89-3.74 (m, 4H), 3.72-3.65 (m, 8H), 2.47 (s, 3H), 2.29-2.18 (m, 4H), 2.11-2.04 (m, 1H), 1.03 (s, 9H); [M/Z] calculated for $C_2H_{60}ClN_5O_9S$: 965.38; Observed from LC-MS ($ES^+$): m/z 966.20 $[M+H]^+$; $t_R$=2.66 min (5.00 minute run).

Example #8: (2S,4R)-4-hydroxy-1-[(2S)-2-(1-[4-[(5-hydroxy-3-methyl-2-phenyl-1H-indol-1-yl)methyl]phenyl]-1,4,7,10-tetraoxadodecan-12-amido)-3,3-dimethylbutanoyl]-N-[[4-(4-methyl-1,3-thiazol-5-yl)phenyl]methyl]pyrrolidine-2-carboxamide

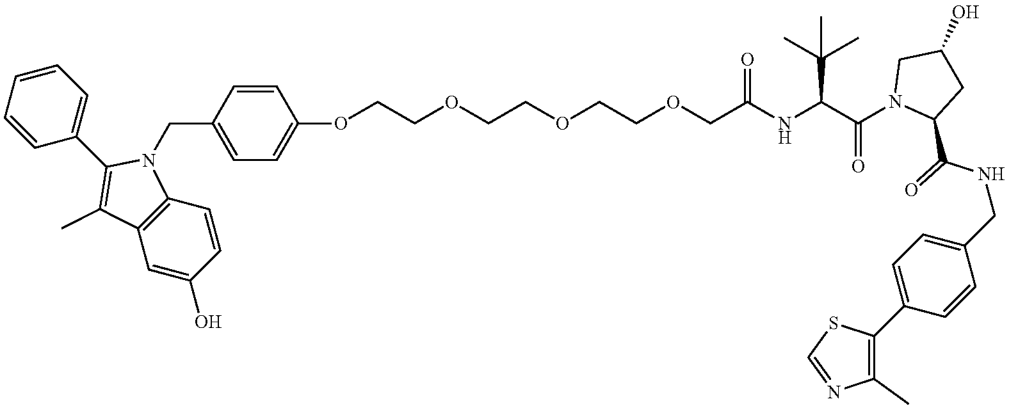 [SMILES: Cc1ncsc1-c1ccc(CNC(=O)[C@@H]2C[C@@H](O)CN2C(=O)[C@@H](NC(=O)COCCOCCOCCOc2ccc(Cn3c(-c4ccccc4)c(C)c4cc(O)ccc43)cc2)C(C)(C)C)cc1]

This compound as a white solid was prepared using the same method as described in Example #1. $^1H$ NMR (400 MHz, $CD_3OD$, ppm): δ 8.82 (s, 1H), 7.48-7.31 (m, 9H), 7.07 (d, J=8.8 Hz, 1H), 6.91 (s, 1H), 6.79-6.65 (m, 5H), 5.14 (s, 2H), 4.69 (s, 1H), 4.58-4.48 (m, 3H), 4.30 (m, 1H), 4.05-3.97 (m, 4H), 3.88-3.73 (m, 4H), 3.72-3.64 (m, 8H), 2.45 (s, 3H), 2.29-2.16 (m, 4H), 2.13-2.05 (m, 1H), 1.01 (s, 9H); [M/Z] calculated for $C_{52}H_{61}N_{50}O_9S$: 931.42; Observed from LC-MS ($ES^+$): m/z 932.25 $[M+H]^+$; $t_R$=1.49 min (3.00 minute run).

Example #9: (2S,4R)-4-hydroxy-1-[(2S)-2-[2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetamido]-3,3-dimethylbutanoyl]-N-[[4-(4-methyl-1,3-thiazol-5-yl)phenyl]methyl]pyrrolidine-2-carboxamide

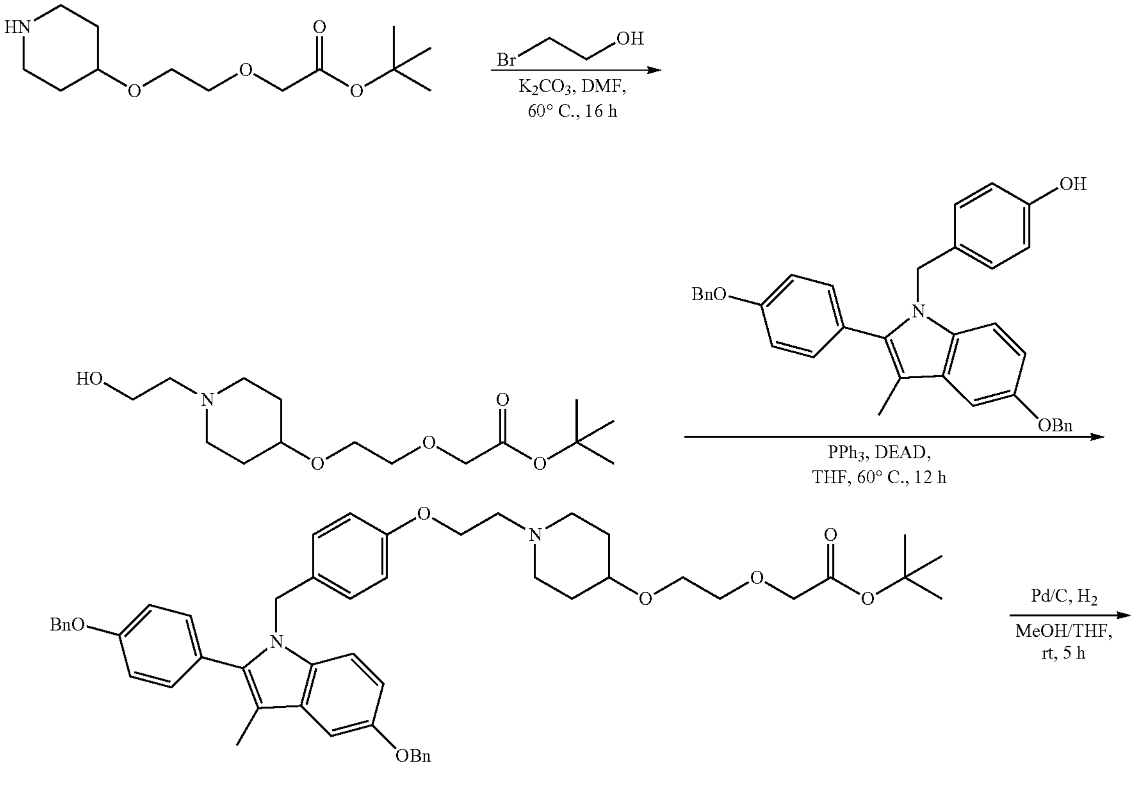

-continued

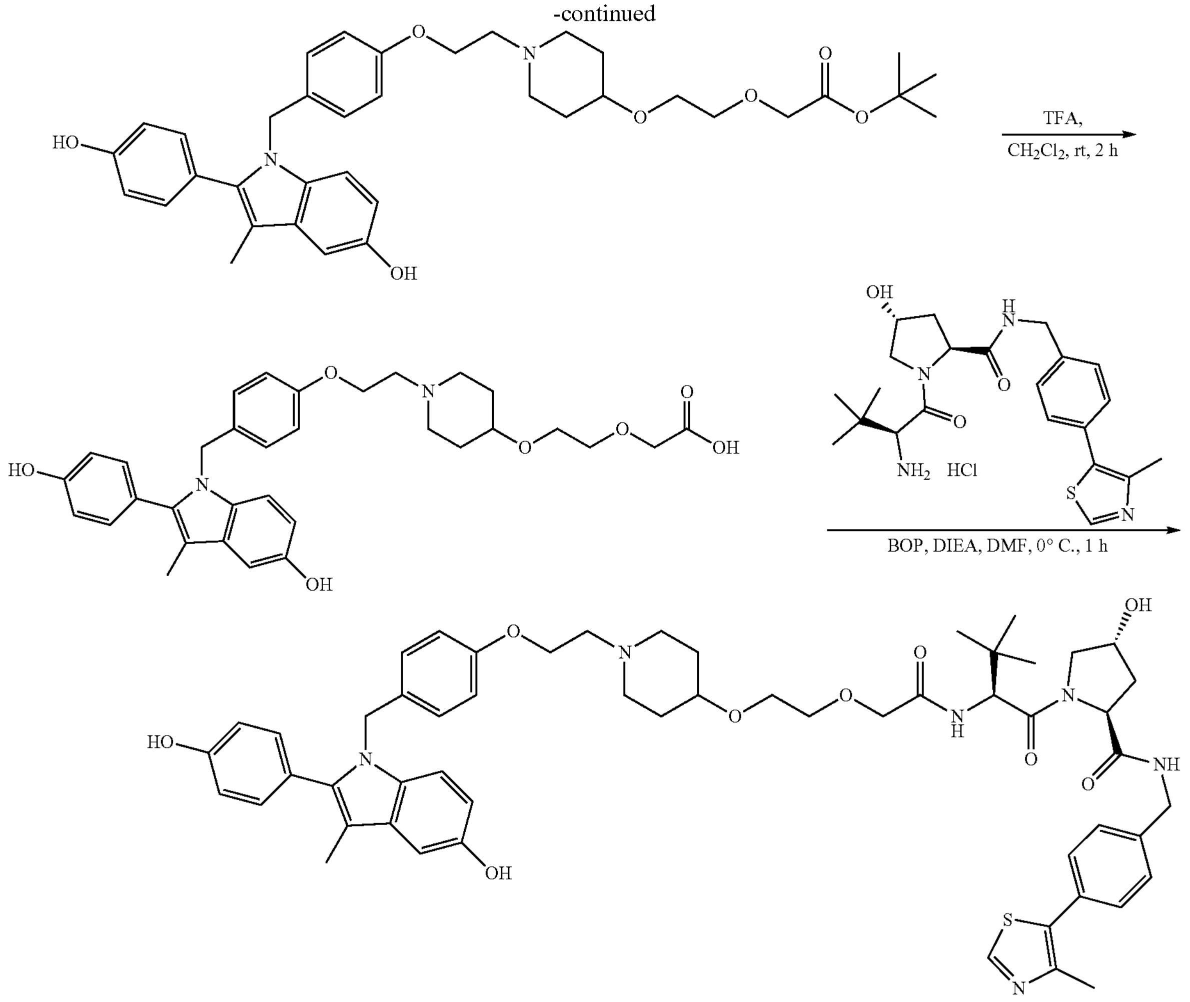

Step 1: Preparation of tert-butyl 2-(2-[[1-(2-hydroxyethyl)piperidin-4-yl]oxy]ethoxy)acetate Into a 50 mL round bottom flask, was placed a solution of tert-butyl 2-[2-(piperidin-4-yloxy)ethoxy]acetate (160.0 mg, 0.62 mmol, 1.00 equiv), 2-bromoethan-1-ol (154.0 mg, 1.23 mmol, 2.00 equiv) and potassium carbonate (170.0 mg, 1.23 mmol, 2.00 equiv) in N,N-dimethylformamide (6 mL) at room temperature. The resulting solution was stirred for 16 hours at 60° C. in an oil bath. The reaction was then quenched by the addition of water. The resulting mixture was extracted with ethyl acetate (20 mL×3) and the organic layers were combined, washed with brine and dried over anhydrous sodium sulfate. The organic solvent was removed under reduced pressure and the residue was applied onto a silica gel column eluting with ethyl acetate/petroleum ether (v:v=1:1). This resulted in 80.0 mg (43%) of tert-butyl 2-(2-[[1-(2-hydroxyethyl)piperidin-4-yl]oxy]ethoxy)acetate as yellow oil. LC-MS ($ES^+$): m/z 304.10 $[M+H]^+$; $t_R$=1.10 min, (2.6 minute run).

Step 2: Preparation of tert-butyl 2-[2-([1-[2-(4-[[5-(benzyloxy)-2-[4-(benzyloxy)phenyl]-3-methyl-1H-indol-1-yl] methyl]phenoxy)ethyl]piperidin-4-yl] oxy)ethoxy]acetate In a 50 mL 3-necked round bottom flask purged and maintained with an inert atmosphere of nitrogen, 4-[[5-(benzyloxy)-2-[4-(benzyloxy)phenyl]-3-methyl-1H-indol-1-yl]methyl]phenol (231.0 mg, 0.44 mmol, 1.00 equiv), tert-butyl 2-(2-[1-(2-hydroxyethyl)piperidin-4-yl]oxy-ethoxy)acetate (160.0 mg, 0.53 mmol, 1.20 equiv) and triphenylphosphine (138.0 mg, 0.53 mmol, 1.20 equiv) were mixed in tetrahydrofuran (15 mL) at room temperature. Diethyl azodicarboxylate (92.0 mg, 0.53 mmol, 1.20 equiv) was added and the resulting solution was heated to 60° C. and stirred for 12 hours at 60° C. The reaction mixture was concentrated under reduced pressure and the residue was applied onto a silica gel column eluting with ethyl acetate/petroleum ether (v:v=1:1). This resulted in 141.0 mg (40%) of tert-butyl 2-[([1-[2-(4-[[5-(benzyloxy)-2-[4-(benzyloxy) phenyl]-3-methyl-1H-indol-1-yl]methyl]phenoxy) ethyl]piperidin-4-yl]oxy)ethoxy]acetate as yellow solid. LC-MS ($ES^+$): m/z 811.40 $[M+H]^+$, $t_R$=1.16 min, (1.9 minute run).

Step 3: Preparation of tert-butyl 2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy] acetate In a 100 mL round bottom flask, palladium(10%) on carbon (20.0 mg) was added to a solution of tert-butyl 2-[2-([1-[2-(4-[[5-(benzyloxy)-2-[4-(benzyloxy)phenyl]-3-methyl-1H-indol-1-yl]methyl]phenoxy)ethyl]piperidin-4- yl]oxy)ethoxy]acetate (140.0 mg, 0.17 mmol, 1.00 equiv) in methanol (20 mL)/tetrahydrofuran (10 mL) at room temperature under nitrogen atmosphere. The reaction flask was vacuumed and charged with a hydrogen balloon. The resulting solution was then stirred for 5 hour at room temperature under hydrogen atmosphere. The reaction mixture was then filtered through a Celite pad and the filtrate was concentrated under reduced pressure. This resulted in 88.0 mg (81%) of tert-butyl 2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetate as light yellow oil. LC-MS ($ES^+$): m/z 631.59 $[M+H]^+$; $t_R$=1.14 min, (2.6 minute run).

Step 4: Preparation of 2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetic acid In a 25 mL round bottom flask, trifluoroacetic acid (1 mL) was added to a solution of tert-butyl 2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetate (77 mg, 0.12 mmol, 1.00 equiv) in dichloromethane (5 mL) at room temperature. The resulting solution was stirred for 2 h at room temperature. After the reaction was done, the reaction mixture was concentrated under reduced pressure. This resulted in 70.0 mg (crude) of 2-[2-([1-[2-(4-[[5-hydroxy-2-(4-hydroxyphenyl)-3-methyl-1H-indol-1-yl]methyl]phenoxy) ethyl]piperidin-4-yl]oxy)ethoxy]acetic acid as yellow solid. LC-MS ($ES^+$): m/z 575.24 $[M+H]^+$; $t_R$=1.02 min, (2.6 minute run).

Step 5: Preparation of (2S,4R)-4-hydroxy-1-[(2S)-2-[2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetamido]-3,3-dimethylbutanoyl]-N-[[4-(4-methyl-1,3-thiazol-5-yl)phenyl]methyl]pyrrolidine-2-carboxamide Into a 25 mL round bottom flask, 2-[2-([l-[2-(4-[[5-hydroxy-2-(4-hydroxyphenyl)-3-methyl-H-indol-1-yl]methyl]phenoxy)ethyl]piperidin-4-yl]oxy)ethoxy]acetic acid (70.0 mg, 0.12 mmol, 1.00 equiv), (2S,4R)-1-[(2S)-2-amino-3,3-dimethylbutanoyl]-4-hydroxy-N-[[4-(4-methyl-1,3-thiazol-5-yl)phenyl]methyl]pyrrolidine-2-carboxamide hydrochloride (68.0 mg, 0.15 mmol, 1.20 equiv) and (benzotriazole-1-yloxy)tris(dimethylamino)phosphonium hexafluorophosphate (65 mg, 0.15 mmol, 1.20 equiv) and N,N-diisopropylethylamine (0.3 ml) were mixed in N,N-dimethylformamide (5 mL) at 0° C. The resulting solution was stirred for 1 hour at 0° C. The reaction was then quenched by the addition of water (20 mL). The resulting mixture was extracted with ethyl acetate (20 mL×3) and the organic layers were combined, washed with brine and dried over anhydrous sodium sulfate. The organic solvent was removed under reduced pressure and the residue was purified by prep-HPLC using the following conditions: column, XBridge Prep C18 OBD Column 19×250 mm, 10 um; mobile phase A, water with ammonium bicarbonate (10 mM), mobile phase B, acetonitrile; flow rate: 30 mL/min; detector, UV 220 &254 nm. This resulted in 38.2 mg (32%) of (2S,4R)-4-hydroxy-1-[(2S)-2-[2-[2-([1-[2-(4-[[5-hydroxy-2-(4-hydroxyphenyl)-3-methyl-1H-indol-1-yl]methyl]phenoxy)ethyl]piperidin-4-yl]oxy)ethoxy]acetamido]-3,3-dimethylbutanoyl]-N-[[4-(4-methyl-1,3-thiazol-5-yl)phenyl]methyl]pyrrolidine-2-carboxamide as white solid. $^1$H NMR (300 MHz, $CD_3OD$, ppm): δ 8.78 (s, 1H), 7.42-7.33 (m, 4H), 7.12-7.09 (d, J=8.7 Hz, 2H), 7.02-6.99 (d, J=8.7 Hz, 1H), 6.88 (d, J=2.1 Hz, 1H), 6.82-6.75 (m, 2H), 6.74-6.61 (m, 5H), 5.09 (s, 2H), 4.68 (s, 1H), 4.59-4.45 (m, 3H), 4.29-4.23 (m, 1H), 4.03-4.00 (m, 2H), 3.98-3.91 (m, 2H), 3.90-3.73 (m, 2H), 3.72-3.61 (m, 4H), 3.48-3.36 (m, 1H), 2.88-2.72 (m, 2H), 2.71-2.64 (m, 2H), 2.43 (s, 3H), 2.37-2.21 (m, 2H), 2.20-2.00 (m, 5H), 1.97-1.85 (m, 2H), 1.71-1.58 (m, 2H), 1.02 (s, 9H); [M/Z] calculated for $C_{55}H_{66}N_6O_9S$: 986.46; Observed from LC-MS ($ES^+$): m/z 987.75 $[M+H]^+$; $t_R$=2.21 min, (5.6 minute run).

Estrogen Receptor-Alpha (ERα) Degradation Assay in MCF-7 Cells

The novel indole-derived ERα degraders were assessed for their activity in degrading ERα in MCF-7 cells using western blot method. The assay was carried out in the presence of 10% female bovine serum (FBS) or high percentage of human or mouse serum. Protocols of the western blot assay were described below:

1. Cells split with Accutase—5 min 37° C.
   a. Carry ⅓ & ⅙ in growth media: DMEM/F12 with 10% FBS
   b. Set 15000/100 uL growth media 96 well plate
   c. Grow till 50-70% confluent (usually 3 day)
2. Gently remove media and replace with 100 uL fresh growth media or 50 uL 25% human or mouse serum
3. Dilute compounds in DMSO 10,000× stock in polypropylene plate—10 mM start for high serum
   a. 2 uL 10 mM+no DMSO
   b. Serial dilutions with ½ log steps
   c. 10 ul into 23 ul DMSO alternating with 10 ul into 20 ul DMSO—6 cmpds, 1/column Make a total of 9 concentrations with 1 DMSO
   1. use 7 high concentrations for high serum (1 uM-1 nM)
   2. skip 2 doses and use the next 7 concentrations (100 nM final-100 pM)
4. Add 99 ul growth media/well of fresh polyprop. plate
5. Transfer 1 ul into media using Integra—this mixes with DMSO/cmpd)—creates 100× stock
6. Add 1 ul 100× stock into 99 ul well of cells—or 0.55 ul/50 ul high serum incubate 4 hr
7. Make 6 ml 1× Cell lysis buffer (cell signaling #9803)—chill 4° C.
8. Aspirate media,
9. wash with 100 ul PBS
10. Aspirate & add 50 ul cold Cell lysis buffer
11. Place on ice 10 min, nutator to mix
12. Transfer to PCR plate
13. CFG 10 min 3900 rpm
14. Aliquot 15 ul into fresh PCR plate
15. Make gel load mix 8.4 ul/well 84×12=1008 120 wells make extra 1260
    a. 150 wells×6 ul=900 ul 4×
    b. 150 wells×2.4 ul=360 ul 10× reducing agent
    c. Aliquot 95 ul/well
16. Aliquot 8.4 ul/well using 12 channel
17. Seal plate, heat to 90° C. 5 min & cool to 4° C. in PCR machine
18. Prep 48 well gels by adding 10 ul water/well using 8 channel adjustable Integra pipetor
19. Load samples DMSO, Low dose-hi dose column 1-6 on gel 1
    a. Use reverse pipetor setting to pick up 15 ul with wide tip spacing 9 mm
    b. Move tips to 4.5 mm setting
    c. Dispense 10 ul/well d. Move tips to 9 mm setting, pipet remainder back into originator well
e. Eject tips
f. Repeat with column 2 ($2^{nd}$ compound)

20. Run gels 24 minutes
21. Transfer gels using program P0 on iBlot
22. Block in 3% BSA TBST 1 hour
23. Add ERα antibody 1/1000 and tubulin antibody 1/5000 4° C. O/N or O/weekend
24. Save antibody with sodium azide@ 4° C.
25. Wash 3× TBST 5 min each
26. Make anti-rabbit HRP 2° 1/200003% BSATBST 30 min-1 hour, RT
27. Wash 3× with TBST, 5 min each
28. Use femto ECL—5 min
29. Image ~5 sec
30. Wash 3×5 min
31. Dilute anti-mouse HRP 2° antibody 1/20000 with 3% BSA TBST and incubate bot 30 min-1 hour, RT
32. Wash 3× with TBST, 5 min each
33. Use femto ECL—5 min
34. Image about 5 seconds FIG. 1 illustrates a western blot analysis of ERα level in MCF-7 cells. Cells were treated with ERα degraders (in the presence of 10% FBS) according the described assay procedure. The Left panel illustrates the effect of Example #1 on degrading ERα. The Right panel illustrates the effect of Example #2 on degrading ERα. D is DMSO and the compound concentration ranged from 0.1 nM to 100 nM.

Figure 2:
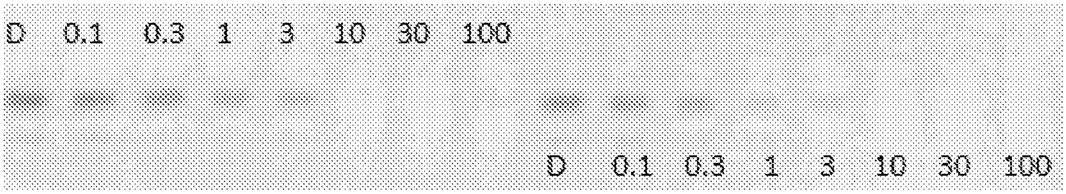
FIG. 2: Western blot analysis of ERα level in MCF-7 cells. Cells were treated with ERα degraders (in the presence of 10% FBS) according the described assay procedure. Left panel: effect of Example #4 on degrading ERα; Right panel: effect of Example #5 on degrading ERα. D: DMSO, compound concentration 0.1 nM to 100 nM.

FIG. 2 illustrates a western blot analysis of ERα level in MCF-7 cells. Cells were treated with ERα degraders (in the presence of 10% FBS) according the described assay procedure. The Left panel illustrates the effect of Example #4 on degrading ERα. The Right panel illustrates the effect of Example #5 on degrading ERα. Again, D is DMSO and the compound concentration ranged from 0.1 nM to 100 nM.

Single Dose Subcutaneous Pharmacokinetics in CD-1 Mice

The subcutaneous bioavailability was determined in the following study: three CD-1 mice were dosed by subcutaneous injection (10 mg/kg) and plasma was collected at the following hourly time points (0.25, 0.5, 1, 2, 4, 8, and 24 h). Plasma compound concentations were determined by HPLC. The results are shown in Table 1.

TABLE 1

Subcutaneous PK of Example #5 in CD-1 mice

| Parameter | Observerd data |
|---|---|
| Route of administration | Subcutaneous |
| Dose (mg/kg) | 10 |
| Cmax (ng/mL) | 687 |
| Tmax (h) | 4 |
| T1/2 (h) | 12 |
| AUC inf (h · ng/mL) | 8275 |
| F % (subcutaneous bioavailability) | 100% |

The contents of all references, patents, pending patent applications and published patents, cited throughout this application are hereby expressly incorporated by reference.

Those skilled in the art will recognize, or be able to ascertain using no more than routine experimentation, many equivalents to the specific embodiments of the invention described herein. Such equivalents are intended to be encompassed by the following claims. It is understood that the detailed examples and embodiments described herein are given by way of example for illustrative purposes only, and are in no way considered to be limiting to the invention. Various modifications or changes in light thereof will be suggested to persons skilled in the art and are included within the spirit and purview of this application and are considered within the scope of the appended claims. For example, the relative quantities of the ingredients may be varied to optimize the desired effects, additional ingredients may be added, and/or similar ingredients may be substituted for one or more of the ingredients described. Additional advantageous features and functionalities associated with the systems, methods, and processes of the present disclosure will be apparent from the appended claims. Moreover, those skilled in the art will recognize, or be able to ascertain using no more than routine experimentation, many equivalents to the specific embodiments of the invention described herein. Such equivalents are intended to be encompassed by the following claims.

What is claimed is:

1. A compound of formula (I):

(I)

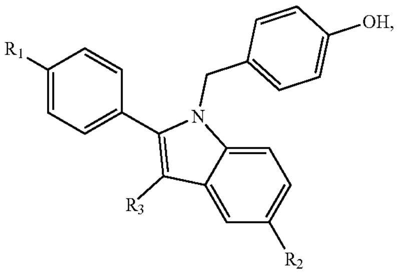

wherein:

$R_1$ is H or a halogen;

$R_2$ is —OH or —$OC_{1-3}$alkyl; and $R_3$ is H or an optionally substituted lower alkyl, or a salt thereof.

2. The compound of claim 1, wherein:

$R_1$ is H, F, Br, or Cl;

$R_2$ is OH or $OCH_3$;

$R_3$ is H or an optionally substituted C1-C4 alkyl; or a combination thereof.

3. The compound of claim 2, wherein $R_1$ is H, F, or Cl.

4. The compound of claim 2, wherein $R_2$ is OH.

5. The compound of claim 2, wherein when $R_3$ is methyl.

6. The compound of claim 1, wherein:

$R_1$ is halogen;

$R_2$ is OH;

$R_3$ is an optionally substituted methyl or an optionally substituted ethyl; or a combination thereof.

7. The compound of claim 1, wherein $R_3$ is methyl.

8. A pharmaceutical composition comprising the compound of claim 1 or a pharmaceutically acceptable salt thereof, and one or more of a pharmaceutically acceptable carrier, diluent, or excipient.

9. A method of making a bifunctional molecule having the chemical structure

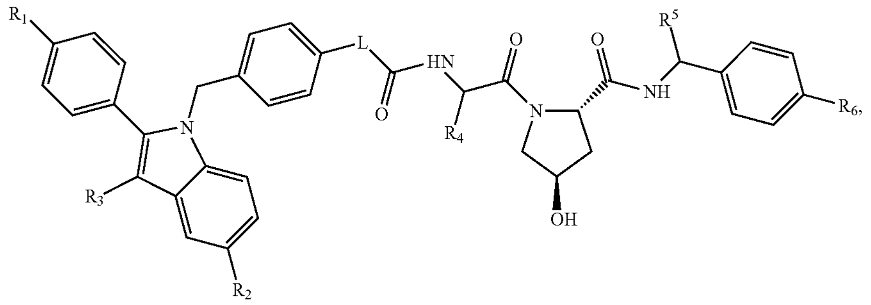

the method comprising:

covalently linking the

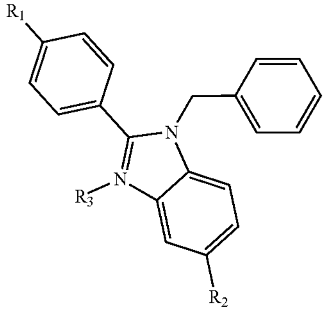

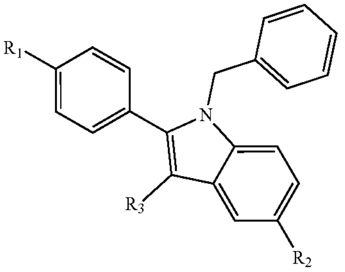

to a chemical linker (L); and covalently linking L to a compound of structure:

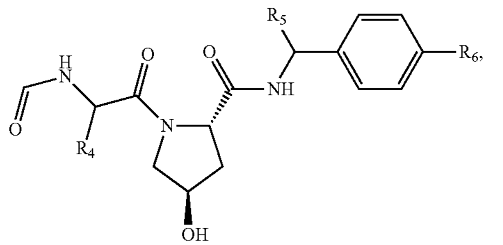

wherein $R_1$ is H, OH, —$OC_{1-3}$ alkyl, or a halogen;

$R_2$ is —OH or —$OC_{1-3}$ alkyl;

$R_3$ is H or an optionally substituted lower alkyl;

L is one or more covalently connected structural units of -$(A)_q$-, wherein A is a chemical moiety, and q is an integer greater than or equal to 1;

$R_4$ is a straight chain or branched $C_{1-6}$alkyl, or $C_{3-6}$ cycloalkyl;

$R_5$ is H or an optionally substituted lower alkyl; and $R_6$ is 4-methylthiazol-5-yl, oxazol-5-yl, optionally substituted imidazole, optionally substituted pyrazole, optionally substituted oxadiazole, optionally substituted triazole, halogen, or cyano group, or a pharmaceutically acceptable salt.

10. The method of claim 9, wherein:

$R_1$ is H, OH, F, Br, Cl, or $OCH_3$;

$R_2$ is OH or $OCH_3$;

$R_3$ is H or an optionally substituted $C_{1-4}$ alkyl; or a combination thereof.

11. The method of claim 10, wherein $R_1$ is H, OH, F, or Cl.

12. The method of claim 10, wherein $R_2$ is OH.

13. The method of claim 10, wherein $R_3$ is methyl.

14. The method of claim 9, wherein:

$R_1$ is OH or halogen;

$R_2$ is OH;

$R_3$ is an optionally substituted methyl or an optionally substituted ethyl; or a combination thereof.

15. The method of claim 14, wherein:

$R_1$ is OH or halogen;

$R_2$ is OH;

$R_3$ is an optionally substituted methyl or an optionally substituted ethyl; or a combination thereof.

16. The method of claim 9, wherein $R_3$ is methyl.

17. The method of claim 9, wherein:

each A is independently selected from $CR^{L1}R^{L2}$, O, SO, $SO_2$, $NR^{L3}$, $SO_2NR^{L3}$, $SONR^{L3}$, $CONR^{L3}$, $NR^{L3}CONR^{L4}$, $NR^{L3}SO_2NR^{L4}$, CO, $CR^{L1}$=$CR^{L2}$, C≡C, $NR^{L3}$C(=NCN)$NR^{L4}$, $NR^{L3}$C(=NCN), $NR^{L3}$C(=$CNO_2$)$NR^{L4}$, $C_{3-11}$cycloalkyl optionally substituted with 1-6 $R^{L1}$ and/or $R^{L2}$ groups, $C_{3-11}$heterocyclyl optionally substituted with 1-6 $R^{L1}$ and/or $R^{L2}$ groups, aryl optionally substituted with 1-6 $R^{L1}$ and/or $R^{L2}$ groups, and heteroaryl optionally substituted with 1-6 $R^{L1}$ and/or $R^{L2}$ groups, wherein $R^{L1}$ or $R^{L2}$, each independently can be linked to other A groups to form a cycloalkyl or heterocyclyl moiety that can be further substituted with 1-4 $R^{L5}$ groups; and each $R^{L1}$, $R^{L2}$, $R^{L3}$, $R^{L4}$ and $R^{L5}$ is independently selected from H, halogen, $C_{1-8}$alkyl, $OC_{1-8}$alkyl, $SC_{1-8}$alkyl, $NHC_{1-8}$alkyl, N($C_{1-8}$alkyl)2, $C_{3-11}$cycloalkyl, aryl, heteroaryl, $C_{3-11}$heterocyclyl, $OC_{3-8}$cycloalkyl, $SC_{3-8}$cycloalkyl, $NHC_{3-8}$cycloalkyl, N($C_{3-8}$cycloalkyl)$_2$, N($C_{3-8}$cycloalkyl)($C_{1-8}$alkyl), OH, $NH_2$, SH, $SO_2C_{1-8}$alkyl, CC—$C_{1-8}$alkyl, CCH, CH=CH($C_{1-8}$alkyl), C($C_{1-8}$alkyl)=CH($C_{1-8}$alkyl), C($C_{1-8}$alkyl)=C $(C_{1-8}alkyl)_2$, $COC_{1-8}alkyl$, $CO_2H$, halogen, CN, $CF_3$, $CHF_2$, $CH_2F$, $NO^2$, $SF_5$, $SO_2NHC_{1-8}alkyl$, $SO_2N(C_{1-8}alkyl)_2$, $SONHC_{1-8}alkyl$, $SON(C_{1-8}alkyl)_2$, $CONHC_{1-8}alkyl$, $CON(C_{1-8}\ alkyl)_2$, $N(C_{1-8}alkyl)CONH(C_{1-8}alkyl)$, $N(C_{1-8}alkyl)CON(C_{1-8}alkyl)_2$, $NHCONH(C_{1-8}alkyl)$, $NHCON(C_{1-8}alkyl)_2$, $NHCONH_2$, $N(C_{1-8}alkyl)SO_2NH(C_{1-8}alkyl)$, $N(C_{1-8}alkyl)\ SO_2N(C_{1-8}alkyl)_2$, $NH\ SO_2NH(C_{1-8}alkyl)$, $NH\ SO_2N(C_{1-8}alkyl)_2$, $NH\ SO_2NH_2$.

18. The method of claim 9, wherein the L is selected from:

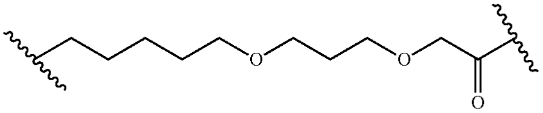
;
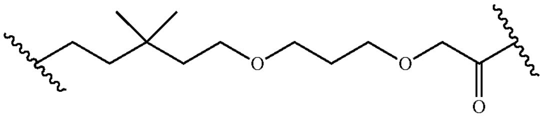
;
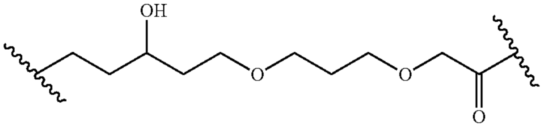
;
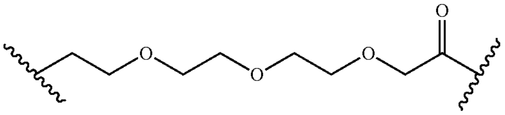
;
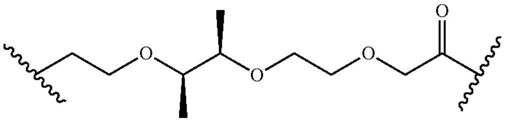
;
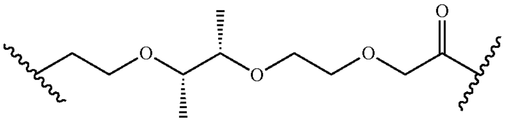
;
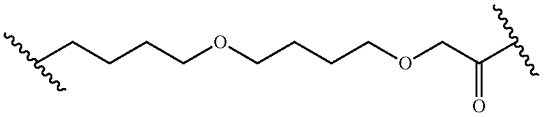
;
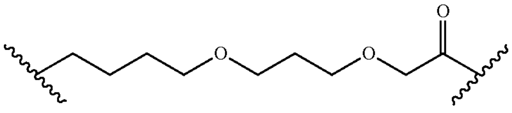
;
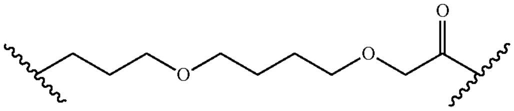
;
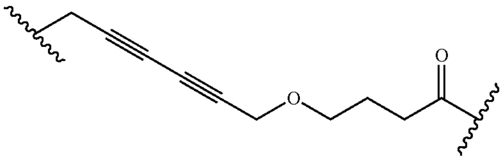
;
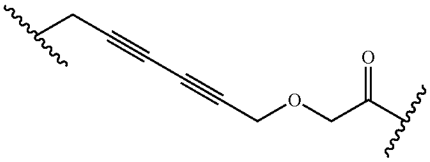
;

-continued

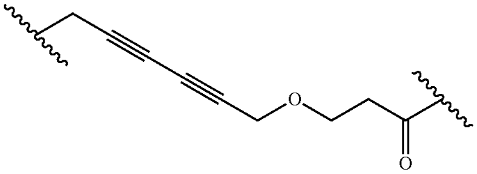
;
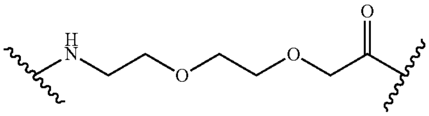
;
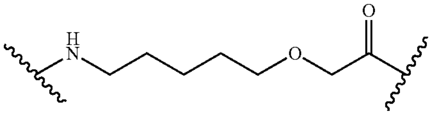
;
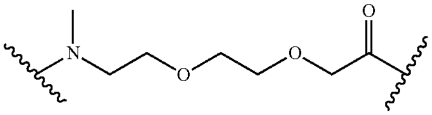
;
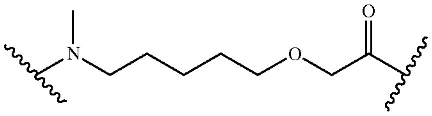
;
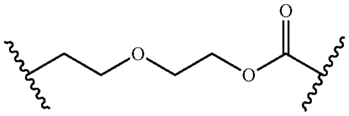
;
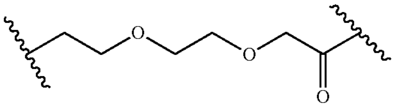
;
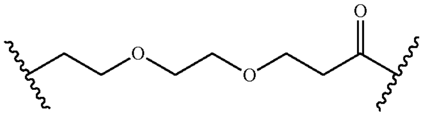
;
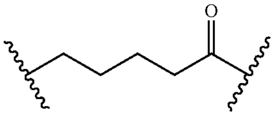
;
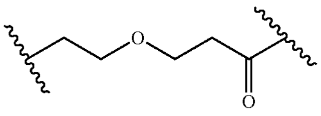
;
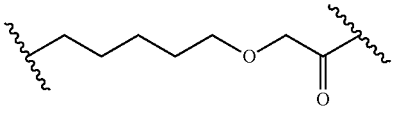
;
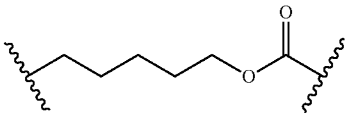
;
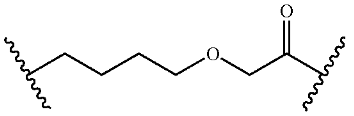
;
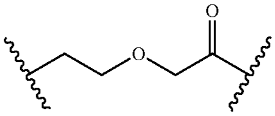
;

-continued
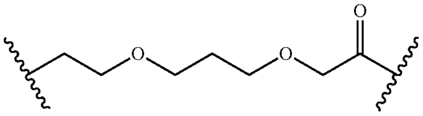
;
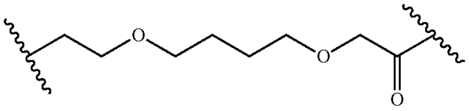
;
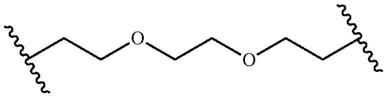
;
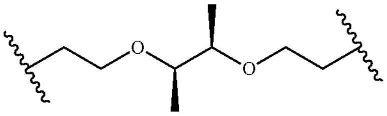
;
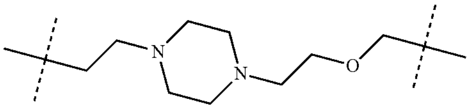
;
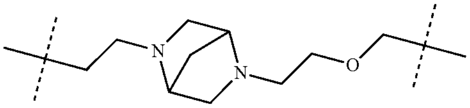
;
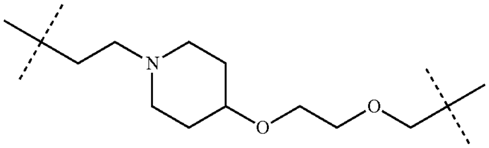
; and
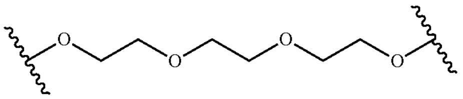
.
19. The method of claim 9, wherein the L has a structure selected from:
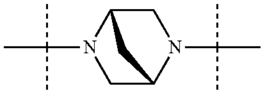
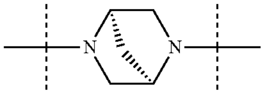
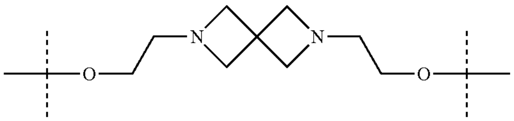
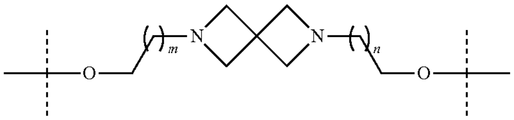
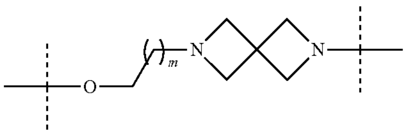
-continued
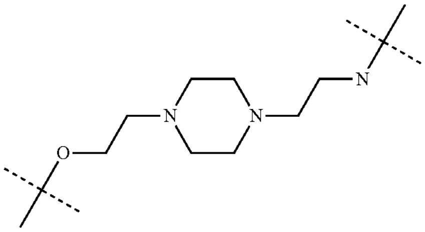
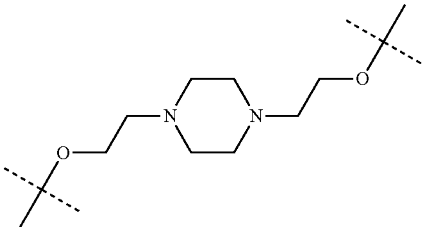
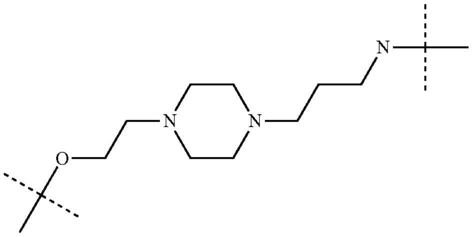
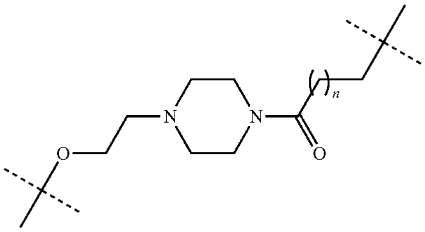
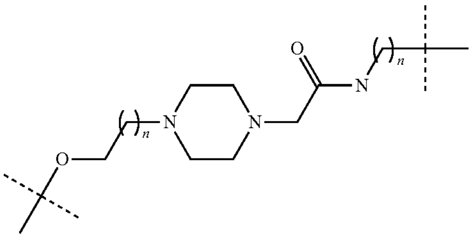
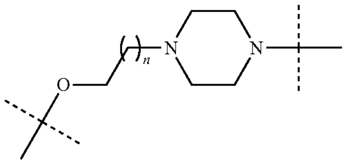
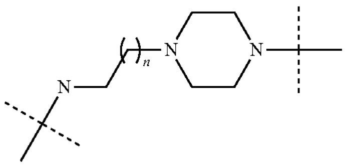
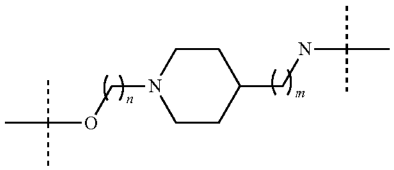

-continued
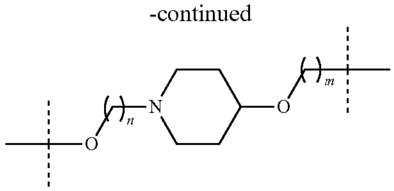
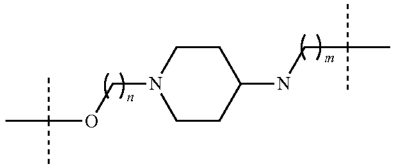
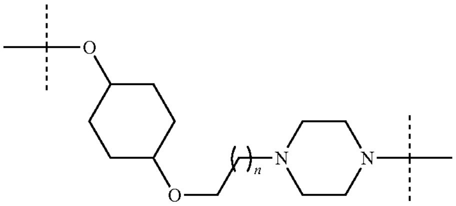
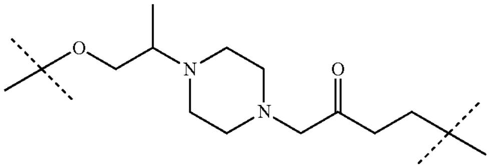
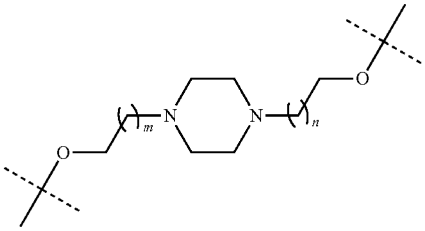
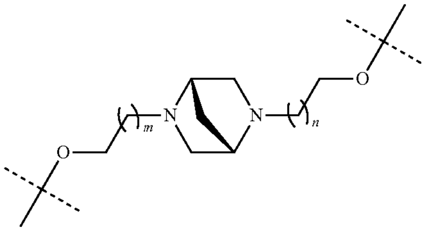
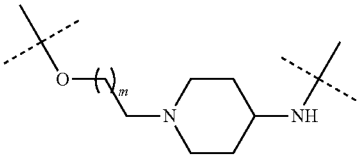
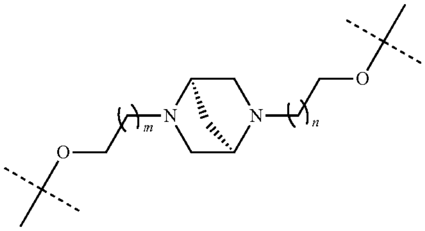
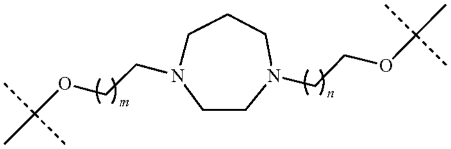
-continued
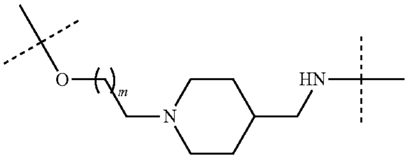
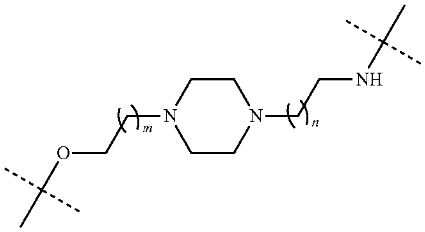
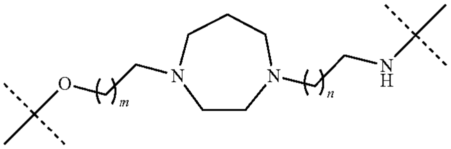
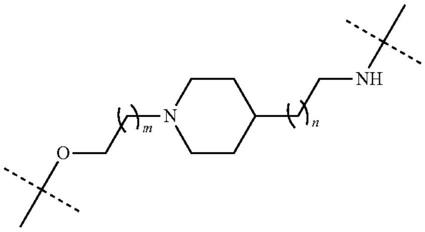
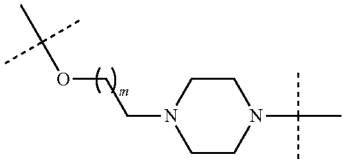
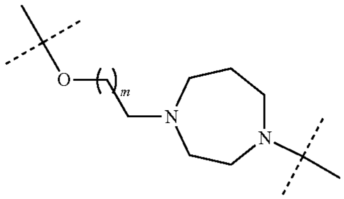
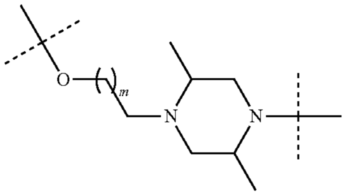
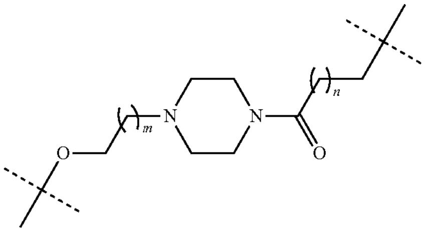

-continued
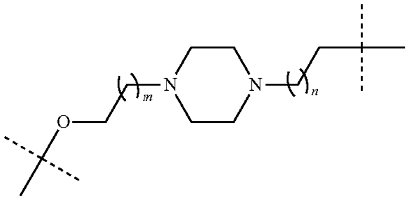
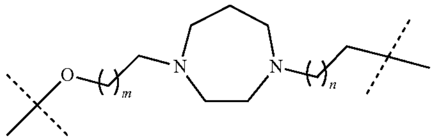
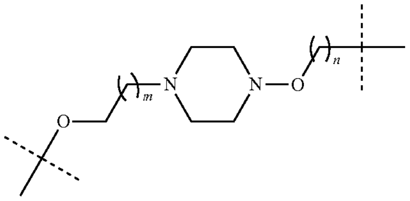
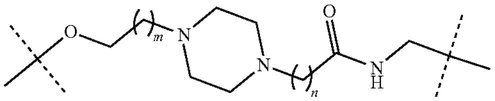
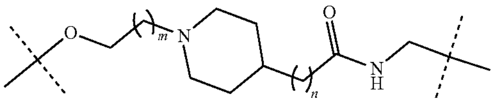
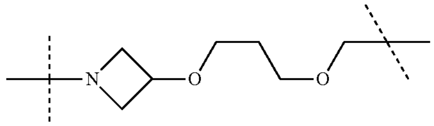
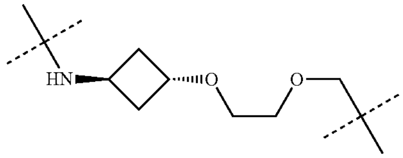
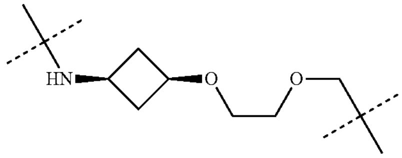
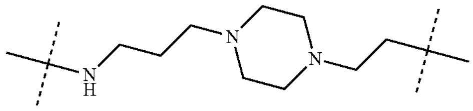
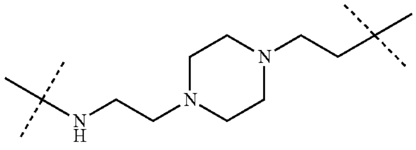
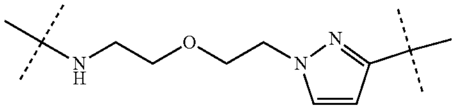
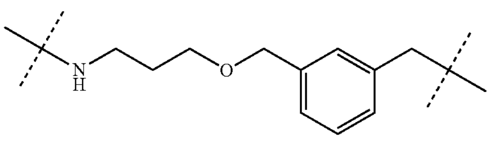
-continued
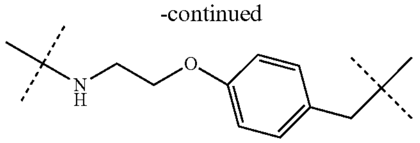
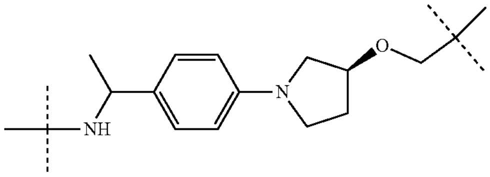
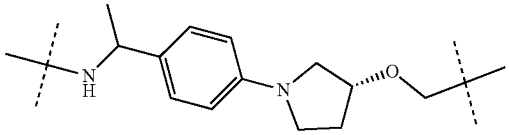
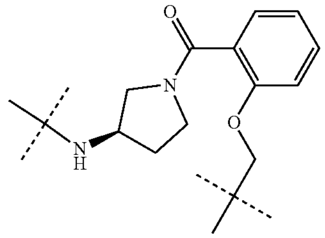
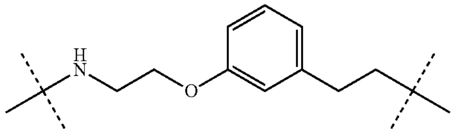
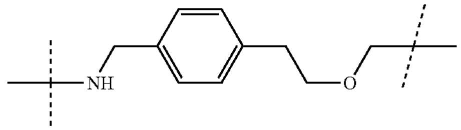
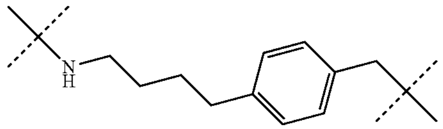
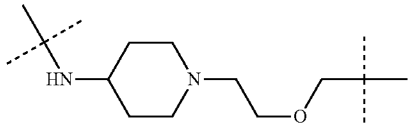
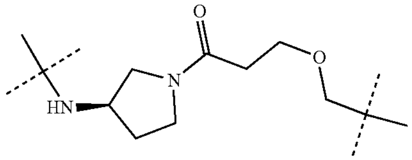
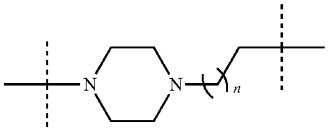
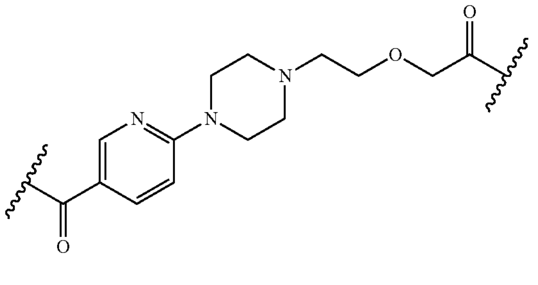
;

-continued
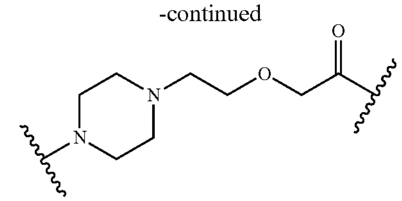
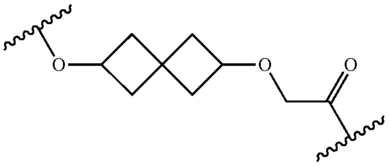
;
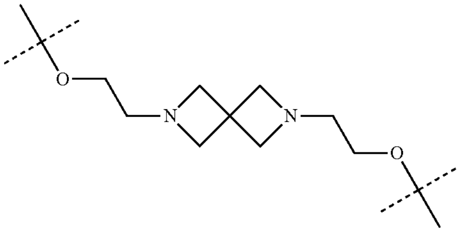
;
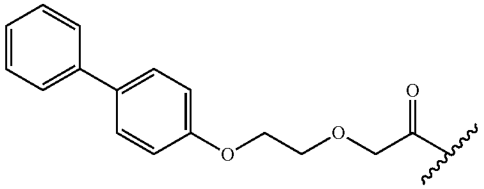
;
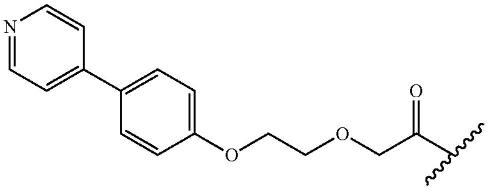
;
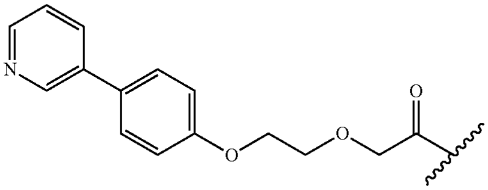
;
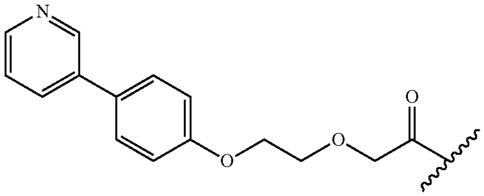
;
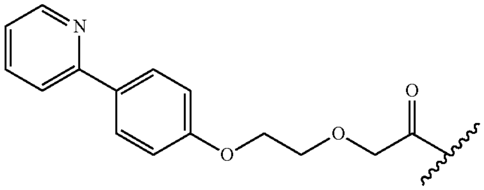
;
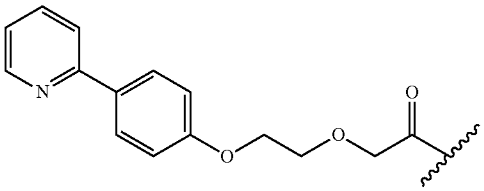
;
-continued
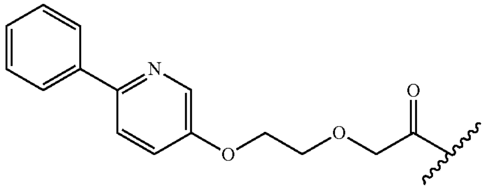
;
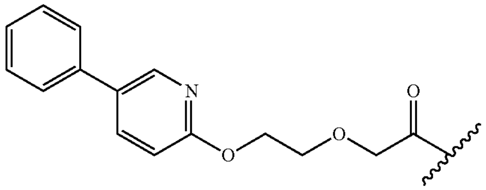
;
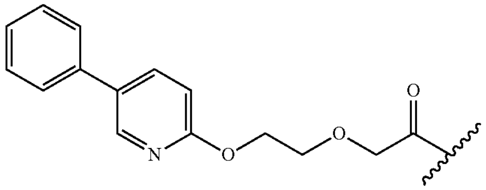
;
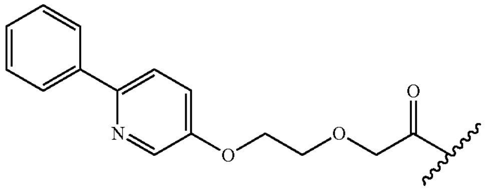
;
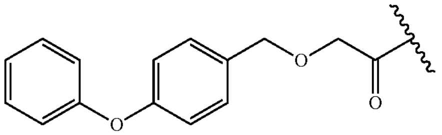
;
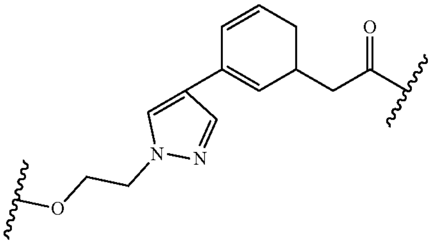
;
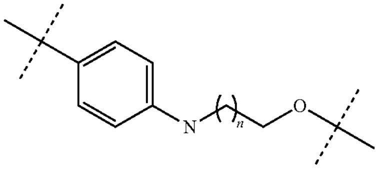
;
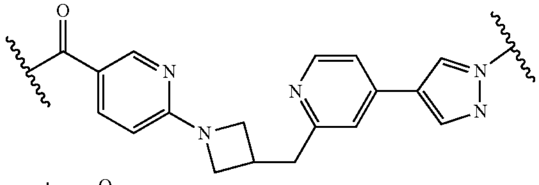
;
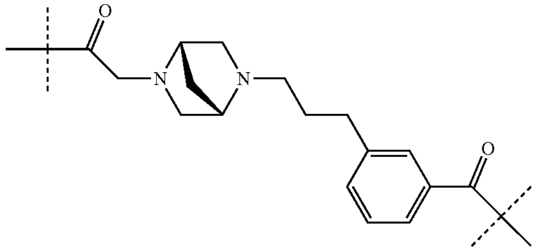
;

-continued
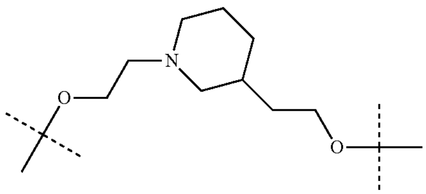
;
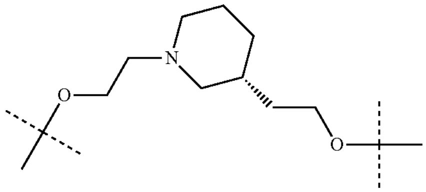
;
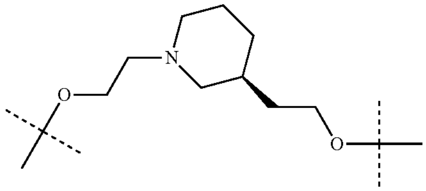
;
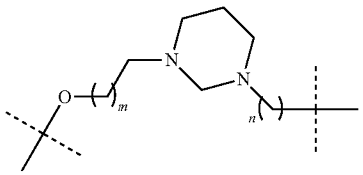
;
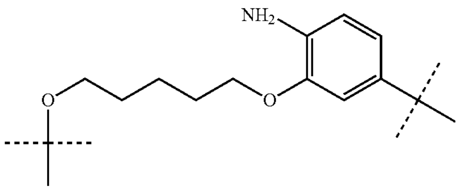
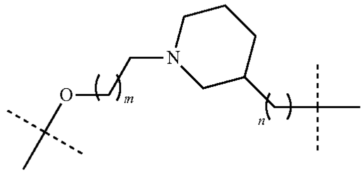
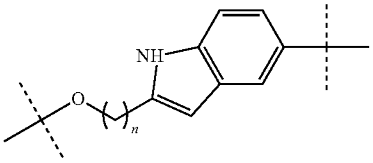
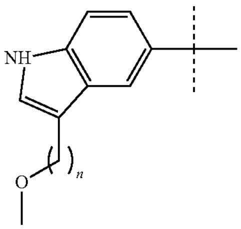
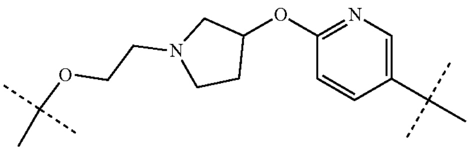
-continued
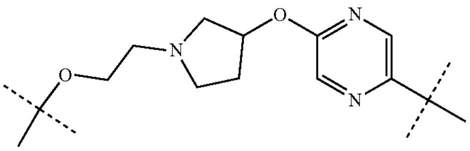
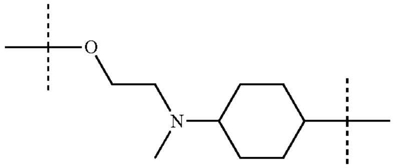
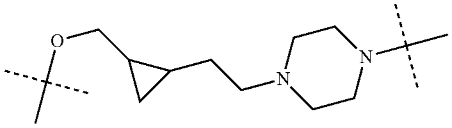
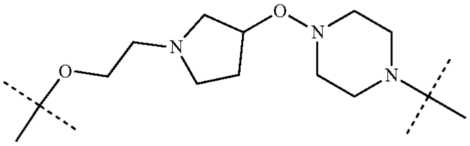
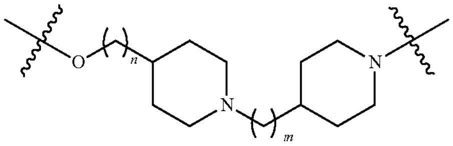
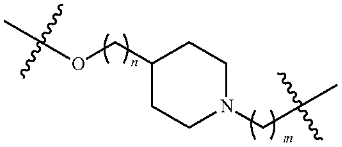
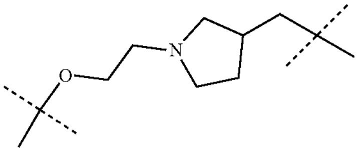
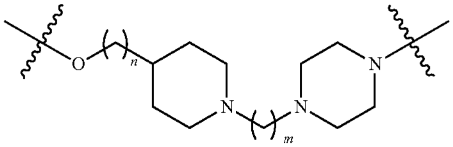
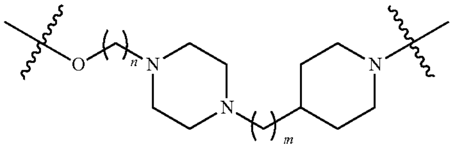
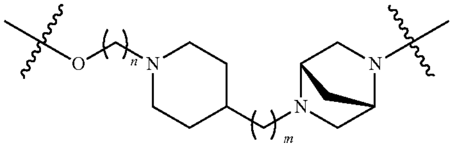
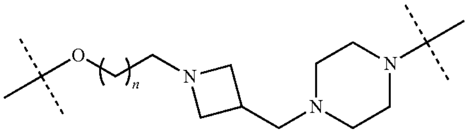

-continued
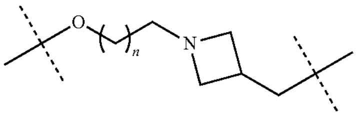
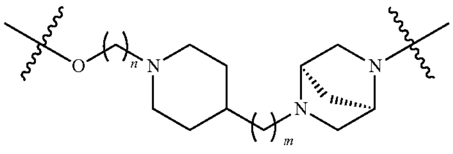
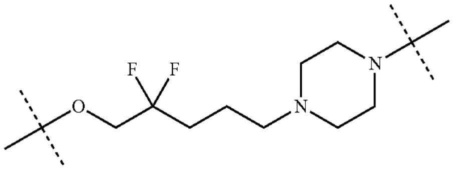
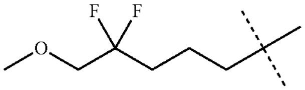
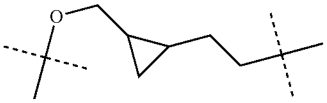
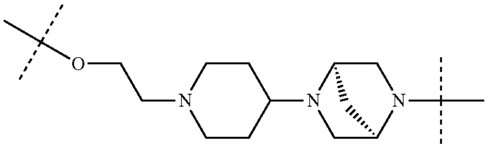
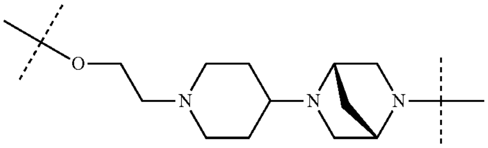
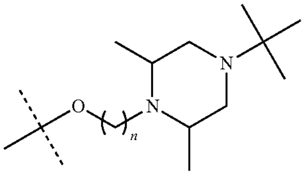
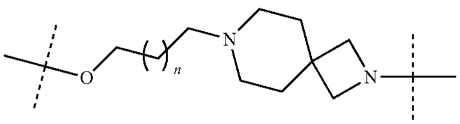
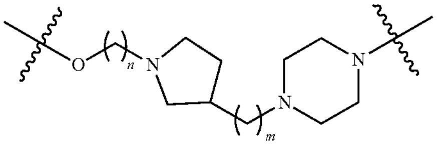
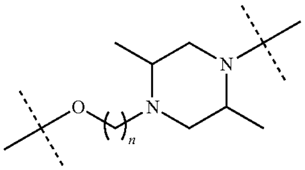
-continued
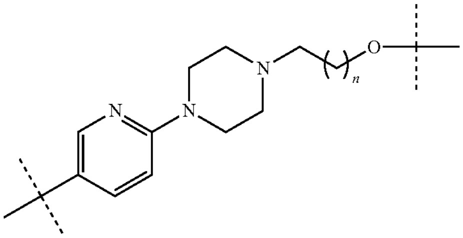
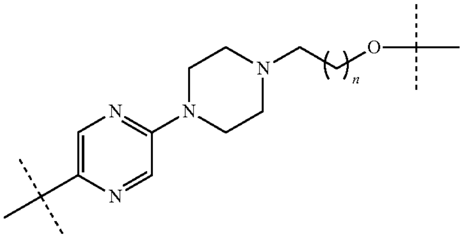
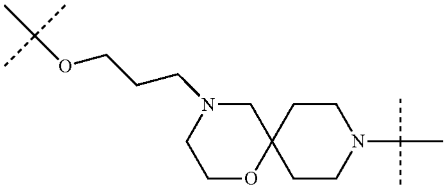
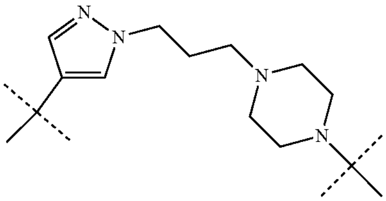
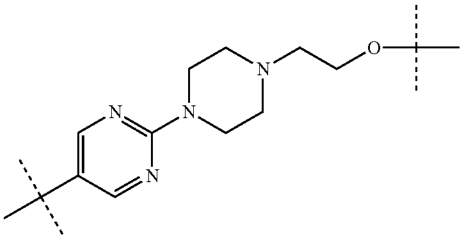
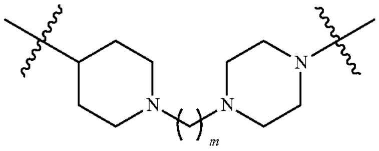
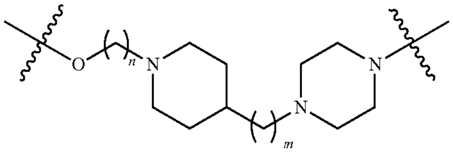
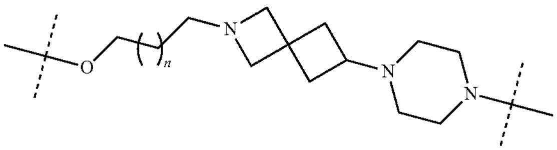
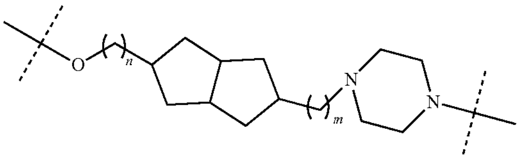

-continued
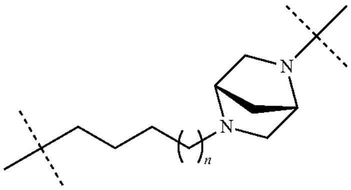
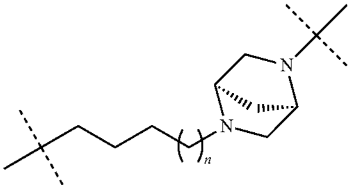
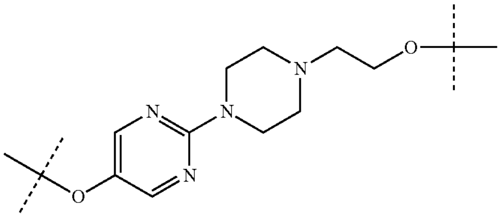
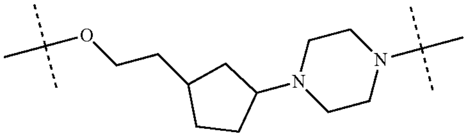
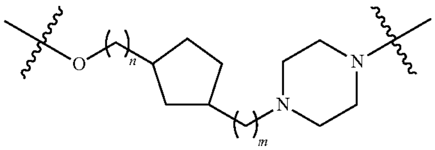
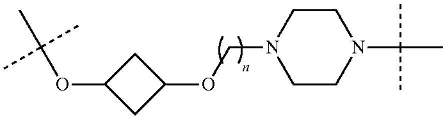
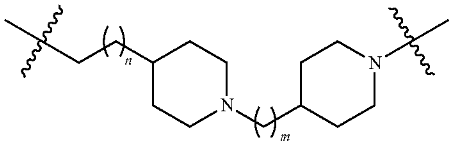
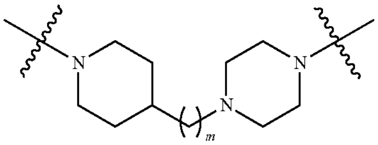
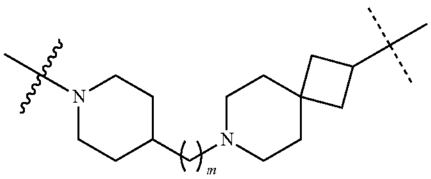
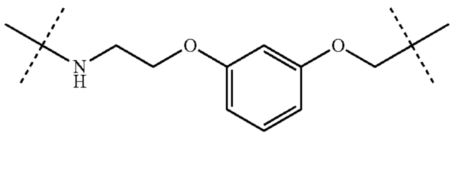
-continued
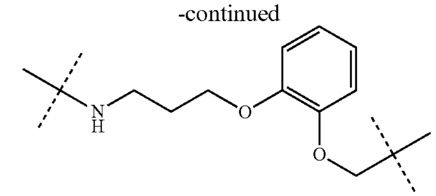
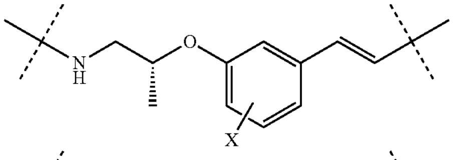
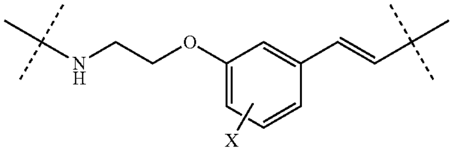
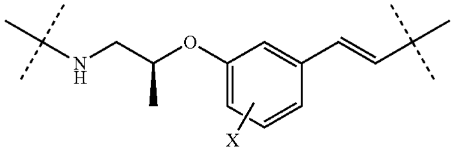
X = H, F
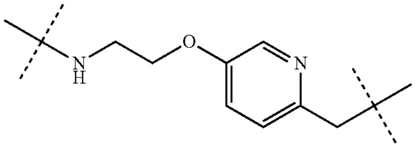
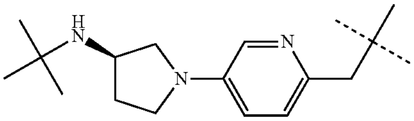
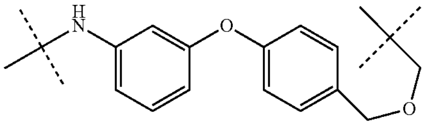
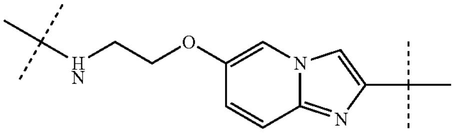
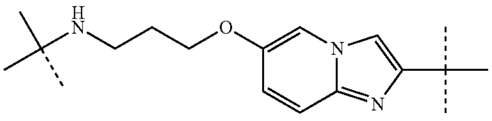
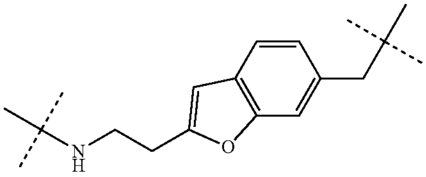
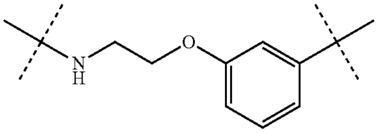
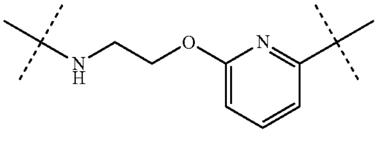

-continued
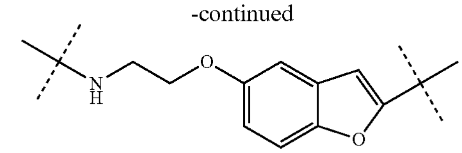
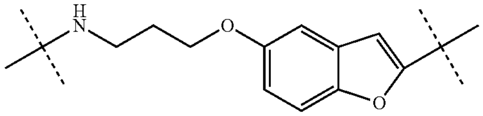
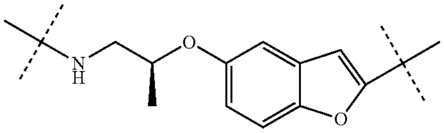
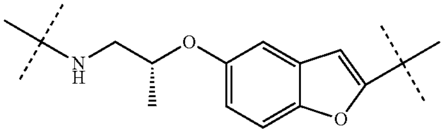
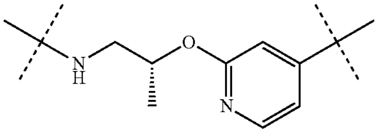
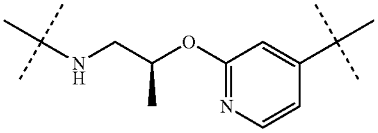
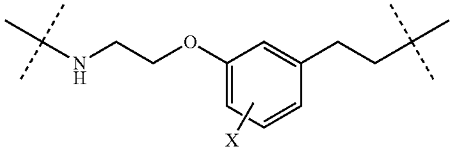
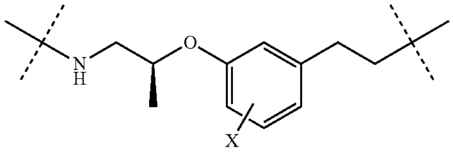
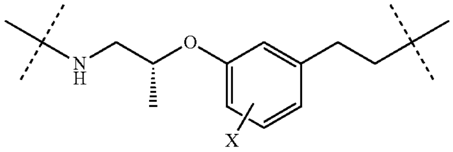
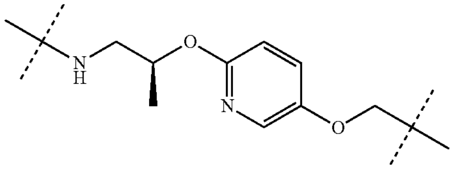
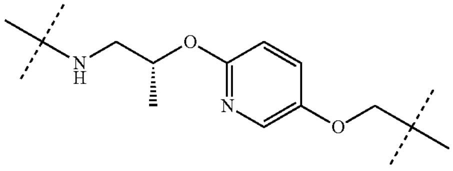
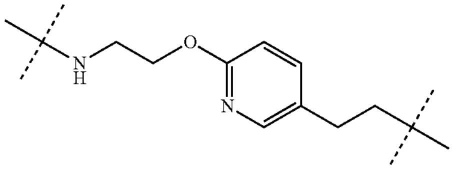
-continued
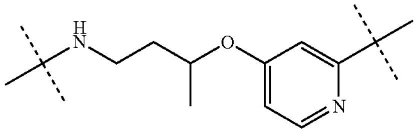
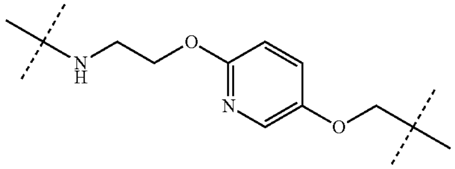
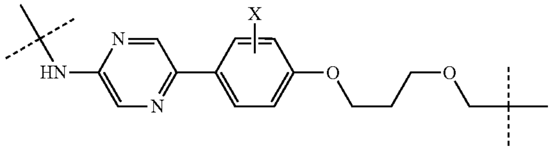
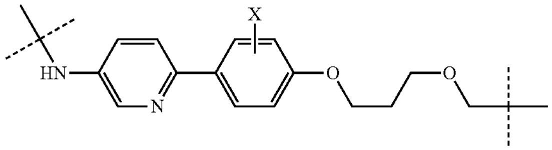
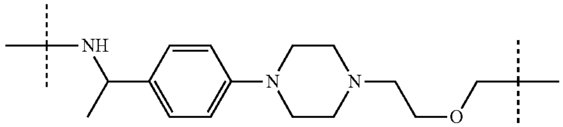
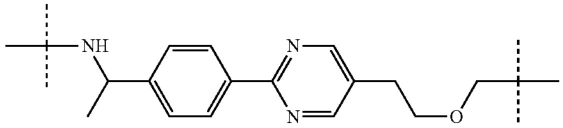
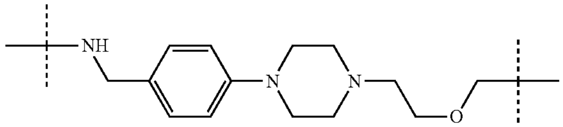
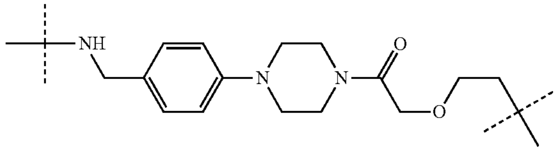
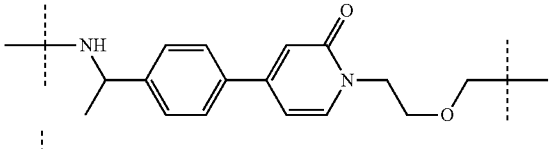
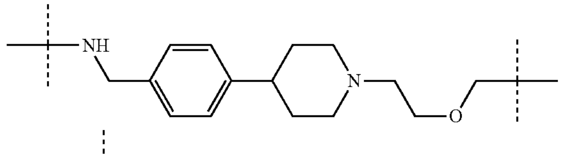
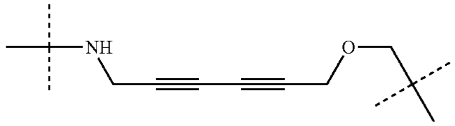
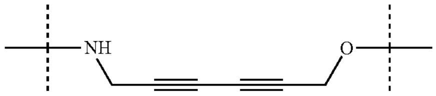
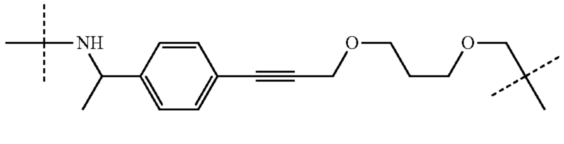

-continued
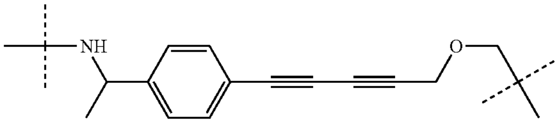
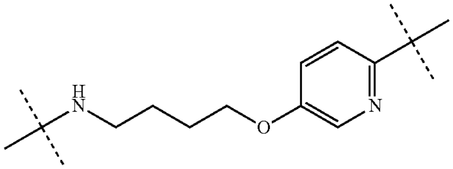
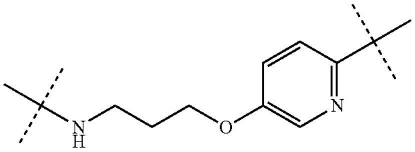
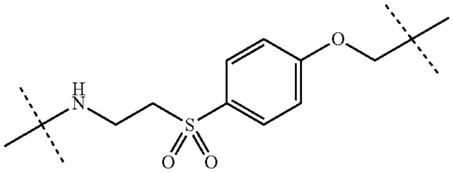
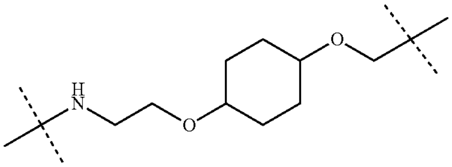
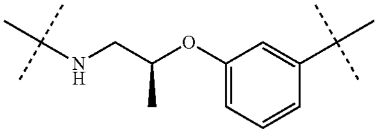
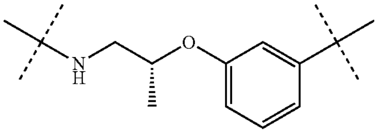
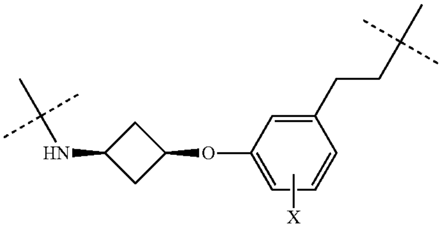
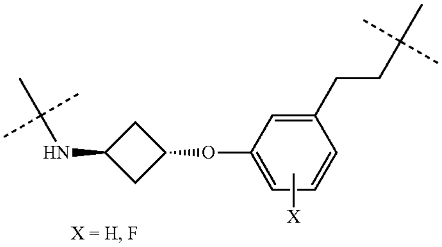
X = H, F
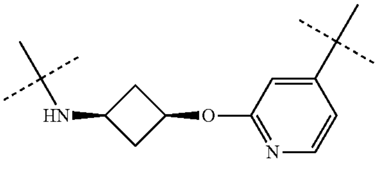
-continued
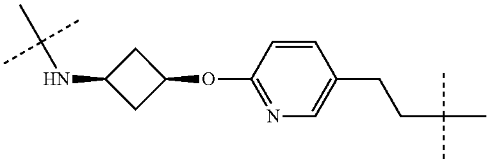
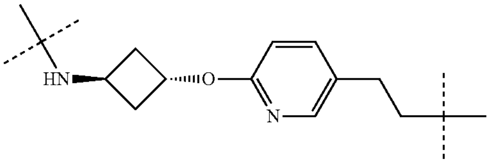
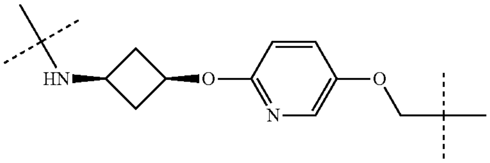
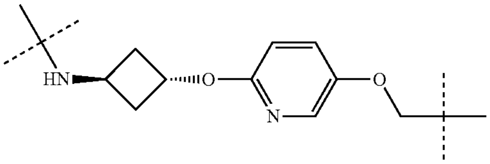
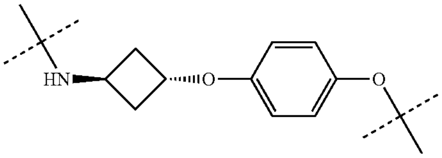
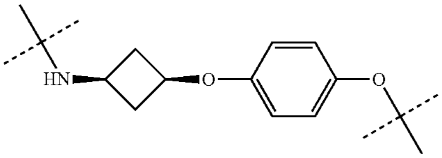
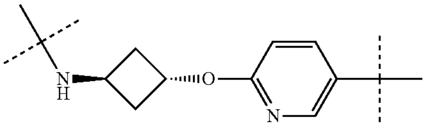
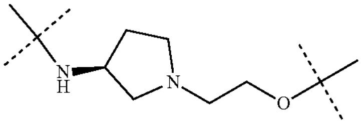
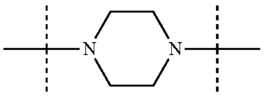
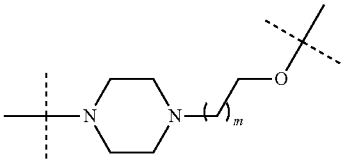
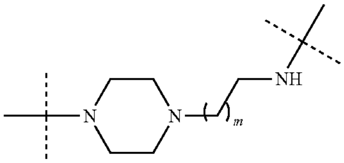

-continued
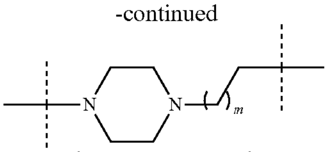
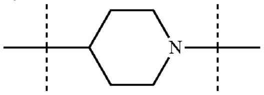
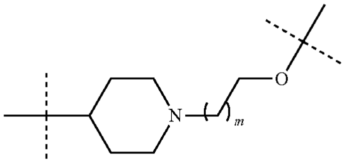
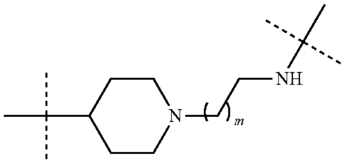
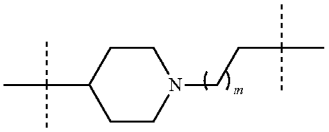
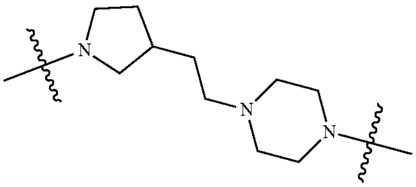
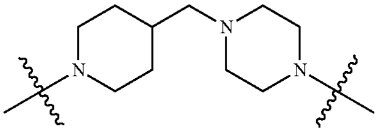
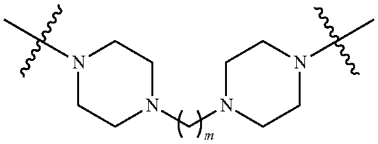
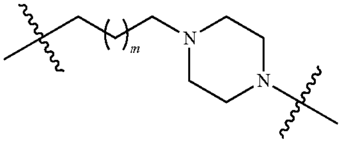
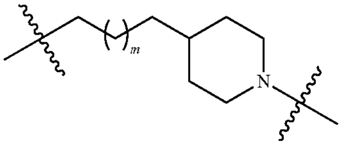
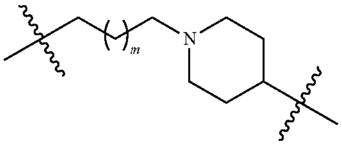
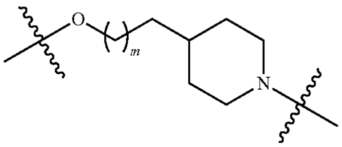
-continued
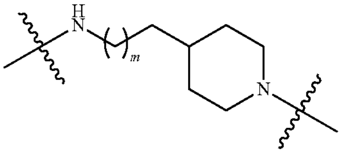
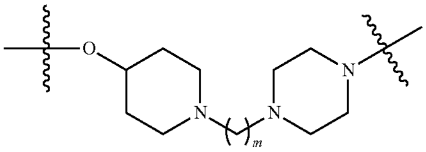
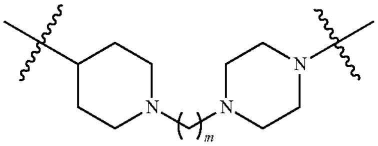
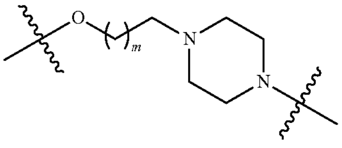
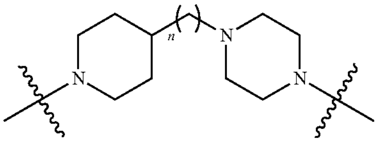
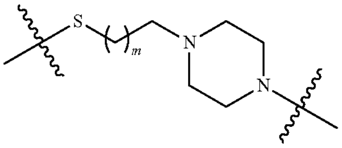
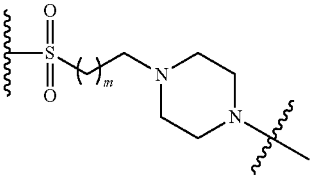
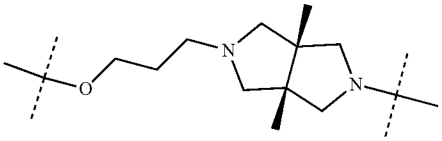
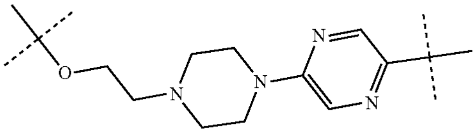
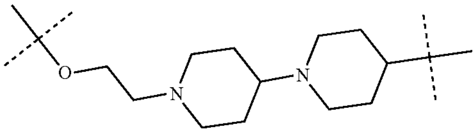
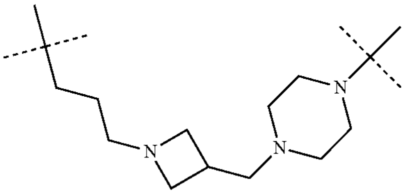

-continued
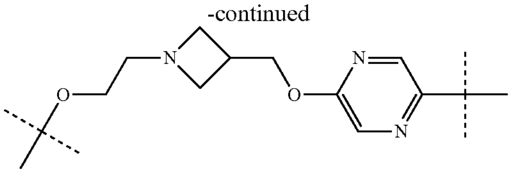
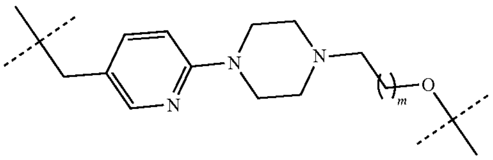
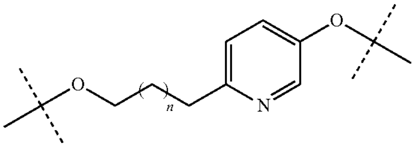
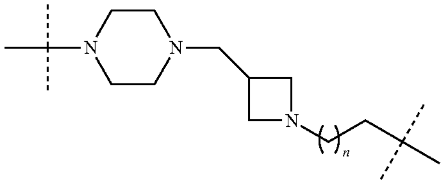
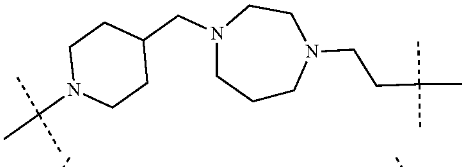
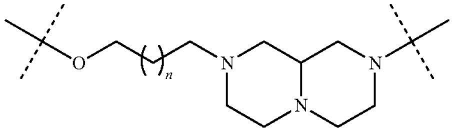
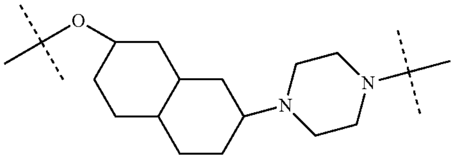
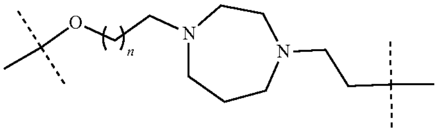
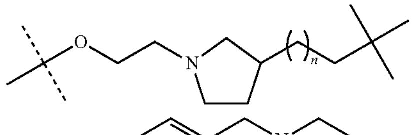
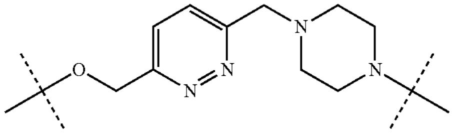
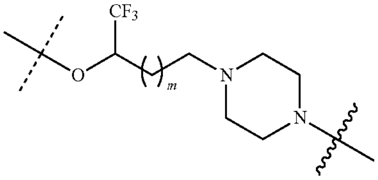
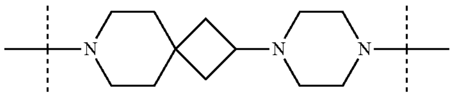
-continued
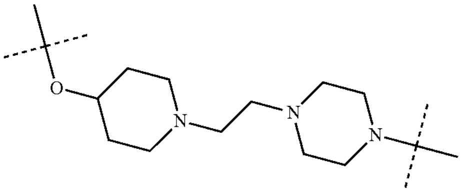
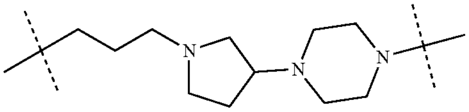
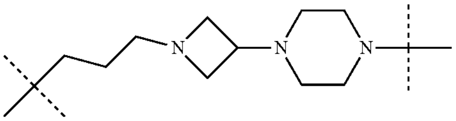
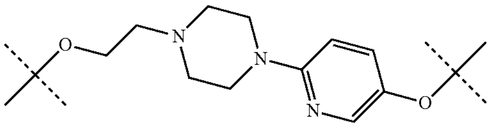
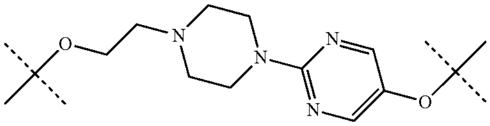
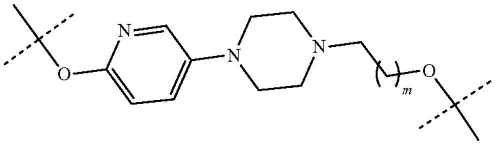
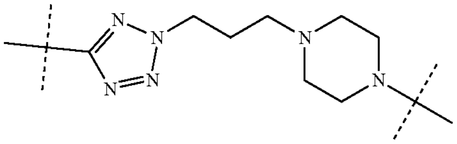
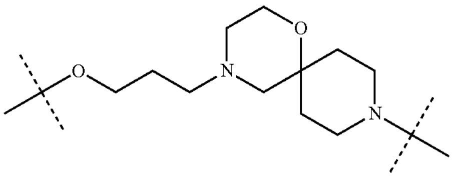
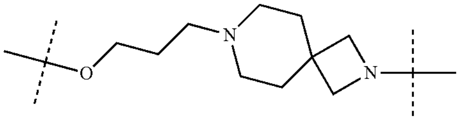
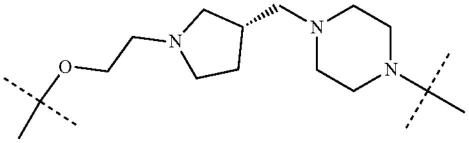
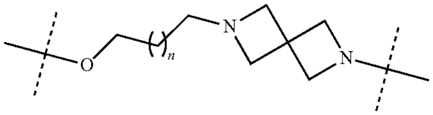
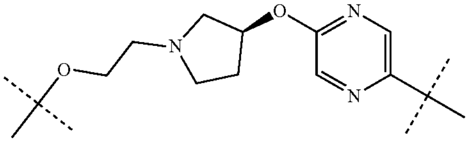

-continued
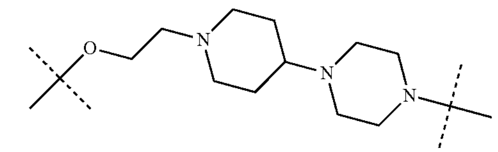
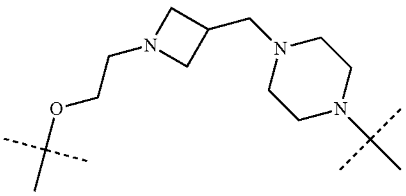
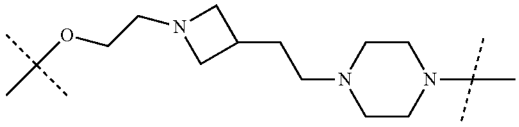
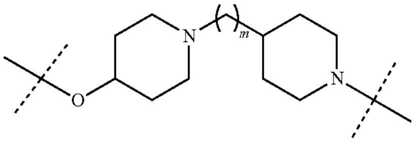
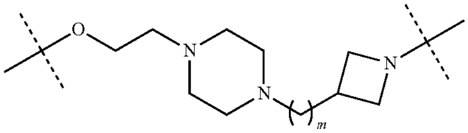
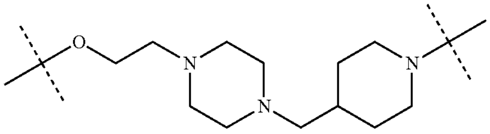
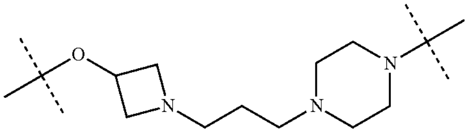
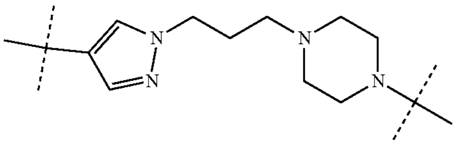
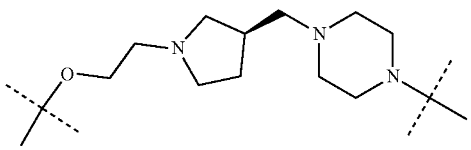
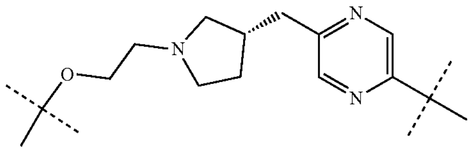
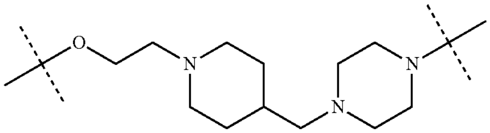
-continued
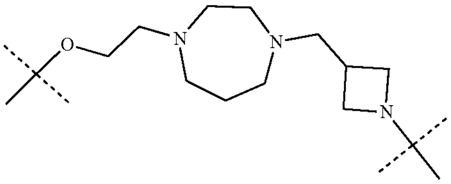
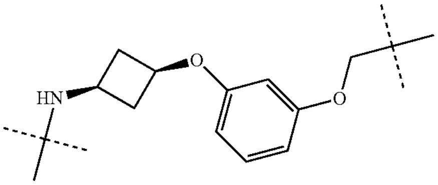
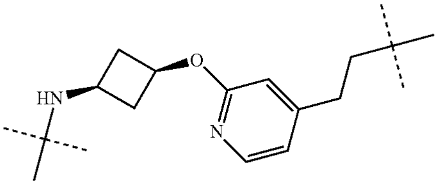
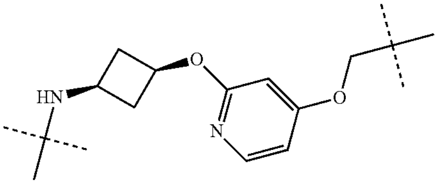
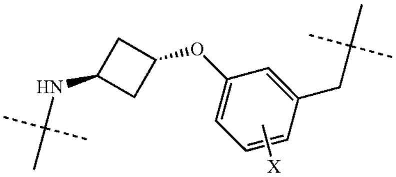
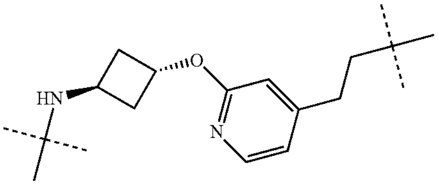
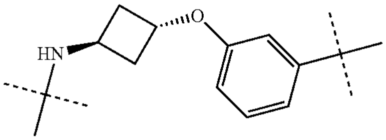
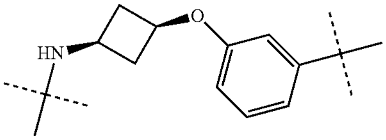
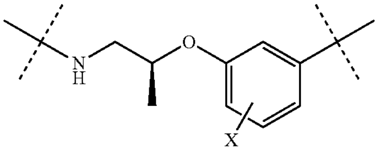
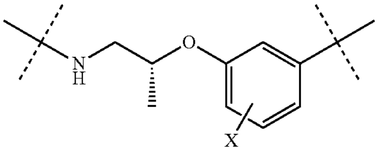

-continued
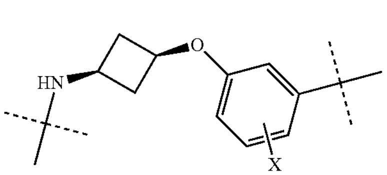
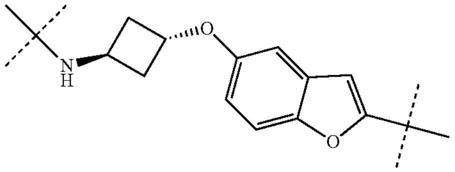
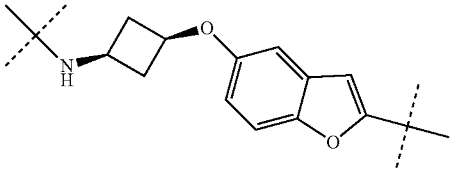
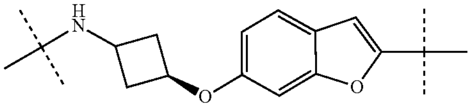
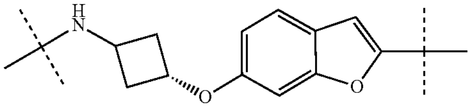
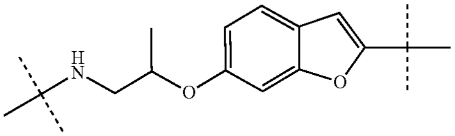
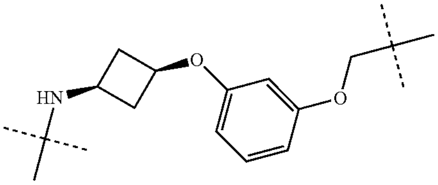
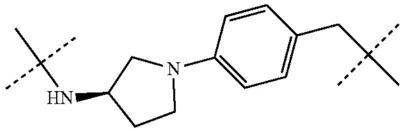
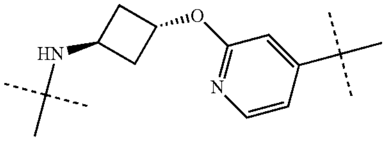
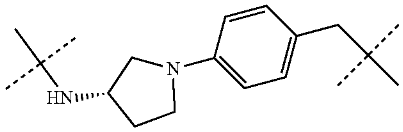
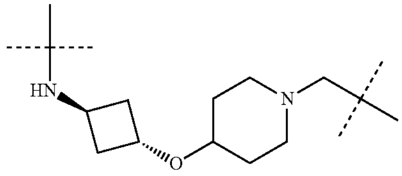
-continued
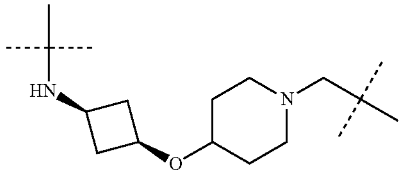
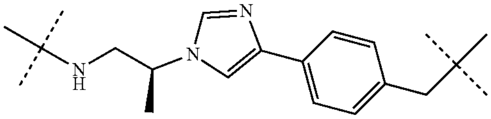
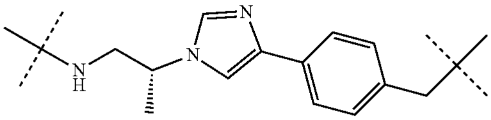
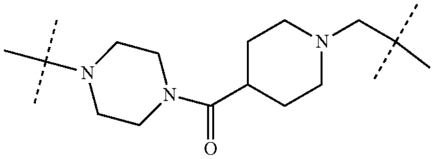
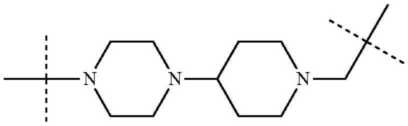
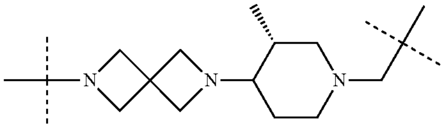
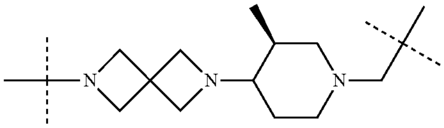
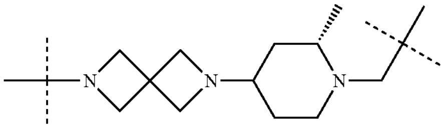
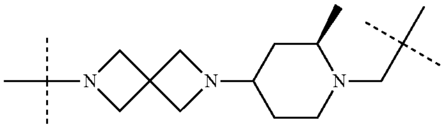
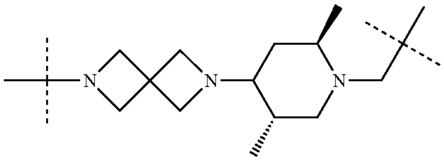
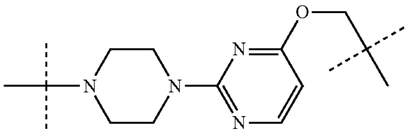
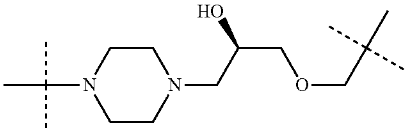

-continued
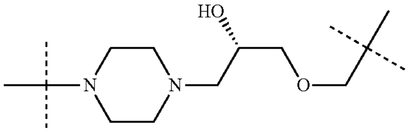
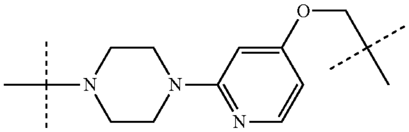
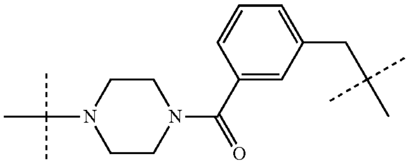
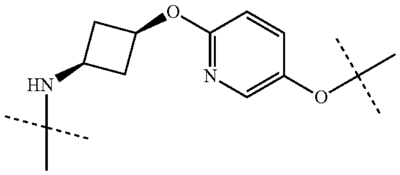
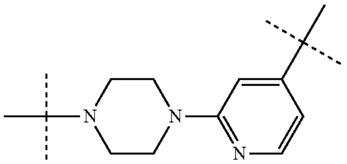
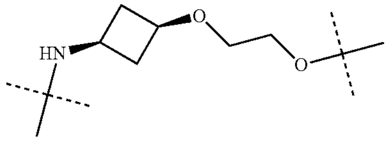
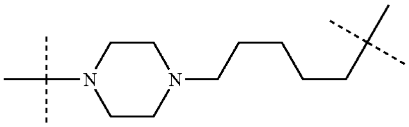
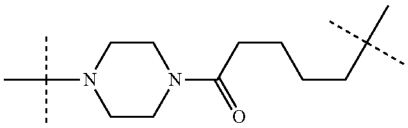
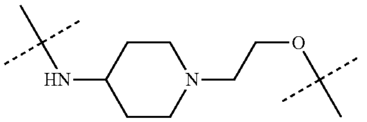
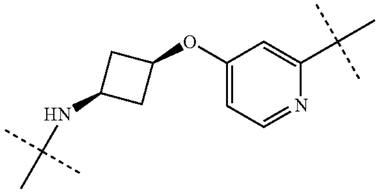
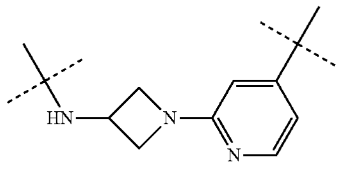
-continued
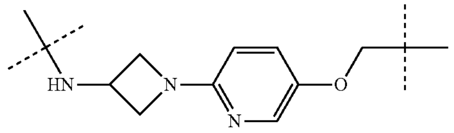
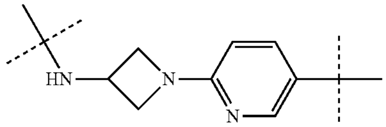
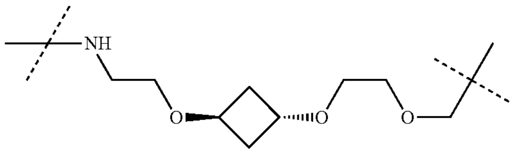
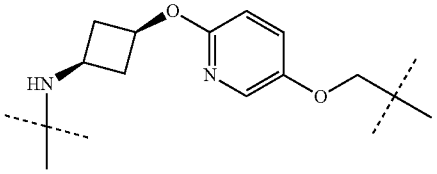
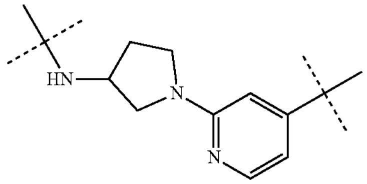
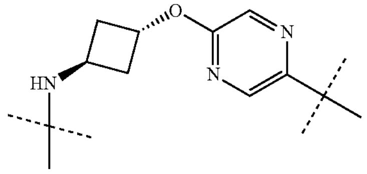
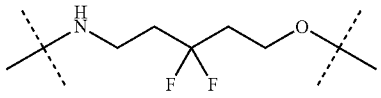
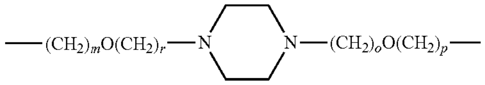
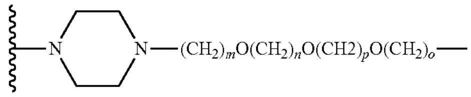
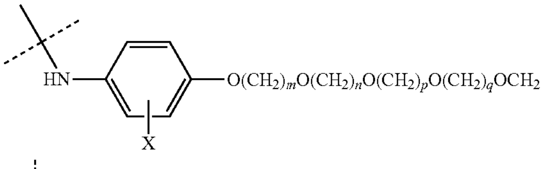
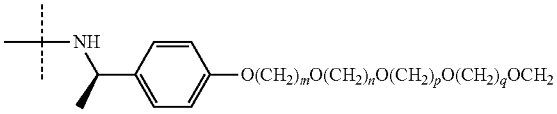
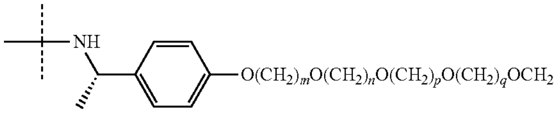
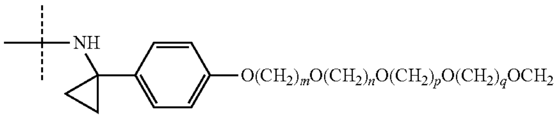

-continued
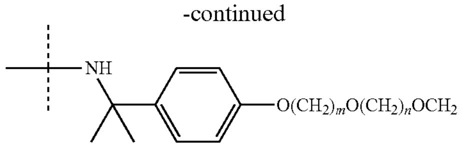
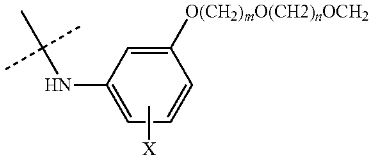
and
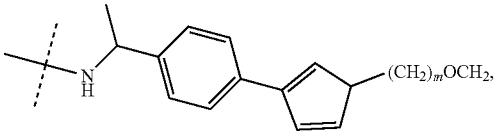
,
wherein:
each m, n, o, p, q, and r of the L is independently selected from 0, 1, 2, 3, 4, 5, and 6, when the number is zero, there is no N—O or O—O bond;
R of L is H, methyl, or ethyl;
X of L is H or F.
* * * * *

UNITED STATES PATENT AND TRADEMARK OFFICE

CERTIFICATE OF CORRECTION

PATENT NO. : 11,584,743 B2
APPLICATION NO. : 17/082839
DATED : February 21, 2023
INVENTOR(S) : Andrew P. Crew et al.

It is certified that error appears in the above-identified patent and that said Letters Patent is hereby corrected as shown below:

In the Claims

In Claim 9, Column 145, Lines 20-30, delete the structure “ 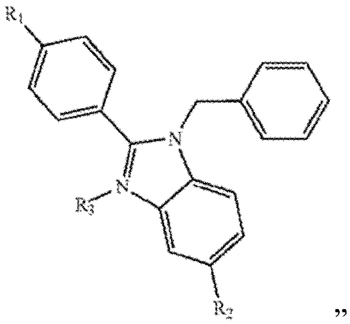 ”.

In Claim 17, Column 147, Line 2, replace the phrase “$NO^2$” with --$NO_2$--.

In Claim 19, Column 153, Lines 15-20, replace the formula

“ 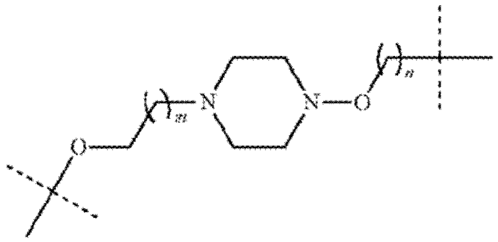 ” with the formulae

-- 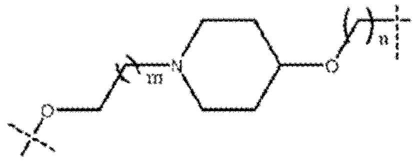 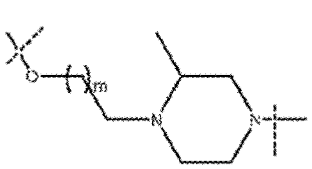 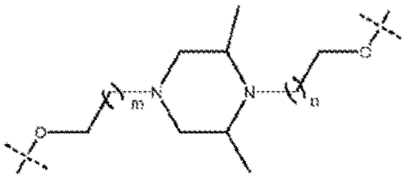 --.

Signed and Sealed this
Ninth Day of May, 2023

Katherine Kelly Vidal

Katherine Kelly Vidal
*Director of the United States Patent and Trademark Office*

In Claim 19, Column 171, Lines 55-60, replace the structure " 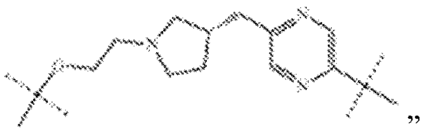 "
with the structure -- 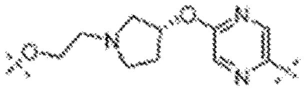 --.